US006951722B2

(12) United States Patent
Mukai et al.

(10) Patent No.: US 6,951,722 B2
(45) Date of Patent: Oct. 4, 2005

(54) METHOD FOR AMPLIFYING NUCLEIC ACID SEQUENCE

(75) Inventors: Hiroyuki Mukai, Moriyama (JP); Hiroaki Sagawa, Kusatsu (JP); Takashi Uemori, Otsu (JP); Junko Yamamoto, Moriyama (JP); Jun Tomono, Otsu (JP); Eiji Kobayashi, Otsu (JP); Tatsuji Enoki, Otsu (JP); Osamu Takeda, Hikone (JP); Kazue Miyake, Uji (JP); Yoshimi Sato, Shiga (JP); Mariko Moriyama, Kyoto (JP); Haruhisa Sawaragi, Otsu (JP); Michio Hagiya, Otsu (JP); Kiyozo Asada, Shiga (JP); Ikunoshin Kato, Uji (JP)

(73) Assignee: Takara Bio Inc., Shiga (JP)

(*) Notice: Subject to any disclaimer, the term of this patent is extended or adjusted under 35 U.S.C. 154(b) by 289 days.

(21) Appl. No.: 09/935,338

(22) Filed: Aug. 23, 2001

(65) Prior Publication Data

US 2003/0073081 A1 Apr. 17, 2003

Related U.S. Application Data

(63) Continuation-in-part of application No. PCT/JP00/01534, filed on Mar. 14, 2000.

(30) Foreign Application Priority Data

| | | |
|---|---|---|
| Mar. 19, 1999 | (JP) | 11-076966 |
| Dec. 27, 1999 | (JP) | 11-370035 |
| Aug. 23, 2000 | (JP) | 2000-251981 |
| Sep. 19, 2000 | (JP) | 2000-284419 |
| Sep. 22, 2000 | (JP) | 2000-288750 |
| Apr. 3, 2001 | (JP) | 2001-104191 |

(51) Int. Cl.$^7$ .................. C12Q 1/68

(52) U.S. Cl. .................. 435/6; 435/7.1; 435/91.1; 435/91.2; 536/22.1; 536/23.1; 536/24.3; 536/24.31; 536/24.32; 536/24.33

(58) Field of Search .................. 435/6, 7.1, 91.1, 435/91.2; 536/22.1, 23.1, 24.3–24.33

(56) References Cited

U.S. PATENT DOCUMENTS

| | | | | |
|---|---|---|---|---|
| 5,648,211 A | | 7/1997 | Fraiser et al. | |
| 5,824,517 A | | 10/1998 | Cleuziat et al. | |
| 6,251,639 B1 | * | 6/2001 | Kurn | 435/91.2 |

FOREIGN PATENT DOCUMENTS

| | | |
|---|---|---|
| EP | 0 496 483 A2 | 7/1992 |
| JP | 05/308963 A | 11/1993 |
| WO | WO 96/19572 A1 | 6/1996 |
| WO | WO 96/40901 A1 | 12/1996 |
| WO | WO 99/09211 | 2/1999 |

OTHER PUBLICATIONS

US 5,711,311, 4/1998, Fraiser et al. (withdrawn)

Sambrook, et al., "Molecular Cloning: A Laboratory Manual, Third Edition", 2001. vol. 3, A4.15, A4.16 and A4.38.

Burrows, et al., "Purification and properties of DNA polymerase from *Bacillus caldotenax*", Biochem Journal. Nov. 1, 1992, vol. 287 (Pt 3), 971–977.

Itaya, M., "Isolation and characterization of a second RNase H (RNase HII) of *Escherichia coli* K–12 encoded by the *rnhB* gene", Proc. Natl. Acad. Sci. Nov. 1990, vol. 87, 8587–8591.

* cited by examiner

*Primary Examiner*—Jeffrey Siew

(74) *Attorney, Agent, or Firm*—Browdy and Neimark, PLLC

(57) ABSTRACT

A convenient and effective method for amplifying a nucleic acid sequence characterized by effecting a DNA synthesis reaction in the presence of chimeric oligonucleotide primers; a method for supplying a large amount of DNA amplification fragments; an effective method for amplifying a nucleic acid sequence by combining the above method with another nucleic acid sequence amplification method; a method for detecting a nucleic acid sequence for detecting or quantitating a microorganism such as a virus, a bacterium, a fungus or a yeast; and a method for detecting a DNA amplification fragment obtained by the above method in situ.

72 Claims, 31 Drawing Sheets

Lane : 1 2 3 4 5 6 7 8 9 10 11

ICAN

Lane : 1 2 3 4 5 6 7 8 9 10 11

PCR

Lane 1 2 3 4 5 6 7

ICAN

Lane 1 2 3 4 5 6 7

PCR

METHOD FOR AMPLIFYING NUCLEIC ACID SEQUENCE

CROSS-REFERENCE TO RELATED APPLICATIONS

This application is a continuation-in-part application of PCT international application No. PCT/JP00/01534 which has an international filing date of Mar. 14, 2000 which designated the United States, the entire contents of which are incorporated by reference.

BACKGROUND OF THE INVENTION

1. Field of the Invention

The present invention relates to a method for detecting a target nucleic acid which is useful in a field of clinical medicine and a method for synthesizing a DNA which is useful in a field of genetic engineering. It relates to a method for amplifying a nucleic acid as a template and a method for detecting a target nucleic acid amplified by said method.

2. Description of Related Art

DNA synthesis is used for various purposes in studies in a field of genetic engineering. Most of the DNA synthesis with the exception of that of a short-chain DNA such as an oligonucleotide is carried out by enzymatic methods in which a DNA polymerase is utilized. An example of the methods is the polymerase chain reaction (PCR) method as described in U.S. Pat. Nos. 4,683,195, 4,683,202 and 4,800,159 in detail. Another example is the reverse transcription-PCR (RT-PCR) method, which is a combination of the PCR and a reverse transcriptase reaction, as described in Trends in Biotechnology, 10:146–152 (1992). The development of the above-mentioned methods has enabled the amplification of a region of interest from a DNA or an RNA.

The above-mentioned DNA synthesis methods are conducted, for example, using a reaction that consists of three steps. The three steps are a step of dissociating (denaturing) a double-stranded DNA into single-stranded DNAs, a step of annealing a primer to the single-stranded DNA and a step of synthesizing (extending) a complementary strand from the primer in order to amplify a region of a DNA of interest. Alternatively, they are conducted using a reaction designated as "the shuttle PCR" ("PCR no saizensen" (Recent advances in PCR methodology: Basic methodology and it's application), Tanpakushitsu Kakusan Kouso, Bessatsu, (Protein, Nucleic Acid and Enzyme, Supplement), 41(5):425–428 (1996)) in which two of the three steps, that is, the step of annealing the primer and the step of extending are carried out at the same temperature.

Alternatively, the ligase chain reaction (LCR) method as described in EP 320,308 published on Jun. 14, 1989 or the transcription-based amplification system (TAS) method as described in PCR Protocols, Academic Press Inc., 1990, pp. 245–252 may be used. The four methods as mentioned above require repeating a reaction at a high temperature and that at a low temperature several times in order to regenerate a single-stranded target molecule for the next amplification cycle. The reaction system should be conducted using discontinuous phases or cycles because the reaction is restricted by temperature as described above.

Thus, the methods require the use of an expensive thermal cycler that can strictly adjust a wide range of temperature over time. Furthermore, the reaction requires time for adjusting the temperature to the two or three predetermined ones. The loss of time increases in proportion to the cycle number.

Nucleic acid amplification methods that can be carried out isothermally have been developed in order to solve the problems. Examples thereof include the strand displacement amplification (SDA) method as described in JP-B 7-114718, the self-sustained sequence replication (3SR) method, the nucleic acid sequence based amplification (NASBA) method as described in Japanese Patent No. 2650159, the transcription-mediated amplification (TMA) method, the Qβ replicase method as described in Japanese Patent No. 2710159 and the various modified SDA methods as described in U.S. Pat. No. 5,824,517, WO 99/09211, WO 95/25180 and WO 99/49081. A method of isothermal enzymatic synthesis of an oligonucleotide is described in U.S. Pat. No. 5,916,777. Extension from a primer and/or annealing of a primer to a single-stranded extension product (or to an original target sequence) followed by extension from the primer take place in parallel in a reaction mixture incubated at a constant temperature in the reaction of these methods of isothermal nucleic acid amplification or synthesis of an oligonucleotide.

Among the isothermal nucleic acid amplification methods, the SDA method is an example of systems in which a DNA is finally amplified. The SDA method is a method for amplifying a target nucleic acid sequence (and a complementary strand thereof) in a sample by displacement of double strands using a DNA polymerase and a restriction endonuclease. The method requires four primers used for the amplification, two of which should be designed to contain a recognition site for the restriction endonuclease. The method requires the use of a modified deoxyribonucleotide triphosphate as a substrate for DNA synthesis in large quantities. An example of the modified deoxyribonucleotide triphosphates is an (α-S) deoxyribonucleotide triphosphate in which the oxygen atom of the phosphate group at the α-position is replaced by a sulfur atom (S). The problem of running cost associated with the use of the modified deoxyribonucleotide triphosphate becomes serious if the reaction is routinely conducted, for example, for genetic test. Furthermore, the incorporation of the modified nucleotide such as the (α-S) deoxyribonucleotide into the amplified DNA fragment in the method may abolish the cleavability of the amplified DNA fragment with a restriction enzyme, for example, when it is subjected to a restriction enzyme fragment length polymorphism (RFLP) analysis.

The modified SDA method as described in U.S. Pat. No. 5,824,517 is a DNA amplification method that uses a chimeric primer that is composed of an RNA and a DNA and has as an essential element a structure in which DNA is positioned at least at the 3'-terminus. The modified SDA method as described in WO 99/09211 requires the use of a restriction enzyme that generates a 3'-protruding end. The modified SDA method as described in WO 95/25180 requires the use of at least two pairs of primers. The modified SDA method as described in WO 99/49081 requires the use of at least two pairs of primers and at least one modified deoxyribonucleotide triphosphate. On the other hand, the method for synthesizing an oligonucleotide as described in U.S. Pat. No. 5,916,777 comprises synthesizing a DNA using a primer having a ribonucleotide at the 3'-terminus, completing a reaction using the primer, introducing a nick between the primer and an extended strand in an primer-extended strand with an endonuclease to separate them, digesting a template and recovering the primer to reuse it. It is required to isolate the primer from the reaction system and then anneal it to the template again in order to reuse the primer in the method. Additionally, the LAMP (Loop-mediated Isothermal Amplification) method as described in WO 00/28082 requires four primers for amplification and the products amplified using the method are DNAs having varying size in which the target regions for the amplification are repeated.

As described above, the conventional isothermal nucleic acid amplification methods still have various problems. Thus, a method for amplifying a nucleic acid at low running cost by which a DNA fragment that can be further genetically engineered is obtained has been desired.

The main object of the present invention is to provide a method for amplifying a target nucleic acid which specifically amplifies with high sensitivity a target nucleic acid in a sample by DNA synthesis reaction using a chimeric oligonucleotide primer, a method for detecting a amplified fragment obtained by said method, a method for producing a target nucleic acid using said amplification method and a chimeric oligonucleotide primer used for these methods.

SUMMARY OF THE INVENTION

As a result of intensive studies, the present inventors have constructed an excellent system for gene amplification reaction. The construction was accomplished by developing a method in which a region of a DNA of interest is amplified in the presence of a chimeric oligonucleotide primer having a ribonucleotide positioned at the 3'-terminus or on the 3'-terminal side, an endonuclease and a DNA polymerase. Thus, the present invention has been completed. The method is a method for amplifying a nucleic acid in which a chimeric oligonucleotide primer is used and herein referred to as ICAN (Isothermal and Chimeric primer-initiated Amplification of Nucleic acids) method.

The first invention of the present invention relates to a method for amplifying a nucleotide sequence, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template, wherein the primer is a chimeric oligonucleotide primer containing a deoxyribonucleotide and a ribonucleotide, the ribonucleotide being positioned at the 3'-terminus or on the 3'-terminal side of the primer for cleavage with an endonuclease;

(b) cleaving the primer-extended strand of a double-stranded nucleic acid obtained in step (a) with the endonuclease at a site that contains the ribonucleotide; and (c) extending a nucleotide sequence that is complementary to the template using a DNA polymerase having a strand displacement activity from the 3'-terminus of the primer portion of the double-stranded nucleic acid in which the primer-extended strand is cleaved obtained in step (b) to effect a strand displacement.

The second invention of the present invention relates to a method for amplifying a nucleotide sequence using at least two primers, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template, wherein the primer is a chimeric oligonucleotide primer containing a deoxyribonucleotide and a ribonucleotide, the ribonucleotide being positioned at the 3'-terminus or on the 3'-terminal side of the primer for cleavage with an endonuclease;

(b) cleaving the primer-extended strand of a double-stranded nucleic acid obtained in step (a) with the endonuclease at a site that contains the ribonucleotide;

(c) extending a nucleotide sequence that is complementary to the template using a DNA polymerase having a strand displacement activity from the 3'-terminus of the primer portion of the double-stranded nucleic acid in which the primer-extended strand is cleaved obtained in step (b) to effect a strand displacement, wherein a double-stranded nucleic acid containing a regenerated primer-extended strand is reused in step (b);

(d) treating a released displaced strand obtained in step (c) as a template with at least one primer that is different from that used in step (a) and a DNA polymerase to synthesize a primer-extended strand that is complementary to the displaced strand, wherein the primer that is different from that used in step (a) is a chimeric oligonucleotide primer that is substantially complementary to the nucleotide sequence of the displaced strand and contains a deoxyribonucleotide and a ribonucleotide, the ribonucleotide being positioned at the 3'-terminus or on the 3'-terminal side of the primer for cleavage with an endonuclease;

(e) cleaving the primer-extended strand of a double-stranded nucleic acid obtained in step (d) with the endonuclease at a site that contains the ribonucleotide; and (f) extending a nucleotide sequence that is complementary to the template using a DNA polymerase having a strand displacement activity from the 3'-terminus of the primer portion of the double-stranded nucleic acid in which the primer-extended strand is cleaved obtained in step (e) to effect a strand displacement, wherein a double-stranded nucleic acid containing a regenerated primer-extended strand is reused in step (e).

The method of the first and second inventions of the present invention may be conducted isothermally. The nucleotide sequence as the template may be a DNA sequence. A step of preparing a single-stranded cDNA by a reverse transcription reaction using reverse transcriptase and an RNA as a template may be comprised prior to step (a) of the first and second inventions. The single-stranded cDNA may be used as the nucleotide sequence as the template. Both of a single-stranded DNA and a double-stranded DNA can be preferably used as the DNA as the template in the first and second inventions of the present inventions. If a double-stranded DNA is used as the template, the method of the present invention may be conducted after a pretreatment step of denaturing the double-stranded DNA into single-stranded DNAs.

In the above-mentioned inventions, the extension from the primer is conducted using a DNA polymerase having a strand displacement activity. A DNA polymerase selected from the group consisting of Klenow fragment of DNA polymerase I from *Escherichia coli*, Bst DNA polymerase lacking 5'→3' exonuclease from *Bacillus stearothermophilus* and Bca DNA polymerase lacking 5'→3' exonuclease from *Bacillus caldotenax* can be preferably used in the present invention. Additionally, an endoribonuclease can be preferably used as the endonuclease. The endoribonuclease that can be used include, but are not limited to, RNase H, for example.

The third invention of the present invention relates to a method for amplifying a nucleotide sequence, characterized in that the method comprises:

(a) preparing a reaction mixture by mixing a nucleic acid as a template, a deoxyribonucleotide triphosphate, a DNA polymerase having a strand displacement activity, at least one primer and an endonuclease that cleaves an extended strand generated from the primer, wherein the primer is a chimeric oligonucleotide primer that is substantially complementary to the nucleotide sequence of the nucleic acid as the template and contains a deoxyribonucleotide and a ribonucleotide, the ribonucleotide being positioned at the 3'-terminus or on the 3'-terminal side of the primer for cleavage with the endonuclease; and (b) incubating the reaction mixture for a sufficient time to generate a reaction product.

Examples of the nucleotide sequences as the templates that can be used in the third invention include a nucleotide sequence selected from the group consisting of a single-stranded DNA, a double-stranded DNA denatured into single-stranded DNAs and a cDNA obtained by a reverse transcription reaction from an RNA. Two or more chimeric oligonucleotide primers may be contained in the reaction mixture. The DNA polymerase having a strand displacement activity and the endonuclease used in the first and second inventions can be preferably used in this invention.

The primer used in the first to third inventions of the present invention is a chimeric oligonucleotide primer. For example, a chimeric oligonucleotide having a structure in which at least one, preferably two or more successive ribonucleotide residues are attached at the 3'-terminus or on the 3'-terminal side of the primer can be used.

The template used in the first to third inventions of the present invention may be a nucleic acid that is amplified beforehand by a nucleic acid amplification method. For example, the TAS method, the 3SR method, the NASBA method, the TMA method, the Qβ replicase method, the PCR method, the LCR method and the SDA method can be utilized as the nucleic acid amplification method although any methods for amplifying a nucleic acid can be used without limitation. The method of the present invention can be used in combination with these nucleic acid amplification methods.

A random primer or a degenerate primer can be used in the nucleic acid amplification reaction. For example, without limitation, a primer having a random sequence or a degenerate sequence at least at the 3'-terminus or on the 3'-terminal side can be preferably used.

The fourth invention of the present invention relates to a chimeric oligonucleotide primer that can be used for the first to third inventions. The primer is characterized in that it contains a deoxyribonucleotide and a ribonucleotide and has a structure in which the ribonucleotide is position at the 3'-terminus or on the 3'-terminal side of the primer. For example, a chimeric oligonucleotide primer that contains at least one, preferably two or more successive ribonucleotide residues and enables the extension of a DNA strand from the 3'-terminus thereof may be used. Such a primer is designed such that it is cleaved by the action of a ribonuclease such as RNase H at the 3'-terminus of the ribonucleotide residue.

The fifth invention of the present invention relates to a DNA polymerase having a strand displacement activity, an endonuclease, and a kit that contains them used for the first to third inventions.

The sixth invention of the present invention relates to a method for detecting a target nucleic acid, characterized in that the method comprises amplifying a target nucleic acid by the method for amplifying a nucleotide sequence of the first to third inventions of the present invention and then detecting the nucleic acid. The methods of detection include a method in which the target nucleic acid is detected using a ribonucleotide (RNA) probe labeled with two or more fluorescent dyes positioned at a distance that results in a quenching state.

The seventh invention of the present invention relates to a DNA polymerase having a strand displacement activity, an endonuclease and a kit that contains them used for the method for detecting a target nucleic acid of the sixth invention of the present invention.

The eighth invention of the present invention relates to a method for producing a material having an immobilized nucleic acid in which the nucleic acid is arrayed in a predefined region, characterized in that the method comprises arraying and immobilizing the nucleic acid amplified by the method for amplifying a nucleotide sequence of the first to third inventions of the present invention in a predefined region on a substrate. A method in which a single-stranded nucleic acid substantially free of a complementary strand thereto is amplified, and arrayed and immobilized in the predefined region is particularly preferable.

The ninth invention of the present invention relates to a material having an immobilized nucleic acid in which the nucleic acid is arrayed in a predefined region produced by the method of the eighth invention of the present invention. A material having an immobilized nucleic acid in which a single-stranded nucleic acid substantially free of a complementary strand thereto is arrayed and immobilized in the predefined region is particularly preferable.

The tenth invention of the present invention relates to a method for detecting a target nucleic acid in a sample, characterized in that the method uses the material having an immobilized nucleic acid in which the nucleic acid is arrayed in a predefined region of the ninth invention of the present invention to detect a nucleic acid that hybridizes with the nucleic acid arrayed and immobilized in the predefined region on the material.

The eleventh invention of the present invention relates to a method for producing a nucleic acid in large quantities, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template, wherein the primer is a chimeric oligonucleotide primer containing a deoxyribonucleotide and a ribonucleotide, the ribonucleotide being positioned at the 3'-terminus or on the 3'-terminal side of the primer for cleavage with an endonuclease;

(b) cleaving the primer-extended strand of a double-stranded nucleic acid obtained in step (a) with the endonuclease at a site that contains the ribonucleotide; and (c) extending a nucleotide sequence that is complementary to the template using a DNA polymerase having a strand displacement activity from the 3'-terminus of the primer portion of the double-stranded nucleic acid in which the primer-extended strand is cleaved obtained in step (b) to effect a strand displacement.

The twelfth invention of the present invention relates to a method for producing a nucleic acid in large quantities using at least two primers, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template, wherein the primer is a chimeric oligonucleotide primer containing a deoxyribonucleotide and a ribonucleotide, the ribonucleotide being positioned at the 3'-terminus or on the 3'-terminal side of the primer for cleavage with an endonuclease;

(b) cleaving the primer-extended strand of a double-stranded nucleic acid obtained in step (a) with the endonuclease at a site that contains the ribonucleotide;

(c) extending a nucleotide sequence that is complementary to the template using a DNA polymerase having a strand displacement activity from the 3'-terminus of the primer portion of the double-stranded nucleic acid in which the primer-extended strand is cleaved obtained in step (b) to effect a strand displacement, wherein a double-stranded nucleic acid containing a regenerated primer-extended strand is reused in step (b);

(d) treating a released displaced strand obtained in step (c) as a template with at least one primer that is different from that used in step (a) and a DNA polymerase to synthesize a primer-extended strand that is complementary to the displaced strand, wherein the primer that is different from that used in step (a) is a chimeric oligonucleotide primer that is substantially complementary to the nucleotide sequence of the displaced strand and contains a deoxyribonucleotide and a ribonucleotide, the ribonucleotide being positioned at the 3'-terminus or on the 3'-terminal side of the primer for cleavage with an endonuclease;

(e) cleaving the primer-extended strand of a double-stranded nucleic acid obtained in step (d) with the endonuclease at a site that contains the ribonucleotide; and (f) extending a nucleotide sequence that is complementary to the template using a DNA polymerase having a strand displacement activity from the 3'-terminus of the primer portion of the double-stranded nucleic acid in which the primer-extended strand is cleaved obtained in step (e) to effect a strand displacement, wherein a double-stranded nucleic acid containing a regenerated primer-extended strand is reused in step (e).

The thirteenth invention of the present invention relates to a method for producing a nucleic acid in large quantities, characterized in that the method comprises:

(a) preparing a reaction mixture by mixing a nucleic acid as a template, a deoxyribonucleotide triphosphate, a DNA polymerase having a strand displacement activity, at least one primer and an endonuclease that cleaves an extended strand generated from the primer, wherein the primer is a chimeric oligonucleotide primer that is substantially complementary to the nucleotide sequence of the nucleic acid as the template and contains a deoxyribonucleotide and a ribonucleotide, the ribonucleotide being positioned at the 3'-terminus or on the 3'-terminal side of the primer for cleavage with the endonuclease; and (b) incubating the reaction mixture for a sufficient time to generate a reaction product.

The fourteenth invention of the present invention relates to a method for amplifying a nucleotide sequence, characterized in that the method comprises:

(a) amplifying a nucleic acid containing a sequence to be amplified by a nucleic acid amplification reaction to prepare a nucleic acid as a template;

(b) treating the nucleic acid as the template obtained in step (a) with at least one primer that is substantially complementary to the nucleotide sequence of the nucleic acid and a DNA polymerase to synthesize a primer-extended strand that is complementary to the template, wherein the primer is a chimeric oligonucleotide primer containing a deoxyribonucleotide and a ribonucleotide, the ribonucleotide being positioned at the 3'-terminus or on the 3'-terminal side of the primer for cleavage with an endonuclease;

(c) cleaving the primer-extended strand of a double-stranded nucleic acid obtained in step (b) with the endonuclease at a site that contains the ribonucleotide; and (d) extending a nucleotide sequence that is complementary to the template using a DNA polymerase having a strand displacement activity from the 3'-terminus of the primer portion of the double-stranded nucleic acid in which the primer-extended strand is cleaved obtained in step (c) to effect a strand displacement.

The fifteenth invention of the present invention relates to a method for amplifying a nucleotide sequence using at least two primers, characterized in that the method comprises:

(a) amplifying a nucleic acid containing a sequence to be amplified by a nucleic acid amplification reaction to prepare a nucleic acid as a template;

(b) treating the nucleic acid as the template obtained in step (a) with at least one primer that is substantially complementary to the nucleotide sequence of the nucleic acid and a DNA polymerase to synthesize a primer-extended strand that is complementary to the template, wherein the primer is a chimeric oligonucleotide primer containing a deoxyribonucleotide and a ribonucleotide, the ribonucleotide being positioned at the 3'-terminus or on the 3'-terminal side of the primer for cleavage with an endonuclease;

(c) cleaving the primer-extended strand of a double-stranded nucleic acid obtained in step (b) with the endonuclease at a site that contains the ribonucleotide;

(d) extending a nucleotide sequence that is complementary to the template using a DNA polymerase having a strand displacement activity from the 3'-terminus of the primer portion of the double-stranded nucleic acid in which the primer-extended strand is cleaved obtained in step (c) to effect a strand displacement, wherein a double-stranded nucleic acid containing a regenerated primer-extended strand is reused in step (c);

(e) treating a released displaced strand obtained in step (d) as a template with at least one primer that is different from that used in step (b) and a DNA polymerase to synthesize a primer-extended strand that is complementary to the displaced strand, wherein the primer that is different from that used in step (b) is a chimeric oligonucleotide primer that is substantially complementary to the nucleotide sequence of the displaced strand and contains a deoxyribonucleotide and a ribonucleotide, the ribonucleotide being positioned at the 3'-terminus or on the 3'-terminal side of the primer for cleavage with an endonuclease;

(f) cleaving the primer-extended strand of a double-stranded nucleic acid obtained in step (e) with the endonuclease at a site that contains the ribonucleotide; and (g) extending a nucleotide sequence that is complementary to the template using a DNA polymerase having a strand displacement activity from the 3'-terminus of the primer portion of the double-stranded nucleic acid in which the primer-extended strand is cleaved obtained in step (f) to effect a strand displacement, wherein a double-stranded nucleic acid containing a regenerated primer-extended strand is reused in step (f).

The sixteenth invention of the present invention relates to a method for amplifying a nucleotide sequence, characterized in that the method comprises:

(a) amplifying a nucleic acid containing a sequence to be amplified by a nucleic acid amplification reaction to prepare a nucleic acid as a template;

(b) preparing a reaction mixture by mixing the nucleic acid as the template obtained in step (a), a deoxyribonucleotide triphosphate, a DNA polymerase having a strand displacement activity, at least one primer and an endonuclease that cleaves an extended strand generated from the primer, wherein the primer is a chimeric oligonucleotide primer that is substantially complementary to the nucleotide sequence of the nucleic acid as the template and contains a deoxyribonucleotide and a ribonucleotide, the ribonucleotide being positioned at the 3'-terminus or on the 3'-terminal side of the primer for cleavage with the endonuclease; and (c) incubating the reaction mixture for a sufficient time to generate a reaction product.

In the fourteenth to sixteenth inventions of the present invention, a nucleic acid containing a sequence to be amplified is amplified beforehand by a nucleic acid amplification reaction. The amplification product is then used as a nucleic acid as a template in the method of the first to third inventions of the present invention. For example, the TAS method, the 3SR method, the NASBA method, the TMA method, the Qβ replicase method, the PCR method, the LCR method and the SDA method can be used as the nucleic acid amplification method used in the fourteenth to sixteenth inventions although any methods for amplifying a nucleic acid can be used without limitation.

A random primer or a degenerate primer can be used in the nucleic acid amplification reaction. For example, without limitation, a primer having a random sequence or a degenerate sequence at least at the 3'-terminus or on the 3'-terminal side can be preferably used.

The seventeenth invention of the present invention relates to a method for amplifying a nucleotide sequence, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template, wherein the primer is a chimeric oligonucleotide primer containing a deoxyribonucleotide and a ribonucleotide, the ribonucleotide being positioned at the 3'-terminus or on the 3'-terminal side of the primer;

(b) cleaving the primer-extended strand of a double-stranded nucleic acid obtained in step (a) with an endonuclease at a site that contains the ribonucleotide; and (c) extending a nucleotide sequence that is complementary to the template using a DNA polymerase having a strand displacement activity from the 3'-terminus of the primer portion of the double-stranded nucleic acid in which the primer-extended strand is cleaved obtained in step (b) to effect a strand displacement.

The eighteenth invention of the present invention relates to a method for amplifying a nucleotide sequence using at least two primers, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template, wherein the primer is a chimeric oligonucleotide primer containing a deoxyribonucleotide and a ribonucleotide, the ribonucleotide being positioned at the 3'-terminus or on the 3'-terminal side of the primer;

(b) cleaving the primer-extended strand of a double-stranded nucleic acid obtained in step (a) with an endonuclease at a site that contains the ribonucleotide;

(c) extending a nucleotide sequence that is complementary to the template using a DNA polymerase having a strand displacement activity from the 3'-terminus of the primer portion of the double-stranded nucleic acid in which the primer-extended strand is cleaved obtained in step (b) to effect a strand displacement, wherein a double-stranded nucleic acid containing a regenerated primer-extended strand is reused in step (b);

(d) treating a released displaced strand obtained in step (c) as a template with at least one primer that is different from that used in step (a) and a DNA polymerase to synthesize a primer-extended strand that is complementary to the displaced strand, wherein the primer that is different from that used in step (a) is a chimeric oligonucleotide primer that is substantially complementary to the nucleotide sequence of the displaced strand and contains a deoxyribonucleotide and a ribonucleotide, the ribonucleotide being positioned at the 3'-terminus or on the 3'-terminal side of the primer;

(e) cleaving the primer-extended strand of a double-stranded nucleic acid obtained in step (d) with an endonuclease at a site that contains the ribonucleotide; and (f) extending a nucleotide sequence that is complementary to the template using a DNA polymerase having a strand displacement activity from the 3'-terminus of the primer portion of the double-stranded nucleic acid in which the primer-extended strand is cleaved obtained in step (e) to effect a strand displacement, wherein a double-stranded nucleic acid containing a regenerated primer-extended strand is reused in step (e).

The nineteenth invention of the present invention relates to a method for amplifying a nucleotide sequence, characterized in that the method comprises:

(a) preparing a reaction mixture by mixing a nucleic acid as a template, a deoxyribonucleotide triphosphate, a DNA polymerase having a strand displacement activity, at least one primer and an endonuclease that cleaves an extended strand generated from the primer, wherein the primer is a chimeric oligonucleotide primer that is substantially complementary to the nucleotide sequence of the nucleic acid as the template and contains a deoxyribonucleotide and a ribonucleotide, the ribonucleotide being positioned at the 3'-terminus or on the 3'-terminal side of the primer; and (b) incubating the reaction mixture for a sufficient time to generate a reaction product.

The twentieth invention of the present invention relates to a method for amplifying a nucleotide sequence, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template, wherein the primer is a chimeric oligonucleotide primer containing a deoxyribonucleotide and a ribonucleotide, the ribonucleotide being positioned at the 3'-terminus or on the 3'-terminal side of the primer, wherein an endonuclease cleaves at a site that contains the ribonucleotide;

(b) cleaving the primer-extended strand of a double-stranded nucleic acid obtained in step (a) with the endonuclease at the site that contains the ribonucleotide; and (c) extending a nucleotide sequence that is complementary to the template using a DNA polymerase having a strand displacement activity from the 3'-terminus of the primer portion of the double-stranded nucleic acid in which the primer-extended strand is cleaved obtained in step (b) to effect a strand displacement.

The twenty-first invention of the present invention relates to a method for amplifying a nucleotide sequence using at least two primers, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template, wherein the primer is a chimeric oligonucleotide primer containing a deoxyribonucleotide and a ribonucleotide, the ribonucleotide being positioned at the 3'-terminus or on the 3'-terminal side of the primer, wherein an endonuclease cleaves at a site that contains the ribonucleotide;

(b) cleaving the primer-extended strand of a double-stranded nucleic acid obtained in step (a) with the endonuclease at the site that contains the ribonucleotide;

(c) extending a nucleotide sequence that is complementary to the template using a DNA polymerase having a strand displacement activity from the 3'-terminus of the primer portion of the double-stranded nucleic acid in which the primer-extended strand is cleaved obtained in step (b) to effect a strand displacement, wherein a double-stranded nucleic acid containing a regenerated primer-extended strand is reused in step (b);

(d) treating a released displaced strand obtained in step (c) as a template with at least one primer that is different from that used in step (a) and a DNA polymerase to synthesize a primer-extended strand that is complementary to the displaced strand, wherein the primer that is different from that used in step (a) is a chimeric oligonucleotide primer that is substantially complementary to the nucleotide sequence of the displaced strand and contains a deoxyribonucleotide and a ribonucleotide, the ribonucleotide being positioned at the 3'-terminus or on the 3'-terminal side of the primer, wherein an endonuclease cleaves at a site that contains the ribonucleotide;

(e) cleaving the primer-extended strand of a double-stranded nucleic acid obtained in step (d) with the endonuclease at the site that contains the ribonucleotide; and (f) extending a nucleotide sequence that is complementary to the template using a DNA polymerase having a strand displacement activity from the 3'-terminus of the primer portion of the double-stranded nucleic acid in which the primer-extended strand is cleaved obtained in step (e) to effect a strand displacement, wherein a double-stranded nucleic acid containing a regenerated primer-extended strand is reused in step (e).

The twenty-second invention of the present invention relates to a method for amplifying a nucleotide sequence, characterized in that the method comprises:

(a) preparing a reaction mixture by mixing a nucleic acid as a template, a deoxyribonucleotide triphosphate, a DNA polymerase having a strand displacement activity, at least one primer and an endonuclease that cleaves an extended strand generated from the primer, wherein the primer is a chimeric oligonucleotide primer that is substantially complementary to the nucleotide sequence of the nucleic acid as the template and contains a deoxyribonucleotide and a ribonucleotide, the ribonucleotide being positioned at the 3'-terminus or on the 3'-terminal side of the primer, wherein the endonuclease cleaves at a site that contains the ribonucleotide; and (b) incubating the reaction mixture for a sufficient time to generate a reaction product.

The twenty-third invention of the present invention relates to a method for determining a nucleotide sequence of a nucleic acid, characterized in that the method comprises amplifying a nucleotide sequence according to the method of any one of the first to third and fourteenth to twenty-second inventions.

The twenty-fourth invention of the present invention relates to a method for amplifying a target nucleic acid, characterized in that the method comprises:

(a) preparing a reaction mixture by mixing a nucleic acid as a template, a deoxyribonucleotide triphosphate, a DNA polymerase having a strand displacement activity, at least one primer and an RNase H, wherein the primer is a chimeric oligonucleotide primer that is substantially complementary to the nucleotide sequence of the nucleic acid as the template and contains a ribonucleotide as well as at least one selected from the group consisting of a deoxyribonucleotide and a nucleotide analog, the ribonucleotide being positioned at the 3'-terminus or on the 3'-terminal side of the primer; and (b) incubating the reaction mixture for a sufficient time to generate a reaction product.

In the twenty-fourth invention of the present invention, a reaction mixture that further contains a chimeric oligonucleotide primer having a sequence that is substantially homologous to the nucleotide sequence of the nucleic acid as the template can be used.

The twenty-fifth invention of the present invention relates to a method for amplifying a nucleic acid, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template and synthesize a double-stranded nucleic acid, wherein the primer is a chimeric oligonucleotide primer containing a ribonucleotide as well as at least one selected from the group consisting of a deoxyribonucleotide and a nucleotide analog, the ribonucleotide being positioned at the 3'-terminus or on the 3'-terminal side of the primer;

(b) extending a nucleic acid that is complementary to the double-stranded nucleic acid as a template obtained in the previous step using a DNA polymerase having a strand displacement activity in the presence of an RNase H to effect a strand displacement and synthesize a displaced strand and a double-stranded nucleic acid; and (c) reusing in step (b) the double-stranded nucleic acid obtained in step (b) as a template.

The twenty-sixth invention of the present invention relates to a method for amplifying a nucleic acid using at least two primers, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template, wherein the primer is a chimeric oligonucleotide primer containing a ribonucleotide as well as at least one selected from the group consisting of a deoxyribonucleotide and a nucleotide analog, the ribonucleotide being positioned at the 3'-terminus or on the 3'-terminal side of the primer;

(b) extending a nucleic acid that is complementary to the double-stranded nucleic acid as a template obtained in the previous step using a DNA polymerase having a strand displacement activity in the presence of an RNase H to effect a strand displacement and synthesize a displaced strand and a double-stranded nucleic acid;

(c) reusing in step (b) the double-stranded nucleic acid obtained in step (b) as a template;

(d) treating a displaced strand obtained in step (b) as a template with at least one primer that is different from that used in step (a) and a DNA polymerase to synthesize a primer-extended strand that is complementary to the displaced strand, wherein the primer that is different from that used in step (a) is a chimeric oligonucleotide primer that is substantially complementary to the nucleotide sequence of the displaced strand and contains a ribonucleotide as well as at least one selected from the group consisting of a deoxyribonucleotide and a nucleotide analog, the ribonucleotide being positioned at the 3'-terminus or on the 3'-terminal side of the primer;

(e) extending a nucleic acid that is complementary to the double-stranded nucleic acid as a template obtained in the previous step using a DNA polymerase having a strand displacement activity in the presence of an RNase H to effect a strand displacement and synthesize a displaced strand and a double-stranded nucleic acid; and (f) reusing in step (e) the double-stranded nucleic acid obtained in step (e) as a template.

In the twenty-fifth or twenty-sixth invention of the present invention, a DNA polymerase having a strand displacement activity can be used as the DNA polymerase.

The twenty-seventh invention of the present invention relates to method for amplifying a nucleic acid, characterized in that the method comprises:

(a) treating a double-stranded nucleic acid as a template with two primers that are substantially complementary to the nucleotide sequences of the respective strands of the double-stranded nucleic acid and a DNA polymerase having a strand displacement activity to synthesize primer-extended strands that are complementary to the template and obtain a double-stranded nucleic acid consisting of the synthesized primer-extended strands being annealed each other, wherein each primer is a chimeric oligonucleotide primer containing a ribonucleotide as well as at least one selected from the group consisting of a deoxyribonucleotide and a nucleotide analog, the ribonucleotide being positioned at the 3'-terminus or on the 3'-terminal side of the primer;

(b) cleaving the double-stranded nucleic acid consisting of the primer-extended strands obtained in step (a) with the endonuclease at sites that contain the ribonucleotides; and (c) extending nucleic acids that are complementary to the template using a DNA polymerase having a strand displacement activity from the 3'-termini of the respective primer portions of the double-stranded nucleic acid in which the primer-extended strands are cleaved obtained in step (b) to effect strand displacements and obtain a double-stranded nucleic acid consisting of the template and the primer-extended strand.

The twenty-eighth invention of the present invention relates to a method for amplifying a nucleic acid, characterized in that the method comprises:

(a) treating a double-stranded nucleic acid as a template with two primers that are substantially complementary to the nucleotide sequences of the respective strands of the double-stranded nucleic acid and a DNA polymerase having a strand displacement activity to synthesize primer-extended strands that are complementary to the template and obtain a double-stranded nucleic acid consisting of the synthesized primer-extended strands being annealed each other, wherein each primer is a chimeric oligonucleotide primer containing a ribonucleotide as well as at least one selected from the group consisting of a deoxyribonucleotide and a nucleotide analog, the ribonucleotide being positioned at the 3'-terminus or on the 3'-terminal side of the primer;

(b) cleaving the double-stranded nucleic acid consisting of the primer-extended strands obtained in step (a) with the endonuclease at sites that contain the ribonucleotides; and (c) extending nucleic acids that are complementary to the template using a DNA polymerase having a strand displacement activity from the 3'-termini of the respective primer portions of the double-stranded nucleic acid in which the primer-extended strands are cleaved obtained in step (b) to effect strand displacements and obtain a double-stranded nucleic acid consisting of the primer-extended strands being annealed each other.

The twenty-ninth invention of the present invention relates to a method for amplifying a nucleic acid, characterized in that the method comprises:

(a) treating a double-stranded nucleic acid as a template with two primers that are substantially complementary to the nucleotide sequences of the respective strands of the double-stranded nucleic acid and a DNA polymerase having a strand displacement activity to synthesize primer-extended strands that are complementary to the template and obtain a double-stranded nucleic acid consisting of the synthesized primer-extended strands being annealed each other, wherein each primer is a chimeric oligonucleotide primer containing a ribonucleotide as well as at least one selected from the group consisting of a deoxyribonucleotide and a nucleotide analog, the ribonucleotide being positioned at the 3'-terminus or on the 3'-terminal side of the primer;

(b) cleaving the double-stranded nucleic acid consisting of the primer-extended strands obtained in step (a) with the endonuclease at sites that contain the ribonucleotides;

(c) extending nucleic acids that are complementary to the template using a DNA polymerase having a strand displacement activity from the 3'-termini of the respective primer portions of the double-stranded nucleic acid in which the primer-extended strands are cleaved obtained in step (b) to effect strand displacements and obtain a double-stranded nucleic acid consisting of the primer-extended strands being annealed each other and a double-stranded nucleic acid consisting of the templates being annealed each other to which the two primers in step (a) are annealed;

(d) extending nucleic acids that are complementary to the template using a DNA polymerase having a strand displacement activity from the 3'-termini of the respective primer portions of the double-stranded nucleic acid to which the two primers are annealed obtained in step (c) to effect strand displacements and obtain a double-stranded nucleic acid consisting of the primer-extended strands being annealed each other and a double-stranded nucleic acid consisting of the templates being annealed each other to which the two primers in step (a) are annealed; and (e) reusing in step (d) the double-stranded nucleic acid to which the two primers are annealed obtained in step (d).

The thirtieth invention of the present invention relates to a method for amplifying a nucleic acid, characterized in that the method comprises:

(a) treating a double-stranded nucleic acid as a template with two primers that are substantially complementary to the nucleotide sequences of the respective strands of the double-stranded nucleic acid and a DNA polymerase having a strand displacement activity to synthesize primer-extended strands that are complementary to the template and obtain a double-stranded nucleic acid consisting of the synthesized primer-extended strands being annealed each other, wherein each primer is a chimeric oligonucleotide primer containing a ribonucleotide as well as at least one selected from the group consisting of a deoxyribonucleotide and a nucleotide analog, the ribonucleotide being positioned at the 3'-terminus or on the 3'-terminal side of the primer;

(b) cleaving the double-stranded nucleic acid consisting of the primer-extended strands obtained in step (a) with the endonuclease at sites that contain the ribonucleotides;

(c) extending nucleic acids that are complementary to the template using a DNA polymerase having a strand displacement activity from the 3'-termini of the respective primer portions of the double-stranded nucleic acid in which the primer-extended strands are cleaved obtained in step (b) to effect strand displacements and obtain a double-stranded nucleic acid consisting of the primer-extended strands being annealed each other and a double-stranded nucleic acid consisting of the templates being annealed each other to which the two primers in step (a) are annealed;

(d) extending nucleic acids that are complementary to the template using a DNA polymerase having a strand displacement activity from the 3'-termini of the respective primer portions of the double-stranded nucleic acid to which the two primers are annealed obtained in step (c) to effect a strand displacement and obtain a double-stranded nucleic acid consisting of the template and the primer-extended strand;

(e) cleaving the double-stranded nucleic acid consisting of the template and the primer-extended strand obtained in step (d) with the endonuclease at a site that contains the ribonucleotide; and (f) extending a nucleic acid that is complementary to the template using a DNA polymerase having a strand displacement activity from the 3'-terminus of the primer portion of the double-stranded nucleic acid in which the primer-extended strand is cleaved obtained in step (e) to synthesize a displaced strand.

In the twenty-seventh to thirtieth invention, an endoribonuclease such as an RNase H can be used as the endonuclease.

In the twenty-fourth to thirtieth invention wherein an RNase H is used, an RNase H from *Escherichia coli*, a bacterium of genus *Thermotoga*, a bacterium of genus *Thermus*, a bacterium of genus *Pyrococcus*, a bacterium of genus *Archaeoglobus*, a bacterium of genus *Bacillus* or the like can be used.

In the twenty-fourth to thirtieth invention, an example of the suitable length of the region to be specifically amplified in the nucleotide sequence of the target nucleic acid is 200 bp or shorter.

For the twenty-fourth to thirtieth invention of the present invention, a chimeric oligonucleotide primer represented by general formula below can be used:

General formula: 5'-dNa-Nb-dNc-3'

(a: an integer of 11 or more; b: an integer of 1 or more; c: 0 or an integer of 1 or more; dN: deoxyribonucleotide and/or nucleotide analog; N: unmodified ribonucleotide and/or modified ribonucleotide, wherein some of dNs in dNa may be replaced by Ns, and the nucleotide at the 3'-terminus may be modified such that extension from the 3'-terminus by the action of the DNA polymerase does not take place).

Such chimeric oligonucleotide primers are exemplified by a primer in which c is 0 and a primer in which the nucleotide analog is deoxyriboinosine nucleotide or deoxyribouracil nucleotide, and the modified ribonucleotide is ($\alpha$-S) ribonucleotide. Furthermore, when such a chimeric oligonucleotide primer is used, the DNA extension reaction is conducted at a DNA extension reaction temperature suitable for the primer.

The amplification method of the twenty-fourth to thirtieth invention can comprise annealing the nucleic acid as the template to the chimeric oligonucleotide primer that is substantially complementary to the nucleotide sequence of the nucleic acid in an annealing solution containing a substance that enhances the annealing of the nucleic acid to the primer. For example, the annealing solution may contain spermidine and/or propylenediamine. The annealing can be conducted by incubating the annealing solution containing the nucleic acid as the template and the chimeric oligonucleotide primer that is substantially complementary to the nucleotide sequence of the nucleic acid at 90° C. or above and then cooling the solution to a temperature at which the amplification reaction is conducted or below.

The amplification reaction of the twenty-fourth to thirtieth invention can be conducted in a buffer containing a buffering component selected from the group consisting of Bicine and HEPES.

In the twenty-fourth to thirtieth invention, for example, a DNA polymerase selected from the group consisting of Klenow fragment of DNA polymerase I from *Escherichia coli*, Bst DNA polymerase lacking 5'→3' exonuclease from *Bacillus stearothermophilus* and Bca DNA polymerase lacking 5'→3' exonuclease from *Bacillus caldotenax* can be used as the DNA polymerase having a strand displacement activity.

In one aspect of the twenty-fourth to thirtieth invention, Bca DNA polymerase lacking 5'→3' exonuclease from *Bacillus caldotenax* is used as the DNA polymerase having a strand displacement activity and an RNase H from *Escherichia coli*, a bacterium of genus *Pyrococcus* or a bacterium of genus *Archaeoglobus* is used as the endonuclease. The RNase H is exemplified by type I RNase H from *Escherichia coli*, or type II RNase H from a bacterium of genus *Pyrococcus* or a bacterium of genus *Archaeoglobus*.

In the twenty-fourth to thirtieth invention, a DNA polymerase having an endonuclease activity can be used. Bca DNA polymerase lacking 5'→3' exonuclease from *Bacillus caldotenax* can be used as such a DNA polymerase and the amplification reaction can be conducted in the presence of a substance that allows the endonuclease activity of the DNA polymerase to express. The substance that allows the endonuclease activity of the Bca DNA polymerase to express is exemplified by a manganese ion.

The method for amplifying a target nucleic acid of the twenty-fourth to thirtieth invention can be conducted in the presence of a substance that inhibits the reverse transcription activity of the DNA polymerase. The substance that inhibits the reverse transcription activity of the DNA polymerase is exemplified by phosphonoformic acid.

The twenty-fourth to thirtieth invention of the present invention can be conducted using a single-stranded DNA or a double-stranded DNA as the template. If the nucleic acid as the template is a double-stranded DNA, the amplification reaction can be conducted after converting it into single-stranded DNAs.

The nucleic acid as the template may be a cDNA obtained by a reverse transcription reaction using an RNA as a template. In one aspect, the amplification reaction is conducted after synthesizing a cDNA by a reverse transcription reaction using an RNA as a template. A DNA polymerase having a reverse transcriptase activity can be used for the reverse transcription reaction. For example, the reverse transcription reaction and the synthesis of the extended strand that is complementary to the template can be conducted using one DNA polymerase having a reverse transcriptase activity and a strand displacement activity. Such a DNA polymerase is exemplified by Bst DNA polymerase lacking 5'→3' exonuclease from *Bacillus stearothermophilus* or Bca DNA polymerase lacking 5'→3' exonuclease from *Bacillus caldotenax*.

In the twenty-fourth to thirtieth invention, the amplification reaction can be conducted under isothermal conditions. In addition, it can be conducted in the presence of a deoxynucleotide triphosphate analog such as deoxyuridine triphosphate or a derivative thereof.

The thirty-first invention of the present invention relates to a composition for amplifying a nucleic acid which contains:

(a) at least one primer that is substantially complementary to a nucleotide sequence of a nucleic acid as a template, wherein the primer is a chimeric oligonucleotide primer that contains a ribonucleotide as well as at least one selected from the group consisting of a deoxyribonucleotide and a nucleotide analog, the ribonucleotide being positioned at the 3'-terminus or on the 3'-terminal side of the primer;

(b) an endonuclease; and (c) a DNA polymerase having a strand displacement activity.

The thirty-second invention of the present invention relates to a composition for amplifying a nucleic acid which contains:

(a) at least two primers that are substantially complementary to nucleotide sequences of respective strands of a double-stranded nucleic acid as a template, wherein each primer is a chimeric oligonucleotide primer that contains a ribonucleotide as well as at least one selected from the group consisting of a deoxyribonucleotide and a nucleotide analog, the ribonucleotide being positioned at the 3'-terminus or on the 3'-terminal side of the primer;

(b) an endonuclease; and (c) a DNA polymerase having a strand displacement activity.

The thirty-third invention of the present invention relates to a composition for amplifying a nucleic acid obtained by mixing a nucleic acid as a template, a deoxyribonucleotide triphosphate, a DNA polymerase having a strand displacement activity, at least one primer and an endonuclease, wherein the primer is a chimeric oligonucleotide primer that is substantially complementary to the nucleotide sequence of the nucleic acid as the template and contains a ribonucleotide as well as at least one selected from the group consisting of a deoxyribonucleotide and a nucleotide analog, the ribonucleotide being positioned at the 3'-terminus or on the 3'-terminal side of the primer.

The thirty-fourth invention of the present invention relates to composition for amplifying a nucleic acid obtained by mixing a nucleic acid as a template, a deoxyribonucleotide triphosphate, a DNA polymerase having a strand displacement activity, at least two primers and an endonuclease, wherein each primer is a chimeric oligonucleotide primer that is substantially complementary to the nucleotide sequence of each strand of the double-stranded nucleic acid as the template and contains a ribonucleotide as well as at least one selected from the group consisting of a deoxyribonucleotide and a nucleotide analog, the ribonucleotide being positioned at the 3'-terminus or on the 3'-terminal side of the primer.

The primer contained in the composition of the thirty-first to thirty-fourth invention of the present invention is exemplified by a chimeric oligonucleotide primer represented by general formula below:

General formula: 5'-dNa-Nb-dNc-3'

(a: an integer of 11 or more; b: an integer of 1 or more; c: 0 or an integer of 1 or more; dN: deoxyribonucleotide and/or nucleotide analog; N: unmodified ribonucleotide and/or modified ribonucleotide, wherein some of dNs in dNa may be replaced by Ns, and the nucleotide at the 3'-terminus may be modified such that extension from the 3'-terminus by the action of the DNA polymerase does not take place).

Such chimeric oligonucleotide primers are exemplified by a primer in which c is 0 and a primer in which the nucleotide analog is deoxyriboinosine nucleotide or deoxyribouracil nucleotide, and the modified ribonucleotide is ($\alpha$-S) ribonucleotide.

The composition of the thirty-first to thirty-fourth invention can contain a buffering component suitable for a nucleic acid amplification reaction. For example, it can contain a buffering component selected from the group consisting of Bicine and HEPES.

The thirty-first to thirty-fourth invention is exemplified by a composition containing a DNA polymerase selected from the group consisting of Klenow fragment of DNA polymerase I from *Escherichia coli*, Bst DNA polymerase lacking 5'→3' exonuclease from *Bacillus stearothermophilus* and Bca DNA polymerase lacking 5'→3' exonuclease from *Bacillus caldotenax* as the DNA polymerase having a strand displacement activity. An endoribonuclease such as an RNase H can be used as the endonuclease. The RNase H is exemplified by an RNase H from *Escherichia coli*, a bacterium of genus *Thermotoga*, a bacterium of genus *Thermus*, a bacterium of genus *Pyrococcus*, a bacterium of genus *Archaeoglobus*, a bacterium of genus *Bacillus* or the like.

In one aspect, the composition of the thirty-first to thirty-fourth invention contains Bca DNA polymerase lacking 5'→3' exonuclease from *Bacillus caldotenax* as the DNA polymerase having a strand displacement activity and an RNase H from *Escherichia coli*, a bacterium of genus *Pyrococcus* or a bacterium of genus *Archaeoglobus* as the endonuclease. The RNase H is exemplified by type I RNase H from *Escherichia coli*, or type II RNase H from a bacterium of genus *Pyrococcus* or a bacterium of genus *Archaeoglobus*.

The composition of the thirty-first to thirty-fourth invention may contain a DNA polymerase having an endonuclease activity. Bca DNA polymerase lacking 5'→3' exonuclease from *Bacillus caldotenax* can be used as such a DNA polymerase, which can be used in the presence of a substance that allows the endonuclease activity of the DNA polymerase to express. The substance that allows the endonuclease activity of the Bca DNA polymerase to express is exemplified by a manganese ion.

The composition of the thirty-first to thirty-fourth invention can contain a substance that inhibits the reverse transcription activity of the DNA polymerase. The substance that inhibits the reverse transcription activity of the DNA polymerase is exemplified by phosphonoformic acid. Furthermore, the composition may contain a deoxynucleotide triphosphate analog such as deoxyuridine triphosphate or a derivative thereof.

The thirty-fifth invention of the present invention relates to a composition for amplifying a nucleic acid used for the method for amplifying a nucleic acid of the twenty-fourth to twenty-sixth invention, which contains:

(a) an RNase H; and (b) a DNA polymerase having a strand displacement activity.

The thirty-sixth invention of the present invention relates to a composition for amplifying a nucleic acid used for the method for amplifying a nucleic acid of the twenty-seventh to thirtieth invention, which contains:

(a) an endonuclease; and (b) a DNA polymerase having a strand displacement activity.

An endoribonuclease such as an RNase H can be used as the endonuclease for the composition of the thirty-sixth invention.

An RNase H selected from the group consisting of an RNase H from *Escherichia coli*, an RNase H from a bacterium of genus *Thermotoga*, an RNase H from a bacterium of genus *Thermus*, an RNase H from a bacterium of genus *Pyrococcus*, an RNase H from a bacterium of genus *Archaeoglobus* and an RNase H from a bacterium of genus *Bacillus* can be used as the RNase H for the composition of the thirty-fifth or thirty-sixth invention which contains an RNase H.

The composition of the thirty-fifth or thirty-sixth invention can further contain a buffering component suitable for a nucleic acid amplification reaction. For example, the composition may contain a buffering component selected from the group consisting of Bicine and HEPES.

The thirty-fifth or thirty-sixth invention is exemplified by a composition that contains a DNA polymerase selected from the group consisting of Klenow fragment of DNA polymerase I from *Escherichia coli*, Bst DNA polymerase lacking 5'→3' exonuclease from *Bacillus stearothermophilus* and Bca DNA polymerase lacking 5'→3' exonuclease from *Bacillus caldotenax* as the DNA polymerase having a strand displacement activity. An endoribonuclease such as an RNase H can be used as the endonuclease. The RNase H is exemplified by an RNase H from *Escherichia coli*, a bacterium of genus *Thermotoga*, a bacterium of genus *Thermus*, a bacterium of genus *Pyrococcus*, a bacterium of genus *Archaeoglobus*, a bacterium of genus *Bacillus* or the like.

In one aspect, the composition of the thirty-fifth or thirty-sixth invention contains Bca DNA polymerase lacking 5'→3' exonuclease from *Bacillus caldotenax* as the DNA polymerase having a strand displacement activity and an RNase H from *Escherichia coli*, a bacterium of genus *Pyrococcus* or a bacterium of genus *Archaeoglobus* as the endonuclease. The RNase H is exemplified by type I RNase H from *Escherichia coli*, or type II RNase H from a bacterium of genus *Pyrococcus* or a bacterium of genus *Archaeoglobus*.

The composition of the thirty-fifth or thirty-sixth invention may contain a DNA polymerase having an endonuclease activity. Bca DNA polymerase lacking 5'→3' exonuclease from *Bacillus caldotenax* can be used as such a DNA polymerase, which can be used in the presence of a substance that allows the endonuclease activity of the DNA polymerase to express. The substance that allows the endonuclease activity of the Bca DNA polymerase to express is exemplified by a manganese ion.

The composition of the thirty-fifth or thirty-sixth invention can contain a substance that inhibits the reverse transcription activity of the DNA polymerase. The substance that inhibits the reverse transcription activity of the DNA polymerase is exemplified by phosphonoformic acid. Furthermore, the composition may contain a deoxynucleotide triphosphate analog such as deoxyuridine triphosphate or a derivative thereof.

The thirty-seventh invention of the present invention relates to a kit for amplifying a nucleic acid used for the method for amplifying a nucleic acid of the twenty-fourth to twenty-sixth of the present invention, which contains:

(a) an RNase H; and (b) a DNA polymerase having a strand displacement activity.

The thirty-eighth invention of the present invention relates to a kit for amplifying a nucleic acid used for the method for amplifying a nucleic acid of the twenty-seventh to thirtieth invention of the present invention, which contains:

(a) an endonuclease; and (b) a DNA polymerase having a strand displacement activity.

An endoribonuclease such as an RNase H can be used as the endonuclease for the kit of the thirty-eighth invention.

The kit of the thirty-seventh or thirty-eighth invention which contains an RNase H is exemplified by a kit containing an RNase H selected from the group consisting of an RNase H from *Escherichia coli*, an RNase H from a bacterium of genus *Thermotoga*, an RNase H from a bacterium of genus *Thermus*, an RNase H from a bacterium of genus *Pyrococcus*, an RNase H from a bacterium of genus *Archaeoglobus* and an RNase H from a bacterium of genus *Bacillus*.

The kit of the thirty-seventh or thirty-eighth invention may further contain a buffering component suitable for a nucleic acid amplification reaction. For example, the composition can contain a buffering component selected from the group consisting of Bicine and HEPES. The kit may contain an annealing solution containing a substance that enhances the annealing of the nucleic acid as the template to the primer that is substantially complementary to the nucleotide sequence of the nucleic acid. For example, the annealing solution may contain spermidine and/or propylenediamine.

The DNA polymerase having a strand displacement activity contained in the kit of the thirty-seventh or thirty-eighth invention of the present invention is exemplified by a DNA polymerase selected from the group consisting of Klenow fragment of DNA polymerase I from *Escherichia coli*, Bst DNA polymerase lacking 5'→3' exonuclease from *Bacillus stearothermophilus* and Bca DNA polymerase lacking 5'→3' exonuclease from *Bacillus caldotenax*.

In one aspect, the kit of the thirty-seventh or thirty-eighth invention contains Bca DNA polymerase lacking 5'→3' exonuclease from *Bacillus caldotenax* and an RNase H from *Escherichia coli*, a bacterium of genus *Pyrococcus* or a bacterium of genus *Archaeoglobus*. The RNase H is exemplified by type I RNase H from *Escherichia coli*, or type II RNase H from a bacterium of genus *Pyrococcus* or a bacterium of genus *Archaeoglobus*.

The kit of the thirty-seventh or thirty-eighth invention of the present invention may contain a DNA polymerase having an endonuclease activity. Bca DNA polymerase lacking 5'→3' exonuclease from *Bacillus caldotenax* can be used as such a DNA polymerase. The kit can contain a substance that allows the endonuclease activity of the DNA polymerase to express. The substance that allows the endonuclease activity of the Bca DNA polymerase to express is exemplified by a manganese ion.

The kit of the thirty-seventh or thirty-eighth invention can contain a substance that inhibits the reverse transcription activity of the DNA polymerase. The substance that inhibits the reverse transcription activity of the DNA polymerase is exemplified by phosphonoformic acid. Furthermore, the kit may contain a deoxynucleotide triphosphate analog such as deoxyuridine triphosphate or a derivative thereof.

The thirty-ninth invention of the present invention relates to a kit for amplifying a nucleic acid used for the method for amplifying a nucleic acid of the twenty-fourth to twenty-sixth invention of the present invention, which is in a packaged form and contains instructions that direct the use of a DNA polymerase having a strand displacement activity and an RNase H.

The fortieth invention of the present invention relates to a kit for amplifying a nucleic acid used for the method for amplifying a nucleic acid of the twenty-seventh to thirtieth invention of the present invention, which is in a packaged form and contains instructions that direct the use of a DNA polymerase having a strand displacement activity and an endonuclease.

The forty-first invention of the present invention relates to a product of a reagent for amplifying a nucleic acid consisting of a packing material and a reagent for amplifying a nucleic acid enclosed in the packing material, wherein the reagent for amplifying a nucleic acid contains a DNA polymerase having a strand displacement activity and/or an RNase H, and description that the reagent for amplifying a nucleic acid can be used for nucleic acid amplification under isothermal conditions is indicated in a label stuck to the packaging material or instructions attached to the packaging material.

The forty-second invention of the present invention relates to a product of a reagent for amplifying a nucleic acid consisting of a packing material and a reagent for amplifying a nucleic acid enclosed in the packing material, wherein the reagent for amplifying a nucleic acid contains a DNA polymerase having a strand displacement activity and/or an endonuclease, and description that the reagent for amplifying a nucleic acid can be used for nucleic acid amplification under isothermal conditions is indicated in a label stuck to the packaging material or instructions attached to the packaging material.

The forty-third invention of the present invention relates to a method for detecting a target nucleic acid in a sample, characterized in that the method comprises:

(a) amplifying a nucleic acid by the method for amplifying a nucleic acid of the twenty-fourth to thirtieth invention of the present invention; and (b) detecting a target nucleic acid amplified in step (a).

The detection method of the forty-third invention of the present invention can comprise detecting the amplified nucleic acid using a probe for detection. The probe may be a probe that has been labeled with a labeling substance. For example, an RNA probe labeled with two or more fluorescent substances positioned at a distance that results in a quenching state can be used.

The forty-fourth invention of the present invention relates to a chimeric oligonucleotide primer used for the forty-third invention. The chimeric oligonucleotide primer is exemplified by a chimeric oligonucleotide primer represented by general formula below:

5'-dNa-Nb-dNc-3' General formula:

(a: an integer of 11 or more; b: an integer of 1 or more; c: 0 or an integer of 1 or more; dN: deoxyribonucleotide and/or nucleotide analog; N: unmodified ribonucleotide and/or modified ribonucleotide, wherein some of dNs in dNa may be replaced by Ns, and the nucleotide at the 3'-terminus may be modified such that extension from the 3'-terminus by the action of the DNA polymerase does not take place).

Such chimeric oligonucleotide primers are exemplified by a primer in which c is 0 and a primer in which the nucleotide analog is deoxyriboinosine nucleotide or deoxyribouracil nucleotide, and the modified ribonucleotide is ($\alpha$-S) ribonucleotide.

The primer of the forty-fourth invention of the present invention is exemplified by a primer for detecting a pathogenic microorganism or a disease-related gene. A chimeric oligonucleotide primer for detecting a pathogenic microorganism such as enterohemorrhagic *Escherichia coli, Clostridium botulinum, Staphylococcus aureus, Mycobacterium tuberculosis, Chlamydia trachomatis*, papilloma virus, hepatitis C virus or a viroid is encompassed by the present invention.

The forty-fifth invention of the present invention relates to a chimeric oligonucleotide primer for detecting enterohemorrhagic *Escherichia coli* having a nucleotide sequence selected from the group consisting of SEQ ID NOS: 31 to 34, 47, 48, 51–53, 64–72, 84, 85, 113, 114, 130 and 131.

The forty-sixth invention of the present invention relates to a chimeric oligonucleotide primer for detecting a viroid having a nucleotide sequence selected from the group consisting of SEQ ID NOS: 59, 60, 119, 120, 122 and 123.

The forty-seventh invention of the present invention relates to a chimeric oligonucleotide primer for detecting *Clostridium botulinum* having a nucleotide sequence represented by SEQ ID NO: 116 or 117.

The forty-eighth invention of the present invention relates to chimeric oligonucleotide primer for detecting papilloma virus having a nucleotide sequence represented by SEQ ID NO: 96 or 97.

The forty-ninth invention of the present invention relates to a chimeric oligonucleotide primer for detecting hepatitis C virus having a nucleotide sequence selected from the group consisting of SEQ ID NOS: 101, 102, 138, 139,200, 201,205 and 206.

The fiftieth invention of the present invention relates to a chimeric oligonucleotide primer for detecting *Staphylococcus aureus* having a nucleotide sequence represented by SEQ ID NO: 136 or 137.

The fifty-first invention of the present invention relates to a chimeric oligonucleotide primer for detecting *Mycobacterium tuberculosis* having a nucleotide sequence selected from the group consisting of SEQ ID NOS: 155, 156, 159 to 162, 194 and 195.

The fifty-second invention of the present invention relates to a chimeric oligonucleotide primer for detecting *Chlamydia trachomatis* having a nucleotide sequence selected from the group consisting of SEQ ID NOS: 157, 158, 203 and 204.

The fifty-third invention of the present invention relates to a kit for amplifying a nucleic acid used for the method for amplifying a nucleic acid of the twenty-fourth to twenty-eighth invention of the present invention, which contains the chimeric oligonucleotide primer of the forty-fourth to fifty-second invention.

The fifty-fourth invention of the present invention relates to a kit for detecting a target nucleic acid used for the method for detecting a target nucleic acid of the forty-third invention of the present invention, which contains the chimeric oligonucleotide primer of the forty-fourth to fifty-second invention.

The fifty-fifth invention of the present invention relates to a probe used in the method of the forty-third invention.

The fifty-sixth invention of the present invention relates to a probe which hybridizes to the nucleic acid amplified by the method of the twenty-third to thirtieth invention.

The fifty-seventh invention of the present invention relates to a probe which hybridizes to a region amplified using the chimeric oligonucleotide primer of the forty-fourth to fifty-second invention.

The probe of the fifty-fifth to fifty-seventh invention may be a probe which has been labeled with a labeling substance, for example, an RNA probe labeled with two or more fluorescent substances positioned at a distance that results in a quenching state The fifty-eighth invention of the present invention relates to a kit used for the detection of the target nucleic acid in the method of the forty-third invention, which contains the probe of the fifty-fifth to fifty-seventh invention.

The fifty-ninth invention of the present invention relates to a method for amplifying a nucleic acid, which comprises using a DNA polymerase having a strand displacement activity to effect a template switching reaction.

The DNA polymerase having a strand displacement activity used in the fifty-ninth invention is exemplified by Klenow fragment of DNA polymerase I from *Escherichia coli*, Bst DNA polymerase lacking 5'→3' exonuclease from *Bacillus stearothermophilus* and Bca DNA polymerase lacking 5'→3' exonuclease from *Bacillus caldotenax*.

The sixtieth invention of the present invention relates to a method for producing a material having an immobilized nucleic acid in which the nucleic acid is arrayed in a predefined region, characterized in that the method comprises:

(a) amplifying a nucleic acid to be immobilized by the method for amplifying a nucleic acid of the twenty-fourth to thirtieth invention of the present invention; and (b) arraying and immobilizing the nucleic acid amplified in step (a) in a predefined region.

The sixty-first invention of the present invention relates to a material having an immobilized nucleic acid in which the nucleic acid is arrayed in a predefined region produced by the method of the sixtieth invention.

The sixty-second invention of the present invention relates to a method for producing a nucleic acid in large quantities, characterized in that the method comprises:

(a) amplifying a nucleic acid by the method for amplifying a nucleic acid of the twenty-fourth to thirtieth invention of the present invention; and (b) collecting the nucleic acid amplified in step (a).

The sixty-third invention of the present invention relates to a method for amplifying a nucleic acid, characterized in that the method comprises:

(a) duplicating a DNA or an RNA containing a sequence to be amplified to prepare a nucleic acid as a template; and (b) amplifying the nucleic acid as the template obtained in step (a) by the method for amplifying a nucleic acid of the twenty-fourth to thirtieth invention.

The sixty-fourth invention of the present invention relates to a method for determining a nucleotide sequence of a nucleic acid, characterized in that the method comprises amplifying a nucleic acid according to the method of the twenty-fourth to thirtieth, sixty-second or sixty-third invention.

The sixty-fifth invention of the present invention relates to a method for preparing a single-stranded nucleic acid, the method comprising a step of generating a single-stranded nucleic acid using the method according to the twenty-fourth to thirtieth invention. In the sixty-fifth invention, at least two primers at different concentrations may be used.

DETAILED DESCRIPTION OF THE INVENTION

Figure 1:
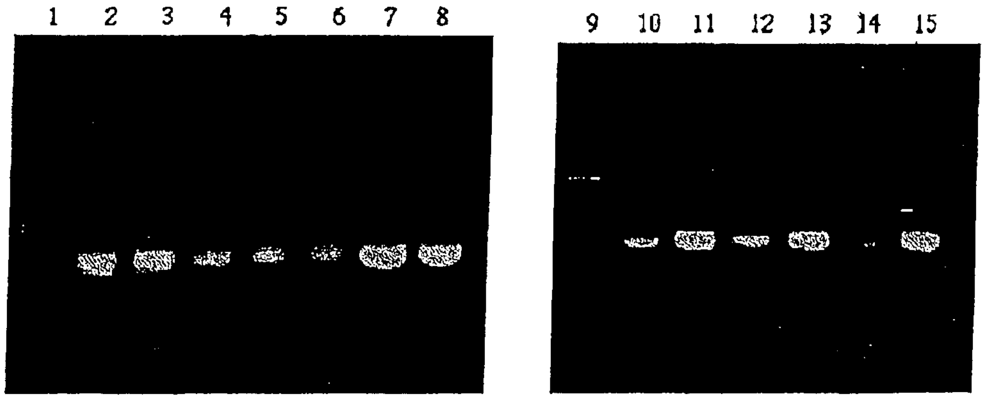
FIG. 1 is a photograph of agarose gel electrophoresis of amplified DNA fragments amplified according to the method of the present invention.

As used herein, a deoxyribonucleotide (also referred to as a dN) refers to a nucleotide of which the sugar portion is composed of D-2-deoxyribose. The deoxyribonucleotides include, for example, ones having adenine, cytosine, guanine or thymine as the base portion. Furthermore, the doxyribonucleotides also include a deoxyribonucleotide having a modified base such as 7-deazaguanosine and a deoxyribonucleotide analog such as deoxyinosine nucleotide.

As used herein, a ribonucleotide (also referred to as an N) refers to a nucleotide of which the sugar portion is composed of D-ribose. The ribonucleotides include ones having adenine, cytosine, guanine or uracil as the base portion. The ribonucleotides also include modified ribonucleotides such as a modified ribonucleotide in which the oxygen atom of the phosphate group at the α-position is replaced by a sulfur atom (also referred to as an (α-S) ribonucleotide or an (α-S) N) or other derivatives.

As used herein, a chimeric oligonucleotide primer refers to a primer that contains a deoxyribonucleotide and a ribonucleotide. The primer may contain a nucleotide analog and/or a modified ribonucleotide.

The chimeric oligonucleotide primers used in the present invention include any chimeric oligonucleotide primer that has a ribonucleotide being positioned at the 3'-terminus or on the 3'-terminal side of the primer, can be used to extend a nucleic acid strand in the method of the present invention, can be cleaved with an endonuclease, and can be used to effect a strand displacement reaction.

As used herein, 3'-terminal side refers to a portion from the center to the 3'-terminus of a nucleic acid such as a primer. Likewise, 5'-terminal side refers to a portion from the center to the 5'-terminus of a nucleic acid.

As used herein, an endonuclease may be any one that acts on a double-stranded DNA generated by extending a DNA from the chimeric oligonucleotide primer which have been annealed to a nucleic acid as a template, and specifically cleaves it at a portion of the primer that contains a ribonucleotide.

As used herein, a DNA polymerase refers to an enzyme that synthesizes a DNA strand de novo using a DNA strand as a template. The DNA polymerases include naturally occurring DNA polymerases and variant enzymes having the above-mentioned activity. For example, such enzymes include a DNA polymerase having a strand displacement activity, a DNA polymerase lacking a 5'→3' exonuclease activity and a DNA polymerase having a reverse transcriptase activity or an endonuclease activity.

As used herein, "a strand displacement activity" refers to an activity that can effect a strand displacement, that is, that can proceed DNA duplication on the basis of the sequence of the nucleic acid as the template while displacing the DNA strand to release the complementary strand that has been annealed to the template strand. In addition, a DNA strand released from a nucleic acid as a template as a result of a strand displacement is referred to as "a displaced strand" herein.

Hereinafter, the present invention will be described in detail.

(1) Chimeric Oligonucleotide Primer Used in the Present Invention.

The primer used in the method of the present invention is a chimeric oligonucleotide primer that contains a ribonucleotide as well as at least one selected from the group consisting of a deoxyribonucleotide and a nucleotide analog. Such primers also include an oligoribonucleotide primer that contains an unmodified ribonucleotide and/or a modified ribonucleotide.

A chimeric oligonucleotide primer used in the method of the present invention is a chimeric oligonucleotide primer that has a nucleotide sequence substantially complementary to a part of the nucleotide sequence of a nucleic acid as a template. It can contribute to extension of a DNA strand under conditions used. Furthermore, a ribonucleotide is positioned at the 3'-terminus or on the 3'-terminal side of the chimeric oligonucleotide primer. The primer is usually designed such that it is complementary to a portion upstream of the region to be amplified, that is, a portion 3' to the nucleotide sequence corresponding to a region to be amplified in a nucleic acid as a template. As used herein, "a substantially complementary nucleotide sequence" means a nucleotide sequence that can anneal to a DNA as a template under reaction conditions used.

The chimeric oligonucleotide primer used in the method of the present invention may contain one or more modified ribonucleotide. As used herein, a ribonucleotide may be an unmodified ribonucleotide and/or a modified ribonucleotide that can be positioned at the 3'-terminus or on the 3'-terminal side of a chimeric oligonucleotide primer and that is recognized by or cleaved with an endonuclease. The ribonucleotides include both of the unmodified ribonucleotide and the modified ribonucleotide as described above. An unmodified ribonucleotide, a modified ribonucleotide or a combination thereof can be used for the chimeric oligonucleotide primer of the present invention as long as it does not abolish the function of the primer. Examples of the modified ribonucleotides include, but are not limited to, an (α-S) ribonucleotide in which the oxygen atom bound to the phosphate group is replaced by a sulfur atom, and a ribonucleotide in which the hydroxy group at the 2-position of the ribose is replaced by a methoxy group. Such a chimeric oligonucleotide primer containing a modified ribonucleotide can be produced by using, for example, an (α-S) ribonucleotide triphosphate, which is prepared by a method using a sulfuration reaction reagent (Glen Research) as described in U.S. Pat. No. 5,003,097, or a 2-OMe-RNA-CE phosphoramidite reagent (Glen Research).

A chimeric oligonucleotide primer that can be used in the amplification method of the present invention may be designed to contain a modified ribonucleotide that confers resistance to the cleavage with an endonuclease. Such a primer is useful in that one can control the cleavage site with an endonuclease during amplification reaction steps.

One or two chimeric oligonucleotide primer may be used in the method of the present invention depending on the desired form of a DNA fragment after amplification (single-stranded or double-stranded). Specifically, one chimeric oligonucleotide primer is used when a single-stranded DNA is desired, whereas two primers are used when a double-stranded DNA is desired.

The length of the chimeric oligonucleotide primer used in the method of the present invention is not specifically limited, but is preferably about 12 nucleotides to about 100 nucleotides, more preferably about 15 nucleotides to about 40 nucleotides. It is preferable that the nucleotide sequence of the chimeric oligonucleotide is substantially complementary to a nucleic acid as a template such that it anneals to the nucleic acid as the template under reaction conditions used. The primer contains a sequence recognized by an endonuclease, which is utilized in a step as described below, at the 3'-terminus or on the 3'-terminal side.

For example, an oligonucleotide having a structure represented by the following general formula can be used in the DNA synthesis method of the present invention as a primer, although it is not intended to limit the present invention:

5'-dNa-Nb-dNc-3' General formula:

(a: an integer of 11 or more; b: an integer of 1 or more; c: 0 or an integer of 1 or more; dN: deoxyribonucleotide and/or nucleotide analog; N: unmodified ribonucleotide and/or modified ribonucleotide, wherein some of dNs in dNa may be replaced by Ns, and the nucleotide at the 3'-terminus may be modified such that extension from the 3'-terminus by the action of the DNA polymerase does not take place).

For example, a chimeric oligonucleotide primer represented by the general formula in which a=an integer of 11 or more; and b=1 and c=0, b=2 and c=0, b=3–5 and c=0, or b=2 and c=0–5 can be preferably used in the present invention. The length of the ribonucleotides at the 3'-terminus or on the 3'-terminal side of the chimeric oligonucleotide primer used in the method of the present invention is preferably 1-mer to 15-mer, more preferably 1-mer to 10-mer, most preferably 1-mer to 5-mer. The number of c in the general formula is not specifically limited, but any number that can be used in the method of the present invention may be selected. Usually, 5 or less is preferably. Better results are obtained in a reaction by selecting 3 rather than 4, 2 rather than 3, and 1 rather than 2 for c. In particular, the most efficient reaction can be accomplished in case of c=0.

The chimeric oligonucleotide primer used in the present invention has a structure in which an endonuclease recognizes or cleaves a DNA strand extended from the primer using a DNA polymerase (a primer-extended strand) at a site that contains a ribonucleotide, which ribonucleotide being positioned at the 3'-terminus or on the 3'-terminal side of the chimeric oligonucleotide primer. Although it is not intended to limit the present invention, for example, when an RNase H acts on a double-stranded DNA generated by extending a DNA from a chimeric oligonucleotide primer represented by the general formula that has been annealed to a nucleic acid as a template, the chimeric oligonucleotide primer is cleaved at the ribonucleotide portion. A double-stranded DNA in which a nick is introduced between the oligonucleotide primer and the DNA strand synthesized by the extension is then generated. Then, a strand displacement reaction with a DNA polymerase proceeds from the nicked site. Thus, any chimeric oligonucleotide primer that can be used to extend a nucleic acid strand from the 3'-terminus of the primer, that can be cleaved with an endonuclease, and with which a DNA polymerase can effect a strand displacement reaction can be used in the method of the present invention. Furthermore, the chimeric oligonucleotide primers of the present invention include one whose 3'-terminus is modified such that extension by the action of the DNA polymerase can not take place, and DNA extension takes place from a 3'-terminus generated upon cleavage by the endonuclease. In addition, a promoter sequence for an RNA polymerase may be included on the 5'-terminal side of the chimeric oligonucleotide primer. Such RNA polymerases are exemplified by T7 RNA polymerase and SP6 RNA polymerase.

Furthermore, the chimeric oligonucleotide primer used in the method of the present invention may contain a nucleotide analog or other substances. That is, one or more nucleotide analog(s) can be contained in the chimeric oligonucleotide primer of the present invention as long as the function of the primer is not abolished. Plural types of the nucleotide analogs can be used in combination. Examples of the nucleotide analogs include, but are not limited to, nucleotide analogs having ribose derivatives such as deoxyinosine nucleotide, deoxyuracil nucleotide and a deoxyribonucleotide analog having a modified base such as 7-deazaguanine. Furthermore, the chimeric oligonucleotides used in the present invention may contain deoxynucleotides, ribonucleotides or nucleotide analogs having various modifications such as addition of labeled compounds as long as they retain the functions as described above.

Incorporation of a nucleotide analog into a primer is effective for suppressing the formation of high-order structure of the primer itself and stabilization of annealing formation with the template. A ribonucleotide may be incorporated into a primer for the same purpose. Although it is not intended to limit the present invention, a modified ribonucleotide such as (α-S) ribonucleotide can be preferably used in order to prevent the digestion of the primer by a non-specific endonuclease (RNase).

The chimeric oligonucleotide primer can be synthesized to have desired nucleotide sequence using, for example, the 394 type DNA synthesizer from Applied Biosystems Inc. (ABI) according to a phosphoramidite method. Alternatively, any methods including a phosphate triester method, an H-phosphonate method and a thiophosphonate method may be used to synthesize the chimeric oligonucleotide primer.

(2) Endonuclease Used in the Present Invention.

Any endonuclease that can act on a double-stranded DNA generated by DNA extension from the chimeric oligonucleotide primer as described above in (1) that has been annealed to a nucleic acid as a template and cleaves the extended strand to effect a strand displacement reaction may be used in the present invention. That is, the endonuclease is an enzyme that can generate a nick in the chimeric oligonucleotide primer portion of the double-stranded DNA. Examples of endonucleases that can be used in the present invention include, but are not limited to, ribonucleases. Among these, endoribonuclease H (RNase H) that acts on an RNA portion of a double-stranded nucleic acid composed of a DNA and an RNA can be preferably used. Any ribonuclease that has the above-mentioned activities can be preferably used in the present invention, including mesophilic and heat-resistant ones. For example, an RNase H from *E. coli* can be used for a reaction at about 50° C. to about 70° C. in the method of the present invention as described below in Examples. A heat-resistant ribonuclease can be preferably used in the method of the present invention. Examples of the heat-resistant ribonucleases which can be preferably used include, but are not limited to, a commercially available ribonuclease, Hybridase™ Thermostable RNase H (Epicenter Technologies) as well as an RNase from a thermophilic bacterium of genus *Bacillus*, a bacterium of genus *Thermus*, a bacterium of genus *Pyrococcus*, a bacterium of genus *Thermotoga*, a bacterium of genus *Archaeoglobus* or the like. Furthermore, both of naturally occurring ribonucleases and variants can be preferably used. The enzymatic unit of RNase H indicated herein is a value expressed according to a method of measuring an enzymatic unit as described in Referential Examples.

The RNase H is not limited to a specific one as long as it can be used in the method of the present invention. For example, the RNase H may be derived from any organisms including various viruses, phages, prokaryotes and eukaryotes. It may be either a bacterial RNase H or a viral RNase H. The bacterial RNase H is exemplified by *Escherichia coli* RNase H I and the viral RNase H is exemplified by HIV-1. Type I, type II or type III RNase H can be used in the method of the present invention. For example, type I RNase H from *Escherichia coli*, or type II RNase H from a bacterium of genus *Pyrococcus* or a bacterium of genus *Archaeoglobus* is preferable, without limitation.

The efficiency of the cleavage reaction with an endonuclease such as RNase H used in the method of the present invention may vary depending on the nucleotide sequence around the 3'-terminus of the primer and influence the amplification efficiency of the desired DNA. Therefore, it is natural to design the optimal primer for the RNase H used.

As used herein, the term "introducing a nick" or "nicking" means internally cleaving one of the two strands of a double-stranded nucleic acid. For example, an RNase H acts on a hybrid double-stranded nucleic acid composed of a DNA and a ribonucleotide-containing DNA to selectively cleave the ribonucleotide-containing strand among the two strands at the ribonucleotide portion, thereby introducing a nick into the hybrid double-stranded nucleic acid.

(3) DNA Polymerase Used in the Present Invention.

A DNA polymerase having a strand displacement activity on a DNA can be used in the present invention. Particularly, a DNA polymerase substantially lacking a 5'→3' exonuclease activity can be preferably used.

As used herein, "a strand displacement activity" refers to an activity that can effect a strand displacement, that is, that can proceed DNA duplication on the basis of a sequence of a nucleic acid as a template while displacing a DNA strand to release a complementary strand that has been annealed to the template strand. Additionally, a DNA strand released from a nucleic acid as a template as a result of a strand displacement is referred to as "a displaced strand" herein.

Any DNA polymerases having the strand displacement activity can be used in the present invention. Examples thereof include variants of DNA polymerases lacking their 5'→3' exonuclease activities derived from thermophilic bacteria of genus *Bacillus* such as *Bacillus caldotenax* (hereinafter referred to as B. ca) and *Bacillus stearothermophilus* (hereinafter referred to as B. st), as well as large fragment (Klenow fragment) of DNA polymerase I from *Escherichia coli* (*E. coli*). Both of mesophilic and heat-resistant DNA polymerases can be preferably used in the present invention.

B. ca is a thermophilic bacterium having an optimal growth temperature of about 70° C. Bca DNA polymerase from this bacterium is known to have a DNA-dependent DNA polymerase activity, an RNA-dependent DNA polymerase activity (a reverse transcription activity), a 5'→3' exonuclease activity and a 3'→5' exonuclease activity. The enzyme may be either an enzyme purified from its original source or a recombinant protein produced by using genetic engineering techniques. The enzyme may be subjected to modification such as substitution, deletion, addition or insertion by using genetic engineering techniques or other means. Examples of such enzymes include BcaBEST DNA polymerase (Takara Shuzo), which is Bca DNA polymerase lacking its 5'→3' exonuclease activity.

It is known that some DNA polymerases have an endonuclease activity such as an RNase H activity under specific conditions. Such a DNA polymerase can be used in the method of the present invention. In one aspect, the DNA polymerase may be used under conditions that allow the RNase H activity to express, e.g., in the presence of $Mn^{2+}$. In this case, the method of the present invention can be conducted without the addition of an RNase H. The present inventors have demonstrated that the Bca DNA polymerase exhibits an RNase activity in a buffer containing $Mn^{2+}$ for the first time, and that the method for amplifying a nucleic acid of the present invention can be carried out in a reaction mixture containing no enzyme other than the Bca DNA polymerase. The above-mentioned aspect is not limited to the use of the Bca DNA polymerase. DNA polymerases that are known to have an RNase H activity such as Tth DNA polymerase from *Thermus thermophilus* can be used in the present invention.

(4) Composition of Reaction Buffer Used in the Present Invention.

A reaction buffer that contains a buffering component, a magnesium salt or another metal salt and dNTPs is used in the present invention. Naturally, the type and the concentration of the salt are optimized depending on the metal requirement or the like of the enzyme to be used. Examples of the buffering components that can be preferably used include, but are not limited to, Bicine, Tricine, HEPES, tris and a phosphate (such as sodium phosphate and potassium phosphate). Among these, a buffer that contains Bicine, Tricine, HEPES or a phosphate as a buffering component is preferable for the present invention. Although it is not intended to limit the present invention, for example, when the reaction temperature is high, a Bicine buffer of which the change in pH due to the change in temperature is little is preferably used. A HEPES buffer may be preferable depending on the type of RNase H used. Thus, the optimal buffer may be selected depending on the reaction temperature, the endonuclease or the DNA polymerase to be used and the like. The final concentration of the buffering component ranges 5–100 mM, preferably 20–50 mM. The pH ranges 6.0–9.5, preferably 7.0–9.2. For example, a buffer containing 22–46 mM Tricine at pH 7.5–9.2 or a buffer containing 25–50 mM potassium phosphate at pH 7.0–8.0 is preferably used. Examples of magnesium salts that can be preferably used include, but are not limited to, magnesium chloride, magnesium acetate or magnesium sulfate. The final concentration of the magnesium salt ranges 1–20 mM, preferably 2–10 mM. The final concentrations of dNTPs (a mixture of dATP, dCTP, dGTP and dTTP) in a mixture as substrates for a DNA extension reaction range 0.1–3.0 mM, preferably 0.2–1.2 mM. The amount of the primers used in a reaction volume of 50 $\mu$l ranges 1–1000 pmol, preferably 10–150 pmol. Additionally, the reaction mixture may contain an additive, for example, in order to stabilize the amplification reaction. Bovine serum albumin (BSA) at a final concentration of 0.1% or less, dimethyl sulfoxide (DMSO) at a final concentration of 10% or less, putrescine dihydrochloride at a final concentration of 4 mM or less, or propylenediamine at a final concentration of 0.01% or less may be added. Additionally, NMP (1-methyl-2-pyrrolidinone), glycerol, polyethylene glycol, dimethyl sulfoxide and/or formamide may be contained. It is expected that the addition of such an organic solvent reduces the non-specific annealing of oligonucleotide primers.

The method of the present invention may be carried out by adding a substance that inhibits the reverse transcription activity of the DNA polymerase such as phosphonoformic acid (PFA). If a substance that inhibits the reverse transcription activity is added, the amplification of non-specific products other than the target nucleic acid is reduced.

In another aspect, annealing of the nucleic acid as the template to the chimeric oligonucleotide primer used in the present invention before the amplification reaction is effective to reduce non-specific annealing of an oligonucleotide primer in the detection, amplification or production method of the present invention. It is preferable to conduct the annealing using an annealing solution that contains a substance that enhances the annealing such as a polyamine (e.g., spermine or spermidine) or propylenediamine. Preferably, the annealing solution containing the polyamine also contains a salt. For example, without limitation, the annealing solution may contain sodium chloride, potassium chloride, potassium acetate, sodium acetate or the like and a polyamine.

The annealing is usually conducted by incubating the annealing solution containing the primer and the nucleic acid as the template at a temperature at which a double-stranded nucleic acid is denatured (e.g., 90° C. or above) and then cooling the solution to a reaction temperature used for the method of the present invention or below.

After annealing, the nucleic acid amplification reaction of the present invention is initiated by further adding other necessary components such as a DNA polymerase, an RNase H and dNTPs to the mixture.

The amount of an RNase H from *Escherichia coli* as an example of endonucleases in a reaction volume of 50 $\mu$l ranges preferably 3–200 U, more preferably 15–60 U. Similarly, the amount of an RNase H from a bacterium of genus *Pyrococcus* or a bacterium of genus *Archaeoglobus* as an example of endonuclease in a reaction volume of 50 $\mu$l ranges preferably 3–200 U, more preferably 4–40 U. The amount of BcaBEST DNA polymerase (Takara Shuzo) as an example of DNA polymerases in a reaction volume of 50 $\mu$l ranges preferably 0.5–100 U, more preferably 1–22 U.

When an endonuclease and a DNA polymerase is used in combination in the method of the present invention, for example, without limitation, a combination of an RNase H from *Escherichia coli*, a bacterium of genus *Pyrococcus* or a bacterium of genus *Archaeoglobus* and BcaBEST DNA polymerase is preferably used. It is considered that the preferable units of the endonuclease and the DNA polymerase may vary depending on the types the enzymes. In such a case, the composition of the buffer used and the amount of the enzymes added may be adjusted using the increase in detection sensitivity or the amount of amplification product as an index. In either case, it is natural to optimize the composition of the reaction buffer and the like depending on the type of the enzyme to be used.

(5) Method for Amplifying Nucleic Acid of the Present Invention.

The method of the present invention can be conducted by using at least one oligonucleotide primer as described above in (1) in combination with the endonuclease as described above in (2) and the DNA polymerase as described above in (3). Alternatively, a DNA polymerase having an RNase H activity can be used under conditions that allow the RNase H activity to express as described above.

dNTPs used for the PCR or the like (a mixture of DATP, dCTP, dGTP and dTTP) can be preferably used as nucleotide triphosphates that serve as substrates in the extension reaction in the method. In addition, dUTP may be used as a substrate. The dNTPs may contain a dNTP (deoxyribonucleotide triphosphate) analog such as 7-deaza-dGTP, triphosphate of dITP or the like as long as it serves as a substrate for the DNA polymerase used. A derivative of a dNTP or a dNTP analog may be used. A derivative having a functional group such as a dUTP having an amino group may be contained. A chimeric oligonucleotide primer is used in the method. The primer can be prepared, for example, using a DNA synthesizer according to a conventional synthesis method. A combination of the chimeric oligonucleotide primer and a normal oligonucleotide primer can be used in the method of the present invention.

If the activity of the enzyme used may be decreased in the course of the reaction, the enzyme can be further added during the reaction in the method of the present invention. Although it is not intended to limit the present invention, for example, an RNase H from *Escherichia coli* may be further added during a reaction in which the RNase H is used. The added enzyme may be the same as that contained in the reaction mixture at the beginning of the reaction or it may be a different enzyme that exhibits the same activity. Thus, the type or the property of the enzyme to be added is not limited to a specific one as long as the addition during the reaction provides effects such as increase in the detection sensitivity or increase in the amount of amplification product.

The nucleic acid (DNA or RNA) used as a template in the method of the present invention may be prepared or isolated from any sample that may contain the nucleic acid. Alternatively, the sample may be used directly in the method for amplifying a nucleic acid of the present invention.

Examples of the samples that may contain the nucleic acid include, but are not limited to, samples from organisms such as a whole blood, a serum, a buffy coat, a urine, feces, a cerebrospinal fluid, a seminal fluid, a saliva, a tissue (e.g., a cancerous tissue or a lymph node) and a cell culture (e.g., a mammalian cell culture or a bacterial cell culture), samples that contain a nucleic acid such as a viroid, a virus, a bacterium, a fungi, a yeast, a plant and an animal, samples suspected to be contaminated or infected with a microorganism such as a virus or a bacterium (e.g., a food or a biological formulation), and samples that may contain an organism such as a soil and a waste water. The sample may be a preparation containing a nucleic acid obtained by processing the above-mentioned samples according to a known method. Examples of the preparations that can be used in the present invention include a cell destruction product or a sample obtained by fractionating the product, the nucleic acid in the sample, or a sample in which specific nucleic acid molecules such as mRNAs are enriched. Furthermore, a nucleic acid such as a DNA or an RNA obtained amplifying a nucleic acid contained in the sample by a known method can be preferably used.

The preparation containing a nucleic acid can be prepared from the above-mentioned materials by using, for example, lysis with a detergent, sonication, shaking/stirring using glass beads or a French press, without limitation. In some cases, it is advantageous to further process the preparation to purify the nucleic acid (e.g., in case where an endogenous nuclease exists). In such cases, the nucleic acid is purified by a know method such as phenol extraction, chromatography, ion exchange, gel electrophoresis or density-gradient centrifugation.

When it is desired to amplify a nucleic acid having a sequence derived from an RNA, the method of the present invention may be conducted using as a template a cDNA synthesized by a reverse transcription reaction that uses the RNA as a template. Any RNA for which one can make a primer to be used in a reverse transcription reaction can be applied to the method of the present invention, including total RNA in a sample, RNA molecules such as, mRNA, tRNA and rRNA as well as specific RNA molecular species.

Any primer that anneals to an RNA as a template under reaction conditions used can be used in the reverse transcription reaction. The primer may be a primer having a nucleotide sequence that is complementary to a specific RNA as a template (a specific primer), an oligo-dT (deoxythymine) primer and a primer having a random sequence (a random primer). In view of specific annealing, the length of the primer for reverse transcription is preferably 6 nucleotides or more, more preferably 9 nucleotides or more. In view of oligonucleotide synthesis, the length is preferably 100 nucleotides or less, more preferably 30 nucleotides or less. A chimeric oligonucleotide primer can be used as a primer for reverse transcription. The chimeric oligonucleotide primer can also be utilized as a primer for a strand displacement reaction in the method for amplifying a nucleic acid of the present invention using a cDNA obtained after reverse transcription as a template. Such a primer may be any one that has the properties as described above in (1) and that can be used in a reverse transcription reaction from an RNA.

Any enzyme that has an activity of synthesizing a cDNA using an RNA as a template can be used in the reverse transcription reaction. Examples thereof include reverse transcriptases originating from various sources such as avian myeloblastosis virus-derived reverse transcriptase (AMV RTase), Molony murine leukemia virus-derived reverse transcriptase (MMLV RTase) and Rous-associated virus 2 reverse transcriptase (RAV-2 RTase). In addition, a DNA polymerase that also has a reverse transcription activity can be used. An enzyme having a reverse transcription activity at a high temperature such as a DNA polymerase from a bacterium of genus *Thermus* (e.g., Tth DNA polymerase) and a DNA polymerase from a thermophilic bacterium of genus *Bacillus* is preferable for the present invention. For example, DNA polymerases from thermophilic bacteria of genus *Bacillus* such as a DNA polymerase from B. st (Bst DNA polymerase) and Bca DNA polymerase are preferable, although it is not intended to limit the present invention. For example, Bca DNA polymerase does not require a manganese ion for the reverse transcription reaction. Furthermore, it can synthesize a cDNA while suppressing the formation of a secondary structure of an RNA as a template under high-temperature conditions. Both a naturally occurring one and a variant of the enzyme having a reverse transcriptase activity can be used as long as they have the activity.

In another aspect, after duplicating a DNA or an RNA containing a nucleotide sequence to be amplified beforehand, the duplicated product may be used as a nucleic acid as a template in the method of the present invention. Examples of the methods for duplication include, but are not limited to, a method in which an appropriate host is transformed with a vector into which the nucleic acid fragment containing the nucleotide sequence to be amplified is inserted, the resulting transformant is cultured, the vector into which the nucleic acid fragment containing the nucleotide sequence to be amplified is inserted is extracted therefrom and used. Any vectors can be used as long as they are stably replicated in the host. For example, pUC series, pBluescript series, pGEM series, cosmid type vectors and phage type vectors are preferably used. Any hosts can be used as long as they can maintain the vectors used. For example, *Escherichia coli*, which is readily cultured, is exemplified.

In another aspect of the duplication method, after an RNA having a nucleotide sequence to be amplified is transcribed using an RNA polymerase and a nucleic acid fragment containing the nucleotide sequence as a template, the RNA may be used as a template for the method of the present invention directly or after converting it into a cDNA by reverse transcription reaction. The nucleic acid fragment containing the nucleotide sequence to be amplified is not limited to a specific one as long as it has a promoter sequence for an RNA polymerase. It may be inserted into a vector having a promoter sequence for an RNA polymerase, ligated with an adapter or a cassette having a promoter sequence for an RNA polymerase at its end or enzymatically synthesized using a primer having a promoter sequence for an RNA polymerase and an appropriate template. Thus, a nucleic acid fragment containing a nucleotide sequence to be amplified can be duplicated or amplified in a form of an RNA using a promoter sequence for an RNA polymerase being positioned as described above. Any vectors can be used as long as they have promoter sequences for RNA polymerases. For example, pUC series, pBluescript series, pGEM series, cosmid type vectors and phage type vectors are preferably used. The vector can be preferably used in its circular form or after being linearized. Any RNA polymerases can be used for the duplication or amplification method. For example, SP6 RNA polymerase, T7 RNA polymerase, T3 RNA polymerase or the like can be preferably used.

Both of a double-stranded DNA such as a genomic DNA isolated as described above or a PCR fragment and a single-stranded DNA such as a cDNA prepared by a reverse transcription reaction from a total RNA or an mRNA can be preferably used as a template DNA in the present invention. The double-stranded DNA is preferably used either after denaturing it into single-stranded DNAs or without the denaturation.

The denaturing step may be eliminated in the nucleic acid amplification method of the present invention if a linear double-stranded DNA such as a PCR amplification product is used as a template. The elimination may be accomplished by locating the annealing site for the primer used in the method of the present invention about 50 bases inside from the terminus of the DNA. If a nucleic acid having a sequence from an RNA is to be amplified, amplification reaction can be initiated by adding an RNA-cDNA double-stranded nucleic acid obtained by reverse transcription reaction using an RNA as a template to the amplification reaction mixture of the present invention containing an RNase H to digest the RNA strand and convert the nucleic acid into a single-stranded cDNA. Furthermore, a reverse transcription reaction using an RNA as a template and a DNA amplification reaction using a cDNA generated by the reverse transcription reaction as a template can be conducted with one DNA polymerase in the DNA synthesis method of the present invention. Such a DNA polymerase has a reverse transcriptase activity and a strand displacement activity.

The suitable length of the template is one that provides a sufficient binding of the primer sequence due to the presence of the whole target sequence or at least a sufficient part of the target sequence in the fragment.

Without limitation, if a DNA as a template is a double-stranded DNA, the DNA can be denatured into single-stranded DNAs to allow a primer to bind to the DNA strand as the template in the method of the present invention. Incubating the double-stranded DNA at a temperature at which it is denatured (e.g., about 95° C.) is preferable for the denaturation. Other processes include one in which an elevated pH is used. In this case, the pH should be lowered upon the amplification reaction in order to allow an oligonucleotide primer to bind to a target. A nucleic acid is successively amplified under isothermal conditions after denaturing a double-stranded DNA into single-stranded DNAs or, if an RNA is used as a template, preparing a cDNA (a single-stranded DNA) by a reverse transcription reaction.

"Successively" means that a reaction proceeds without a change in the reaction temperature or the composition of the reaction mixture. As used herein, "isothermal" means conditions of a substantially constant temperature under which an enzyme and a nucleic acid strand function in each step.

The nucleic acid amplification reaction of the present invention may be conducted at a normal temperature (e.g., 37° C.) by using a mesophilic DNA polymerase such as Klenow fragment. It can also be conducted at a high temperature (e.g., 50° C. or higher, or 60° C. or higher) by using heat-resistant enzymes (an endonuclease and a DNA polymerase). In this case, non-specific annealing of a primer is suppressed, resulting in increase in the specificity of DNA amplification. Furthermore, the problem of forming secondary structure of a DNA as a template is solved, resulting in increase in the ability of extension of a DNA polymerase. A reverse transcription reaction and the nucleic acid amplification can be successively conducted in the method. In this case, a DNA having a sequence derived from an RNA can be amplified by combining the use of a reverse transcriptase with the above-mentioned reaction or by using a DNA polymerase having a reverse transcription activity.

In each aspect of the present invention, preferably, a chimeric oligonucleotide primer that is complementary to a single-stranded DNA as a template is first annealed to the DNA, although it is not intended to limit the present invention. A DNA that is complementary to the DNA as the template (a primer-extended strand) is then extended along the remained sequence of the DNA as the template from the 3'-terminus of the primer by the action of a DNA polymerase to synthesize a double-stranded DNA. An endonuclease acts on the double-stranded DNA and begins to reextend a DNA from the primer portion of the primer-extended strand de novo. In one aspect of the present invention, the endonuclease acts as a nicking enzyme that introduces a nick into the double-stranded DNA or it alters the structure of the double-stranded DNA composed of the chimeric oligonucleotide primer and the DNA as the template, although the present invention is not restricted by a theory. A DNA polymerase having a strand displacement activity re-extends a DNA strand from the 3'-terminus of the nick introduced in the double-stranded DNA to generate a new primer-extended strand while releasing the DNA downstream from the 3'-terminus of the nick. Thus, the new primer-extended strand replaces the previously synthesized primer-extended strand.

The method for amplifying a nucleic acid of the present invention can be carried out using two primers, i.e., a chimeric oligonucleotide primer that is complementary to a nucleic acid as a template and another chimeric oligonucleotide primer that is complementary to a displaced strand. In this case, one primer binds to a DNA strand as a template to cause a strand displacement reaction, whereas another primer binds to a displaced strand released as a result of the strand displacement reaction to initiate another strand displacement reaction. It is clear that a reaction product with one primer can function as a template for another primer if this aspect is used. Thus, the amount of amplification product increases in a non-linear manner as the amount of the template increases.

When the method for amplifying a nucleic acid of the present invention is conducted using a double-stranded DNA as a template, both strands can serve as templates in the amplification reaction by using chimeric oligonucleotide primers that anneal to the respective two strands. If the reaction is initiated after denaturing the double-stranded DNA, a chimeric oligonucleotide primer, four deoxyribonucleotide triphosphates (dNTPs), a DNA polymerase and an endonuclease are added to a reaction mixture before or after the double-stranded DNA is denatured. If heat treatment is used for denaturing the double-stranded DNA and a heat-resistant enzyme is not used, it is preferable to add the enzyme after the denaturation.

In the aspect of the nucleic acid amplification method of the present invention in which a double-stranded DNA as a template and two chimeric oligonucleotide primers are used, switching of templates may occur among the template-extended strand intermediates during the extension reaction from the primers to generate a double-stranded nucleic acid consisting of the synthesized primer-extended strands being annealed each other, although it depends on the reaction conditions or the like. The double-stranded nucleic acid has chimeric oligonucleotide primers at both ends. Then, reaction of extending complementary strands comprising strand displacement can be initiated from both of the ends again. As a result of the reaction, an amplification product having the primer sequence at one end is generated. Furthermore, if switching of templates occurs during the reaction, a double-stranded nucleic acid similar to one that described above is generated again.

The present invention provides a method for amplifying a nucleic acid which comprises using a DNA polymerase having a strand displacement activity to effect a template switching reaction. In the template switching reaction in the presence of a double-stranded nucleoc acid as a template, two chimeric oligonucleotide primers substantially complementary to the nucleotide sequences of the respective strands and a DNA polymerase having a strand displacement activity, two primer-extended strands complementary to the template are synthesized. Template switching of each of the primer-extended strands from the template to the other primer-extended strand takes place during the synthesis of the primer-extended strands.

As used herein, a template switching reation refers to a reaction in which when complementary strands are synthesized by strand displacement reactions from the both sides of a double-stranded nucleic acid, a DNA polymerase switches the template and synthesizes a complementary strand thereafter using the other complementary strand newly synthesized by another DNA polymerase as a template. In other words, a template switching reaction refers to a reaction in which a double-stranded nucleic acid as a template is treated with primers and a DNA polymerase having a strand displacement activity to generate extended strands complementary to the template, wherein a DNA polymerase that synthesized the primer-extended strands actively switches the template from the original templates to the other primer-extended strands during the synthesis of the extended strands. The ability of the DNA polymerase to effect a template switching reaction can be determined, for example, according to the method as described in Example 45 below, although it is not intended to limit the present invention.

A DNA polymerase capable of an effect the template switching reaction during strand displacement reaction can be preferably used for the present invention. For example, a variant enzyme of Bca DNA polymerase lacking a 5'→3' exonuclease activity is preferably used in particular. Such an enzyme is commercially available as BcaBEST DNA polymerase (Takara Shuzo). It can also be prepared from *Escherichia coli* HB101/pU1205 (FERM BP-3720) which contains the gene for the enzyme according to the method as described in Japanese Patent No. 2978001.

Although it is not intended to limit the present invention, the mode of reaction of the method for amplifying a nucleic acid of the present invention is considered as follows, for example.

In the method for amplifying a nucleic acid of the present invention, a double-stranded nucleic acid as a template is treated in the presence of an RNase H with two chimeric oligonucleotide primers that are substantially complementary to the nucleotide sequences of the respective strands and a DNA polymerase having a strand displacement activity to synthesize primer-extended strands that are complementary to the template. A double-stranded nucleic acid consisting of the synthesized primer-extended strands being annealed each other and a double-stranded nucleic acid consisting of the templates being annealed each other to which the two primers are annealed as a result of template switching reaction can be obtained. The latter double-stranded nucleic acid is reused as a template.

The double-stranded nucleic acid consisting of the primer-extended strands being annealed each other is cleaved with an RNase H at sites that contain the ribonucleotides. Nucleic acids that are complementary to the template are extended using a DNA polymerase having a strand displacement activity from the 3'-termini of the respective primer portions of the double-stranded nucleic acid by an effect of strand displacements. A double-stranded nucleic acid consisting of the primer-extended strands being annealed each other and a double-stranded nucleic acid consisting of the templates being annealed each other to which the two primers are annealed as a result of template switching reaction can be obtained.

If the template switching reaction does not take place, two types of double-stranded nucleic acids each consisting of the template and the primer-extended strand can be obtained.

Nucleic acids that are complementary to the template are extended using a DNA polymerase having a strand displacement activity from the 3'-termini of the respective primer portions of the double-stranded nucleic acid. As a result of template switching reaction, a double-stranded nucleic acid consisting of the primer-extended strands being annealed each other and a double-stranded nucleic acid consisting of the templates being annealed each other to which the two primers are annealed can be obtained. The double-stranded nucleic acid to which the two primers are annealed is reused as a template.

If the template switching reaction does not take place, two types of double-stranded nucleic acids each consisting of the template and the primer-extended strand can be obtained.

The two types of double-stranded nucleic acids are cleaved with an RNase H at sites that contain the ribonucleotides. Nucleic acids that are complementary to the template are extended using a DNA polymerase having a strand displacement activity from the 3'-termini of the respective primer portions of the double-stranded nucleic acid by an effect of strand displacements.

In the method for amplifying a nucleic acid of the present invention, a double-stranded nucleic acid as a template is treated in the presence of an RNase H with two chimeric oligonucleotide primers that are substantially complementary to the nucleotide sequences of the respective strands and a DNA polymerase having a strand displacement activity and primer-extended strands that are complementary to the template are synthesized. If the template switching reaction does not take place, two types of double-stranded nucleic acids each consisting of the template and the primer-extended strand can be obtained.

In the amplification method of the present invention, the chimeric oligonucleotide primer-extended strand may be cleaved at a site that contains the ribonucleotide such that the 5' fragment (primer portion) resulting from the cleavage does not contain the ribonucleotide. A primer-extended strand extended from the thus generated primer portion is no longer cleaved by an endonuclease. As a result, an amplification product having the primer sequence at its end is generated.

As described above, an amplification product without the primer sequence and a product having the primer sequence(s) at one or both of the ends may be generated in the nucleic acid amplification method of the present invention. These products are included in the amplification products herein.

An example of the method for amplifying a nucleic acid of the present invention is illustrated in FIGS. 33 to 36. In other words, FIGS. 33 to 36 illustrate an exemplary nucleic acid amplification in the nucleic acid amplification method of the present invention.

FIGS. 33 to 36 illustrate an exemplary nucleic acid amplification in the presence of a DNA as a template which is a double-stranded nucleic acid, a pair of chimeric oligonucleotide primers synthesized on the basis of the nucleotide sequence information of the DNA as the template (in the figures, the chimeric oligonucleotide primers have three ribonucleotides at their 3'-termini; open circles in the figures represent the ribonucleotides), a strand displacement type DNA synthetase (DNA polymerase) having a strand displacement activity, an RNase H which is a ribonuclease that cleaves at a DNA-RNA hybrid site, and dNTPs which are substrates to be incorporated into the extended strands.

Figure 33:
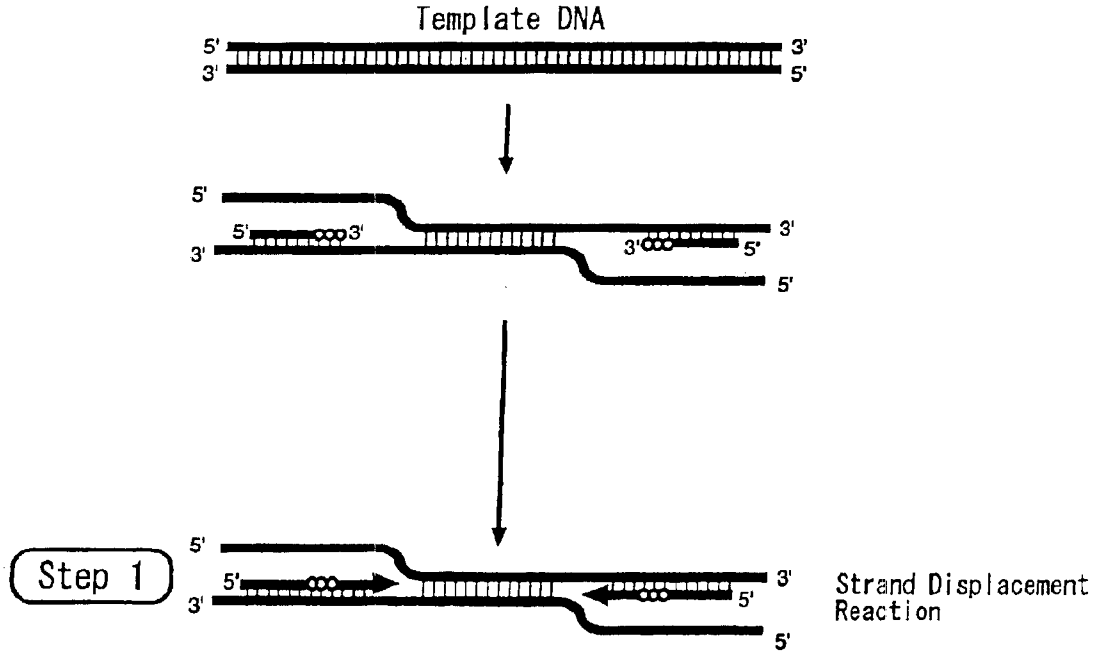
FIG. 33 is a figure illustrating one aspect of the method for amplifying a nucleic acid of the present invention.

As shown in FIG. 33, the chimeric oligonucleotide primers synthesized on the basis of the nucleotide sequence information of the DNA as the template are annealed to the specific portions of the DNA as the template. DNA strands are extended from the 3'-termini of the respective chimeric oligonucleotide primers as a result of the strand displacement reaction as indicated with Step 1.

Figure 34:
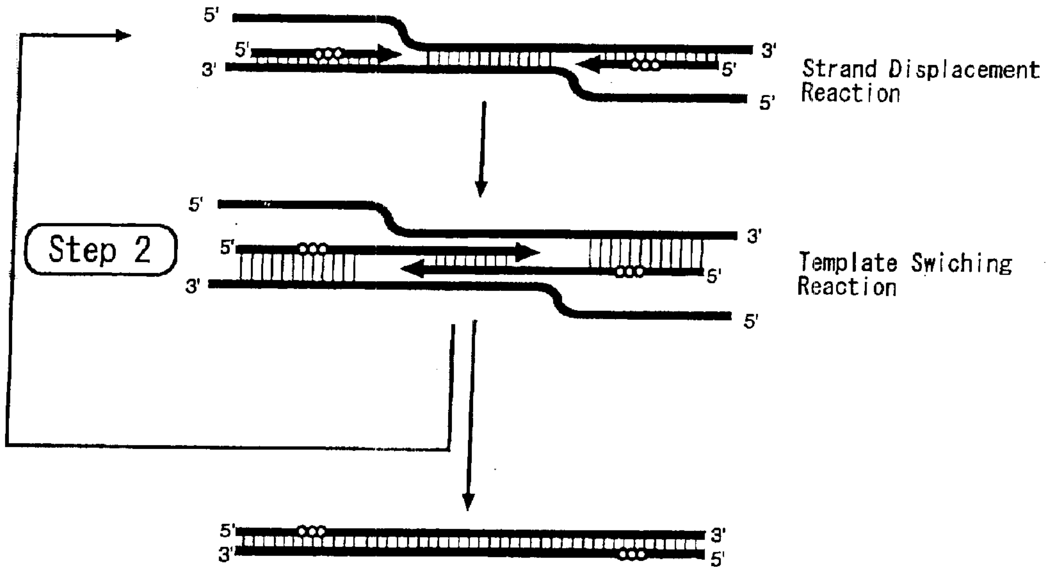
FIG. 34 is a figure illustrating one aspect of the method for amplifying a nucleic acid of the present invention.

Next, as shown in FIG. 34, some of the primer-extended strands extended from upstream and downstream are released from the original templates as a result of the template switching reaction as indicated with Step 2. The primer-extended strands are annealed each other at their 3' portions. Complementary strands are extended from the annealed extended strands, forming a double-stranded DNA consisting of the primer-extended strands being annealed each other. Additionally, a double-stranded DNA consisting of the displaced strands being annealed each other to which the above-mentioned chimeric oligonucleotide primers are annealed is generated. This is utilized as the starting material in FIG. 34.

Figure 35:
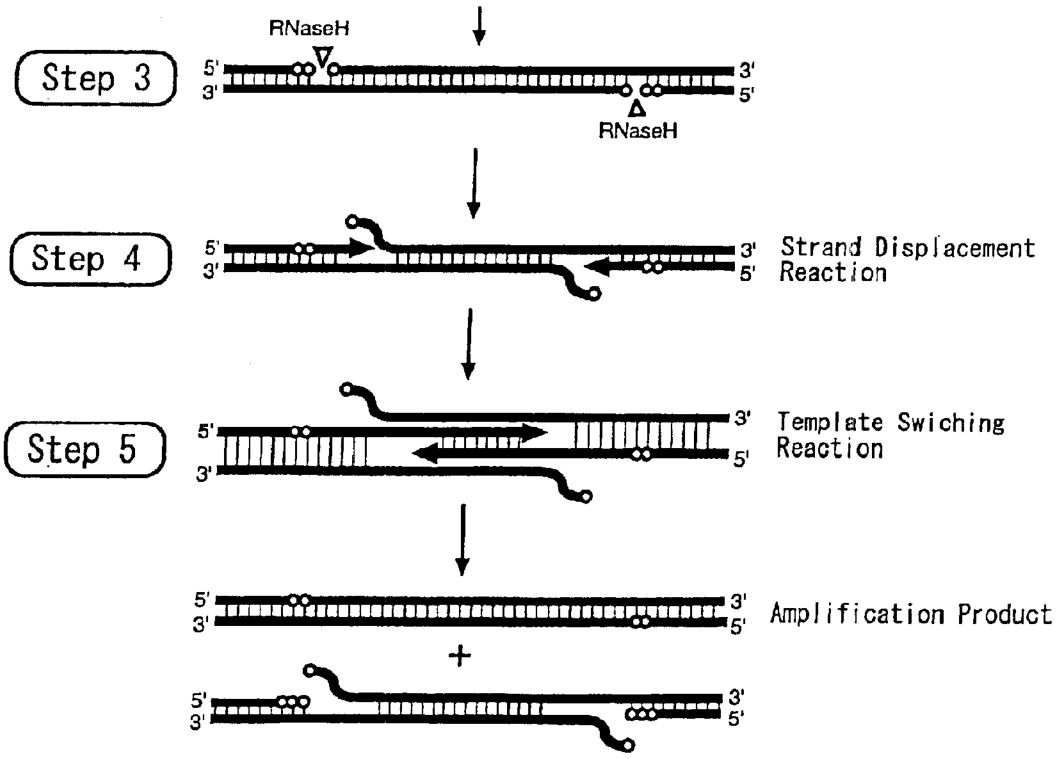
FIG. 35 is a figure illustrating one aspect of the method for amplifying a nucleic acid of the present invention.

As indicated with Step 3 in FIG. 35, only one strand containing an RNA derived from the chimeric oligonucleotide primer of the double-stranded DNA in FIG. 34 consisting of the primer-extended strands being annealed each other is cleaved by the action of an RNase H at the DNA/RNA hybrid site of the double-stranded DNA, resulting in introduction of a nick in the double-stranded DNA.

Subsequently, the strand displacement reaction takes place from the nick in the double-stranded DNA and a DNA is extend as indicated with Step 4 in FIG. 35. Next, a template switching reaction like that in Step 2 in FIG. 34 takes place in some degree or at some ratio as indicated with Step 5 in FIG. 35, resulting in a double-stranded DNA consisting of the amplification products, i.e., the primer-extended strands being annealed each other.

In addition, a double-stranded DNA consisting of the displaced strands being annealed each other to which the above-mentioned chimeric oligonucleotide primers are annealed are generated.

Figure 36:
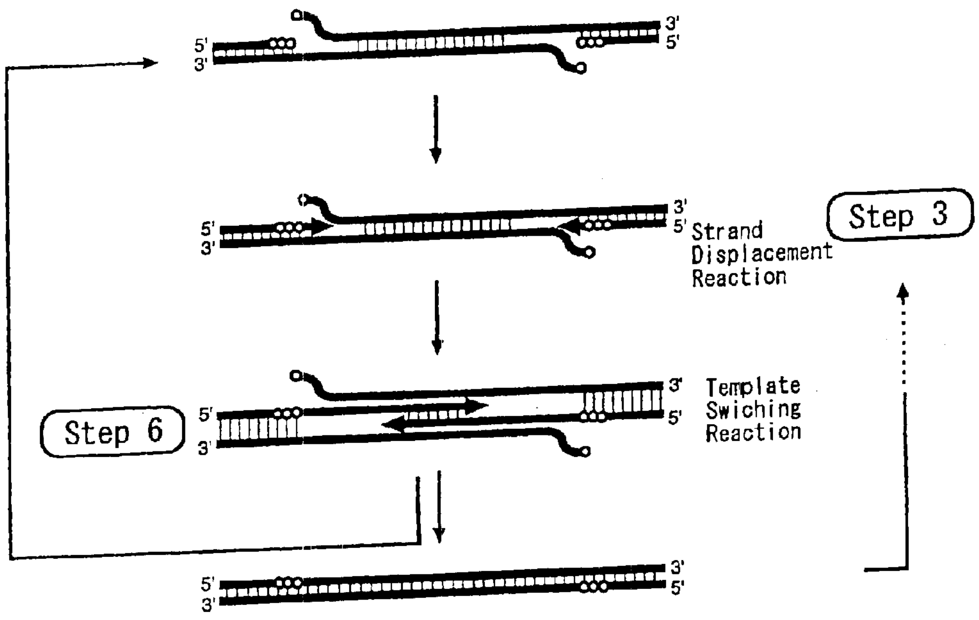
FIG. 36 is a figure illustrating one aspect of the method for amplifying a nucleic acid of the present invention.

Next, as shown in FIG. 36, DNA strands are extended as a result of the strand displacement reaction from the 3'-termini of the respective chimeric oligonucleotide primers in the double-stranded DNA in FIG. 35 which consists of the displaced strands being annealed each other to which the chimeric oligonucleotide primers are annealed. Similar template switching reactions take place in Step 2 and Step 5 in some degree, resulting in a double-stranded DNA consisting of the primer-extended strands being annealed each other. This double-stranded DNA is brought back to Step 3 in FIG. 35. The reaction starts on Step 3 again. A double-stranded DNA which consists of the displaced strands being annealed each other to which the chimeric oligonucleotide primers are annealed is generated and utilized as a starting material in FIG. 36. As a result, a chain reaction, in which these double-stranded nucleic acids are repeatedly generated, takes place to specifically amplify and produce a region bounded by a pair of chimeric oligonucleotide primers.

In the nucleic acid amplification method of the present invention using a chimeric oligonucleotide, a polymer in which the regions to be amplified are connected each other may be generated. The polymer has a structure in which plural regions to be amplified are repeated in the same direction. The polymers are observed upon electrophoretic analysis of amplification products as laddered bands. It is considered that the generation of such polymers is influenced by the region to be amplified, the size of the region, the flanking regions, the nucleotide sequence of the chimeric oligonucleotide primer to be used, the reaction conditions and the like.

The polymer as described above contains plural regions to be amplified. For example, the polymer is useful when detection of a nucleic acid containing a region to be amplified is intended because it hybridizes to a number of probes upon hybridization using an appropriate probe and generates a intensive signal. The region to be amplified or a portion thereof can be obtained from the polymer as a monomer by using digestion with a restriction enzyme or the like in combination.

The DNA polymerase used in the present invention should synthesize an extended strand from the 3'-terminus of the primer portion towards the downstream while displacing a previously extended DNA strand. It is important that the DNA polymerase should not exhibit a 5'→3' exonuclease activity that may digest the displaced strand. For example, Klenow fragment, which is an exonuclease-deficient variant of DNA polymerase I from *Escherichia coli*, a similar fragment derived from Bst DNA polymerase (New England Biolabs), and BcaBEST DNA polymerase from B. ca (Takara Shuzo) are useful as such a DNA polymerase. Sequenase 1.0 and Sequenase 2.0 (United States Biochemical), and T5 DNA polymerase and ϕ29 DNA polymerase as described in Gene, 97:13–19 (1991) can also be used. A polymerase that normally has a 5'→3' exonuclease activity can be used in the DNA synthesis method of the present invention if addition of an appropriate inhibitor can inhibit the activity.

The method for amplifying a nucleic acid of the present invention may be conducted at varying temperatures or it may be conducted isothermally. Varying temperatures means that the reaction temperatures are changed for respective steps such that the change does not interfere with the reactions in the steps. Specifically, varying temperatures refers to change in temperature to that suitable for, for example, each of annealing of a primer, synthesis reaction of a complementary strand, nicking of a complementary strand and a displacement reaction.

On the other hand, isothermal means that the reaction temperature for each step is unchanged and each step is conducted at a substantially constant temperature. It is natural to select the temperature to optimize the reaction conditions in both cases.

One feature of the method for amplifying a nucleic acid of the present invention is that the method does not require adjusting the temperature up and down during the nucleic acid synthesis. Thus, the present invention provides a method for isothermally synthesizing a nucleic acid. Many of conventional nucleic acid amplification methods require adjusting the temperature up and down to dissociate a target from a synthesized strand. These methods require a special reaction equipment such as a thermal cycler for this purpose. However, the method of the present invention can be conducted only using an equipment that can keep a constant temperature. As described above, the method of the present invention can be conducted at a single temperature. Preferably, it is conducted by selecting the reaction temperature and the stringency level such that non-specific annealing of a primer is reduced and such that the primer specifically anneals to a nucleic acid as a template. Although it is not intended to limit the present invention, the method of the present invention can be conducted under high-temperature conditions by using a heat-resistant enzyme as described above. In addition, it is preferable to conduct the method of the present invention at an appropriate temperature for sufficiently retaining the activity of the enzyme used in order to maintain the reaction efficiency at high level. Thus, the reaction temperature is preferably about 20° C. to about 80° C., more preferably about 30° C. to about 75° C., most preferably about 50° C. to about 70° C. although it varies depending on the enzyme used. When the reaction is conducted under high-temperature conditions in particular, it is preferable to use a longer primer than that for a reaction at a normal temperature. The sequence and the length of the primer appropriate for the reaction temperature may be determined, for example, with reference to its Tm value. Alternatively, a commercially available software for designing a primer such as OLIGO™ Primer Analysis software (Takara Shuzo) may be used. For example, when a reaction temperature of 55° C. to 60° C. or 65° C. is used, the primer used for the method of the present invention may be, for example, without limitation, 12–100 nucleotides in length, preferably 14–50 nucleotides in length, more preferably 15–40 nucleotides in length. An example of effects brought by the elevated reaction temperature is the solution of a problem of forming secondary structure of a DNA as a template. The elevated reaction temperature enables amplification of a desired nucleic acid even if a nucleic acid having a high GC content is used as a template. Furthermore, it is similarly effective in amplifying a region of a long chain length. Such effect is observed in a range between about 60 bp and about 20 kbp, specifically between about 110 bp and about 4.3 kbp, more specifically about 130 bp and about 1500 bp.

The amplification efficiency can be increased by adjusting the reaction temperature in accordance with the GC content of the nucleic acid as the template. For example, if a nucleic acid having a low GC content is used as a template, the amplification reaction of the present invention can be conducted at 50 to 55° C., although the temperature depends on the chain length to be amplified and the Tm value of the primer.

Use of a DNA polymerase having a reverse transcriptase activity (e.g., BcaBEST DNA polymerase) in the method of the present invention can make the amplification of a nucleic acid from an RNA, which comprises a step of preparing a cDNA from an RNA (a reverse transcription reaction), be conveniently conducted. Alternatively, a product obtained by independently conducting a step of preparing a cDNA from an RNA, i.e., a cDNA, can be used in the method of the present invention as the DNA as a template.

In each case, the reaction in the method of the present invention is repeated until it is terminated by appropriate means, for example, by inactivating the enzyme or by lowering the reaction temperature, or until the reaction is deprived of one of the substrates.

Figure 40:
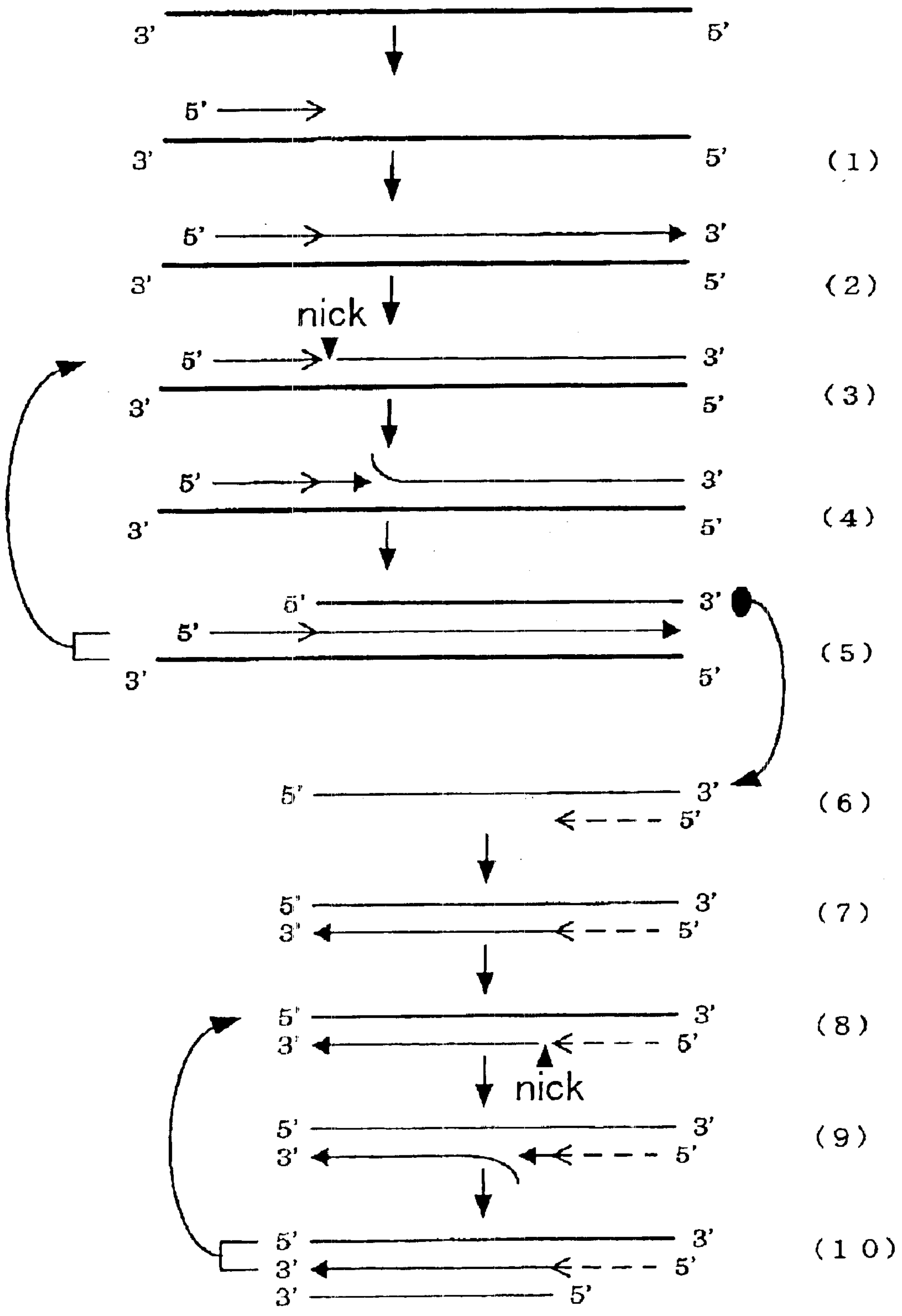
FIG. 40 is a flow chart that illustrates an example of the method of the present invention in which a single-stranded DNA is used. In the figure, the released DNA strand marked with the closed circle serves as a template DNA in (6).

FIG. 40 illustrates one embodiment in which a single-stranded DNA as a template and two primers are used. Respective steps, which are successively conducted in parallel, are described below:

(1) a step of annealing a single-stranded DNA as a template with a chimeric oligonucleotide primer;

(2) a step of effecting a DNA extension reaction from the 3'-terminus of the primer to form a primer-extended strand;

(3) a step of cleaving at a site that contains a ribonucleotide in the primer with an endonuclease;

(4) a step of effecting a strand displacement using a DNA polymerase from the cleavage site in step (3);

(5) a step of reusing a double-stranded DNA, which is composed of a template obtained in step (4) and a regenerated primer-extended strand, in step (3), while utilizing a released displaced strand in a reaction of step (6) and the following steps;

(6) a step annealing an oligonucleotide primer that is different from that in step (1) with the released displaced strand in step (5) as a template;

(7) a step of effecting a DNA extension reaction from the 3'-terminus of the primer to form a primer-extended strand;

(8) a step of cleaving at a site that contains a ribonucleotide in the primer with an endonuclease;

(9) a step of effecting a strand displacement using a DNA polymerase from the cleavage site in step (8); and

(10) a step of reusing a template obtained in step (9) and a regenerated primer-extended strand in step (8).

When a double-stranded DNA is used as a template, each of the single-stranded DNAs obtained after denaturing the double-stranded DNA serves as the template in step (1). Therefore, the amount of amplification product is more than that obtained with a single-stranded DNA as a template. In addition, detection of the amplification product can be conducted in a shorter time than that required when a single-stranded DNA is used as a template.

The method for amplifying a nucleic acid of the present invention can be used for various experimental procedures that utilize amplification of a nucleic acid including detection, labeling and sequencing of a nucleic acid.

Furthermore, the method for amplifying a nucleic acid of the present invention can be used for an in situ nucleic acid amplification method, a method for amplifying a nucleic acid on a solid substrate such as a DNA chip, or a multiplex nucleic acid amplification method in which plural regions are simultaneously amplified.

One of the features of the method for amplifying a nucleic acid of the present invention is its ability to prepare a single-stranded DNA. One or two chimeric oligonucleotide primers can be used in the method for this purpose. For example, if two oligonucleotide primers are used, the method of the present invention can be conducted applying a similar primer ratio to the so-called asymmetric-PCR in which an amplification reaction is carried out by using an excess amount of one oligonucleotide primer relative to another. The primer ratio is, without limitation, preferably in a range of 1:10 to 1:500, more preferably in a range of 1:10 to 1:100. As a result, the amount of the replacement product from one strand becomes excessive relative to that from another.

According to the method for amplifying a nucleic acid of the present invention, a single-stranded DNA substantially free of a complementary strand thereto can be prepared. For example, a single-stranded DNA for producing a material having an immobilized nucleic acid such as a DNA chip, a single-stranded DNA probe for detecting a target nucleic acid, or a mega-primer for the long-chain PCR can be readily produced in a short time. Only a sense sequence or an antisense sequence can be selectively amplified by using the method of the present invention. Thus, the present invention is also useful as a method for producing a nucleic acid having a sense sequence or a antisense sequence.

A region of a nucleic acid of interest can be amplified even from a trace amount of a nucleic acid as a template by conducting the method of the present invention in a buffer of Bicine, Tricine, HEPES, phosphate or tris.

Furthermore, the methods for amplifying a nucleic acid of the present invention does not require the specific reaction equipment that can adjust a temperature with the passage of time. Therefore, an amplification reaction can be conducted in a large volume of reaction mixture. Thus, a nucleic acid (e.g., for medical use) can be industrially produced in large quantities.

The utilization efficiency of the primer in the method for amplifying a nucleic acid of the present invention is about 100%, which may be 5- to 10-fold higher than that in a conventional method such as the PCR.

The nucleic acid amplification method of the present invention can produce an amplification product with high fidelity to the nucleotide sequence of the template nucleic acid. When the frequency of error in the DNA synthesis in the method of the present invention was confirmed by analyzing the nucleotide sequences of resulting amplification products, the frequency of error found in amplification products obtained by the method of the present invention was equivalent to that by LA-PCR which is known to be able to amplify a nucleic acid with high fidelity. In other words, the method of the present invention has fidelity equivalent to that of the LA-PCR.

(6) Method for Detecting Target Nucleic Acid of the Present Invention and Kit for the Method.

A target nucleic acid in a sample can be detected by using the method for amplifying a nucleic acid of the present invention. The detection method comprises:

(a) amplifying a target nucleic acid by the method for amplifying a nucleic acid of the present invention as described above; and (b) detecting the target nucleic acid amplified in the step above.

In step (a) above, if an RNA is used as a template, the reverse transcription reaction and the nucleic acid amplification reaction may be conducted in one step. Although it is not intended to limit the present invention, for example, a combination of AMV RTase, MMLV RTase or RAV-2 RTase and Bca DNA polymerase lacking 5'→3' exonuclease can be preferably used as a combination of a reverse transcriptase and a strand displacement-type DNA polymerase.

The method can be utilized to detect or quantify a specific gene in a sample. In other words, a specific gene can be detected or quantified from all samples suspected to contain a nucleic acid such as a DNA or an RNA. Examples of the samples from which a specific gene can be detected or quantified include, but are not limited to, samples from organisms such as a whole blood, a serum, a buffy coat, a urine, feces, a cerebrospinal fluid, a seminal fluid, a saliva, a tissue (e.g., a cancerous tissue or a lymph node) and a cell culture (e.g., a mammalian cell culture or a bacterial cell culture), samples that contain a nucleic acid such as a viroid, a virus, a bacterium, a fungi, a yeast, a plant and an animal, samples suspected to be contaminated or infected with a microorganism such as a virus or a bacterium (e.g., a food or a biological formulation), and samples that may contain an organism such as a soil and a waste water. For example, a viroid, a virus, a fungi, a bacterium or other microorganisms in a sample can be detected or quantified on the basis of the presence or the content of a specific gene derived from these microorganisms as a target. Particularly, a method for detecting a pathogenic microorganism is useful in fields of sanitation and environment. Furthermore, the method of the present invention can be used to distinguish a genotype of an organism or to determine the expression level of a gene. Particularly, detection or confirmation of the expression state of a disease-related gene, e.g., a gene related to canceration of cells is useful in a field of medicine. Both of an RNA and a DNA can be preferably used as the nucleic acid as the template in the detection.

The method for detecting a target nucleic acid of the present invention can be used to distinguish the difference in the nucleotide sequence of the target nucleic acid. In this aspect, the chimeric oligonucleotide primer to be used is designed such that the 3'-terminal portion of the primer is positioned close to the specific base of the target nucleotide sequence to be distinguished. For example, it is designed such that a hydrogen bond is formed between the base and the 3'-terminal base of the primer. If a mismatch exists between the nucleotide sequence of the 3'-terminal portion of the primer and the nucleotide sequence of the template, amplification from the target nucleic acid does not take place and no amplification product is generated using the above-mentioned chimeric oligonucleotide primer for amplification reaction. Information concerning a specific base in a gene such as a point mutation or a single nucleotide polymorphism (SNP) can be obtained using the method.

The method for detecting a target nucleic acid of the present invention can be conducted by amplifying the target nucleic acid directly from a sample containing the nucleic acid. In this case, the chain length of the target nucleic acid to be amplified is not limited to a specific one. For example, a region of 200 bp or shorter, preferably 150 bp or shorter is effective for sensitive detection of the target nucleic acid. The target nucleic acid in the sample can be detected with high sensitivity by designing the chimeric oligonucleotide primers of the present invention to result in the chain length to be amplified as described above.

In addition, a target nucleic acid can be detected with more sensitivity even from a trace amount of a nucleic acid sample in the detection method of the present invention by using a reaction buffer containing Bicine, Tricine, HEPES, phosphate or tris as a buffering component and an annealing solution containing spermidine or propylenediamine as exemplified in (4) above. In this case, the endonuclease and the DNA polymerase to be used are not limited to specific ones. For example, a combination of an RNase H from *Escherichia coli*, a bacterium of genus *Pyrococcus* or a bacterium of genus *Archaeoglobus* and BcaBEST DNA polymerase is preferable. It is considered that the preferable units of the endonuclease and the DNA polymerase may vary depending on the types the enzymes. In such a case, the composition of the buffer and the amount of the enzymes added may be adjusted using the increase in detection sensitivity or the amount of amplification product as an index.

In the detection method of the present invention, dUTP may be incorporated as a substrate during amplification of a target nucleic acid. Thus, if dUTP is used as a substrate, it is possible to prevent carry-over contamination of amplification products by degrading amplification products utilizing uracil N-glycosidase (UNG)

Known methods for detecting a nucleic acid can be used for step (b). Examples of such methods include detection of a reaction product having a specific size by electrophoresis, and detection by hybridization with a probe. Furthermore, a detection method in which magnetic beads are combined can be preferably used. A fluorescent substance such as ethidium bromide is usually used in the detection by electrophoresis. The hybridization with a probe may be combined with the detection by electrophoresis. The probe may be labeled with a radioisotope or with a non-radioactive substance such as biotin or a fluorescent substance. Additionally, use of a labeled nucleotide in step (a) may facilitate the detection of amplification product into which the labeled nucleotide is incorporated, or may enhance the signal for detection utilizing the label. Furthermore, a fluorescence polarization method, a fluorescence energy transition or the like can also be utilized for the detection. The target nucleic acid can be detected automatically or quantified by constructing a suitable detection system. In addition, detection with naked eyes by a hybrid chromatography method can be preferably used.

A ribonucleotide (RNA) probe labeled with two or more fluorescent substances positioned at a distance that results in a quenching state can be used in the detection method of the present invention. The probe does not emit fluorescence. When it is annealed to a DNA amplified from a target nucleic acid that is complementary to the probe, RNase H digests the probe. The distance between the fluorescent substances on the probe then increases, resulting in the emission of fluorescence. Thus, the emission reveals the presence of the target nucleic acid. If RNase H is used in the method for amplifying a nucleic acid of the present invention, a target nucleic acid can be detected only by adding the probe to the reaction mixture. For example, a combination of fluorescent substances, 6-carboxyfluorescein (6-FAM) and N,N,N',N'-tetramethyl-6-carboxyhydramine (TAMRA), can be preferably used for labeling the probe.

The present invention further provides a probe used in the above-mentioned method for detecting a target nucleic acid. The probe of the present invention is not limited to specific one as long as it can hybridize to a target nucleic acid amplified by the nucleic acid amplification method of the present invention under normal hybridization conditions. In view of specific detection of amplification product, a probe that hybridizes under conditions, for example, known to those skilled in the art as being stringent is preferable. The stringent hybridization conditions are described in, for example, T. Maniatis et al. (eds.), Molecular Cloning: A Laboratory Manual 2nd ed., 1989, Cold Spring Harbor Laboratory. Specifically, the stringent conditions are exemplified by the following: incubation at a temperature about 25° C. lower than the Tm of the probe to be used for 4 hours to overnight in 6×SSC (1×SSC: 0.15 M NaCl, 0.015 M sodium citrate, pH 7.0) containing 0.5% SDS, 5×Denhardt's (0.1% bovine serum albumin (BSA), 0.1% polyvinylpyrrolidone, 0.1% Ficoll 400) and 100 mg/ml salmon sperm DNA. A probe having a label as described above may be used as the probe for facilitating the detection of the target nucleic acid.

The method for amplifying a nucleic acid under isothermal conditions of the present invention does not require the use of an equipment such as a thermal cycler. The number of primers used in the amplification method of the present invention can be one or two, which is less than that used in a conventional method. Since reagents such as dNTPs used for PCR and the like can be applied to the method of the present invention, the running cost can be reduced as compared with a conventional method. Therefore, the method of the present invention can be preferably used, for example, in a field of genetic test in which the detection is routinely conducted. The method of the present invention provides a greater amount of an amplification product in a shorter time than the PCR. Therefore, the method of the present invention can be utilized as a convenient, rapid and sensitive method for detecting a gene.

In genetic analysis on a genomic level, attempts are made to make the reaction system small and to increase the degree of integration in order to analyze a large amount of nucleotide sequences. An system has been developed for this purpose by utilizing the latest hyperfine processing techniques in which basic processes for genome analysis (e.g., extraction of DNA from cells, DNA amplification reaction, electrophoresis, hybridization, detection of the DNA of interest, etc.) are integrated on a microchip of several square centimeters to fingertip size. Such a system is called as a microchip or a nanochip.

Application of the PCR to the system as a gene amplification reaction is currently considered. However, since the PCRs requires means for repeatedly controlling temperature up and down over time, the system would become complicated. By contrast, since the system can be simplified using the method of the present invention which can amplify a nucleic acid under isothermal conditions, the method is quite suitably utilized for the integrated system as described above. A highly integrated system can be constructed by utilizing the techniques of the present invention.

(7) Kit of the Present Invention

The present invention provides a kit used for the method for amplifying or detecting a nucleic acid of present invention as described above. In one embodiment, the kit is in a packaged form and contains instructions regarding the use of a DNA polymerase and an endonuclease in a strand displacement reaction. Also, a kit that contains a DNA polymerase having a strand displacement activity, an endonuclease, and a buffer for a strand displacement reaction is preferably used for the method of the present invention. Alternatively, a commercially available DNA polymerase having a strand displacement activity and/or endonuclease may be selected and used according to the instructions. Additionally, the kit may contain a reagent for a reverse transcription reaction that is used when an RNA is used as a template. The DNA polymerase can be selected from the DNA polymerases to be used in the present invention as described above in (3). The endonuclease can be selected from the endonucleases as described above in (2). One having the reaction buffer composition as described above in (4) can be preferably used as the buffer for the strand displacement reaction.

"Instructions" are printed matters describing a method of using the kit, e.g., a method for preparing a reagent solution for a strand displacement reaction, recommended reaction conditions and the like. The instructions include an instruction manual in a form of a pamphlet or a leaflet, a label stuck to the kit, and description on the surface of the package containing the kit. The instructions also include information disclosed or provided through electronic media such as the Internet.

The kit of the present invention may further contain a reaction buffer containing Bicine, Tricine, HEPES, phosphate or tris as a buffering component and an annealing solution as exemplified in (4) above. Additionally, it may contain a DNA polymerase having a strand displacement activity and an RNase H. Furthermore, the kit may contain a modified deoxyribonucleotide or a deoxynucleotide triphosphate analog.

The kit used in the method for detecting a target nucleic acid may further contain an appropriate chimeric oligonucleotide primer for amplifying the target nucleic acid and a reagent for detecting the amplified target nucleic acid such as a probe in addition to the instructions and the reagents for amplification reaction as described above.

In addition, the kits of the present invention include a kit containing the chimeric oligonucleotide primer used in the present invention and/or the probe of the present invention as described above.

(8) Composition of the Present Invention.

The present invention provides a composition used for the method for amplifying a nucleic acid of the present invention or the method for detecting a nucleic acid of the present invention as described above. For example, the composition may contain the endonuclease as described in (2) above and the DNA polymerase as described in (3) above. The composition may further contain a buffering component, a magnesium salt, dNTPs and the like as components for conducting an amplification reaction. Furthermore, it may contain a modified deoxyribonucleotide or a deoxynucleotide triphosphate analog. Those as described in (4) above can be used as the buffering component and other additives.

In a particularly preferable aspect, the composition may contain suitable amounts of the various components as listed above for the nucleic acid amplification method of the present invention. Amplification reaction can be conducted only by adding an appropriate template and chimeric oligonucleotide primer(s) to the composition. If the object to be amplified is known beforehand, the composition preferably contains chimeric oligonucleotide primer(s) suitable for amplifying the object.

(9) Material having Immobilized Nucleic Acid Arrayed in Predefined Region of the Present Invention and Method for Producing the Same.

A DNA chip (also referred to as a DNA microarray or a DNA array) is a material having an immobilized nucleic acid in which various fragments of genes or DNAs are arrayed and immobilized in a predefined region or at a predefined position on a solid substrate such as a slide glass. The DNA chip is used for examining the presence of a nucleic acid in a nucleic acid sample that has a sequence complementary to an arrayed and immobilized DNA in a predefined region on the DNA chip. The examination is carried out by contacting the DNA chip with the nucleic acid sample prepared from a sample, preferably a labeled nucleic acid sample, for hybridization. Since the DNA chip can be used to detect or quantify a number of nucleic acids in a sample in one procedure, it is a very useful means that dramatically promotes the analysis of gene expression, or the analysis of a mutation or polymorphism. A DNA chip in which a double-stranded nucleic acid is arrayed and immobilized in a predefined region is used for hybridization after it is subjected to appropriate denaturation. A DNA chip in which a single-stranded DNA complementary to a target nucleic acid to be detected is arrayed and immobilized in a predefined region is particularly preferable for the detection of a target nucleic acid.

As described above, a desired DNA can be amplified in a single-stranded form by the method of the present invention. Although any method for purifying an amplification product can be used, purification using isopropanol precipitation is preferable. The thus obtained DNA, preferably a single-stranded DNA substantially free of a complementary strand thereto, can be preferably used as a DNA fragment to be immobilized onto a DNA chip. Thus, the method of the present invention is preferably used as a method for preparing a DNA to be arrayed and immobilized in a predefined region for producing a DNA chip. Any insoluble substrate can be used as a substrate onto which the thus obtained DNA is arrayed and immobilized in a predefined region, but a plate-shaped substrate made from glass or plastic, and a membrane-shaped substrate made from nitrocellulose or nylon are preferably used. A known method for immobilizing a nucleic acid can be used for the immobilization. The DNA may be directly immobilized onto a substrate. Alternatively, the DNA may be immobilized through a suitable linker or after ligating plural DNA molecules. Furthermore, since a modified deoxyribonucleotide can be incorporated into an amplified nucleic acid by the method of the present invention, the material having an immobilized nucleic acid can be produced utilizing the modification group.

A target nucleic acid that hybridizes with a nucleic acid on a material having an immobilized nucleic acid in which a DNA amplified by the method of the present invention is arrayed and immobilized in a predefined region (e.g., a DNA chip) can be detected or quantified. Such detection or quantification can be accomplished by contacting the material with a nucleic acid sample prepared from a sample suspected to contain the target nucleic acid for hybridization. Among these, a DNA chip in which a single-stranded DNA amplified by the method of the present invention is arrayed and immobilized in a predefined region allows the detection of a target nucleic acid with more convenient operation, higher sensitivity and higher reproducibility as compared with a conventional material.

(10) Method for Producing Nucleic Acid in Large Quantities of the Present Invention.

As described above, one aspect of the present invention provides a method for amplifying a nucleic acid that can be carried out under isothermal conditions. A desired nucleic acid can be produced in the method by mixing a nucleic acid as a template for the nucleic acid to be amplified and various components required for a reaction and reacting the mixture under isothermal conditions. Since the PCR requires changing the temperature of the reaction mixture over time, the reaction volume is limited to one in which the temperature can be controlled (usually, 200 $\mu$l or less). Therefore, it is difficult to scale up the volume. On the other hand, there is no such limitation in the method of the present invention. A large amount of nucleic acid can be produced by increasing the volume of the reaction mixture. In the method of the present invention, the volume is, for example, preferably more than 200 $\mu$l, more preferably 300 $\mu$l or more, and most preferably 500 $\mu$l or more, although it is not intended to limit the present invention. In the method of the present invention, a number of complementary strand molecules are synthesized from one template molecule. Furthermore, nucleic acids can be synthesized using these complementary strand molecules as templates. Thus, a desired nucleic acid can be efficiently produced in large quantities by suitably selecting the template and the primer. Additionally, the fact that, unlike the PCR, the method of the present invention does not require a special equipment or a complicated temperature change makes it advantageous in view of the cost of equipment and energy. Therefore, the method is an excellent industrial method for producing a nucleic acid in large quantities.

The nucleic acid of interest can be amplified or produced even from a trace amount of a nucleic acid as a template in the production method of the present invention by using the reaction buffer and the annealing solution as exemplified in (4) above. In this case, the endonuclease and the DNA polymerase to be used are not limited to specific ones. For example, a combination of an RNase H from *Escherichia coli* and BcaBEST DNA polymerase is preferable. It is considered that the preferable units of the endonuclease and the DNA polymerase may vary depending on the types of the enzymes. In such a case, the composition of the buffer and the amount of the enzymes added may be adjusted using the maximal amount of amplification product as an index.

Furthermore, the method of the present invention is useful as a method for supplying a variety of DNA fragments in large quantities, such as those to be immobilized onto the DNA chip. Specifically, DNA fragments can be obtained in large quantities in simple reaction steps in one embodiment. In another embodiment, a limited number of primers can be used to obtain a variety of DNA fragments. A step of amplifying the nucleic acid that serves as the template in the method of the present invention beforehand by a known nucleic acid amplification method such as the PCR can be incorporated in the latter embodiment. All kinds of nucleic acids as templates can be amplified using a limited number of primers, for example, based on the method for amplifying a nucleic acid using a random primer having a tag sequence (Nucleic Acids Research, 24(19):3778–3783 (1996)) or the degenerate oligonucleotide-primed PCR (DOP-PCR; Genomics, 13:718–725 (1992)), which uses a degenerate primer. The nucleic acid amplification method of the present invention can be conducted using one or several primers for all of the nucleic acids as templates produced in the above-mentioned step. This can be accomplished by designing the primer used in the nucleic acid amplification method of the present invention such that it corresponds to the tag sequence added to the random or degenerate primer. Thus, a combination of a suitable step for preparing a nucleic acid as a template and the method of the present invention can supply a variety of DNA fragments in larger quantities and at a lower cost as compared with a conventional method.

A pharmaceutical composition containing a nucleic acid may contain a double-stranded DNA for expressing a useful polypeptide in a cell or a single-stranded antisense DNA for suppressing the expression of a gene of interest. Such a nucleic acid is administered into an organism using suitable means, for example, a carrier for gene transfer such as liposome. The method for producing a nucleic acid of the present invention is preferable for producing a single-stranded or double-stranded nucleic acid for medical use in large quantities. Additionally, a nucleic acid containing a dNTP analog that, for example, suppresses the degradation of the nucleic acid in vivo can be readily produced by the method of the present invention.

Since the DNA fragment amplified in the present invention is composed of normal nucleotides, the amplified DNA can be, for example, subcloned into a suitable vector utilizing a restriction enzyme site in the DNA. Furthermore, the DNA can be treated with a restriction enzyme for RFLP without a problem, for example. Therefore, the DNA can be widely utilized in a field of genetic test. In addition, a promoter sequence for an RNA polymerase can be incorporated into the amplified fragment. The amplified fragment can be used as a template to synthesize an RNA, which can be used as a probe, for example. Of course, a fluorescence-labeled DNA probe can be produced by conducting the method for amplifying a nucleic acid of the present invention using a fluorescence-labeled dNTP instead of a normal dNTP.

Features of the method for amplifying a nucleic acid of the present invention are listed below.

1. It can amplify a large amount of a nucleic acid from a small amount of a template. The amplification product increases quadratically when two primers are used.

2. It can be conducted isothermally. In this case, it does not require the use of an equipment such as a thermal cycler. Therefore, the reaction volume can be readily scaled up.

3. Usually, the amplification reaction is conducted using one or two chimeric oligonucleotide primer and two enzymes (a DNA polymerase and an endonuclease).

4. Since a number of DNA strands are synthesized from one molecule of a primer, the amount of the primer does not restrict the amount of the amplification product. Furthermore, the primer utilization efficiency is about 100%, which is very higher than that of the PCR.

5. A single-stranded or double-stranded DNA can be selectively amplified depending on the purpose.

6. Since it does not require a dNTP analog such as an (α-S) dNTP for the amplification reaction, the cost of reagents is low. Furthermore, a nucleic acid in a natural form without a dNTP analog can be obtained.

7. It can supply an amplified DNA fragment at low cost and in large quantities by combining the method of the present invention with another nucleic acid duplication method.

8. The detection method of the present invention has an equal or higher detection sensitivity as compared with that of a conventional method. The detection method of the present invention can be conducted in a shorter time than that required for a conventional method having the equal sensitivity.

9. The method is suitable for amplification of a nucleic acid, automated detection, detection in a small amount and highly integrated detection on a microchip or a nanochip.

As described above, the method of the present invention is suitable for detection of a gene and industrial production of a nucleic acid. Examples The following Examples illustrate the present invention in more detail, but are not to be construed to limit the scope thereof.

REFERENTIAL EXAMPLE 1

Preparation of RNase H from Thermophile *Bacillus caldotenax*

*Bacillus caldotenax* YT-G (purchased from Deutsche Sammlung von Mikroorganismen; DSM406) was inoculated into 100 ml of a medium containing 0.2% Tryptone (Difco Laboratories) and 1.5% yeast extract (Difco Laboratories) (pH 6.5), cultured at 60° C. for 140 minutes with shaking and used as a pre-culture. 30 ml of the pre-culture was inoculated into 3 L of a medium having the same composition and cultured with aeration at 2.5 L/minute and stirring at 250 rpm at a temperature of 60° C. for 5 hours.

The cells were collected by centrifuging the culture at 5000×g for 15 minutes. 402 g (wet weight) of the cells were suspended in 1000 ml of 50 mM tris-HCl buffer (pH 7.5) containing 10 mM mercaptoethanol, 0.5 M NaCl, 1 mM EDTA and 20 μM PAPMSF and disrupted using MINI-Lab (APV GAULIN/RANNIE). Cell debris were removed by centrifugation to recover a supernatant.

A polyethylene imine solution was added to the resulting supernatant at a final concentration of 0.1%. After stirring, the mixture was allowed to stand for 1 hour. A supernatant was then recovered by centrifugation. Ammonium sulfate was added to the supernatant to 50% saturation. A precipitate obtained by centrifugation was dissolved in 20 mM tris-HCl buffer (pH 7.5) containing 10 mM mercaptoethanol, 0.1 mM EDTA, 50 mM NaCl and 10% glycerol. The solution was dialyzed against the same buffer. The dialyzed sample was loaded onto a 280-ml DE52 column (Whatman) equilibrated with the same buffer and non-adsorptive fractions were collected.

The column was further washed with 420 ml of the buffer used for the equilibration and washing fractions were collected. The non-adsorptive fractions and the washing fractions from the DE52 column chromatography were mixed together and loaded onto a 240-ml P-11 column (Whatman) equilibrated with 20 mM tris-HCl buffer (pH 7.5) containing 10 mM mercaptoethanol, 0.1 mM EDTA, 50 mM NaCl and 10% glycerol. Elution was then carried out using the equilibration buffer containing 0 to 0.5 M NaCl.

The resulting active fractions were placed in a dialysis tube. The tube was placed on solid polyethylene glycol 20000 for dehydration-concentration at 4° C. The enzyme concentrate was then loaded onto a 300-ml Superdex G-200 column (Amersham Pharmacia Biotech) equilibrated with 25 mM tris-HCl buffer (pH 7.5) containing 5 mM mercaptoethanol, 0.5 mM EDTA, 30 mM NaCl and 50% glycerol. Elution was carried out using the buffer used for equilibration to obtain active fractions. The active fractions were loaded onto a 15-ml Heparin-Sepharose column (Amersham Pharmacia Biotech) equilibrated with 20 mM tris-HCl buffer (pH 7.5) containing 10 mM mercaptoethanol, 0.1 mM EDTA, 50 mM NaCl and 10% glycerol. Elution was carried out using the equilibration buffer containing 0 to 0.5 M NaCl.

The resulting active fractions were loaded onto a 5-ml Hitrap-SP column (Amersham Pharmacia Biotech) equilibrated with 20 mM tris-HCl buffer (pH 7.5) containing 10 mM mercaptoethanol, 0.1 mM EDTA, 50 mM NaCl and 10% glycerol. Elution was carried out using the equilibration buffer containing 0 to 0.5 M NaCl. The resulting active fractions were loaded onto a 300-ml Superdex G-200 column (Amersham Pharmacia Biotech) equilibrated with 25 mM tris-HCl buffer (pH 7.5) containing 5 mM mercaptoethanol, 0.5 mM EDTA, 30 mM NaCl and 50% glycerol again. The resulting active fractions were used as an RNase H preparation (an enzyme solution).

A heat-resistant RNase H activity was measured as follows.

1 mg of poly(rA) or poly(dT) (both from Amersham Pharmacia Biotech) was dissolved in 1 ml of 40 mM tris-HCl (pH 7.7) containing 1 mM EDTA to prepare a poly(rA) solution and a poly(dT) solution.

The poly(rA) solution (to a final concentration of 20 $\mu$g/ml) and the poly(dT) solution (to a final concentration of 30 $\mu$g/ml) were then added to 40 mM tris-HCl (pH 7.7) containing 4 mM $MgCl_2$, 1 mM DTT, 0.003% BSA and 4% glycerol. The mixture was reacted at 37° C. for 10 minutes and then cooled to 4° C. at prepare a poly(rA)-poly(dT) solution.

1 $\mu$l of an enzyme solution was added to 100 $\mu$l of the poly(rA)-poly(dT) solution. The mixture was reacted at 40° C. for 10 minutes. 10 $\mu$l of 0.5 M EDTA was added thereto to terminate the reaction. Absorbance at 260 nm was then measured. As a control, 10 $\mu$l of 0.5 M EDTA was added to the reaction mixture, the resulting mixture was reacted at 40° C. for 10 minutes, and the absorbance was then measured. A value (difference in absorbance) was obtained by subtracting the absorbance for the control from the absorbance for the reaction in the absence of EDTA. Thus, the concentration of nucleotide released from poly(rA)-poly(dT) hybrid by the enzymatic reaction was determined on the basis of the difference in absorbance. One unit of an RNase H was defined as an amount of enzyme that increases $A_{260}$ corresponding to release of 1 nmol of ribonucleotide in 10 minutes calculated according to the following equation. If a diluted enzyme solution is used, the value obtained using the following equation was corrected based on the dilution rate:

Unit=[Difference in Absorbance×Reaction Volume (ml)]/0.0152

REFERENTIAL EXAMPLE 2

Cloning of *Bacillus caldotenax* RNase HII gene (1) Preparation of Genomic DNA from *Bacillus caldotenax*

*Bacillus caldotenax* YT-G (DSM406) was inoculated into 60 ml of LB medium (1% Tryptone, 0.5% yeast extract and 0.5% NaCl, pH 7.2) and cultured at 65° C. for 20 hours. After culturing, the culture was centrifuged to collect cells. The cells were suspended in 2 ml of 25% sucrose and 50 mM tris-HCl (pH 8.0). 0.2 ml of 10 mg/ml lysozyme chloride (Nacalai Tesque) in water was added thereto. The mixture was reacted at 20° C. for 1 hour. After reaction, 12 ml of a mixture containing 150 mM NaCl, 1 mM EDTA and 20 mM tris-HCl (pH 8.0), 0.1 ml of 20 mg/ml proteinase K (Takara Shuzo) and 1 ml of a 10% aqueous solution of sodium lauryl sulfate were added to the reaction mixture. The mixture was incubated at 37° C. for 1 hour.

2.1 ml of 5 M NaCl and 2 ml of a CTAB-NaCl solution [10% cetyltrimethylammonium bromide (Nacalai Tesque) and 0.7 M NaCl] were then added to the mixture and the resulting mixture was mixed thoroughly and incubated at 65° C. for 10 minutes. An equal volume of a mixture of chloroform/isoamyl alcohol (24:1, v/v) was added thereto. The resulting mixture was gently mixed for 10 minutes and then centrifuged for 10 minutes at 10000×g. After centrifugation, an equal volume of a mixture of phenol saturated with 100 mM tris-HCl (pH 8.0)/chloroform/isoamyl alcohol (25:24:1, v/v) was added to the resulting supernatant. The resulting mixture was gently mixed for 10 minutes and then centrifuged for 10 minutes at 10000×g. After centrifugation, 0.6 volume of 2-propanol was added to the resulting supernatant. The resulting fibrous precipitate was wound using a glass bar, washed with 70% ethanol in water, air-dried and then dissolved in 0.5 ml of TE buffer to obtain a genomic DNA solution.

(2) Cloning of a Middle Portion of RNase HII Gene

Oligonucleotides BsuII-3 and BsuII-6 represented by SEQ ID NOS:97 and 98 were synthesized on the basis of Motif I and Motif III, portions conserved among amino acid sequences of RNase HIIs from various organisms (Biochemistry, 38:605–608 (1999)).

A PCR was carried out in a volume of 100 $\mu$l using 1 $\mu$l of the *Bacillus caldotenax* genomic DNA solution as prepared in Referential Example 2-(1) as a template, and 100 pmol of BsuII-3 and 100 pmol of BsuII-6 as primers. TaKaRa Taq polymerase (Takara Shuzo) was used as a DNA polymerase for the PCR according to the attached protocol. The PCR was carried out as follows: 50 cycles of 94° C. for 30 seconds, 45° C. for 30 seconds and 72° C. for 1 minute. After reaction, the reaction mixture was subjected to phenol treatment followed by ethanol precipitation to purify a DNA. The resulting DNA was blunt-ended using T4 DNA polymerase (Takara Shuzo) and then subjected to agarose gel electrophoresis to recover an amplified DNA fragment of about 0.4 kb from the gel. The about 0.4-kb DNA fragment was ligated with pUC119 (Takara Shuzo) digested with SmaI (Takara Shuzo) using T4 DNA ligase (Takara Shuzo). The ligation mixture was used to transform *Escherichia coli* JM109. The resulting transformants were cultured to obtain a plasmid 21-12 into which the about 0.4-kb DNA was inserted.

(3) Cloning of Upstream Portion of RNase II Gene

The nucleotide sequence of the inserted fragment of about 0.4 kb in the plasmid 21-12 obtained in Referential Example 2-(2) was determined. Oligonucleotides RNII-S1 and RNII-S2 represented by SEQ ID NOS:99 and 100 were synthesized on the basis of the determined nucleotide sequence.

The *Bacillus caldotenax* genomic DNA as prepared in Referential Example 2-(1) was digested with BamHI (Takara Shuzo) and ligated with a Sau3AI cassette (Takara Shuzo) using T4 DNA ligase. A procedure was carried out according to the protocol attached to TaKaRa LA PCR in vitro cloning kit (Takara Shuzo) using the ligation mixture as a template, RNII-S2 as a primer for a primary PCR and RNII-S1 as a primer for a secondary PCR. A DNA was purified from the solution after the secondary PCR by phenol extraction followed by ethanol precipitation. The DNA was blunt-ended using T4 DNA polymerase and then subjected to agarose gel electrophoresis to recover an amplified DNA fragment of about 1.5 kb from the gel. The about 1.5-kb DNA fragment was ligated with pUC119 digested with SmaI using T4 DNA ligase. The ligation mixture was used to transform *Escherichia coli* JM109.

The resulting transformants were cultured to obtain a plasmid B25N16 into which the about 1.5-kb DNA was inserted.

(4) Cloning of the Entire RNase II Gene

Oligonucleotides RNII-S5 and RNII-S6 represented by SEQ ID NOS:101 and 102 were synthesized on the basis of the nucleotide sequence of the inserted fragment of about 0.4 kb in the plasmid 21-12 as determined in Referential Example 2-(3).

A PCR was carried out using the plasmid 21-12 as prepared in Referential Example 2-(2) as a template, and RNII-S5 and RNII-S6 as primers. TaKaRa Ex Taq polymerase (Takara Shuzo) was used as a DNA polymerase for the PCR according to the attached protocol. The PCR was carried out as follows: 25 cycles of 94° C. for 30 seconds, 55° C. for 30 seconds and 72° C. for 30 seconds. After reaction, the reaction mixture was subjected to agarose gel electrophoresis. An amplified DNA fragment of about 0.3 kb was recovered from the gel. The about 0.3-kb DNA fragment was labeled with digoxigenin using DIG High-prime (Roche Diagnostics).

Southern Hybridization was carried out for digests of the *Bacillus caldotenax* genomic DNA as prepared in Referential Example 2-(1) with HindIII (Takara Shuzo), SacI (Takara Shuzo), or HindIII and SacI using the digoxigenin-labeled DNA as a probe. Hybridization and detection were carried out using DIG Luminescent Detection Kit (Roche Diagnostics) according to the protocol attached thereto. As a result, DNA fragments of about 4.5 kb, about 5.8 kb and about 1.3 kb were hybridized with the probe for the digests with HindIII, SacI, and HindIII and SacI, respectively.

Based on these results, the *Bacillus caldotenax* genomic DNA was digested with HindIII and subjected to agarose gel electrophoresis to recover DNAs of about 4.5 kb from the gel. The resulting DNA fragments were digested with SacI and subjected to agarose gel electrophoresis to recover DNAs of about 1.3 kb from the gel. The resulting DNAs were ligated with pUC19 (Takara Shuzo) digested with HindIII and SacI using T4 DNA ligase. The ligation mixture was used to transform *Escherichia coli* HB101.

The resulting transformants were replica-plated onto Hybond-N™ (Amersham Pharmacia Biotech). Colony hybridization was then carried out using the above-mentioned digoxigenin-labeled probe according to a conventional method. A plasmid pRHB1 was prepared from the thus obtained positive clone.

The nucleotide sequence of the DNA inserted into pRHB1 was then determined. Comparison of the amino acid sequence deduced from the nucleotide sequence with the amino acid sequence of the RNase HII from *Bacillus subtilis* suggested that a region of about 40 bp from the initiation codon was missing in the DNA in pRHB1. Then, the full-length RNase H gene was constructed as follows.

B25N16 as prepared in Referential Example 2-(3) was digested with HindIII and subjected to agarose gel electrophoresis to recover a DNA fragment of about 160 bp from the gel. The about 160-bp DNA fragment was ligated with pRHB1 digested with HindIII using T4 DNA ligase. The ligation mixture was used to transform *Escherichia coli* HB101. Plasmids were prepared from the resulting transformants.

Next, an oligonucleotide RNII-Nde represented by SEQ ID NO:103 was synthesized on the basis of the presumed nucleotide sequence around the initiation codon. PCRs were carried out using the plasmids prepared from the transformants as templates, and RNII-Nde and RNII-S6 as primers. A plasmid from which a DNA fragment of about 0.7 kb was amplified was selected and designated as pRHB11.

The nucleotide sequence of the DNA fragment inserted into the thus obtained plasmid pRHB11 was determined. Analysis of the results revealed an open reading frame presumably encoding RNase HII. This nucleotide sequence is shown in SEQ ID NO:104. The amino acid sequence of RNase HII deduced from the nucleotide sequence is shown in SEQ ID NO:105.

*Escherichia coli* HB101 transformed with the plasmid pRHB11 is designated and indicated as *Escherichia coli* JM109/pRHB11, and deposited on Sep. 5, 2000 at the International Patent Organism Depositary, National Institute of Advanced Industrial Science and Technology under accession number FERM P-18021.

(5) Expression of *Bacillus caldotenax* RNase HII Gene

*Escherichia coli* HB101 transformed with pRHB11 or pRHB1 was inoculated into 5 ml of LB medium containing 100 μg/ml of ampicillin and cultured with shaking at 37° C. overnight. After cultivation, cells collected by centrifugation were suspended in 0.5 ml of TE buffer and sonicated. A supernatant obtained by centrifugation was used as a cell crude extract.

10 mM tris-HCl (pH 8.0), 1 mM dithiothreitol (Nacalai Tesque), 0.003% bovine serum albumin (fraction V, Sigma), 4% glycerol, 20 μg/ml poly(dT) (Amersham Pharmacia Biotech) and 30 μg/ml poly(rA) (Amersham Pharmacia Biotech) were mixed together. The mixture was incubated at 37° C. for 10 minutes and used as a substrate solution for measuring an RNase H activity.

1 μl of 1 M $MnCl_2$ was added to 100 μl of the substrate solution. The mixture was incubated at 40° C. 10 μl of a 10-fold dilution of the cell crude extract was added to the mixture to initiate a reaction. After reacting at 40° C. for 30 minutes, 10 μl of 0.5 M EDTA was added thereto to terminate the reaction. Absorbance at 260 nm was then measured. As a result, the absorbance at 260 nm from a reaction in which a cell crude extract prepared from *Escherichia coli* HB101 harboring pRHB11 was used was clearly higher than that from a reaction in which a cell crude extract prepared from *Escherichia coli* HB101 harboring pRHB1 was used. Thus, it was demonstrated that pRHB11 contained an RNase H gene and that *Escherichia coli* harboring pRHB11 expressed an RNase H activity.

(6) Preparation of Purified RNase HII Preparation

*Escherichia coli* HB101 transformed with pRHB11 obtained in Referential Example 2-(4) was inoculated into 1 L of LB medium containing 100 μg/ml of ampicillin and cultured with shaking at 37° C. for 16 hours. After cultivation, cells collected by centrifugation were suspended in 52.3 ml of a sonication buffer [50 mM tris-HCl (pH 8.0), 2 mM 2-mercaptoethanol, 10% glycerol, 2 mM phenylmethanesulfonyl fluoride] and sonicated. A supernatant obtained by centrifuging the sonicated suspension at 12000 rpm for 10 minutes was heated at 60° C. for 15 minutes. It was then centrifuged at 12000 rpm for 10 minutes again to collect a supernatant. Thus, 50.0 ml of a heated supernatant was obtained.

The solution was subjected to RESOURSE Q column (Amersham Pharmacia Biotech) equilibrated with Buffer C [50 mM tris-HCl (pH 8.0), 2 mM 2-mercaptoethanol, 10% glycerol] and chromatographed using FPLC system (Amersham Pharmacia Biotech). As a result, RNase HII flowed through the RESOURSE Q column. 51 ml of the flow-through RNase HII fraction was subjected to RESOURSE S column (Amersham Pharmacia Biotech) equilibrated with Buffer C and eluted with a linear gradient of 0 to 500 mM NaCl using FPLC system. A fraction containing RNase II eluted with about 240 mM NaCl was obtained. 3.0 ml of the RNase II fraction was subjected in two portions to PD-10 column (Amersham Pharmacia Biotech) equilibrated with Buffer C containing 50 mM NaCl. 7.0 ml the resulting eluate was subjected to HiTrap-heparin column (Amersham Pharmacia Biotech) equilibrated with Buffer C containing 50 mM NaCl and eluted with a linear gradient of 50 to 550 mM NaCl using FPLC system. A fraction containing RNase II eluted with about 310 mM NaCl was obtained. 4.4 ml of the RNase II fraction was concentrated by ultrafiltration using Centricon-10 (Amicon). 280 $\mu$l of the concentrate was subjected to Superdex 200 gel filtration column (Amersham Pharmacia Biotech) equilibrated with 50 mM tris-HCl (pH 8.0) containing 100 mM NaCl and 0.1 mM EDTA and eluted with the same buffer. As a result, RNase HII was eluted at a position corresponding to a molecular weight of 35 kilodalton. This molecular weight corresponds to that of RNase HII in a form of a monomer. The thus eluted RNase HII was used as Bca RNase HII preparation.

The enzymatic activity of the thus obtained Bca RNase HII preparation was measured as follows.

100 $\mu$l of a reaction mixture [20 mM HEPES-potassium hydroxide (pH 7.8), 0.01% bovine serum albumin (Takara Shuzo), 1% dimethyl sulfoxide, 10 mM manganese chloride, 20 $\mu$g/ml poly(dT) (Amersham Pharmacia Biotech), 30 $\mu$g/ml poly(rA) (Amersham Pharmacia Biotech)] which had been incubated at 40° C. was added to 1 $\mu$l of the Bca RNase HII preparation. The mixture was reacted at 40° C. for 10 minutes. The reaction was then terminated by adding 10 $\mu$l of 0.5 M EDTA (pH 8.0). Absorbance at 260 nm was then measured.

As a result, an RNase H activity was observed for the Bca RNase HII preparation.

REFERENTIAL EXAMPLE 3

Cloning of *Bacillus caldotenax* RNase HIII Gene (1) Cloning of Fragment of RNase HIII Gene Primers BsuIII-1, BsuIII-3, BsuIII-6 and BsuIII-8 represented by SEQ ID NOS:106–109 for screening a gene encoding RNase HIII were synthesized based on the amino acid sequences of regions well conserved among *Bacillus subtilis* and other organisms determined on the basis of the homology among the amino acid sequences of RNase HIIIs from *Bacillus subtilis* [Biochemistry, 38:605–608 (1999)] and other organisms.

A first PCR was carried out in a volume of 50 $\mu$l using 200 ng of the *Bacillus caldotenax* genomic DNA as prepared in Referential Example 2-(1) as a template, and 100 pmol of BsuIII-1 and 100 pmol of BsuIII-8 as primers. A second PCR was then carried out in a volume of 100 $\mu$l using 1 $\mu$l of the reaction mixture as a template, and 100 pmol of BsuIII-3 and 100 pmol of BsuIII-6 as primers. TaKaRa Taq polymerase (Takara Shuzo) was used as a DNA polymerase for the two PCRs according to the attached protocol. The PCRs were carried out as follows: 25 (the first PCR) or 30 (the second PCR) cycles of 94° C. for 30 seconds, 45° C. for 30 seconds and 72° C. for 1 minute.

An amplified DNA fragment of about 450 bp was blunt-ended using T4 DNA polymerase (Takara Shuzo) and then subjected to agarose gel electrophoresis to recover the amplified DNA fragment of about 450 bp. The about 450-bp DNA fragment was ligated with pUC119 (Takara Shuzo) digested with SmaI (Takara Shuzo) using T4 DNA ligase (Takara Shuzo). The ligation mixture was used to transform *Escherichia coli* JM109. The resulting transformants were cultured to obtain a plasmid pBCA3204 into which the about 450-bp DNA fragment was inserted.

(2) Cloning of RNase HIII gene using Southern Hybridization Method

The nucleotide sequence of the DNA fragment inserted in pBCA3204 obtained in Referential Example 3-(1) was determined. Primers RNIII-S3 and BcaRNIII-3 represented by SEQ ID NOS:110 and 111 were synthesized on the basis of the determined nucleotide sequence. A PCR was carried out in a volume of 100 $\mu$l using RNIII-S3 and BcaRNIII-3 as primers and pBCA3204 as a template. TaKaRa Z-Taq (Takara Shuzo) was used as a DNA polymerase for the PCR according to the attached protocol. The PCR was carried out as follows: 30 cycles of 98° C. for 0 second, 55° C. for 0 second and 72° C. for 20 seconds. After reaction, the reaction mixture was subjected to phenol-chloroform extraction, ethanol precipitation and agarose gel electrophoresis to recover a DNA fragment of about 0.4 kb from the gel. The about 0.4-kb DNA fragment was labeled using DIG DNA Labeling Kit (Boehringer Mannheim) to prepare a probe.

20 $\mu$g of the *Bacillus caldotenax* genomic DNA prepared in Referential Example 2-(1) was completely digested with BamHI, EcoRI, HindIII, PstI or XbaI (all from Takara Shuzo). The half of each of the digests was then subjected to agarose gel electrophoresis. The DNAs were transferred from the agarose gel to a nylon membrane using 0.4 N sodium hydroxide and fixed at 120° C. for 30 minutes. The membrane was pre-incubated in a sealed bag containing 30 ml of a hybridization buffer [43.4 g/L sodium chloride, 17.6 g/L sodium citrate, 1% blocking agent (Boehringer Mannheim), 0.1% N-lauroyl sarcosine, 0.02% sodium lauryl sulfate (SDS)] at 60° C. for 4 hours and then incubated in a sealed bag containing 5 ml of a hybridization buffer containing the probe at 60° C. for 16 hours.

The membrane was washed twice in 50 ml of 2×SSC (17.5 g/L NaCl, 8.8 g/L sodium citrate) containing 0.1% SDS at room temperature, and twice in 50 ml of 0.5×SSC (4.3 g/L sodium chloride, 1.9 g/L sodium citrate) containing 0.1% SDS at 45° C. Then, an EcoRI fragment of about 8 kb, a PstI fragment of about 4.5 kb and a HindIII fragment of about 1 kb which have sequences complementary to the probe were detected using DIG nucleic acid detection kit (Boehringer Mannheim).

The remaining half of the *Bacillus caldotenax* genomic DNA completely digested with PstI was subjected to agarose gel electrophoresis. PstI fragments of about 4.5 kb were recovered from the gel. The DNA fragments were then ligated with a plasmid vector pTV119N, which had been digested with PstI and dephosphorylated with alkaline phosphatase (Takara Shuzo). The ligation mixture was used to transform *Escherichia coli* JM109.

A PCR was carried out in a volume of 50 $\mu$l using RNIII-S3 and BcaRNIII-3 as primers, and one of the colonies as a template to select a colony presumably harboring an RNase HIII gene. TaKaRa-Z Taq (Takara Shuzo) was used for the PCR according to the attached protocol. The PCR was carried out as follows: 30 cycles of 98° C. for 0 second, 55° C. for 0 second and 72° C. for 20 seconds. As a result, it was found that the gene of interest was contained in the colony No. 88.

A PCR was carried out using a plasmid prepared from the colony No. 88 as a template, and a primer pair RN-N (Takara Shuzo) and BcaRNIII-3 or a primer pair M4 (Takara Shuzo) and RNIII-S3 to examine whether or not the entire RNase HIII gene was contained in the plasmid. As a result, it was found that the entire RNase HIII gene was contained in the plasmid, which was designated as pBCA3P88.

(3) Determination of Nucleotide Sequence of DNA Fragment Containing RNase HIII Gene The nucleotide sequence of the DNA fragment inserted into the plasmid pBCA3P88 obtained in Referential Example 3-(2) was determined according to a dideoxy method.

Analysis of the determined nucleotide sequence revealed the existence of an open reading frame encoding an amino acid sequence including the N-terminal amino acid sequence of RNase HIII. The nucleotide sequence of the open reading frame and the amino acid sequence of RNase HIII deduced from the nucleotide sequence are shown in SEQ ID NO:112 and SEQ ID NO:113, respectively.

(4) Construction of Plasmid for Expressing RNase HIII

A PCR was carried out in a volume of 100 μl using the plasmid pBCA3P88 as described in Referential Example 3-(2) as a template, BcaRNIIINde represented by SEQ ID NO:114 designed with reference to the sequence around the above-mentioned open reading frame for RNase HIII and M13 primer M4 (Takara Shuzo). Pyrobest DNA polymerase (Takara Shuzo) was used as a DNA polymerase for the PCR according to the attached protocol. The PCR was carried out as follows: 30 cycles of 94° C. for 30 seconds, 55° C. for 30 seconds and 72° C. for 3 minutes. An amplified DNA fragment of about 4 kb was digested with NdeI (Takara Shuzo) and subjected to agarose gel electrophoresis to recover an NdeI fragment of about 1.4 kb from the gel. The about 1.4-kb DNA fragment was ligated with pTV119Nd (a plasmid in which the NcoI site in pTV119N is converted into a NdeI site) which had been digested with NdeI and dephosphorylated with alkaline phosphatase (Takara Shuzo). The ligation mixture was used to transform *Escherichia coli* JM109.

Next, a PCR was carried out in a volume of 50 μl using one of the colonies as a template, and RN-N (Takara Shuzo) and BcaRNIII-3 as primers in order to screen for a plasmid in which the RNase HIII gene in the NdeI fragment was linked downstream from the lac promoter in the vector pTV119Nd. A colony presumably harboring the RNase HIII gene was then selected. TaKaRa-Z Taq (Takara Shuzo) was used as a DNA polymerase for the PCR according to the attached protocol. The PCR was carried out as follows: 30 cycles of 98° C. for 0 second, 55° C. for 0 second and 72° C. for 20 seconds. As a result, it was found that the colony No. 2 contained a plasmid in which the RNase HIII gene in the NdeI fragment was linked downstream from the lac promoter in the vector pTV119Nd. This plasmid was designated as pBCA3Nd2.

The determination of the nucleotide sequence of the DNA fragment inserted into the plasmid by a dideoxy method revealed that there was no mutation due to the PCR except that the initiation codon GTG was changed to ATG.

*Escherichia coli* JM109 transformed with the plasmid pBCA3Nd2 is designated and indicated as *Escherichia coli* JM109/pBCA3Nd2, and deposited on Sep. 5, 2000 at the International Patent Organism Depositary, National Institute of Advanced Industrial Science and Technology under accession number FERM P-18019.

(5) Preparation of Purified RNase HIII Preparation

*Escherichia coli* JM109 transformed with pBCA3Nd2 obtained in Referential Example 3-(4) was inoculated into 2 L of LB medium containing 100 μg/ml of ampicillin and cultured with shaking at 37° C. for 16 hours. After cultivation, cells collected by centrifugation were suspended in 39.6 ml of a sonication buffer [50 mM tris-HCl (pH 8.0), 1 mM EDTA, 2 mM phenylmethanesulfonyl fluoride] and sonicated. A supernatant obtained by centrifuging the sonicated suspension at 12000 rpm for 10 minutes was heated at 60° C. for 15 minutes. It was then centrifuged at 12000 rpm for 10 minutes again to collect a supernatant. Thus, 39.8 ml of a heated supernatant was obtained.

The heated supernatant was subjected to RESOURSE Q column (Amersham Pharmacia Biotech) equilibrated with Buffer A [50 mM tris-HCl (pH 8.0), 1 mM EDTA] and chromatographed using FPLC system (Amersham Pharmacia Biotech). As a result, RNase HIII flowed through the RESOURSE Q column.

45 ml of the flow-through RNase HIII fraction was dialyzed against 2 L of Buffer B [50 mM tris-HCl (pH 7.0), 1 mM EDTA] for 2 hours. The dialysis was repeated for two more times under the same conditions. 55.8 ml of the dialyzed enzyme solution was subjected to RESOURSE S column (Amersham Pharmacia Biotech) equilibrated with Buffer B and eluted with a linear gradient of 0 to 500 mM NaCl using FPLC system. A fraction containing RNase HIII eluted with about 105 mM NaCl was obtained.

Buffer B containing 1 M NaCl was added to 7.0 ml of the fraction to make the NaCl concentration to 150 mM. The mixture was subjected to HiTrap-heparin column (Amersham Pharmacia Biotech) equilibrated with Buffer B containing 150 mM NaCl. As a result, RNase HIII flowed through the HiTrap-heparin column.

7.5 ml of the flow-through RNase HIII fraction was concentrated by ultrafiltration using Centricon-10 (Amicon). 190 μl of the concentrate was subjected to Superdex 200 gel filtration column (Amersham Pharmacia Biotech) equilibrated with 50 mM tris-HCl (pH 7.0) containing 100 mM NaCl and 0.1 mM EDTA and eluted with the same buffer. As a result, RNase HIII was eluted at a position corresponding to a molecular weight of 33 kilodalton. This molecular weight corresponds to that of RNase HIII in a form of a monomer.

The thus eluted RNase HIII was used as Bca RNase HIII preparation.

The enzymatic activity of the thus obtained Bca RNase HIII preparation was measured as follows.

100 μl of a reaction mixture [20 mM HEPES-potassium hydroxide (pH 7.8), 0.01% bovine serum albumin (Takara Shuzo), 1% dimethyl sulfoxide, 4 mM magnesium acetate, 20 μg/ml poly(dT) (Amersham Pharmacia Biotech), 30 μg/ml poly(rA) (Amersham Pharmacia Biotech)] which had been incubated at 40° C. was added to 1 μl of the Bca RNase HIII preparation. The mixture was reacted at 40° C. for 10 minutes. The reaction was terminated by adding 10 μl of 0.5 M EDTA (pH 8.0). Absorbance at 260 nm was then measured. As a result, an RNase H activity was observed for the Bca RNase HIII preparation.

REFERENTIAL EXAMPLE 4

Cloning of *Pyrococcus furiosus* RNase HII Gene (1) Preparation of Genomic DNA from *Pyrococcus furiosus*

2 L of a medium containing 1% Tryptone (Difco Laboratories), 0.5% yeast extract (Difco Laboratories), 1% soluble starch (Nacalai Tesque), 3.5% Jamarine S Solid (Jamarine Laboratory), 0.5% Jamarine S Liquid (Jamarine Laboratory), 0.003% $MgSO_4$, 0.001% NaCl, 0.0001% $FeSO_4.7H_2O$, 0.0001% $COSO_4$, 0.0001% $CaCl_2.7H_2O$, 0.0001% $ZnSO_4$, 0.1 ppm $CuSO_4.5H_2O$, 0.1 ppm $KAl(SO_4)_2$, 0.1 ppm $H_3BO_4$, 0.1 ppm $Na_2MoO_4.2H_2O$ and 0.25 ppm $NiCl_2.6H_2O$ was placed in a 2 L medium bottle, sterilized at 120° C. for 20 minutes, bubbled with nitrogen gas to remove dissolved oxygen, then *Pyrococcus furiosus* (purchased from Deutsche Sammlung von Mikroorganismen; DSM3638) was inoculated into the medium and cultured at 95° C. for 16 hours without shaking. After cultivation, cells were collected by centrifugation.

The resulting cells were then suspended in 4 ml of 25% sucrose, 50 mM tris-HCl (pH 8.0). 0.4 ml of 10 mg/ml lysozyme chloride (Nacalai Tesque) in water was added thereto. The mixture was reacted at 20° C. for 1 hour. After reaction, 24 ml of a mixture containing 150 mM NaCl, 1 mM EDTA and 20 mM tris-HCl (pH 8.0), 0.2 ml of 20 mg/ml proteinase K (Takara Shuzo) and 2 ml of 10% aqueous solution of sodium lauryl sulfate and were added to the reaction mixture. The mixture was incubated at 37° C. for 1 hour. After reaction, the mixture was subjected to phenol-chloroform extraction followed by ethanol precipitation to prepare about 1 mg of genomic DNA.

(2) Cloning of RNase HII Gene

The entire genomic sequence of *Pyrococcus horikoshii* was published [DNA Research, 5:55–76 (1998)]. The existence of a gene encoding a homologue of RNase HII (PH1650) in the genome was known (SEQ ID NO:115, the home page of National Institute of Technology and Evaluation, Ministry of International Trade and Industry of Japan: http://www/nite.go.jp/).

Homology between the PH1650 gene and the partially published genomic sequence of *Pyrococcus furiosus* (the home page of University of Utah, Utah Genome Center: http://www.genome.utah.edu/sequence.html) was searched. As a result, a highly homologous sequence was found. Primers 1650Nde (SEQ ID NO:116) and 1650Bam (SEQ ID NO:117) were synthesized on the basis of the homologous sequence.

A PCR was carried out in a volume of 100 μl using 200 ng of the *Pyrococcus furiosus* genomic DNA obtained in Referential Example 4-(1) as a template, and 20 pmol of 1650Nde and 20 pmol of 1650Bam as primers. TaKaRa Ex Taq (Takara Shuzo) was used as a DNA polymerase for the PCR according to the attached protocol. The PCR was carried out as follows: 30 cycles of 94° C. for 30 seconds, 55° C. for 30 seconds and 72° C. for 1 minute. An amplified DNA fragment of about 0.7 kb was digested with NdeI and BamHI (both from Takara Shuzo). The resulting DNA fragment was inserted between the NdeI site and the BamHI site in a plasmid vector pET3a (Novagen) to make a plasmid pPFU220.

(3) Determination of Nucleotide Sequence of DNA Fragment Containing RNase HII Gene The nucleotide sequence of the DNA fragment inserted into pPFU220 obtained in Referential Example 4-(2) was determined according to a dideoxy method.

Analysis of the determined nucleotide sequence revealed the existence of an open reading frame presumably encoding RNase HII. The nucleotide sequence of the open reading frame is shown in SEQ ID NO:118. The amino acid sequence of RNase HII deduced from the nucleotide sequence is shown in SEQ ID NO:119.

*Escherichia coli* JM109 transformed with the plasmid pPFU220 is designated and indicated as *Escherichia coli* JM109/pPFU220, and deposited on Sep. 5, 2000 at the International Patent Organism Depositary, National Institute of Advanced Industrial Science and Technology under accession number FERM P-18020.

(4) Preparation of Purified RNase HII Preparation

*Escherichia coli* HMS174(DE3) (Novagen) was transformed with pPFU220 obtained in Referential Example 4-(2). The resulting *Escherichia coli* HMS174(DE3) harboring pPFU220 was inoculated into 2 L of LB medium containing 100 μg/ml of ampicillin and cultured with shaking at 37° C. for 16 hours. After cultivation, cells collected by centrifugation were suspended in 66.0 ml of a sonication buffer [50 mM tris-HCl (pH 8.0), 1 mM EDTA, 2 mM phenylmethanesulfonyl fluoride] and sonicated. A supernatant obtained by centrifuging the sonicated suspension at 12000 rpm for 10 minutes was heated at 60° C. for 15 minutes. It was then centrifuged at 12000 rpm for 10 minutes again to collect a supernatant. Thus, 61.5 ml of a heated supernatant was obtained.

The heated supernatant was subjected to RESOURSE Q column (Amersham Pharmacia Biotech) equilibrated with Buffer A [50 mM tris-HCl (pH 8.0), 1 mM EDTA] and chromatographed using FPLC system (Amersham Pharmacia Biotech). As a result, RNase HIT flowed through the RESOURSE Q column.

60.0 ml of the flow-through RNase HIT fraction was subjected to RESOURSE S column (Amersham Pharmacia Biotech) equilibrated with Buffer A and eluted with a linear gradient of 0 to 500 mM NaCl using FPLC system. A fraction containing RNase HIT eluted with about 150 mM NaCl was obtained. 2.0 ml of the RNase HII fraction was concentrated by ultrafiltration using Centricon-10 (Amicon) 250 μl of the concentrate was subjected to Superdex 200 gel filtration column (Amersham Pharmacia Biotech) equilibrated with 50 mM tris-HCl (pH 8.0) containing 100 mM NaCl and 0.1 mM EDTA and eluted with the same buffer. As a result, RNase HIT was eluted at a position corresponding to a molecular weight of 17 kilodalton. This molecular weight corresponds to that of RNase HIT in a form of a monomer.

The thus eluted RNase HIT was used as Pfu RNase HIT preparation.

The enzymatic activity of the thus obtained Pfu RNase HII preparation was measured as described in Referential Example 3-(5). As a result, an RNase H activity was observed for the Pfu RNase HII preparation.

REFERENTIAL EXAMPLE 5

Cloning of *Thermotoga maritima* RNase HII Gene (1) Preparation of Genomic DNA from *Thermotoga maritima*

2 L of a medium containing 1% Tryptone, 0.5% yeast extract, 1% soluble starch, 3.5% Jamarine S Solid, 0.5% Jamarine S Liquid, 0.003% $MgSO_4$, 0.001% NaCl, 0.0001% $FeSO_4.7H_2O$, 0.0001% $COSO_4$, 0.0001% $CaCl_2.7H_2O$, 0.0001% $ZnSO_4$, 0.1 ppm $CuSO_4.5H_2O$, 0.1 ppm $KAl(SO_4)_2$, 0.1 ppm $H_3BO_3$, 0.1 ppm $Na_2MoO_4.2H_2O$ and 0.25 ppm $NiCl_2.6H_2O$ was placed in a 2 L medium bottle, sterilized at 120° C. for 20 minutes, bubbled with nitrogen gas to remove dissolved oxygen, then *Thermotoga maritima* (purchased from Deutsche Sammlung von Mikroorganismen und Zellkulturen GmbH; DSM3109) was inoculated into the medium and cultured at 85° C. for 16 hours without shaking.

Cells collected by centrifugation from 300 ml of the culture were then suspended in 3 ml of TE buffer [10 mM tris-HCl (pH 7.5), 1 mM EDTA]. 150 μl of 10% aqueous solution of sodium lauryl sulfate (Nacalai Tesque) and 15 μl of 20 mg/ml proteinase K (Takara Shuzo) were added thereto. The mixture was incubated at 37° C. for 1 hour. After reaction, 0.5 ml of 5 M NaCl was added to the mixture. After thoroughly mixing, 0.4 ml of a CTAB-NaCl solution [10% cetyltrimethylammonium bromide (Nacalai Tesque), 0.7 M NaCl] was added to the mixture. After thoroughly mixing, the mixture was incubated at 65° C. for 10 minutes. 1.5 ml of a mixture of chloroform/isoamyl alcohol (24:1, v/v) was added thereto. The mixture was gently mixed for 10 minutes and centrifuged at 20000×g for 5 minutes. After centrifugation, an equal volume of a mixture of phenol saturated with 100 mM tris-HCl (pH 8.0)/chloroform/isoamyl alcohol (25:24:1, v/v) was added to the resulting supernatant. The mixture was gently mixed for 10 minutes and then centrifuged at 20000×g for 5 minutes. After centrifugation, 0.6 volume of 2-propanol was added to the supernatant. The precipitate obtained by centrifugation at 10000×g for 5 minutes was washed with 70% ethanol in water, air-dried and then dissolved in 200 μl of TE to obtain a genomic DNA solution.

(2) Cloning of RNase HII Gene

Oligonucleotides 915-F1, 915-F2, 915-R1 and 915-R2 represented by SEQ ID NOS:120–123 were synthesized on the basis of the nucleotide sequence of a portion that had been identified as an RNase HII gene in the nucleotide sequence of the genomic DNA of *Thermotoga maritima* (http://www.tigr.org/tdb/CMR/btm/htmls/SplashPage.html) in order to obtain an amplified DNA fragment containing an RNase H gene by carrying out a PCR using the *Thermotoga maritima* genomic DNA as a template.

PCRs were carried out using the *Thermotoga maritima* genomic DNA as prepared in Referential Example 5-(1) as a template, and 915-F1 and 915-R1, 915-F1 and 915-R2, 915-F2 and 915-R1, or 915-F2 and 915-R2 as a primer pair. TaKaRa Ex Taq was used as a DNA polymerase for the PCRs according to the attached protocol. The PCRs were carried out as follows: 25 cycles of 95° C. for 0.5 minute, 55° C. for 0.5 minute and 72° C. for 1.5 minute. After reactions, the respective PCR products were subjected to agarose gel electrophoresis to extract and purify amplified DNA fragments of about 0.7 kb. The DNAs amplified using a primer pair 915-F1 and 915-R1 or 915-F1 and 915-R2 were digested with HindIII and XbaI (both from Takara Shuzo) and ligated with pUC19 digested with HindIII and XbaI using T4 DNA ligase. The ligation mixture was used to transform *Escherichia coli* JM109. The resulting transformants were cultured to prepare plasmid DNAs into which the about 0.7-kb DNAs were inserted. As a result, plasmids No. 1 and No. 2 having DNAs amplified using 915-F1 and 915-R1, and plasmids No. 3 and No. 4 having DNAs amplified using 915-F1 and 915-R2 were obtained.

In addition, the DNAs amplified using a primer pair 915-F2 and 915-R1 or 915-F2 and 915-R2 were doubly digested with NcoI (Takara Shuzo) and XbaI and ligated with pTV119N (Takara Shuzo) doubly digested with NcoI and XbaI using T4 DNA ligase. The ligation mixture was used to transform *Escherichia coli* JM109.

The resulting transformants were cultured to prepare plasmid DNAs into which the about 0.7-kb DNAs were inserted. As a result, plasmids No. 5 and No. 6 having DNAs amplified using 915-F2 and 915-R1, and a plasmid No. 7 having a DNA amplified using 915-F2 and 915-R2 were obtained.

*Escherichia coli* JM109 transformed with the plasmid No. 7 is designated and indicated as *Escherichia coli* JM109/pTM-RNH, and deposited on Sep. 5, 2000 at the International Patent Organism Depositary, National Institute of Advanced Industrial Science and Technology under accession number FERM P-18018.

(3) Expression of *Thermotoga maritima* RNase HII Gene

*Escherichia coli* JM109 transformed with one of the plasmids No. 1 to 7 or pUC19 was inoculated into 5 ml of LB medium (10 g/L Tryptone, 5 g/L yeast extract, 5 g/L NaCl, pH 7.2) containing 100 μg/ml of ampicillin and cultured with shaking at 37° C. When the absorbance at 660 nm reached 0.5, isopropyl-β-D-thiogalactopyranoside was added thereto to a final concentration of 1 mM and the cells were cultured overnight. After cultivation, cells collected by centrifugation were suspended in 1 ml of TE buffer and sonicated. The sonicated suspension was heated at 80° C. for 10 minute. A supernatant obtained by centrifugation was used as a cell crude extract. Absorbance was measured using the cell crude extract as described in Referential Example 2-(5). As a result, when reactions were carried out in the presence of $MnCl_{21}$ the absorbance at 260 nm from each of the reactions in which cell crude extracts prepared from *Escherichia coli* JM109 harboring the plasmid No. 3, 5, 6 or 7 were used was clearly higher than that from a reaction in which a crude extract prepared from *Escherichia coli* JM109 harboring pUC19 was used. Thus, it was demonstrated that the plasmids No. 3, 5, 6 and 7 contained RNase H genes and that *Escherichia coli* harboring one of these plasmids expressed an RNase H activity.

The partial nucleotide sequences of the DNA fragments inserted into the plasmids which were demonstrated to express RNase activities in *Escherichia coli* as described above were determined. Analysis of the determined nucleotide sequences revealed an open reading frame presumably encoding RNase HII. The nucleotide sequence of the open reading frame is shown in SEQ ID NO:232. The amino acid sequence of RNase HII deduced from the nucleotide sequence is shown in SEQ ID NO:233. Then, it was found that one base substitution that was presumably generated upon the PCR was observed in a portion of the nucleotide sequence of the DNA fragment inserted in the plasmid No. 7, resulting in the change in the encoded amino acid residue.

(4) Preparation of Purified RNase HII Preparation

*Escherichia coli* JM109 was transformed with pTM-RNH obtained in Referential Example 5-(2). The resulting *Escherichia coli* JM109 harboring pTM-RNH was inoculated into 1 L of LB medium containing 100 μg/ml of ampicillin and cultured with shaking at 37° C. for 16 hours. After cultivation, cells collected by centrifugation were suspended in 31.0 ml of a sonication buffer [50 mM tris-HCl (pH 8.0), 2 mM 2-mercaptoethanol, 10% glycerol, 2 mM phenylmethanesulfonyl fluoride] and sonicated. A supernatant obtained by centrifuging the sonicated suspension at 12000 rpm for 10 minutes was heated at 70° C. for 15 minutes. It was then centrifuged at 12000 rpm for 10 minutes again to collect a supernatant. Thus, 32.0 ml of a heated supernatant was obtained.

The heated supernatant was subjected to RESOURSE Q column (Amersham Pharmacia Biotech) equilibrated with Buffer C [50 mM tris-HCl (pH 8.0), 2 mM 2-mercaptoethanol, 10% glycerol] and chromatographed using FPLC system (Amersham Pharmacia Biotech). As a result, RNase HII flowed through the RESOURSE Q column. 32.5 ml of the flow-through RNase HII fraction was subjected to RESOURSE S column (Amersham Pharmacia Biotech) equilibrated with Buffer C and eluted with a linear gradient of 0 to 500 mM NaCl using FPLC system. A fraction containing RNase II eluted with about 240 mM NaCl was obtained. 2.0 ml of the RNase II fraction was subjected to PD-10 column (Amersham Pharmacia Biotech) equilibrated with Buffer C containing 50 mM NaCl. 3.5 ml of the resulting eluate was subjected to HiTrap-heparin column (Amersham Pharmacia Biotech) equilibrated with Buffer C containing 50 mM NaCl and eluted with a linear gradient of 50 to 550 mM NaCl using FPLC system. As a result, a fraction containing RNase II eluted with about 295 mM NaCl was obtained. The thus eluted RNase HII was used as Tma RNase HII preparation.

The enzymatic activity of the thus obtained Tma RNase HII preparation was measured as described in Referential Example 2-(6). As a result, an RNase H activity was observed for the Tma RNase HII preparation.

REFERENTIAL EXAMPLE 6

Cloning of RNase HII Gene from *Pyrococcus horikoshii*

(1) Preparation of Genomic DNA from *Pyrococcus horikoshii*

2 L of a medium containing 1% Tryptone (Difco Laboratories), 0.5% yeast extract (Difco Laboratories), 1% soluble starch (Nacalai Tesque), 3.5% Jamarine S Solid (Jamarine Laboratory), 0.5% Jamarine S Liquid (Jamarine Laboratory), 0.003% $MgSO_4$, 0.001% NaCl, 0.0001% $FeSO_4.7H_2O$, 0.0001% $CoSO_4$, 0.0001% $CaCl_2.7H_2O$, 0.0001% $ZnSO_4$, 0.1 ppm $CuSO_4.5H_2O$, 0.1 ppm $KAl(SO_4)_2$, 0.1 ppm $H_3BO_4$, 0.1 ppm $Na_2MoO_4.2H_2O$ and 0.25 ppm $NiCl_2.6H_2O$ was placed in a 2-L medium bottle, sterilized at 120° C. for 20 minutes, bubbled with nitrogen gas to remove dissolved oxygen, then *Pyrococcus horikoshii* OT3 (purchased from the Institute of Physical and Chemical Research (RIKEN); JCM9974) was inoculated into the medium and cultured at 95° C. for 16 hours without shaking. After cultivation, cells were collected by centrifugation.

The cells were then suspended in 4 ml of 25% sucrose, 50 mM tris-HCl (pH 8.0). 0.4 ml of 10 mg/ml lysozyme chloride (Nacalai Tesque) in water was added thereto. The mixture was reacted at 20° C. for 1 hour. After reaction, 24 ml of a mixture containing 150 mM NaCl, 1 mM EDTA and 20 mM tris-HCl (pH 8.0), 0.2 ml of 20 mg/ml proteinase K (Takara Shuzo) and 2 ml of 10% aqueous solution of sodium lauryl sulfate were added to the reaction mixture. The mixture was incubated at 37° C. for 1 hour.

After reaction, the mixture was subjected to phenol-chloroform extraction followed by ethanol precipitation to prepare about 1 mg of genomic DNA.

(2) Cloning of RNase HII Gene

The entire genomic sequence of the *Pyrococcus horikoshii* has been published [DNA Research, 5:55–76 (1998)]. The existence of one gene encoding a homologue of RNase HII (PH1650) was known (SEQ ID NO:234, the home page of National Institute of Technology and Evaluation: http://www/nite.go.jp/).

Primers PhoNde (SEQ ID NO:235) and PhoBam (SEQ ID NO:236) were synthesized on the basis of the sequence of the PH1650 gene (SEQ ID NO:234).

A PCR was carried out using 100 ng of the *Pyrococcus horikoshii* genomic DNA prepared in Referential Example 6-(1) as a template, and 20 pmol each of PhoNde and PhoBam as primers in a volume of 100 μl. TaKaRa Ex Taq (Takara Shuzo) was used as a DNA polymerase for the PCR according to the attached protocol. The PCR was carried out as follows: 40 cycles of 94° C. for 30 seconds, 55° C. for 30 seconds and 72° C. for 1 minute. An amplified DNA fragment of about 0.7 kb was digested with NdeI and BamHI (both from Takara Shuzo). Then, a plasmid pPHO238 was constructed by incorporating the resulting DNA fragment between NdeI and BamHI sites in a plasmid vector pET3a (Novagen).

(3) Determination of Nucleotide Sequence of DNA Fragment Containing RNase HII Gene The nucleotide sequence of the DNA fragment inserted into pPHO238 obtained in Referential Example 6-(2) was determined according to a dideoxy method.

Analysis of the determined nucleotide sequence revealed an open reading frame presumably encoding RNase HII. The nucleotide sequence of the open reading frame is shown in SEQ ID NO:237. The amino acid sequence of RNase HII deduced from the nucleotide sequence is shown in SEQ ID NO:238.

*Escherichia coli* JM109 transformed with the plasmid pPHO238 is designated and indicated as *Escherichia coli* JM109/pPHO238, and deposited on Feb. 22, 2001 at International Patent Organism Depositary, National Institute of Advanced Industrial Science and Technology under accession number FERM P-18222.

(4) Preparation of Purified RNase HII Preparation

*Escherichia coli* HMS174(DE3) (Novagen) was transformed with pPHO238 obtained in Referential Example 6-(2). The resulting *Escherichia coli* HMS174(DE3) harboring pPHO238 was inoculated into 1 L of LB medium containing 100 μg/ml of ampicillin and cultured with shaking at 37° C. for 16 hours. After cultivation, cells collected by centrifugation were suspended in 34.3 ml of a sonication buffer [50 mM tris-HCl (pH 8.0), 1 mM EDTA, 2 mM phenylmethanesulfonyl fluoride] and sonicated. A supernatant obtained by centrifuging the sonicated suspension at 12000 rpm for 10 minutes was heated at 80° C. for 15 minutes. It was then centrifuged at 12000 rpm for 10 minutes again to collect a supernatant. Thus, 33.5 ml of a heated supernatant was obtained.

The heated supernatant was subjected to RESOURSE Q column (Amersham Pharmacia Biotech) equilibrated with Buffer A [50 mM tris-HCl (pH 8.0), 1 mM EDTA] and chromatographed using FPLC system (Amersham Pharmacia Biotech). As a result, RNase HII flowed through the RESOURSE Q column.

35.0 ml of the flow-through RNase HII fraction was dialyzed against 2 L of Buffer B (50 mM tris-HCl (pH 7.0), 1 mM EDTA) for 2 hours. The dialysis was repeated two more times. 34.5 ml of the dialyzed enzyme solution was subjected to RESOURSE S column (Amersham Pharmacia Biotech) equilibrated with Buffer B and eluted with a linear gradient of 0 to 500 mM NaCl using FPLC system. A fraction containing RNase HII eluted with about 155 mM NaCl was obtained.

Buffer B was added to 4.0 ml of the fraction to make the NaCl concentration to 50 mM. The mixture was subjected to HiTrap-heparin column (Amersham Pharmacia Biotech) equilibrated with Buffer B containing 50 mM NaCl and eluted with a linear gradient of 50 to 550 mM NaCl using FPLC system. As a result, a fraction containing RNase HII eluted with about 160 mM NaCl was obtained.

6.9 ml of the RNase HII fraction was concentrated by ultrafiltration using Centricon-10 (Amicon). Two portions each separated from 250 μl of the concentrate were subjected to Superose 6 gel filtration column (Amersham Pharmacia Biotech) equilibrated with 50 mM tris-HCl (pH 7.0) containing 100 mM NaCl and 0.1 mM EDTA and eluted with the same buffer. As a result, RNase HII was eluted at a position corresponding to a molecular weight of 24.5 kilodalton. This molecular weight corresponds to that of RNase HII in a form of a monomer.

The RNase HII eluted as described above was used as Pho RNase HII preparation.

The enzymatic activity of the thus obtained Pho RNase HII preparation was measured as described in Referential Example 3-(5). As a result, an RNase H activity was observed for the Pho RNase HII preparation.

REFERENTIAL EXAMPLE 7

Cloning of RNase HII Gene from *Archaeoglobus fulgidus*

(1) Preparation of Genomic DNA from *Archaeoglobus fulgidus*

Cells of *Archaeoglobus fulgidus* (purchased from Deutsche Sammlung von Mikroorganismen und Zellkulturen GmbH; DSM4139) collected from 8 ml of a culture was suspended in 100 μl of 25% sucrose, 50 mM tris-HCl (pH 8.0). 20 μl of 0.5 M EDTA and 10 μl of 10 mg/ml lysozyme chloride (Nacalai Tesque) in water was added thereto. The mixture was reacted at 20° C. for 1 hour. After reaction, 800 μl of a mixture containing 150 mM NaCl, 1 mM EDTA and 20 mM tris-HCl (pH 8.0), 10 μl of 20 mg/ml proteinase K (Takara Shuzo) and 50 μl of 10% aqueous solution of sodium lauryl sulfate and were added to the reaction mixture. The mixture was incubated at 37° C. for 1 hour. After reaction, the mixture was subjected to phenol-chloroform extraction, ethanol precipitation and air-drying, and then dissolved in 50 μl of TE to obtain a genomic DNA solution.

(2) Cloning of RNase HII Gene

The entire genomic sequence of the *Archaeoglobus fulgidus* has been published [Nature, 390:364–370 (1997)]. The existence of one gene encoding a homologue of RNase HII (AF0621) was known (SEQ ID NO:239, http://www.tigr.org/tdb/CMR/btm/htmls/SplashPage.htlm).

Primers AfuNde (SEQ ID NO:240) and AfuBam (SEQ ID NO:241) were synthesized on the basis of the sequence of the AF0621 gene (SEQ ID NO:239).

A PCR was carried out using 30 ng of the *Archaeoglobus fulgidus* genomic DNA prepared in Referential Example 7-(1) as a template, and 20 pmol each of AfuNde and AfuBam as primers in a volume of 100 μl. Pyrobest DNA polymerase (Takara Shuzo) was used as a DNA polymerase for the PCR according to the attached protocol. The PCR was carried out as follows: 40 cycles of 94° C. for 30 seconds, 55° C. for 30 seconds and 72° C. for 1 minute. An amplified DNA fragment of about 0.6 kb was digested with NdeI and BamHI (both from Takara Shuzo). Then, a plasmid pAFU204 was constructed by incorporating the resulting DNA fragment between NdeI and BamHI sites in a plasmid vector pTV119Nd (a plasmid in which the NcoI site in pTV119N is converted into a NdeI site).

(3) Determination of Nucleotide Sequence of DNA Fragment Containing RNase HII Gene The nucleotide sequence of the DNA fragment inserted into pAFU204 obtained in Referential Example 7-(2) was determined according to a dideoxy method.

Analysis of the determined nucleotide sequence revealed an open reading frame presumably encoding RNase HII. The nucleotide sequence of the open reading frame is shown in SEQ ID NO:242. The amino acid sequence of RNase HII deduced from the nucleotide sequence is shown in SEQ ID NO:243.

*Escherichia coli* JM109 transformed with the plasmid pAFU204 is designated and indicated as *Escherichia coli* JM109/pAFU204, and deposited on Feb. 22, 2001 at International Patent Organism Depositary, National Institute of Advanced Industrial Science and Technology under accession number FERM P-18221.

(4) Preparation of Purified RNase HII Preparation

*Escherichia coli* JM109 was transformed with pAFU204 obtained in Referential Example 7-(2). The resulting *Escherichia coli* JM109 harboring pAFU204 was inoculated into 2 L of LB medium containing 100 μg/ml of ampicillin and cultured with shaking at 37° C. for 16 hours. After cultivation, cells collected by centrifugation were suspended in 37.1 ml of a sonication buffer [50 mM tris-HCl (pH 8.0), 1 mM EDTA, 2 mM phenylmethanesulfonyl fluoride] and sonicated. A supernatant obtained by centrifuging the sonicated suspension at 12000 rpm for 10 minutes was heated at 70° C. for 15 minutes. It was then centrifuged at 12000 rpm for 10 minutes again to collect a supernatant. Thus, 40.3 ml of a heated supernatant was obtained.

The heated supernatant was subjected to RESOURSE Q column (Amersham Pharmacia Biotech) equilibrated with Buffer A [50 mM tris-HCl (pH 8.0), 1 mM EDTA] and chromatographed using FPLC system (Amersham Pharmacia Biotech). As a result, RNase HII flowed through the RESOURSE Q column.

The flow-through RNase HII fraction was subjected to RESOURSE S column (Amersham Pharmacia Biotech) equilibrated with Buffer A and chromatographed using FPLC system (Amersham Pharmacia Biotech). As a result, RNase HII flowed through the RESOURSE S column.

40.0 ml of the flow-through RNase HII fraction was dialyzed against 2 L of Buffer B (50 mM tris-HCl (pH 7.0), 1 mM EDTA) containing 50 mM NaCl for 2 hours. The dialysis was repeated two more times. 40.2 ml of the dialyzed enzyme solution was subjected to HiTrap-heparin column (Amersham Pharmacia Biotech) equilibrated with Buffer B containing 50 mM NaCl and eluted with a linear gradient of 50 to 550 mM NaCl using FPLC system. As a result, a fraction containing RNase HII eluted with about 240 mM NaCl was obtained.

7.8 ml of the RNase HII fraction was concentrated by ultrafiltration using Centricon-10 (Amicon). Four portions each separated from about 600 μl of the concentrate were subjected to Superose 6 gel filtration column (Amersham Pharmacia Biotech) equilibrated with 50 mM tris-HCl (pH 7.0) containing 100 mM NaCl and 0.1 mM EDTA and eluted with the same buffer. As a result, RNase HII was eluted at a position corresponding to a molecular weight of 30.0 kilodalton. This molecular weight corresponds to that of RNase HII in a form of a monomer.

The RNase HII eluted as described above was used as Afu RNase HII preparation.

The enzymatic activity of the thus obtained Afu RNase HII preparation was measured as described in Referential Example 3-(5). As a result, an RNase H activity was observed for the Afu RNase HII preparation.

REFERENTIAL EXAMPLE 8

Unit value of RNase H from *Escherichi coli* used in the method of the present invention was measured according to the following method.

(1) Preparation of Reagent Solutions Used

Reaction mixture for determining activity: The following substances at the indicated final concentrations were contained in sterile water: 40 mM tris-hydrochloride (pH 7.7 at 37° C.), 4 mM magnesium chloride, 1 mM DTT, 0.003% BSA, 4% glycerol and 24 $\mu$M poly(dT).

Poly[8-$^3$H]adenylic acid solution: 370 kBq of a poly[8-$^3$H]adenylic acid solution was dissolved in 200 $\mu$l of sterile water.

Polyadenylic acid solution: Polyadenylic acid was diluted to a concentration of 3 mM with sterile ultrapure water.

Enzyme dilution solution: The following substances at the indicated final concentrations were contained in sterile water: 25 mM tris-hydrochloride (pH 7.5 at 37° C.), 5 mM 2-mercaptoethanol, 0.5 mM EDTA (pH 7.5 at 37° C.), 30 mM sodium chloride and 50% glycerol.

Preparation of heat-denatured calf thymus DNA: 200 mg of calf thymus DNA was suspended and allowed to swell in 100 ml of TE buffer. The solution was diluted to a concentration of 1 mg/ml with sterile ultrapure water based on the absorbance measured at UV 260 nm. The diluted solution was heated at 100° C. for 10 minutes and then rapidly cooled in an ice bath.

(2) Method for Measuring Activity

7 $\mu$l of the poly[8-$^3$H]adenylic acid solution was added to 985 $\mu$l of the reaction mixture for determining activity prepared in (1) above. The mixture was incubated at 37° C. for 10 minutes. 8 $\mu$l of polyadenylic acid was added to the mixture to make the final concentration to 24 $\mu$M. The mixture was further incubated at 37° C. for 5 minutes. Thus, 1000 $\mu$l of a poly[8-$^3$H]rA-poly-dT reaction mixture was prepared. 200 $\mu$l of the reaction mixture was then incubated at 30° C. for 5 minutes. 1 $\mu$l of an appropriate serial dilution of an enzyme solution was added thereto. 50 $\mu$l each of samples was taken from the reaction mixture over time for use in subsequent measurement. The period of time in minutes from the addition of the enzyme to the sampling is defined as Y. 50 $\mu$l of a reaction mixture for total CPM or for blank was prepared by adding 1 $\mu$l of the enzyme dilution solution instead of an enzyme solution. 100 $\mu$l of 100 mM sodium pyrophosphate, 50 $\mu$l of the heat-denatured calf thymus DNA solution and 300 $\mu$l of 10% trichloroacetic acid (300 $\mu$l of ultrapure water for measuring total CPM) were added to the sample. The mixture was incubated at 0° C. for 5 minutes, and then centrifuged at 10000 rpm for 10 minutes. After centrifugation, 250 $\mu$l of the resulting supernatant was placed in a vial. 10 ml of Aquasol-2 (NEN Life Science Products) was added thereto. CPM was measured in a liquid scintillation counter.

(3) Calculation of Units

Unit value for each enzyme was calculated according to the following equation.

$$\text{Unit/ml}=\{(\text{measured } CPM-\text{blank } CPM)\times 1.2^{*}\times 20\times 1000\times \text{dilution rate}\}200\ (\mu l)/(\text{total } CPM\times Y\ (\text{min.})\times 50\ (\mu l)\times 9^{**})$$

1.2*: Amount in nmol of poly[8-$^3$H]rA-poly-dT contained in total CPM per 50 $\mu$l.

9**: Correction coefficient.

EXAMPLE 1

(1) Synthesis of Template DNA and Primers

A single-stranded DNA of 99 bases as a template and primers used in this Example were synthesized using a DNA synthesizer (Applied Biosystems). The nucleotide sequence of the single-stranded DNA of 99 bases is shown in SEQ ID NO:1 of the Sequence Listing. The structures of the primers used in this Example are described below in detail:

Primer Pair 1: A combination of primers having a nucleotide sequence as shown in SEQ ID NO:2 or 3 of the Sequence Listing and wholly composed of deoxyribonucleotides;

Primer Pair 2: A combination of primers having a nucleotide sequence as shown in SEQ ID NO:4 or 5 of the Sequence Listing in which the first and second nucleotides from the 3'-terminus are ribonucleotides and the phosphate bond on the 5'-terminal side of the second ribonucleotide from the 3'-terminus is replaced by a phosphorothioate bond;

Primer Pair 3: A combination of primers having a nucleotide sequence as shown in SEQ ID NO:6 or 7 of the Sequence Listing in which the nucleotide at the 3'-terminus is a ribonucleotide and the phosphate bond on the 5'-terminal side of the ribonucleotide is replaced by a phosphorothioate bond;

Primer Pair 4: A combination of primers having a nucleotide sequence as shown in SEQ ID NO:8 or 9 of the Sequence Listing in which the first and second nucleotides from the 3'-terminus are ribonucleotides; and Primer Pair 5: A combination of primers having a nucleotide sequence as shown in SEQ ID NO:10 or 11 of the Sequence Listing in which the third and fourth nucleotides from the 3'-terminus are ribonucleotides and the phosphate bond on the 5'-terminal side of the fourth ribonucleotide form the 3'-terminus is replaced by a phosphorothioate bond.

(2) Amplification Reaction

Bca BEST DNA polymerase (Takara Shuzo), which is a DNA polymerase lacking a 5'→3' exonuclease activity from *Bacillus caldotenax*, and cloned ribonuclease H (Takara Shuzo), which is RNase H from *E. coli*, were used to examine the reaction systems of Models 1 to 7 as described below.

A reaction mixture was prepared as follows.

35 mM tris-hydrochloride buffer (pH 7.5), 0.1 mg/ml bovine serum albumin (BSA), 2.7% glycerol, 5% dimethyl sulfoxide, 1.4 mM each of dNTPs, 10 mM magnesium chloride, 20 pmol of one or both of the primers of one of the primer pairs as described above in (1), 0.6 ng of the synthetic single-stranded DNA as the template, 5 U of Bca BEST DNA polymerase and 60 U of cloned ribonuclease H to a final reaction volume of 50 $\mu$l. The reaction mixture was mixed to homogeneity, incubated at 55° C. for 60 minutes, and then heated at 90° C. for 2 minutes to inactivate the enzymes. 8 $\mu$l of the reaction mixture was subjected to electrophoresis on 3% NuSieve 3:1 agarose (Takara Shuzo) gel. The primers used in the respective Models are described below:

Models 1–5: One of the Primer Pairs 1–5 was used;

Model 6: Only the downstream primer of the Primer Pair 2 was used; and

Model 7: The Primer Pair 4 was used without the addition of RNase H.

As a result, amplified fragments having a size of interest ranging from about 40 base pairs (bp) to about 90 bp were observed when the reaction mixtures of the Models 2 to 5 were used, indicating that DNAs are amplified using these reaction systems. An amplified fragment having an expected size of about 70 bases (b) (a single-stranded DNA fragment) was observed for the Model 6 in which only one of the two primers was used. No DNA amplification was observed for the reaction of the Model 1 or 7.

(3) Confirmation of Amplification Products

The reaction mixture obtained by the reaction of the Model 4 as described in (2) was filtrated using Microcon-100 (Takara Shuzo) to recover an amplified DNA fragment entrapped on the filter. The nucleotide sequence of the DNA fragment was determined by the dideoxy method. As a result, the fragment amplified by the above-mentioned reaction was confirmed to be a DNA having the same nucleotide sequence as that of the DNA as the template.

(4) Examination of Reaction Time

Figure 41:
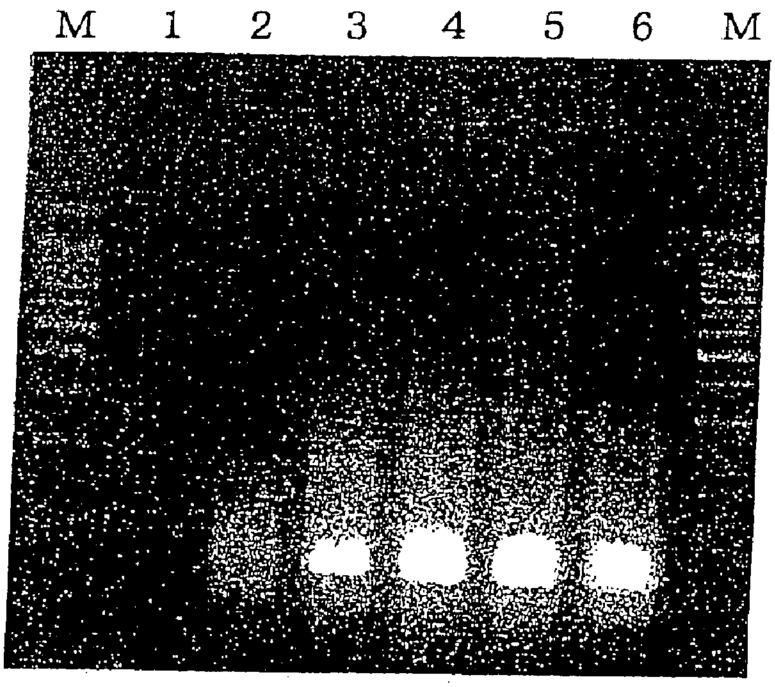
FIG. 41 shows the results of agarose gel electrophoresis of DNA fragments amplified by the method of the present invention using varying reaction time.

The reaction mixture of the Model 2 as described above in (2) was prepared to study the change in the amount of the amplification product when it was reacted for a varying time. The reaction mixture was incubated for 0, 15, 30, 60, 90 or 120 minutes at 55° C. The mixture was then treated at 90° C. for 2 minutes to inactivate the enzymes. 8 of the reaction mixture was analyzed by electrophoresis on 3% NuSieve 3:1 agarose gel. The results of the electrophoresis are shown in FIG. 41. Numbers 1 to 6 in the figure represent lanes to which the reaction mixture reacted for 0, 15, 30, 60, 90 or 120 minutes was applied, respectively. M represents a lane to which 100 bp DNA ladder marker (Takara Shuzo) was applied as a molecular weight marker.

As shown in FIG. 41, no amplification product was observed for a reaction time of 0 minute. It was confirmed that the amount of the amplification product increased as the reaction time became longer from 15 minutes to 30 or 60 minutes. However, the amount of the amplification product as observed by electrophoresis was almost unchanged for a reaction time of 60 minutes or longer, indicating that the amplification in the reaction system used reached the plateau at about 60 minutes.

EXAMPLE 2

(1) Preparation of RNA

An RNA used as a template in this Example was prepared from human cultured cell HT29 (ATCC HTB-38) (Dainippon Pharmaceutical) using TRIzol reagent (Life Technologies). The concentration of the resulting total RNA was adjusted to 1 $\mu$g/$\mu$l. The OD260/OD280 value was 1.8, which indicates the spectrophotometric purity of the RNA.

(2) Amplification Reaction

Bca BEST DNA polymerase, which has a reverse transcription activity and a DNA polymerase activity, as well as RNase H endonuclease were used to determine if a cDNA is amplified from an RNA.

A reaction mixture having the composition as described in Example 2 was prepared with the addition of 1 $\mu$g of the above-mentioned total RNA. A targeted region encoding human transferrin receptor (GenBank accession no. X01060) was amplified using the Primer Pair 2 in Example 1 as primers.

The reaction mixture was incubated at 55° C. for 60 minutes, and then heated at 90° C. for 2 minutes to inactivate the enzymes. When 8 $\mu$l of the reaction mixture was subjected to electrophoresis on 3% NuSieve 3:1 agarose gel, an amplified fragment having an expected size of 56 bp was observed. Furthermore, Southern hybridization was carried out using a probe having the targeted nucleotide sequence. A DNA probe having a nucleotide sequence as shown in SEQ ID NO:12 of the Sequence Listing labeled with biotin at the 5'-terminus was used to conduct Southern hybridization. As a result, the probe hybridized with the above-mentioned amplified fragment, confirming that the targeted region was correctly amplified by the method of the present invention.

EXAMPLE 3

(1) Synthesis of Primers

The amplification method of the present invention was examined using a double-stranded DNA as a template. Primers used were synthesized using a DNA synthesizer (Applied Biosystems). Nucleotide sequences of primers are shown in SEQ ID NOS:13–22 of the Sequence Listing. The structures of the primers used in this Example are described below in detail. The pUC19 DNA (Takara Shuzo) was used as a template for the Primer Pairs A-F. The nucleotide sequence of pUC19 is available from a database (GenBank accession no. L09137). An amplified double-stranded DNA fragment was used as a template for the Primer Pair G. The fragment was prepared from the human total RNA obtained in Example 2 using primers having a sequence as shown in SEQ ID NOS:95 or 96 of the Sequence Listing and TaKaRa RNA PCR Kit (AMV) Ver. 2.1 (Takara Shuzo) according to the attached standard protocol.

Primer Pair A (amplified fragment length: about 450 bp): A combination of primers having a nucleotide sequence as shown in SEQ ID NO:13 or 14 of the Sequence Listing in which the first and second bases from the 3'-terminus are ribonucleotides;

Primer Pair B (amplified fragment length: about 250 bp): A combination of primers having a nucleotide sequence as shown in SEQ ID NO:13 or 15 of the Sequence Listing in which the first and second bases from the 3'-terminus are ribonucleotides;

Primer Pair C (amplified fragment length: about 520 bp): A combination of primers having a nucleotide sequence as shown in SEQ ID NO:13 or 16 of the Sequence Listing in which the first and second bases from the 3'-terminus are ribonucleotides;

Primer Pair D (amplified fragment length: about 890 bp): A combination of primers having a nucleotide sequence as shown in SEQ ID NO:13 or 17 of the Sequence Listing in which the first and second bases from the 3'-terminus are ribonucleotides;

Primer Pair E (amplified fragment length: about 130 bp): A combination of primers having a nucleotide sequence as shown in SEQ ID NO:18 or 19 of the Sequence Listing in which the first to third bases from the 3' terminus are ribonucleotides;

Primer Pair F (amplified fragment length: about 220 bp): A combination of primers having a nucleotide sequence as shown in SEQ ID NO:20 or 19 of the Sequence Listing in which the first to third bases from the 3'-terminus are ribonucleotides; and Primer Pair G (amplified fragment length: about 320 bp): A combination of primers having a nucleotide sequence as shown in SEQ ID NO:21 or 22 of the Sequence Listing in which the first to third bases from the 3'-terminus are ribonucleotides.

(2) Amplification Reaction

A reaction mixture was prepared as follows.

35 mM potassium phosphate buffer (pH 7.5), 0.1 mg/ml bovine serum albumin (BSA), 5% dimethyl sulfoxide, 1.4 mM each of dNTPs, 10 mM magnesium chloride, 60 pmol each of the primers of one of the primer pairs as described above in (1), 100 ng of the pUC19 DNA as the template, 5.5 U of Bca BEST DNA polymerase and 60 U of RNase H to a final reaction volume of 50 μl.

The reaction conditions were as follows. The reaction mixture without the DNA polymerase or RNase H was heat-denatured at 98° C. for 1 minute, and then cooled to 55° C. The DNA polymerase and RNase H were then added thereto and the mixture was incubated at 55° C. for 60 minutes. After the completion of the reaction, the mixture was heated at 90° C. for 2 minutes to inactivate the enzymes. 8 μl of the reaction mixture was then subjected to electrophoresis on 3% NuSieve 3:1 agarose gel.

As a result, it was confirmed that an amplified fragment of interest was obtained using either of the Primer Pairs. Thus, it was confirmed that a double-stranded DNA can be used as a template to conduct an amplification reaction in the amplification method of the present invention.

(3) Digestion of Amplification Product with Restriction Enzyme

Digestion of an amplified fragment obtained using the amplification method of the present invention with a restriction enzyme was examined. The pUC19 plasmid DNA was used as a template DNA. pUC19 upper (2) NN primer and pUC19 lower NN primer as shown in SEQ ID NOS:13 and 14 of the Sequence Listing, respectively, were used. In the primers, the first and second bases from the 3'-terminus are ribonucleotides. The composition of the reaction mixture was as follows.

Reaction Mixture A: 35 mM potassium phosphate buffer (pH 7.5), 10 mM magnesium chloride, 1.4 mM each of dNTPs, 0.01% BSA, 5% DMSO, 2.7% glycerol, 100 pmol each of the pUC19 upper (2) NN primer and the pUC19 lower NN primer, 500 ng of the pUC19 DNA and sterile distilled water to a reaction volume of 48 μl.

The reaction mixture was heat-denatured at 98° C. for 1 minute, and then cooled to 55° C. 60 U of *E. coli* RNase H and 5.5 U of Bca BEST were then added thereto to make the reaction volume to 50 μl. The reaction mixture was incubated at 55° C. for 1 hour. After the completion of the reaction, the mixture was heated at 90° C. for 2 minutes to inactivate the enzymes. The reaction mixture was subjected to electrophoresis on 3% agarose gel to purify the resulting amplification product. The recovered amplification product was resupended in 100 μl of sterile distilled water.

The thus obtained DNA solution was used for restriction enzyme digestion. Restriction enzymes used were AccII (Takara Shuzo) and BcnI (Takara Shuzo). The composition of the reaction mixture was as follows.

3 μl of the DNA solution, 1 μl of 10×AccII buffer or 10×BcnI buffer attached to each of the enzymes, 1 μl of the restriction enzyme AccII or BcnI and sterile distilled water to a reaction volume of 10 μl. The reaction mixture was reacted at 37° C. for 30 minutes. 1.5 μl of 10× loading buffer was added thereto. 6 μl of the mixture was subjected to electrophoresis on 3% NuSieve agarose gel.

As a result, restriction enzyme-digested DNA fragments of interest were obtained using both of the restriction enzymes AccII and BcnI.

(4) Detection of Mutation

Detection of a mutation using the amplification method of the present invention was examined. pUC19 was used as a template. Nucleotide sequences of pUC19 upper 5 (2) NN-U primer, pUC19 upper (2) NN-A primer, pUC19 upper (2) NN-C primer and pUC19 upper (2) NN-G primer are shown in SEQ ID NOS:23–26 of the Sequence Listing, respectively. Nucleotide sequences of pUC19 lower NN primer is shown in SEQ ID NOS:14 of the Sequence Listing. Any one of these primers is a chimeric oligonucleotide primer in which the first and second bases from the 3'-terminus are ribonucleotides. The combinations of these primers were as follows.

Primer Pair 1: pUC19 upper (2) NN-U and pUC19 lower NN;

Primer Pair 2: pUC19 upper (2) NN-A and pUC19 lower NN;

Primer Pair 3: pUC19 upper (2) NN-C and pUC19 lower NN; and

Primer Pair 4: pUC19 upper (2) NN-G and pUC19 lower NN.

A reaction mixture was prepared as follows.

30 mM potassium phosphate buffer (pH 7.3), 0.01% bovine serum albumin (BSA), 5% DMSO, 1 mM each of dNTPs, 8 mM magnesium acetate, 60 pmol each of the primers, 50 ng of the DNA as the template and sterile distilled water to a reaction volume of 48 μl.

The reaction mixture was heat-denatured at 98° C. for 1 minute, and then cooled to 55° C. 5.5 U of Bca BEST DNA polymerase and 60 U of *E. coli* RNase H were then added thereto and the reaction mixture was incubated at 55° C. for 60 minutes. The mixture was then heated at 90° C. for 2 minutes to inactivate the enzymes. 8 μl of the reaction mixture was subjected to electrophoresis on 4% NuSieve 3:1 agarose (Takara Shuzo) gel. As a result, an amplified fragment of about 450 bp of interest was detected only when the combination of the primers that included the primer having a complementary base at the 3'-terminus of pUC19 upper (2) NN was used. On the other hand, no amplified fragment was observed for the combinations including the primer having a mismatched base at the 3'-terminus of pUC19 upper (2) NN.

EXAMPLE 4

(1) Reaction in Microtube

Reaction volume for the amplification method of the present invention was examined. A region encoding human transferrin receptor was selected as a region to be amplified. Primers having a sequence as shown in SEQ ID NO:27 or 28 of the Sequence Listing were used. In the primers, the first and second bases from the 3'-terminus are ribonucleotides. A fragment of about 750 bp amplified by RT-PCR was used as a template DNA. The reaction volume was adjusted to 50, 100, 300 or 500 μl. The composition of the reaction mixture was as follows.

Reaction Mixture A: 10 μl of 5× specialized buffer (135 mM potassium phosphate buffer (pH 7.5), 0.5 mg/ml BSA, 2.5% DMSO), 4 μl of 100 mM magnesium acetate, 5 μl of 10 mM dNTPs, 10 μl of 10 μM ATP, 1 μl of Bca BEST DNA polymerase (22 U/μl), 1 μl of RNase H (60 U/μl) and sterile distilled water to 39 μl.

Reaction Mixture B: 3 μl each of 20 μM human transferrin receptor S primer (SEQ ID NO:27) and 20 μM human transferrin receptor A primer (SEQ ID NO:28), about 100 ng of the DNA as the template and sterile distilled water to 11 μl. If the volume became 50 μl or more, it was scaled up to have the above-mentioned composition.

For an amplification reaction, the Reaction Mixture B was treated at 98° C. for 2 minutes, and then incubated at 55° C. for 3 minutes. The Reaction Mixture B was added to the Reaction Mixture A which had been pre-incubated in a 1500-μl microtube at 55° C. After mixing, the reaction mixture was incubated at 55° C. for 1 hour. After the completion of the reaction, the mixture was transferred to an ice bath. 8 μl of the reaction mixture was subjected to electrophoresis on 3% agarose gel.

As a result, a fragment of about 300 bp of interest was efficiently amplified using each of the reaction volumes. In addition, it was confirmed that an amplified fragment of interest can be obtained without a problem using a PCR-amplified fragment as a template DNA.

(2) Reaction in Petri Dish

Use of a Petri dish for preventing the heterogeneous temperature in a reaction mixture due to increased reaction volume was examined. A region encoding human transferrin receptor was selected as a region to be amplified. Primers having a sequence as shown in SEQ ID NO:12 or 13 of the Sequence Listing were used. In the primers, the first and second bases from the 3'-terminus are ribonucleotides. A fragment of about 750 bp amplified by RT-PCR was used as a template DNA. The reaction volume was adjusted to 10 ml. The composition of the reaction mixture was as follows.

Reaction Mixture A: 2000 μl of 5× specialized buffer (135 mM potassium phosphate buffer (pH 7.5), 0.5 mg/ml BSA, 2.5% DMSO), 800 μl of 100 mM magnesium acetate, 1000 μl of 10 mM dNTPs and sterile distilled water to 9.1 ml.

Reaction Mixture B: 200 μl each of 60 μM human transferrin receptor S primer (SEQ ID NO:12) and 60 μM human transferrin receptor primer (SEQ ID NO:13), about 10 μg of the DNA as the template and sterile distilled water to 500 μl.

Reaction Mixture C: 200 μl of Bca BEST DNA polymerase (22 U/μl) and 200 μl of RNase H (60 U/μl)

For an amplification reaction, the Reaction Mixture B was treated at 98° C. for 1 minute, and then incubated at 55° C. for 3 minutes. The Reaction Mixture B was added to the Reaction Mixture A which had been pre-incubated in a 60-mm (diameter) plastic Petri dish at 55° C. The Reaction Mixture C was further added thereto. After mixing, the reaction mixture was incubated at 55° C. for 1 hour. After the completion of the reaction, the reaction mixture was transferred to an ice bath. 8 μl of the reaction mixture was then subjected to electrophoresis on 3% agarose gel.

As a result, a fragment of about 300 bp of interest was efficiently amplified even if the reaction volume of 10 ml was used. In addition, it was confirmed that an amplified fragment of interest can be obtained without a problem using a PCR-amplified fragment as a template DNA. Thus, it was confirmed that the method of the present invention can be more preferably used for making a DNA chip, which requires a large amount of a DNA fragment, as compared to the conventional PCR method.

EXAMPLE 5

(1) Relationship Between Type of Buffer and Amount of RNase H Used The relationship between the type of buffer and the amount of RNase H used was examined. Plasmid DNAs, in which a fragment of 249 bp or 911 bp was cloned into the pUC19 vector (designated as pUC19-249 and pUC19-911) were used as templates. Chimeric oligonucleotide primers, in which the first to third bases from the 3'-terminus of MF2N3 (24) primer or MR1N3 (24) primer having a sequence as shown in SEQ ID NO:29 or 30 of the Sequence Listing are ribonucleotides, were used as primers. By using the combination of these primers, amplified fragments of about 450 bp and about 1100 bp are obtained for pUC19-249 and pUC19-911, respectively.

A tris-hydrochloride buffer, a potassium phosphate buffer and Tricine buffer were selected as buffer systems to be examined. The amounts of RNase H examined were no addition and a final concentration ranging from 0.3 to 1.2 U/μl. The tris-hydrochloride buffer system was prepared as described in Example 1 (2), except that 10 ng of pUC19-249 or 200 ng of pUC19-911, 60 pmol each of the primers and 11 U/50 μl reaction volume of Bca BEST DNA polymerase were used. The potassium phosphate buffer system was prepared to have a similar composition. The Tricine buffer system was prepared to contain the following at the indicated final concentration: 34 mM Tricine buffer (pH 8.7), 10 mM potassium chloride, 10 mM ammonium sulfate, 0.01% BSA, 1% DMSO, 4 mM magnesium acetate and 0.5 mM each of dNTPs. 10 ng/50 μl reaction volume of the pUC19-249 plasmid or 200 ng/50 μl reaction volume of the pUC19-911 plasmid, 60 pmol/50 μl reaction volume each of primers, RNase H at a predetermined concentration and 11 U/50 μl reaction volume of Bca BEST DNA polymerase were added to the buffer system.

For an amplification reaction, a mixture of pUC19-249 or pUC19-911 as a template and the respective primers was heat-denatured at 98° C. for 1 minute, and then cooled to 55° C. A mixture of the remaining reaction components was added thereto. The mixture was reacted at 55° C. for 60 minutes. After the completion of the reaction, the mixture was cooled to 4° C. and 1/10 volume of 0.5 M EDTA was added thereto to terminate the reaction. 3 μl of the reaction mixture was subjected to electrophoresis on 3% NuSieve 3:1 agarose (Takara Shuzo) gel.

As a result, when pUC19-249 was used as a template, increase in amplification efficiency was observed depending on the buffer system used in the following order: tris-hydrochloride<potassium phosphate<Tricine. When pUC19-911 was used as a template, increase in amplification efficiency was observed depending on the buffer system used in the following order: tris-hydrochloride<Tricine<potassium phosphate. The use of RNase H at a final concentration ranging from 0.3 to 1.2 U/μl resulted in the amplified fragment of interest, although no amplified fragment of interest was observed for no addition.

(2) Examination of Amount of Primer

The effect of the amount of a primer used on the amplification method of the present invention was examined. A reaction mixture system having a composition in which pUC19-249 was used as a template among the compositions as described above in (1) was used. 60 U/50 μl reaction volume of RNase H was used for the potassium phosphate buffer system, whereas 30 U/50 μl reaction volume of RNase H was used for the tris-hydrochloride or Tricine buffer system. The examined concentration of the primer ranged from 10 to 100 pmol/50 μl. Reaction conditions and confirmation of amplification were as described above in (1).

As a result, an amplified fragment of interest was observed using each of the reaction buffer systems containing the primer at a concentration ranging from 10 to 100 pmol/50 μl.

(3) Effect of pH of Reaction Buffer

The effect of the pH of a reaction mixture on the amplification method of the present invention was examined. The composition of the reaction mixture was as described above in (2). The pH examined were 7.0–8.0 for the potassium phosphate buffer system, 7.5–9.2 for the Tricine buffer system, and 7.5–9.0 for the tris-hydrochloride buffer system. Reaction conditions and confirmation of amplification were as described above in (1).

As a result, an amplified fragment of interest was observed at pH within the range used for the respective buffer systems.

(4) Effect of Additive

The effect of addition of dimethyl sulfoxide (DMSO) was examined using the reaction mixture composition of the phosphate buffer system (pH 7.5) as described above in (3). Additionally, the effect of addition of a polyamine was also examined. The examined amount of added DMSO ranged from no addition to 10%. On the other hand, spermine tetrahydrochloride (Sigma), spermidine trihydrochloride (Sigma), acetylputrescine (Nacalai Tesque), putrescine dihydrochloride (Nacalai Tesque), trimethylene diamine (Nacalai Tesque), propylenediamine (Nacalai Tesque) and diaminomethane dihydrochloride (Nacalai Tesque) were used as a polyamine. The amounts of propylenediamine and trimethylene diamine added were within the range between no addition and 2%. Other polyaminies were used within the range between no addition and 5 mM. Reaction conditions and confirmation of amplification were as described above in (1).

As a result, a DNA fragment of interest was efficiently amplified using the additive at a concentration within the indicated range: no addition to 5% of DMSO; no addition to 200 μM of spermine tetrahydrochloride or spermidine; 40 μM to 40 mM of acetylputrescine or putrescine dihydrochloride; 0.002% to 0.02% of trimethylene diamine; 0.0001% to 0.01% of propylenediamine; and 0.1 μM to 10 μM of diaminomethane dihydrochloride.

(5) Examination of Type of Magnesium Salt

The effect of the type of a magnesium salt on the amplification method of the present invention was examined. The pUC19 DNA was used as a template. pUC19 upper NN 249 primer and pUC19 lower NN primer having sequences as shown in SEQ ID NOS:31 and 14 of the Sequence Listing, respectively, were used as primers. An amplified fragment of about 225 bp is obtained using a pair of these primers. Magnesium chloride, magnesium acetate and magnesium sulfate were used as magnesium salts. The composition of the reaction mixture was as follows.

35 mM potassium phosphate buffer (pH 7.3), 8 mM (final concentration) magnesium chloride, magnesium acetate or magnesium sulfate, 1.0 mM (final concentration) each of dNTPs, 50 ng of the pUC19 DNA, 60 pmol each of the primers, 60 U of RNase H, 5.5 U of Bca BEST DNA polymerase and sterile distilled water to a reaction volume of 50 μl. Reaction conditions and confirmation of amplification were as described above in (3).

As a result, an amplified fragment of interest was observed using each of the magnesium salts.

(6) Examination of Concentrations of Magnesium and dNTPs

The effects of the concentrations of magnesium and dNTPs on the amplification method of the present invention were examined. The composition of the reaction mixture was as described above in (5), except that 25 ng of the pUC19 DNA, and magnesium and dNTPs at various concentrations were used. Reaction conditions and confirmation of amplification were as described above in (1).

In a reaction system in which the final concentration of each of dNTPs was fixed at 1 mM, an amplified fragment of interest was obtained when a final magnesium concentration ranging from 6 mM to 10 mM was used. In a reaction system in which the final magnesium concentration of was fixed at 8 mM, an amplified fragment of interest was obtained when a final concentration of each of dNTPs ranging from 0.6 mM to 1.2 mM was used. Furthermore, in a reaction system in which the final concentration of each of dNTPs was fixed at 0.5 mM, an amplified fragment of interest was obtained when a final magnesium concentration ranging from 2 mM to 6 mM was used. In a reaction system in which the final magnesium concentration was fixed at 4 mM, an amplified fragment of interest was obtained when a final concentration of each of dNTPs ranging from 0.2 mM to 0.8 mM was used.

(7) Examination of Change in Concentration of Potassium Phosphate Buffer or Tricine Buffer and Reactivity The effect of the concentration of the potassium phosphate buffer or the Tricine buffer on the amplification method of the present invention was examined. The composition of the reaction mixture was as described above in (1) for a case where pUC19-249 was used as a template, except that a potassium phosphate buffer at a final concentration of 20–50 mM or a Tricine buffer at a final concentration of 22–46 mM was used.

As a result, an amplified fragment of interest was obtained when the potassium phosphate buffer at a final concentration ranging from 20 to 50 mM or the Tricine buffer at a final concentration ranging from 22 to 46 mM was used.

(8) Examination of Concentration of Bca BEST DNA Polymerase

The effect of the concentration of Bca BEST DNA polymerase on the amplification method of the present invention was examined. The composition of the reaction mixture was as described above in (1) for a case where pUC19-249 was used as a template, except that a potassium phosphate buffer system or a Tricine buffer system and Bca BEST DNA polymerase at a concentration within a range of 1–22 U/50 μl reaction volume was used. Reaction conditions and confirmation of amplification were as described above in (1).

As a result, an amplified fragment of interest was obtained when Bca BEST DNA polymerase was used at a concentration within a range of 1–22 U/50 μl.

EXAMPLE 6

Comparison with the PCR Method

The amplification method of the present invention was compared with the PCR method. Ones in which a DNA fragment of about 150 bp or about 250 bp is inserted into a multi-cloning site in the pUC19 plasmid DNA were used as templates. The templates were prepared as follows.

pUC19 upper 150 PCR primer, pUC19 upper 249 PCR primer and pUC19 lower PCR primer, which have sequences as shown in SEQ ID NOS:32, 33 and 34 of the Sequence Listing, respectively, were used to conduct a PCR reaction using 100 pg of the pUC19 plasmid DNA as a template. An amplified fragment of about 150 bp was obtained by using a combination of the pUC19 upper 150 primer and the pUC19 lower NN primer. An amplified fragment of about 250 bp was obtained by using a combination of the pUC19 upper 249 primer and the pUC19 lower NN primer. Each of these amplified fragments was purified using Microcon-100, blunt-ended using DNA blunting kit (Takara Shuzo), and then subcloned into a HincII site in the pUC19 plasmid. Plasmids into which one of the amplified fragments is inserted were used to transform *E. coli* JM109. The resulting transformants were cultivated and plasmids with inserted DNA were purified from the cells using QIAGEN plasmid mini kit (Qiagen). The plasmids with inserted DNA were used as templates.

The sequences of the primers used in this Example are shown in SEQ ID NOS:35 and 36 of the Sequence Listing. Primers in which the first to third bases from the 3'-terminus are ribonucleotides were used for the amplification method of the present invention. The composition of the reaction mixture was as follows.

27 mM phosphate buffer (pH 7.3), 0.01% bovine serum albumin (BSA), 5% DMSO, 1 mM each of dNTPs, 8 mM magnesium acetate, 60 pmol each of the primers, 1 ng of the DNA as the template and sterile distilled water to a reaction volume of 48 μl.

The reaction mixture was heat-denatured at 98° C. for 1 minute, and then cooled to 55° C. 5.5 U of Bca BEST DNA polymerase and 60 U of *E. coli* RNase H were added thereto, and the mixture was incubated at 55° C. for 60 minutes. Thereafter, the mixture was heated at 90° C. for 2 minutes to inactivate the enzymes. 3 μl of the reaction mixture was subjected to electrophoresis on 4% NuSieve 3:1 agarose (Takara Shuzo) gel.

On the other hand, amplification using the PCR method was conducted as a control. PCR Amplification kit (Takara Shuzo), 10 pmol each of primers having a sequence as shown in SEQ ID NO:37 or 38 of the Sequence Listing, 1 ng of the DNA as the template and sterile distilled water to a reaction volume of 50 μl were used for the reaction. The reaction conditions were 25 cycles of 94° C. for 30 seconds, 55° C. for 30 seconds and 72° C. for 40 seconds. After the completion of the reaction, 3 μl of the reaction mixture was subjected to electrophoresis on 4% NuSieve 3:1 agarose (Takara Shuzo) gel.

As a result, more amount of a fragment of interest was amplified from each of the plasmids having an insert of 150 bp or 249 bp as a template in the amplification method of the present invention as compared with the PCR method. 20 μl of the reaction mixture was purified using Microcon-100, and the amount of the amplification product was quantified using Beckman DU-640 spectrophotometer (Beckman) in order to express numerically the amount of the amplification product. The amount of the fragment amplified from the plasmid having an insert of 150 bp as the template in the amplification method of the present invention was confirmed to be about 60-fold higher than that in the PCR method. The amount of the fragment amplified from the plasmid having an insert of 250 bp as the template in the amplification method of the present invention was confirmed to be about 40-fold higher than that in the PCR methods. Based on these results, it was confirmed that the method of the present invention can be more preferably used for making a DNA chip, for which a large amount of a DNA fragment is required, as compared with the conventional PCR method.

EXAMPLE 7

(1) Preparation of RNA Probe

A method for detecting an amplified fragment obtained by the amplification method of the present invention was examined. A probe for detection composed of ribonucleotides in which two different fluorescent substances are attached to the ribonucleotides on both ends of the probe was prepared. The RNA probe for detection was synthesized using a DNA synthesizer (Applied Biosystems). The nucleotide sequence of the probe is shown in SEQ ID NO:39 of the Sequence Listing. 6-FAM (Glen Research) and TAMRA (Glen Research) were used as fluorescent substances to label the probe at the 5'-terminus and the 3'-terminus, respectively.

(2) Amplification Reaction and Detection 0.1 or 1 ng of the pUC19 DNA was used as a template. pUC19 upper 150 2N primer and pUC19 lower 542 2N primer having sequences as shown in SEQ ID NOS:40 and 16 of the Sequence Listing, respectively, in which the first and second bases from the 3'-terminus of the primer are ribonucleotides were used as primers.

The composition of the reaction mixture was as follows.

27 mM phosphate buffer (pH 7.3), 0.01% BSA, 5% DMSO, 1 mM each of dNTPs, 8 mM magnesium acetate, 60 pmol each of the primers, 0.1 or 1 ng of the DNA as the template, 0.1 μg of the RNA probe and sterile distilled water to a reaction volume of 48 μl. One without the DNA as the template was also prepared as a control.

The reaction mixture was heat-denatured at 98° C. for 1 minute, and then cooled to 55° C. 22 U of Bca BEST DNA polymerase or sterile water, and 60 U of *E. coli* RNase H were added thereto, and the mixture was incubated at 55° C. for 60 minutes. Thereafter, 5 μl of 10% sodium dodecyl sulfate (SDS; Nacalai Tesque) was added to the mixture to inactivate the enzymes. 50 μl of the reaction mixture was diluted with an equal volume of sterile water and transferred to a microplate. An image analyzer FM BIO II Multi-View (Takara Shuzo) was used for detection at an excitation wavelength of 505 nm.

As a result, no fluorescent signal was detected using either of the templates when Bca BEST DNA polymerase was not added. Also, no fluorescent signal was detected for the reaction mixture containing Bca BEST DNA polymerase when the DNA as the template was not added. On the other hand, a fluorescent signal was detected when either 0.1 or 1 ng of the DNA as the template was added. An amplified fragment of about 190 bp of interest was also observed by electrophoresis on 3% agarose gel containing 0.00003% ethidium bromide only when 0.1 or 1 ng of the DNA as the template was added in the presence of Bca BEST DNA polymerase. That is, the same results were obtained by the detection method using an RNA probe and the conventional electrophoretic detection method. Thus, a method for detecting an amplified fragment obtained by the amplification method of the present invention using an RNA probe was established.

EXAMPLE 8

Use of a primer composed of deoxyribonucleotides as one of the two primers in the method of the present invention was examined. MR1N3 (30) having a sequence as shown in SEQ ID NO:41 of the Sequence Listing and M4 primer (Takara Shuzo) having a sequence as shown in SEQ ID NO:42 of the Sequence Listing were used as primers. In the MR1N3 primer, the first to third bases from the 3'-terminus are ribonucleotides. The composition of the reaction mixture was as follows.

27 mM phosphate buffer (pH 7.3), 0.01% bovine serum albumin (BSA), 5% DMSO, 1 mM each of dNTPs, 8 mM magnesium acetate, 30 pmol each of the primers, 1 ng of the DNA as the template and sterile distilled water to a reaction volume of 24 μl.

The reaction mixture was heat-denatured at 98° C. for 2 minutes, and then cooled to 55° C. 11 U of Bca BEST DNA polymerase and 30 U of *E. coli* RNase H were added thereto to make the reaction volume to 25 μl. The reaction mixture was incubated at 55° C. for 60 minutes. Thereafter, the mixture was heated at 90° C. for 2 minutes to inactivate the enzymes. 5 μl of the reaction mixture was subjected to electrophoresis on 4% NuSieve 3:1 agarose gel. As a result, an amplified fragment of interest was observed.

EXAMPLE 9

The method of the present invention was used to detect hemorrhagic *E. coli* O-157.

Sequences of the primers used in this Example are shown in SEQ ID NOS:43–46 of the Sequence Listing. In the primers, the first, second and the third bases from the 3'-terminus are ribonucleotides. A combination of primers having a sequence of SEQ ID NO:40 or 41, and a combination of primers having a sequence of SEQ ID NO:42 or 43 were constructed for detecting a sequence encoding vero toxin 1 or vero toxin 2 of O-157 according to the description of Rinsho To Biseibutsu (Clinical Microbiology), 18(4) :507–513 (1991). Primers in which the first to third bases from the 3'-terminus are ribonucleotides were used for the amplification method of the present invention. A heat-extract prepared by harvesting a culture of hemorrhagic *E. coli* O-157 (ATCC accession no. 43895), suspending it in sterile water at an appropriate cell density and treating it at 98° C. for 10 minutes was used as a template. The composition of the reaction mixture was as follows.

27 mM phosphate buffer (pH 7.3), 0.01% bovine serum albumin (BSA), 5% DMSO, 1 mM each of dNTPs, 8 mM magnesium acetate, 60 pmol each of the primers, the DNA as the template (the heat-extract) corresponding to 104–106 cells and sterile distilled water to a reaction volume of 48 μl.

The reaction mixture was heat-denatured at 98° C. for 1 minute, and then cooled to 55° C. 5.5 U of Bca BEST DNA polymerase and 60 U of *E. coli* RNase H were added thereto. The reaction mixture was incubated at 55° C. for 60 minutes. Thereafter, the mixture was heated at 90° C. for 2 minutes to inactivate the enzymes. 3 μl of the reaction mixture was subjected to electrophoresis on 4% NuSieve 3:1 agarose (Takara Shuzo) gel.

As a result, O-157 vero toxin 1 and 2 could be detected using either one of the primer pairs and the DNA as the template corresponding to $10^4$ cells, confirming that the method of the present invention can be utilized as a method for detecting a virulent bacterium.

EXAMPLE 10

Amplification of a long-chain DNA fragment by the method of the present invention was examined. A double-stranded DNA as a template was prepared as follows. First, a library was constructed from mRNA derived from a normal gastric tissue using Uni-ZAP XR vector (Stratagene) according to a conventional method. The library was screened to select clones having an insert of about 2.1 kbp or about 4.3 kbp. The clones were used to obtain pBluescript SK (−) phage vectors by in vitro excision. Amplified fragments of about 2.2 kbp and about 4.4 kbp were obtained using the plasmids as templates, MCR-F primer and MCR-R primer having sequences as shown in SEQ ID NOS:47 and 48 of the Sequence Listing, respectively, and PCR Amplification kit (Takara Shuzo). These PCR fragments were used as templates for the amplification method of the present invention. MF2N3 (24) primer and MR1N3 (24) primer having sequences as shown in SEQ ID NOS:49 and 50 of the Sequence Listing, respectively, in which the first to third bases from the 3'-terminus are ribonucleotides were used as primers. The composition of the reaction mixture was as follows.

28 mM phosphate buffer (pH 7.5), 0.01% bovine serum albumin (BSA), 1% DMSO, 0.5 mM each of dNTPs, 4 mM magnesium acetate, 30 pmol each of the primers, 0.2 mM putrescine and sterile distilled water to 24.25 μl. The reaction mixture was treated at 92° C. for 2 minutes, and then cooled to 55° C. 30 U of RNase H and 5.5 U of Bca BEST DNA polymerase were added thereto to make the reaction volume to 25 μl. The reaction mixture was incubated for 1 hour. After the completion of the reaction, the mixture was cooled at 4° C., and 2.5 μl of a 0.5 M EDTA solution added thereto to terminate the reaction. 5 μl of the mixture was subjected to electrophoresis on 1% agarose gel.

As a result, an amplified fragment of about 2.2 kbp or about 4.4 kbp was obtained by the method of the present invention, confirming that the method of the present invention can be used to amplify a long-chain DNA fragment.

EXAMPLE 11

A DNA microarray onto which a λ DNA fragment of about 400 bp amplified by the amplification method of the present invention and λ DNA fragments of 300 bp and 1000 bp amplified by PCR were spotted was produced. The nucleotide sequence of the λ DNA is available from GenBank accession nos. V00636, J02459, M17233 and X00906. A reaction mixture for the amplification method of the present invention was prepared as follows.

34 mM Tricine-hydrochloride buffer (pH 8.7), 10 mM potassium chloride, 10 mM ammonium sulfate, 0.01% bovine serum albumin (BSA), 1% dimethyl sulfoxide, 4 mM magnesium acetate, 0.5 mM each of dNTPs, 500 pmol each of the primers, 100 ng of the PCR amplification product as the template, 110 U of Bca BEST DNA polymerase and 300 U of cloned RNase H in a final reaction volume of 500 11. The reaction mixture was mixed to homogeneity, incubated at 55° C. for 60 minutes, and then heated at 90° C. for 2 minutes to inactivate the enzymes. This solution was used in the subsequent steps. The spotted DNA fragments were as follows.

1. Sample: A PCR amplification product (300 bp) obtained by using a λ DNA as a template and a combination of primers having a sequence as shown in SEQ ID NO:51 or 52 of the Sequence Listing was subcloned into the pUC19 vector. The subcloned product was then PCR-amplified using MCR-F primer and MCR-R primer as shown in example 10. The thus obtained product as a template and chimeric oligonucleotide primers having a sequence as shown in SEQ ID NO:53 or 54 of the Sequence Listing, in which the first and second bases from the 3'-terminus of the primer are ribonucleotides, were used to amplify a product of about 400 bp by the amplification method of the present invention to obtain the Sample. Five DNA solutions, i.e., the reaction mixture at its original concentration or 2-, 4-, 8- or 16-fold dilutions of the reaction mixture with a carbonate buffer (a carbonate buffer at a concentration of 50 mM were used for dilution in each case) were used for spotting.

2. Sample: The DNA fragment amplified in 1 above was treated with Microcon-100 (Takara Shuzo). Then, five DNA solutions were prepared by adjusting the concentrations to 0.125 μg/μl, 0.25 μg/μl, 0.5 μg/μl, 1.0 μg/μl and 2.0 μg/μl with the 50 mM carbonate buffer.

3. Positive Control: A PCR amplification product (300 bp) amplified in 1 above was treated with Microcon-100. Then, five DNA solutions were prepared by adjusting the concentrations to 0.125 μg/μl, 0.25 μg/μl, 0.5 μg/μl, 1.0 μg/μl and 2.0 μg/μl with the 50 mM carbonate buffer.

4. Positive Control: A PCR amplification product (1000 bp) obtained by using the λ DNA as a template and a combination of primers having a sequences as shown in SEQ ID NO:55 or 56 of the Sequence Listing was treated with Microcon-100. Then, four DNA solutions were prepared by adjusting the concentrations to 0.125 μg/μl, 0.25 μg/μl, 0.5 μg/μl and 1.0 μg/μl with the 50 mM carbonate buffer.

5. Negative Control: A PCR amplification product (300 bp) obtained by using the λ DNA as a template and a combination of primers having a sequence as shown in SEQ ID NO:55 or 57 of the Sequence Listing was subcloned into the pUC19 vector. The subcloned product was then PCR-amplified using primers having a sequence as shown in SEQ ID NO:47 or 48 of the Sequence Listing. The thus obtained product as a template and primers having a sequence as shown in SEQ ID NO:53 or 54 of the Sequence Listing as primers were used to amplify a product of about 400 bp by the amplification method of the present invention to obtain the Negative Control. Five DNA solutions, i.e., the reaction mixture at its original concentration or 2-, 4-, 8- or 16-fold dilutions of the reaction mixture with a carbonate buffer (a carbonate buffer at a concentration of 50 mM were used for dilution in each case) were used for spotting.

6. Negative Control: The DNA fragment obtained in 5 above was treated with Microcon-100. Then, five DNA solutions were prepared by adjusting the concentrations to 0.125 μg/μl, 0.25 μg/μl, 0.5 μg/μl, 1.0 μg/μl and 2.0 μg/μl with the 50 mM carbonate buffer.

The respective DNA solutions thus prepared were spotted onto a slide glass to which amino groups had been introduced (Matsunami Glass) using an equipment for making DNA chips (Genetic Microsystems (GMS)), and were immobilized using UV irradiation. The slide was washed with 0.2% SDS followed by distilled water, dried, and then used as a DNA array.

A PCR amplification product (300 bp) amplified in 1 above was labeled with Cy5 using Label IT Cy5$^R$ Labeling Kit (Takara Shuzo) for use as a probe. Hybridization was carried out using a prehybridization solution and a hybridization solution as described in the instructions attached to IntelliGene (Takara Shuzo). First, the DNA array was subjected to prehybridization at room temperature for 2 hours. The hybridization solution containing the denatured Cy5-labeled probe was dripped onto the DNA array. A cover glass was mounted thereon. The sides of the cover glass were sealed with a film. The sealed DNA array was incubated at 65° C. for 13 hours. After the cover glass was removed, the DNA array was washed in 2×SSC at 65° C. for 5 minutes, in a solution containing 0.2×SSC and 0.1% SDS at 65° C. for 5 minutes, and finally in 0.2×SSC at room temperature for 5 minutes, and air-dried. The DNA array was then subjected to a microarray scanner (GMS) to analyze the fluorescent signals from the respective spots.

As a result, a fluorescent signal was observed at each of the positions onto which fragments amplified by the PCR method (the Positive Controls as described above in 3 and 4) and the method of the present invention (the Samples as described above in 1 and 2) were spotted. The intensities of the signals were as follows: the Sample 2>the Positive Control 4>the Sample 1>the Positive Control 3. On the other hand, no signal was observed at all for the Negative Controls 5 and 6. From these results, it was confirmed that an unpurified or purified DNA fragment amplified by the method of the present invention can be preferably used as a DNA fragment to be immobilized to make a DNA chip.

EXAMPLE 12

(1) The designing of a primer used in the method of the present invention in which a PCR-amplified fragment was used as a template was examined. First, R1-S1 primer, R1-A3 primer, R2-S1 primer, R2-A3 primer, R3-S1 primer and R3-A3 primer having sequences as shown in SEQ ID NOS:58–63 of the Sequence Listing respectively, were synthesized according to a conventional method. The structures of the respective primers are as follows.

(i) R1-S1 primer: From the 5'-terminus, 7 bases of a spacer sequence, 17 bases of a M13RV sequence (or RV sequence; the nucleotide sequence of M13RV primer (Takara Shuzo)) and 20 bases of a sense primer sequence for λ DNA-specific PCR;

(ii) R1-A3 primer: From the 5'-terminus, 7 bases of a spacer sequence, 17 bases of the M13RV sequence and 20 bases of an antisense primer sequence for λ DNA-specific PCR;

(iii) R2-S1 primer: From the 5'-terminus, 25 bases of a spacer sequence, 17 bases of the M13RV sequence and 20 bases of a sense primer sequence for λ DNA-specific PCR;

(iv) R2-A3 primer: From the 5'-terminus, 25 bases of a spacer sequence, 17 bases of the M13RV sequence and 20 bases of an antisense primer sequence for λ DNA-specific PCR;

(v) R3-S1 primer: From the 5'-terminus, 58 bases of a spacer sequence, 17 bases of the M13RV sequence and 20 bases of a sense primer sequence for λ DNA-specific PCR; and (vi) R3-A3 primer: From the 5'-terminus, 58 bases of a spacer sequence, 17 bases of the M13RV sequence and 20 bases of an antisense primer sequence for λ DNA-specific PCR.

M13RV 20 mer has a sequence of a total of 20 bases consisting of 17 bases of the M13RV sequence and 3 bases at the 5'-terminus. Therefore, when M13RV 20 mer is used in the method of the present invention, the lengths of the spacer sequences in the above-mentioned primers become 4 bases, 22 bases and 55 bases, respectively. Primers without a spacer sequence were also made as controls for the above-mentioned primers.

For example, when the primer pair, R1-S1 primer/R1-A3 primer, is used, an amplified fragment of 348 bp is obtained. 7 bases on both ends of the amplified fragment correspond to the spacer portions. The RV sequences are located inside the spacer portions. The λ DNA sequences are located inside the RV sequences.

Similarly, when the primer pair, R2-S1 primer/R2-A3 primer, is used, an amplified fragment of 384 bp in which 25 bases on both ends of the amplified fragment correspond to the spacer portions is obtained. In addition, when the primer pair, R3-S1 primer/R3-A3 primer, is used, an amplified fragment of 450 bp in which 58 bases on both ends of the amplified fragment correspond to the spacer portions is obtained. On the other hand, a fragment amplified using control primers has no spacer portion. These PCR-amplified fragments were used as templates for the following examination.

One of two primers, M13RV-2N 17 mer primer or M13RV-2N 20 mer having a sequence as shown in SEQ ID NO:64 or 65 of the Sequence Listing was used in this Example. In the primers, the first and second bases from the 3'-terminus are ribonucleotides. The reaction was carried out as follows. 5 μl of a mixture of 20 μM of the primer, about 20 ng of the template and 0.01% propylenediamine was denatured at 98° C. for 2 minutes, and then cooled to 55° C. Thereafter, 34 mM Tricine buffer (pH 8.7), 10 mM potassium chloride, 10 mM ammonium sulfate, 0.01% BSA, 1% DMSO, 4 mM magnesium acetate, 0.5 mM each of dNTPs, 1 U of Bca BEST DNA polymerase and 15 U of RNase H were added thereto to make the final reaction volume to 25 μl. The reaction mixture was incubated at 55° C. for 1 hour. After the completion of the reaction, the mixture was cooled to 4° C., and then 2.5 μl of a 0.5 M EDTA solution was added thereto to terminate the reaction. 3 μl of the reaction mixture was subjected to electrophoresis on 3% NuSieve 3:1 agarose (Takara Shuzo) gel. As a result, when M13RV-2N 17 mer was used, increase in amplification efficiency was observed depending on the length of the spacer sequence in the following order: 25 mer>7 mer>58 mer>no spacer sequence. When M13RV-2N 20 mer was used, increase in amplification efficiency was observed depending on the length of the spacer sequence in the following order: 22 mer>4 mer>S5 mer>no spacer sequence. Furthermore, when the M13RV sequences in the primers described above in (i) to (vi) were replaced by M13M4 sequences, a similar tendency was observed for the relationship between the spacer sequence and the amplification efficiency. Thus, it was confirmed that, when a linear DNA fragment such as a PCR-amplified fragment is used as a template, the designing of primers used in the method of the present invention to generate a spacer sequence (portion) leads to an increased amplification efficiency.

(2) Amplification of a template having a high GC content in the method for amplifying a nucleotide sequence using an elevated reaction temperature was examined. First, primers having a sequence as shown in SEQ ID NO:66 or 67 of the Sequence Listing for PCR amplification of a 307-bp region (GC content: 62.5%) of CDC2-related protein kinase PISS LRE gene (GenBank accession no. AA789328) were produced. In addition, primers having a sequence as shown in SEQ ID NO:68 or 69 of the Sequence Listing for PCR amplification of a 284-bp region (GC content: 61.3%) of Type II cytoskeltal 1 keratin gene (GenBank accession no. AA706022) were produced. PCR amplification was carried out using these primers and commercially available DNA fragments (Research Genetics) as templates. The respective PCR-amplified fragments obtained by using the above-mentioned primer pairs have spacer sequences and the M13RV sequences on both ends. The fragments were used as templates for the present invention.

M13RV-2N 17 mer primer having a sequence as shown in SEQ ID NO:64 of the Sequence Listing or M13RV-2N 20 mer primer having a sequence as shown in SEQ ID NO:65 of the Sequence Listing was used in this Example. In the primers, the first and second bases from the 3'-terminus are ribonucleotides. The reaction was carried out as follows. 10 μl of a mixture of 100 pmol of the primer, 20 ng of the template and 0.01% propylenediamine was denatured at 98° C. for 2 minutes, and then cooled to 55° C. or 60° C. Thereafter, 34 mM Tricine buffer (pH 8.7), 10 mM KCl, 10 mM ammonium sulfate, 0.01% BSA, 1% DMSO, 4 mM magnesium acetate, 0.5 mM each of dNTPs, 11 U of Bca BEST DNA polymerase and 30 U of RNase H were added thereto to make the final reaction volume to 50 μl. The reaction mixture was incubated at 55° C. or 60° C. for 1 hour. After the completion of the reaction, the mixture was cooled to 4° C. 3 μl of the reaction mixture was subjected to electrophoresis on 3% agarose gel. The results are shown in Table 1 below.

TABLE 1

| Reaction temperature | Primers used | Gene and results of amplification: CDC2-related | Type II cytoskeltal |
|---|---|---|---|
| 55° C. | M13RV-2N 17mer | ++ | ++ |
| | M13RV-2N 20mer | ++ | ++ |
| 60° C. | M13RV-2N 17mer | + | + |
| | M13RV-2N 20mer | ++++ | ++++ |

+ to ++++: The degree of amplification was scored in four grades.
−: No amplification was observed.

As shown in Table 1, the region of interest was efficiently amplified even if a template having a high GC content was used. This amplification was accomplished by elevating the reaction temperature (from 55° C. to 60° C.) and by using a primer having a higher Tm value as compared with an optimal primer for a reaction at 55° C. when the reaction was carried at 60° C.

(3) The relationship between the length of an amplified fragment and the amount of the amplification product in the method for amplifying a nucleotide sequence under high reaction temperature conditions was examined. First, a pair of primers having a sequence as shown in SEQ ID NO:70 or 71 of the Sequence Listing for amplifying a 800-bp region of the lambda DNA (Takara Shuzo) and a pair of primers having a sequence as shown in SEQ ID NO:72 or 73 of the Sequence Listing for amplifying a 400-bp region of the lambda DNA were synthesized according to a conventional method. PCR was conducted using one of these primer pairs and the λ DNA as a template to obtain an amplified fragment. An amplified fragment of about 1.1 kbp was also prepared using the pUC19-911 plasmid as described in Example 5 (1) as a template and MF2 (24) PCR primer and MR1 (24) PCR primer, which have sequences as shown in SEQ ID NOS:74 and 75 of the Sequence Listing, respectively. The PCR-amplified fragments obtained by using the above-mentioned primer pairs have spacer sequences and the M13RV or M4 sequences on both ends. These fragments were used as templates for the present invention.

M13RV-2N 17 mer primer or M13RV-2N 20 mer primer as shown in (2) above was used as a primer in this Example. In the primers, the first and second bases from the 3'-terminus are ribonucleotides. A combination of M13M4-3N 20 mer primer having a sequence as shown in SEQ ID NO:76 of the Sequence Listing and M13RV-3N 20 mer primer having a sequence as shown in SEQ ID NO:77 of the Sequence Listing, and a combination of M13M4-3N 24 mer primer and M13RV-3N 24 mer primer having sequences as shown in SEQ ID NO:78 and 79 of the Sequence Listing, respectively, were used for amplifying a region of about 1 kbp. In the primers, the first to third bases from the 3'-terminus are ribonucleotides. The reaction was carried out as follows. 10 μl of a mixture of 10 pmol of the primer, about 20 ng of the template and 0.01% propylenediamine was denatured at 98° C. for 2 minutes, and then cooled to 55° C. or 60° C. Thereafter, 34 mM Tricine buffer (pH 8.7), 10 mM potassium chloride, 10 mM ammonium sulfate, 0.01% BSA, 1% DMSO, 4 mM magnesium acetate, 0.5 mM each of dNTPs, 11 U of Bca BEST DNA polymerase and 30 U of RNase H were added thereto to make the final reaction volume to 50 μl. The reaction mixture was incubated at 55° C. or 60° C. for 1 hour. After the completion of the reaction, the mixture was cooled to 4° C., and then 5 μl of a 0.5 M EDTA solution was added thereto to terminate the reaction.

3 μl of the reaction mixture was subjected to electrophoresis on 3% NuSieve 3:1 agarose (Takara Shuzo) gel. The results are shown in Tables 2 and 3 below.

TABLE 2

| Reaction temperature | Primers used | Length of amplified fragment and results 400 bp | 800 bp |
|---|---|---|---|
| 55° C. | M13RV-2N 17mer | ++ | ++ |
| | M13RV-2N 20mer | ++ | ++ |
| 60° C. | M13RV-2N 17mer | + | + |
| | M13RV-2N 20mer | ++++ | ++++ |

+ to ++++: The degree of amplification was scored in four grades.
−: No amplification was observed.

As shown in Table 2, fragments for regions of 400 bp and 800 bp were efficiently amplified by making the length of the primer for amplification from 7 mer to 20 mer and by elevating the reaction temperature from 55° C. to 60° C.

TABLE 3

| Reaction temperature | Primers used | Length of amplified fragment and results 1034 bp |
|---|---|---|
| 55° C. | M13RV-3N 20mer & M13M4-3N 20mer | ++ |
| | M13RV-3N 24mer & M13M4-3N 24mer | ++ |
| 65° C. | M13RV-3N 20mer & M13M4-3N 20mer | + |
| | M13RV-3N 24mer & M13M4-3N 24mer | ++++ |

+ to ++++: The degree of amplification was scored in four grades.
−: No amplification was observed.

Furthermore, as shown in Table 3, a fragment for a region of about 1 kbp was efficiently amplified by making the length of the primer for amplification from 20 mer to 24 mer and by elevating the reaction temperature from 55° C. to 65° C. Additionally, similar results were obtained for amplification of a long-chain DNA fragment as described in Example 10 by using longer primers and an elevated reaction temperature. Increase in amplification efficiency was observed when a region of about 2 kbp or longer was amplified.

EXAMPLE 13

(1) Use of a heat-resistant DNA polymerase other than Bca BEST DNA polymerase in the method of the present invention was examined. Bst DNA polymerase (New England Biolabs) was used as a heat-resistant DNA polymerase. A pair of primers, 5'-ID primer and 3'-ID primer having sequences as shown in SEQ ID NOS:80 and 81 of the Sequence Listing, respectively, were synthesized according to a conventional method. PCR was carried out using the primer pair and a commercially available DNA fragment for cyclin A gene (Research Genetics) as a template, resulting in an amplified fragment of about 300 bp. The PCR-amplified fragment obtained by using the primer pair has the M13RV sequences on both ends. The fragment was used as a template for the present invention.

M13RV-2N 17 mer primer having a sequence as shown in SEQ ID NO:64 of the Sequence Listing was used as a primer in this Example. In the primer, the first and second bases from the 3'-terminus are ribonucleotides. The reaction was carried out as follows. 10 μl of a mixture of 20 μM of the primer, about 20 ng of the template and 0.01% propylenediamine was denatured at 98° C. for 2 minutes, and then cooled to 55° C. Thereafter, 34 mM Tricine buffer (pH 8.7), 10 mM potassium chloride, 10 mM ammonium sulfate, 0.01% BSA, 1% DMSO, 4 mM magnesium acetate, 0.5 mM each of dNTPs, 4, 8, 12 or 16 U of Bst DNA polymerase and 30 U of RNase H were added thereto to make the final reaction volume to 50 μl. As a control, a reaction mixture having a composition identical with the above-mentioned one was prepared, except that 11 U of Bca BEST DNA polymerase was used. The reaction mixture was incubated at 55° C. for 1 hour. After the completion of the reaction, the mixture was cooled to 4° C., and then 5 μl of a 0.5 M EDTA solution was added thereto to terminate the reaction. 3 μl of the reaction mixture was subjected to electrophoresis on 3% NuSieve 3:1 agarose (Takara Shuzo) gel. As a result, an amplified fragment of interest was obtained using each of the various units of Bst DNA polymerase. Thus, it was confirmed that heat-resistant DNA polymerases can be preferably used in the method of the present invention.

(2) Use of a mesophilic DNA polymerase in the method of the present invention was examined. 5'→3' exo activity (−) Klenow fragment (Takara Shuzo) was used as a mesophilic DNA polymerase. The DNA prepared in (1) above was used a template DNA for the method of the present invention.

M13RV-2N 16 mer primer having a sequence as shown in SEQ ID NO:82 of the Sequence Listing was used as a primer in this Example. In the primer, the first and second bases from the 3'-terminus are ribonucleotides. The reaction was carried out as follows. 10 μl of a mixture of 20 μM of the primer, about 20 ng of the template and 0.01% propylenediamine was denatured at 98° C. for 2 minutes, and then cooled to 40° C. Thereafter, 34 mM Tricine buffer (pH 8.7), 10 mM potassium chloride, 10 mM ammonium sulfate, 0.01% BSA, 1% DMSO, 4 mM magnesium acetate, 0.5 mM each of dNTPs, 0, 2, 4, 6 or 8 U of Klenow fragment and 30 U of RNase H were added thereto to make the final reaction volume to 50 μl. The reaction mixture was incubated at 40° C. for 1 hour. After the completion of the reaction, the mixture was cooled to 4° C., and then 5 μl of a 0.5 M EDTA solution was added thereto to terminate the reaction. 3 μl of the reaction mixture was subjected to electrophoresis on 3% NuSieve 3:1 agarose (Takara Shuzo) gel. As a result, an amplified fragment of interest was obtained in cases where the various units of Klenow fragment were used excluding the case where no Klenow fragment was added. Thus, it was confirmed that mesophilic DNA polymerases can be preferably used in the method of the present invention.

EXAMPLE 14

Chimeric oligonucleotide primers to be used in the method of the present invention were examined. A DNA as a template and primers were synthesized as described in Example 1 (1). The structures of the primers used in this Examples are described below in detail:

Primer Pair 1: A combination of primers having a nucleotide sequence as shown in SEQ ID NO:2 or 3 of the Sequence Listing and wholly composed of deoxyribonucleotides;

Primer Pair 2: A combination of primers having a nucleotide sequence as shown in SEQ ID NO:83 or 84 of the Sequence Listing in which the sixth and seventh deoxyribonucleotides from the 3'-terminus are ribonucleotides;

Primer Pair 3: A combination of primers having a nucleotide sequence as shown in SEQ ID NO:85 or 86 of the Sequence Listing in which the fifth and sixth deoxyribonucleotides from the 3'-terminus are ribonucleotides;

Primer Pair 4: A combination of primers having a nucleotide sequence as shown in SEQ ID NO:87 or 88 of the Sequence Listing in which the fourth and fifth deoxyribonucleotides from the 3'-terminus are ribonucleotides;

Primer Pair 5: A combination of primers having a nucleotide sequence as shown in SEQ ID NO:89 or 90 of the Sequence Listing in which the third and fourth deoxyribonucleotides from the 3'-terminus are ribonucleotides;

Primer Pair 6: A combination of primers having a nucleotide sequence as shown in SEQ ID NO: 91 or 92 of the Sequence Listing in which the second and third deoxyribonucleotides from the 3'-terminus are ribonucleotides;

Primer Pair 7: A combination of primers having a nucleotide sequence as shown in SEQ ID NO:93 or 94 of the Sequence Listing in which the first and second deoxyribonucleotides from the 3'-terminus are ribonucleotides; and Primer Pair 8: A combination of primers having a nucleotide sequence as shown in SEQ ID NO:91 or 92 of the Sequence Listing in which the second and third deoxyribonucleotides from the 3'-terminus are ribonucleotides and the phosphate bond on the 5'-terminal side of the third ribonucleotide from the 3'-terminus is replaced by a phosphorothioate bond.

Amplification conditions and detection method were as described in Example 1 (2) and (3). As a result, an amplified fragment having a length of interest was observed for each of the Primer Pairs 2–8. For the Primer Pairs 2–7, the amount of the amplification product increased as the number of deoxyribonucleotides at the 3'-terminus decreased. Particularly, the most abundant amplification product was observed for the Primer Pair 7 having no deoxyribonucleotide at the 3'-terminus. On the other hand, no amplified fragment was observed for the Primer Pair 1. Furthermore, the fact that amplified fragments of interest were observed for both of the Primer Pairs 6 and 8 confirms that both of a modified ribonucleotide and a unmodified ribonucleotide can be preferably used as a ribonucleotide contained in a primer in the method of the present invention.

EXAMPLE 15

(1) The effect of the type of the buffer used in the method of the present invention was examined. Primers for amplifying λ DNA having sequences represented by SEQ ID NOS:128 and 129 were used in this Example. The reaction was carried out as follows. Briefly, 10 μl of a mixture containing 120 pmol each of the primers, 0.01% aqueous solution of propylenediamine and 10 ng or 1 ng of a DNA as a template was heat-denatured at 98° C. for 2 minutes, and then cooled on ice to anneal the primers to the template DNA. An amplified product (1005 bp) obtained by a PCR using A DNA (Takara Shuzo) as a template and primers represented by SEQ ID NOS:130 and 131, which was then purified using Suprec02 (Takara Shuzo), was used as the template.

After annealing, 40 μl of one of three types of buffers for reaction (42.5 mM Tricine-potassium hydroxide buffer (pH 8.5), 42.5 mM Bicine-potassium hydroxide buffer (pH 8.3) and 42.5 mM HEPES-potassium hydroxide buffer (pH 7.8)) each containing 0.625 mM each of dNTPs, 5.0 mM magnesium acetate, 0.0125% bovine serum albumin (BSA), 1.25% dimethyl sulfoxide (DMSO), 30 U of *E. coli* RNase H and 11 U of BcaBEST DNA polymerase was added to the mixture to make the final volume to 50 μl. The reaction mixtures were incubated at 60° C. for 1 hour. After reaction, 3 μl each of the reaction mixtures was subjected to electrophoresis on 3.0% agarose gel for confirmation. Then, the amplified fragments of interest were observed for both of the amounts of the template. In particular, a greater amount of amplification product was obtained for the reaction system containing Bicine-potassium hydroxide buffer (pH 8.5).

(2) Improvement of reactivity by the use of HEPES-potassium hydroxide buffer was examined. pUC19 plasmid DNA with a DNA fragment of about 150 bp being inserted into the multi-cloning site was used as a template. This template was prepared as follows.

A PCR was carried out using pUC19 upper 150 PCR primer and pUC19 lower PCR primer having sequences represented by SEQ ID NOS:223 and 224, and 100 pg of pUC19 plasmid DNA as a template. The resulting amplified fragment was purified using Microcon-100, blunt-ended using DNA blunting kit (Takara Shuzo) and subcloned into a HincII site of the plasmid pUC19. The plasmid with the amplified fragment being inserted was used to transform *Escherichia coli* JM109. The transformant was cultured. The plasmid having the inserted DNA was purified from the cells using QIAGEN plasmid mini kit (Qiagen) and used as a template.

A DNA fragment PCR-amplified using the pUC19-150 plasmid DNA prepared as described above as a template, and primers MCS-F and MCS-R having nucleotide sequences represented by SEQ ID NOS:124 and 125 was used as a template. Primers MF2N3(24) and MR1N3(24) having nucleotide sequences represented by SEQ ID NOS:126 and 127 were used as chimeric oligonucleotide primers. The expected size of the amplified fragment obtained using the combination of these primers was about 350 bp.

An HEPES-potassium hydoxide buffer system was selected as a buffer to be examined. A potassium phosphate buffer system and a Tricine buffer system were used as controls. The compositions of the reaction mixtures are shown below.

Reaction mixture A: 10 ng of the PCR-amplified fragment, 50 pmol each of the primers MF2N3(24) and MR1N3(24), 0.01% aqueous solution of propylenediamine and sterile distilled water to a reaction volume of 10 μl.

Reaction mixtures B: The following three types were prepared.

Potassium phosphate buffer system: 40 μl of a reaction mixture containing, at final concentrations, 35 mM potassium phosphate buffer (pH 7.5), 1.25% DMSO, 0.0125% BSA, 5 mM magnesium acetate, 0.625 mM each of dNTPs, 60 U of *E. coli* RNase H and 5.5 U of BcaBEST DNA polymerase was prepared.

Tricine buffer system: 40 μl of a reaction mixture containing, at final concentrations, 42.5 mM Tricine buffer (pH 8.7), 12.5 mM potassium chloride, 12.5 mM ammonium sulfate, 1.25% DMSO, 0.0125% BSA, 5 mM magnesium acetate, 0.625 mM each of dNTPs, 30 U of *E. coli* RNase H and 5.5 U of BcaBEST DNA polymerase was prepared.

HEPES-potassium hydroxide buffer system: 40 μl of a reaction mixture containing, at final concentrations, 25 mM HEPES-potassium hydroxide buffer (pH 7.8), 125 mM potassium acetate, 1.25% DMSO, 0.0125% BSA, 5 mM magnesium acetate, 0.625 mM each of dNTPs, 30 U of *E. coli* RNase H and 5.5 U of BcaBEST DNA polymerase was prepared.

The reaction mixture A was heat-denatured at 98° C. for 2 minutes, cooled to 60° C. or 65° C. and then allowed to stand on ice. One of the reaction mixtures B was added to the reaction mixture A on ice and mixed to make the reaction volume to 50 $\mu$l. The reaction mixtures were incubated at 60° C. or 65° C. for 1 hour. After reaction, they were cooled to 4° C., and 1/10 volume of 0.5 M EDTA was added to each of the mixtures to terminate the reaction. 3 $\mu$l each of the reaction mixtures was subjected to electrophoresis on 3% NuSieve 3:1 agarose gel. As a result, the amplified fragments of interest were observed for the three buffer systems regardless of the reaction temperature used. In particular, the largest amount of the amplification product and the highest reactivity were observed for the HEPES-potassium hydroxide buffer system in this Example.

EXAMPLE 16

(1) Conditions used in the method of the present invention for annealing primers to a template were examined. Primers having nucleotide sequences represented by SEQ ID NOS:132 and 133 based on the partial nucleotide sequence of a bacterium *Flavobacterium* sp. SA-0082 as described in WO 97/32010 (deposited at the International Patent Organism Depositary, National Institute of Advanced Industrial Science and Technology, AIST Tsukuba Central 6, 1–1, Higashi 1-chome, Tsukuba-shi, Ibaraki-ken 305-8566, Japan on Mar. 29, 1995 under accession number FERM P-14872, and deposited at the International Patent Organism Depositary, National Institute of Advanced Industrial Science and Technology under accession number FERM BP-5402 (date of request for transmission to international depositary authority: Feb. 15, 1996)) were used. An amplified product (573 bp) obtained by a PCR using a genomic DNA from *Flavobacterium* sp. SA-0082 as a template and a combination of primers represented by SEQ ID NOS:134 and 135, which was then purified using Suprec02 (Takara Shuzo), was used as the DNA as the template in this Example. The reaction was carried out as follows. Briefly, 2 $\mu$l of one of two annealing solutions (500 mM potassium chloride and 8 $\mu$M spermidine, or 0.05% propylenediamine) was added to 120 pmol each of the primers. A final volume of 10 $\mu$l of each of the mixtures further containing 10 ng or 1 ng of the PCR-amplified fragment was heat-denatured at 98° C. for 2 minute. After denaturation, the mixtures were rapidly cooled on ice to anneal the primers to the template.

After annealing, 40 $\mu$l of one of three types of buffers (42.5 mM Tricine-potassium hydroxide buffer (pH 8.5), 42.5 mM Bicine-potassium hydroxide buffer (pH 8.3) and 42.5 mM HEPES-potassium hydroxide buffer (pH 7.8)) each containing 0.625 mM each of dNTPs, 5.0 mM magnesium acetate, 0.0125% bovine serum albumin (BSA), 1.25% dimethyl sulfoxide (DMSO), 30 U of *E. coli* RNase H and 11 U of BcaBEST DNA polymerase was added to the mixture to make the final volume to 50 $\mu$l. The reaction mixtures were incubated at 52° C. for 1 hour. After reaction, 3 $\mu$l each of the reaction mixtures was subjected to electrophoresis on 3.0% agarose gel. The results are shown in FIG. 1. FIG. 1 is a photograph of electrophoresis of reactions using the respective combinations of the annealing solutions and the buffers. Lane 1: molecular weight marker (100 bp ladder, Takara Shuzo); lane 2: propylenediamine/Tricine (template: 10 ng); lane 3: propylenediamine/HEPES (template: 10 ng); lane 4: propylenediamine/HEPES (template: 1 ng); lane 5: propylenediamine/Bicine (template: 10 ng); lane 6: propylenediamine/Bicine (template: 1 ng); lane 7: 500 mM potassium chloride and 8 $\mu$M spermidine/Bicine (template: 10 ng); lane 8: 500 mM potassium chloride and 8 $\mu$M spermidine/Bicine (template: 1 ng); lane 9: molecular weight marker (100 bp ladder); lane 10: propylenediamine/Tricine (template: 1 ng); lane 11: 500 mM potassium chloride and 8 $\mu$M spermidine/Tricine (template: 1 ng); lane 12: propylenediamine/HEPES (template 1 ng); lane 13: 500 mM potassium chloride and 8 $\mu$M spermidine/HEPES (template: 1 ng); lane 14: propylenediamine/Bicine (template: 1 ng); and lane 15: 500 mM potassium chloride and 8 $\mu$M spermidine/Bicine (template: 1 ng).

As shown in FIG. 1, a greater amount of the amplification product of interest was obtained when the annealing solution containing 500 mM potassium chloride+8 $\mu$M spermidine was used for the annealing of the primers to the template DNA for either of the three buffers regardless of the amount of the DNA as the template. In particular, the combination of the annealing solution containing 500 mM potassium chloride+8 $\mu$M spermidine and the Bicine-potassium hydroxide buffer yielded good results in this Example.

(2) The effect of an annealing solution in case where a PCR-amplified fragment from λ DNA was used as a template was examined. The chimeric oligonucleotide primers as described in Example 15(1) were used in this Example. The PCR-amplified fragment as prepared in Example 15(1) or λ DNA was used as a template DNA. The reaction was carried out as follows. Briefly, 2 $\mu$l of one of three types of annealing solutions (500 mM potassium chloride and 8 $\mu$M spermidine, 0.05% propylenediamine, or sterile water) was added to 120 pmol each of the primers. 10 $\mu$l of the mixtures further containing 10 ng or 1 ng of the PCR-amplified fragment were prepared. The mixtures were heat-denatured at 98° C. for 2 minutes, and then rapidly cooled on ice to anneal the primers to the template.

Figure 2:
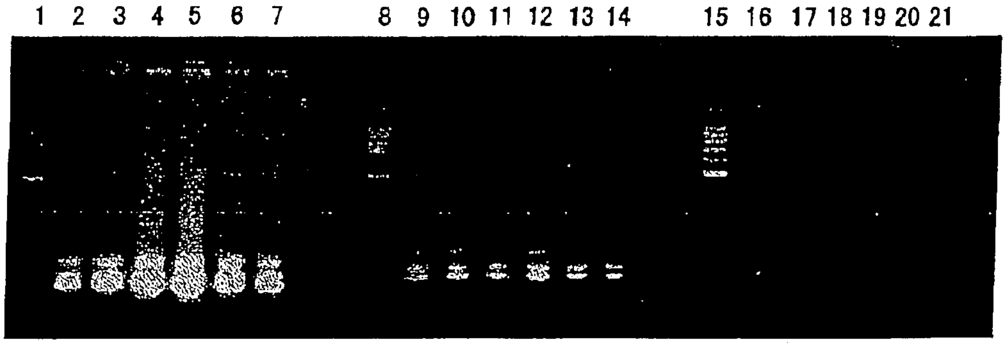
FIG. 2 is a photograph of agarose gel electrophoresis of amplified DNA fragments amplified according to the method of the present invention.

After annealing, 40 $\mu$l of one of three types of buffers (42.5 mM Tricine-potassium hydroxide buffer (pH 8.5), 42.5 mM Bicine-potassium hydroxide buffer (pH 8.3) and 42.5 mM HEPES-potassium hydroxide buffer (pH 7.8)) each containing 0.625 mM each of dNTPs, 5.0 mM magnesium acetate, 0.0125% BSA, 1.25% DMSO, 30 U of *E. coli* RNase H and 11 U of BcaBEST DNA polymerase was added to the mixture to make the final volume to 50 $\mu$l. The reaction mixtures were incubated at 60° C. for 1 hour. After reaction, 3 $\mu$l each of the reaction mixtures was subjected to electrophoresis on 3.0% agarose gel. The results are shown in FIG. 2. FIG. 2 is a photograph of electrophoresis showing the results for the examination of combinations of the amounts of the template, the reaction buffers and the annealing solutions. Lane 1: marker (100 bp ladder); lane 2: 10 ng of the template, a combination of Tricine/500 mM potassium chloride and 8 $\mu$M spermidine; lane 3: 1 ng of the template, a combination of Tricine/500 mM potassium chloride and 8 $\mu$M spermidine; lane 4: 10 ng of the template, a combination of Bicine/500 mM potassium chloride and 8 $\mu$M spermidine; lane 5: 1 ng of the template, a combination of Bicine/500 mM potassium chloride and 8 $\mu$M spermidine; lane 6: 10 ng of the template, a combination of HEPES/500 mM potassium chloride and 8 $\mu$M spermidine; lane 7: 1 ng of the template, a combination of HEPES/500 mM potassium chloride and 8 $\mu$M spermidine; lane 8: molecular weight marker (100 bp ladder); lane 9: 10 ng of the template, a combination of Tricine/propylenediamine; lane 10: 1 ng of the template, a combination of Tricine/propylenediamine; lane 11: 10 ng of the template, a combination of Bicine/propylenediamine; lane 12: 1 ng of the template, a combination of Bicine/propylenediamine; lane 13: 10 ng of the template, a combination of HEPES/propylenediamine; lane 14: 1 ng of the template, a combination of HEPES/propylenediamine; lane 15: molecular weight marker (100 bp ladder); lane 16: 10 ng of the template, a combination of Tricine/water; lane 17: 1 ng of the template, a combination of Tricine/water; lane 18: 10 ng of the template, a combination of Bicine/water; lane 19: 1 ng of the template, a combination of Bicine/water; lane 20: 10 ng of the template, a combination of HEPES/water; and lane 21: 1 ng of the template, a combination of HEPES/water.

As shown in FIG. 2, the amplified fragments of interest were observed for the respective combinations of the three buffers and the three annealing solutions regardless of the amount of the template DNA. In particular, it was confirmed that a greater amount of the amplified fragment was obtained using the combination of the Bicine buffer and the annealing solution containing 500 mM potassium chloride and 8 μM spermidine.

EXAMPLE 17

The effect of the presence of an inhibitor of reverse transcriptase (RTase) on the method of the present invention was examined. Phosphonoformic acid (PFA) was used as an inhibitor of RTase. Primers represented by SEQ ID NOS:136 and 137 were used in this Example. An amplified product (576 bp) obtained by a PCR using a genomic DNA from enterohemorrhagic *Escherichia coli* O-157 as a template and primers represented by SEQ ID NOS:138 and 139, which was then purified using Suprec02 (Takara Shuzo), was used as the template DNA. The reaction was carried out as follows. Briefly, 10 μl of a mixture prepared by adding 1 ng of the PCR-amplified fragment to 120 pmol each of the primers and 2 μl of an annealing solutions containing 500 mM potassium chloride and 8 μM spermidine was heat-denatured at 98° C. for 2 minutes, and then rapidly cooled on ice to anneal the primers to the template.

Figure 3:
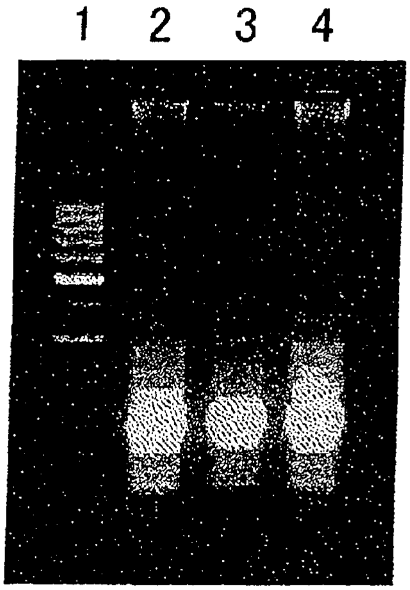
FIG. 3 is a photograph of agarose gel electrophoresis of amplified DNA fragments amplified according to the method of the present invention.

After annealing, 40 μl of a mixture containing 0.625 mM each of dNTPs, 42.5 mM Tricine-potassium hydroxide buffer (pH 8.5), 5.0 mM magnesium acetate, 0.0125% bovine serum albumin (BSA), 1.25% dimethyl sulfoxide (DMSO), 30 U of *E. coli* RNase H and 11 U of BcaBEST DNA polymerase as well as PFA to a concentration of 500 μg/ml or 50 μg/ml were added to the annealing mixture to make the final volume to 50 μl. The reaction mixtures were incubated at 55° C. for 1 hour. A system without the addition of PFA was also prepared as a control. After reaction, 9 μl each of the reaction mixtures was subjected to electrophoresis on 3.0% agarose gel. The results are shown in FIG. 3. FIG. 3 is a photograph of electrophoresis which shows the effect of the inhibitor of RTase. Lane 1: molecular weight marker (100 bp ladder); lane 2: without the addition of PFA; lane 3: with the addition of PFA at a concentration of 500 μg/ml; lane 4: with the addition of PFA at a concentration of 50 μg/ml.

As shown in FIG. 3, when PFA was added, non-specific amplification was suppressed and the amplified fragment of interest was observed. In particular, it was confirmed that the non-specific amplification products which were observed in the system without the addition of PFA was not observed and the amplified fragment of interest was clearly amplified in the system to which PFA was added at a concentration of 500 μg/ml.

EXAMPLE 18

The relationship between the length of a fragment to be amplified and the detection sensitivity in the method of the present invention was examined.

(1) Primers for amplifying *Escherichia coli* O-157 vero toxin represented by SEQ ID NOS:140–142 were synthesized. The chimeric oligonucleotide primers used in Example 17 were also used. The length of a fragment to be amplified using each of the combinations of primers was as follows: 247 bp (SEQ ID NOS:140 and 137); 168 bp (SEQ ID NOS:141 and 142); 206 bp (SEQ ID NOS:141 and 137); 135 bp (SEQ ID NOS:136 and 142); and 173 bp (SEQ ID NOS:136 and 137). The purified PCR-amplified 576-bp fragment prepared in Example 17 was used as a template DNA in this Example. The reaction was carried out as follows. Briefly, 10 μl of a mixture containing 60 pmol each of the primers, 2 μl of 0.05% aqueous solution of propylenediamine and 10 fg to 10 ng of the PCR-amplified fragment was heat-denatured at 98° C. for 2 minutes and then cooled to 55° C. in Thermal Cycler Personal (Takara Shuzo) to anneal the primers to the template.

After annealing, 40 μl of a mixture containing 0.625 mM each of dNTPs, 42.5 mM Tricine-potassium hydroxide buffer (pH 8.5), 5.0 mM magnesium acetate, 0.0125% bovine serum albumin (BSA), 1.25% dimethyl sulfoxide (DMSO), 30 U of *E. coli* RNase H, 5.5 U of BcaBEST DNA polymerase and sterile water was added to the mixture to make the final volume to 50 μl. The reaction mixtures were incubated at 55° C. for 1 hour. After reaction, 5 μl each of the reaction mixtures was subjected to electrophoresis on 3.0% agarose gel. As a control, detection of 10 fg to 1 pg of the PCR-amplified fragment was carried out using primers represented by SEQ ID NOS:143 and 144. A 135-bp fragment is amplified using the combination of these primers. 50 μl of a PCR solution containing 60 pmol each of the primers, 5 μl of 10×Ex Taq buffer (Takara Shuzo), 1.25 U of TaKaRa Ex Taq DNA polymerase (Takara Shuzo) and 0.2 mM each of dNTPs was prepared. The PCR was carried out as follows: 25 or 30 cycles of 94° C. for 30 seconds, 55° C. for 30 seconds and 72° C. for 30 seconds (2 min. 38 sec./cycle). After reaction, 1 μl (ICAN) or 5 μl (PCR) each of the reaction mixtures was subjected to electrophoresis on 3.0% agarose gel. The results are shown in FIG. 4 and Table 4.

TABLE 4

| Amplification size (bp) | Detection limit |
|---|---|
| ICAN (total time: 70 minutes) | |
| 247 | 100 pg |
| 168 | 100 fg |
| 206 | 100 pg |
| 135 | 10 fg |
| 173 | 100 fg |
| PCR (25 cycles; total time: about 66 minutes) | |
| 135 | 100 fg |
| PCR (30 cycles; total time: about 80 minutes) | |
| 135 | 10 fg |

Figure 4:
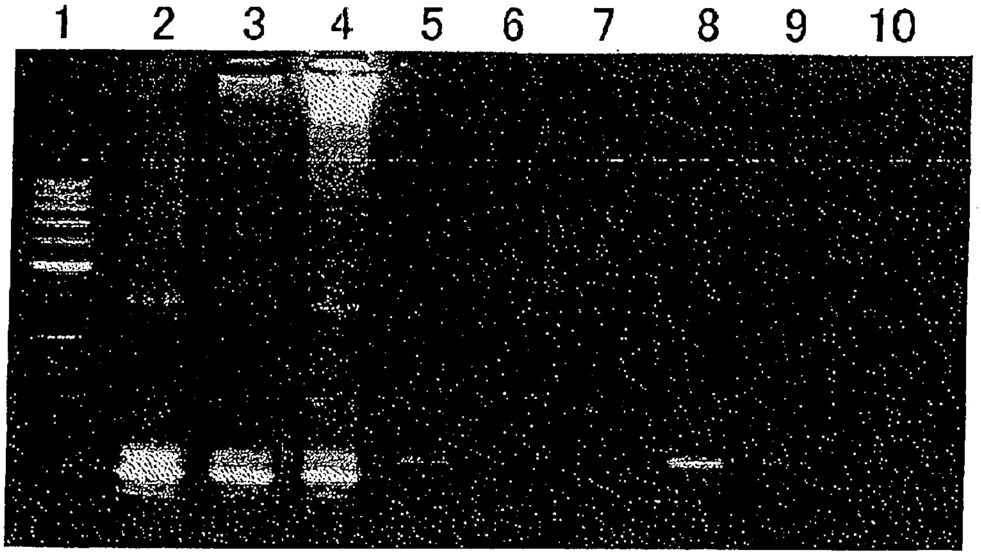
FIG. 4 is a photograph of agarose gel electrophoresis of amplified DNA fragments amplified according to the method of the present invention.

FIG. 4 is a photograph of electrophoresis which shows the detection limits for amplifying a chain length of 135 bp accomplished by the ICAN (1/50 of the reaction mixture was loaded) and the PCR (1/10 of the reaction mixture was loaded). Lane 1: molecular weight marker (100 bp ladder); lane 2: ICAN using 1 pg of the template; lane 3: ICAN using 100 fg of the template; lane 4: ICAN using 10 fg of the template; lane 5: PCR (25 cycles) using 1 pg of the template; lane 6: PCR (25 cycles) using 100 fg of the template; lane 7: PCR (25 cycles) using 10 fg of the template; lane 8: PCR (30 cycles) using 1 pg of the template; lane 9: PCR (30 cycles) using 100 fg of the template; lane 10: PCR (30 cycles) using 10 fg of the template.

As shown in Table 4, it was confirmed that almost the same detection sensitivity as that of the PCR was accomplished by the ICAN. Furthermore, the total reaction time for the PCR was about 80 minutes, whereas the reaction time required for accomplishing the same detection sensitivity using the method of the present invention was 70 minutes, confirming that the reaction time can be shortened by using the method of the present invention.

(2) Primers for amplifying λ DNA having nucleotide sequences represented by SEQ ID NOS:128, 129 and 145 were synthesized. The length of a fragment to be amplified using each of the combinations of primers was as follows: 151 bp (SEQ ID NOS:128 and 129); and 125 bp (SEQ ID NOS:145 and 129). The template DNA prepared in Example 15(1) was used in this Example. The reaction was carried out as follows. Briefly, 2 μl of an annealing solution (500 mM potassium chloride and 8 μM spermidine), 1 fg to 1 ng of the template were added to 120 pmol each of the primers and fill up to 10 μl by sterile water. The mixture was heat-denatured at 98° C. for 2 minutes, and then rapidly cooled on ice to anneal the primers to the template.

After annealing, 40 μl of a mixture containing 0.625 mM each of dNTPs, 42.5 mM Tricine-potassium hydroxide buffer (pH 8.5), 5.0 mM magnesium acetate, 0.0125% BSA, 1.25% DMSO, 30 U of *E. coli* RNase H and 11 U of BcaBEST DNA polymerase was added to the mixture to make the final volume to 50 μl. The reaction mixtures were incubated at 60° C. for 1 hour. After reaction, 3 μl each of the reaction mixtures was subjected to electrophoresis on 3.0% agarose gel. The results are shown in Table 5.

TABLE 5

| Amplification size (bp) | Detection limit |
|---|---|
| 125 | 10 fg |
| 151 | 100 fg |

As shown in Table 5, it was confirmed that, when λ DNA was used as a template, a detection sensitivity of as low as 10 fg could be also accomplished by examining the optimal region.

(3) A plasmid was prepared by inserting an amplified fragment (length: 340 bp) into a plasmid T7Blue T-Vector (Takara Shuzo). The fragment was prepared as described in JP-A 9-140383 using synthetic primers for amplifying a chrysanthemum viroid gene having nucleotide sequences represented by SEQ ID NOS:146 and 147, and an RNA from chrysanthemum infected with the viroid as a template. The plasmid was used to transform *Escherichia coli* JM109 competent cells (Takara Shuzo). The transformant was cultured in 5 ml of LB medium at 37° C. for 16 hour. The plasmid was purified from the collected cells using QIAGEN Plasmid Mini Kit (Qiagen) according to the manual. Dilutions containing 0 fg, 1 fg, 10 fg, 100 fg, 1 pg, 10 pg, 100 pg or 1 ng of the plasmid in 1 μl of sterile water were prepared based on the concentration of the plasmid as measured using Beckman DU-600 (Beckman). 1 μl of one of the thus prepared plasmid solutions was used as a template for 50 μl each of ICAN reaction systems. Primers CSVD-F2 and CSVD-R6 having nucleotide sequences represented by SEQ ID NOS:148 and 149 were used in this Example. The reaction was carried out as follows. Briefly, 10 μl of a mixture containing 50 pmol each of the primers, 1 μl of the prepared plasmid solution and propylenediamine at a final concentration of 0.01% was prepared. The mixture was heated at 98° C. for 2 minutes, cooled to 60° C., incubated at the temperature for 1 minute in Thermal Cycler Personal (Takara Shuzo), and then placed on ice.

After annealing, at final concentrations, 20 mM HEPES-potassium hydroxide buffer (pH 7.8), 100 mM potassium acetate, 1% DMSO, 0.01% BSA, 4 mM magnesium acetate, 500 μM each of dNTPs, 30 U of *E. coli* RNase H and 5.5 U of BcaBEST DNA polymerase were added to the mixture to make the final volume to 50 μl with sterile water. The reaction mixtures were placed in Thermal Cycler Personal which had been set at 60° C. and reacted for 60 minutes. After reaction, 3 μl each of the reaction mixtures was subjected to electrophoresis on 3% NuSieve 3:1 agarose. As a result, the amplification products of interest (about 90 bp, about 70 bp and about 50 bp) were observed using a template at a concentration of 10 fg.

EXAMPLE 19

Primers to be used in the method of the present invention were examined.

(1) The Tm value of a primer and the reaction temperature were examined. Primers for amplifying *Flavobacterium* sp. SA-0082 having nucleotide sequences represented by SEQ ID NOS:132 and 150–152 were synthesized. These primers were constructed such that a region of 160 bp or shorter having a GC content of about 20% was amplified. The length of a fragment to be amplified using each of the combinations of primers was as follows: 126 bp (SEQ ID NOS:132 and 151); 158 bp (SEQ ID NOS:132 and 152); 91 bp (SEQ ID NOS:150 and 151); and 123 bp (SEQ ID NOS:150 and 152). The PCR-amplification product as prepared in Example 16(1) was used as a DNA as the template in this Example. The reaction was carried out as follows. Briefly, 10 μl of a mixture containing 120 pmol each of the primers, 2 μl of one of three types of annealing solutions (500 mM potassium chloride and 8 μM spermidine, 0.05% propylenediamine, or water) and 1 fg to 10 ng of the template was prepared. The mixture was heat-denatured at 98° C. for 2 minutes, and then cooled on ice to anneal the primers to the template.

After annealing, 40 μl of one of three types of buffers (17 mM Tricine-potassium hydroxide buffer (pH 8.5), 17 mM Bicine-potassium hydroxide buffer (pH 8.3) and 20 mM HEPES-potassium hydroxide buffer (pH 7.8)) containing 0.625 mM each of dNTPs, 5.0 mM magnesium acetate, 0.0125% bovine serum albumin (BSA), 1.25% dimethyl sulfoxide (DMSO), 30 U of *E. coli* RNase H and 11 U of BcaBEST DNA polymerase was added to the mixture to make the final volume to 50 μl. The reaction mixtures were incubated at 52, 55 or 60° C. for 1 hour. After reaction, 3 μl each of the reaction mixtures was subjected to electrophoresis on 3.0% agarose gel. As a result, the amplified fragment of interest was observed using the reaction temperature of 52° C. In particular, a greater amount of amplified fragment of interest was obtained using the combination of the annealing solution containing 500 mM potassium chloride and 8 μM spermidine and Tricine or Bicine buffer. The primer pair, the length of the amplified fragment and the detection sensitivity for the reaction temperature of 52° C. are shown in FIG. 5 and Table 6.

TABLE 6

| Amplification size (bp) | Detection limit |
|---|---|
| 126 | 100 fg |
| 158 | 1 pg |
| 91 | 1 fg |
| 123 | 100 fg |

Figure 5:
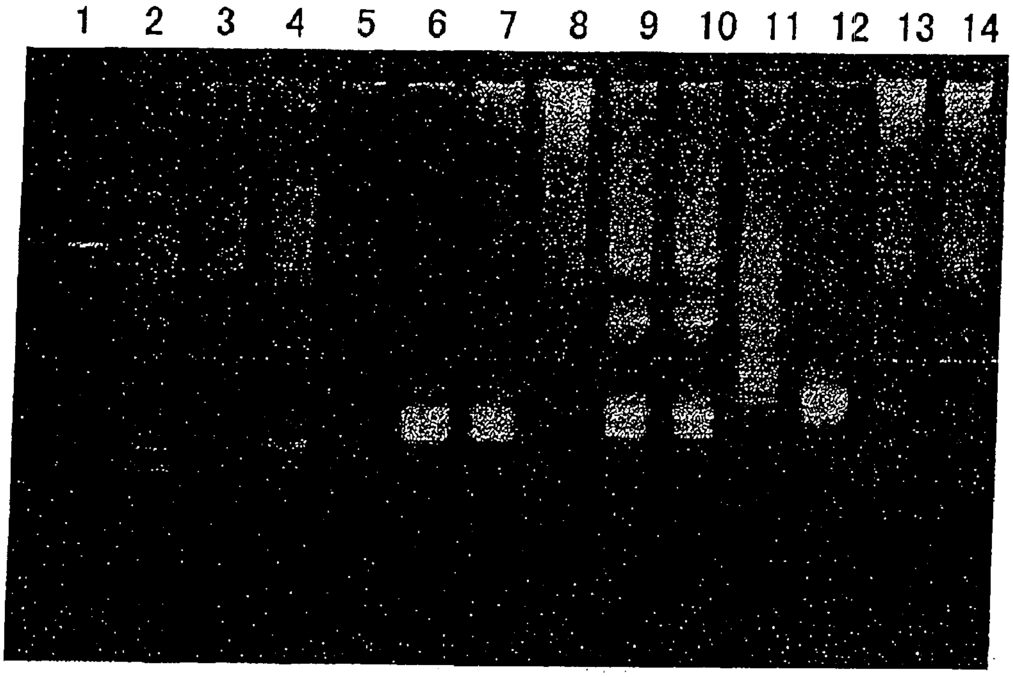
FIG. 5 is a photograph of agarose gel electrophoresis of amplified DNA fragments amplified according to the method of the present invention.

FIG. 5 is a photograph of electrophoresis which shows the relationship between the length of the amplified fragment and the amount of the DNA as the template when an AT-rich region was amplified. Lane 1: molecular weight marker (100 bp ladder); lane 2: amplification of a fragment of 91 bp in length using 1 pg of the template; lane 3: amplification of a fragment of 91 bp in length using 100 fg of the template; lane 4: amplification of a fragment of 91 bp in length using 10 fg of the template; lane 5: amplification of a fragment of 91 bp in length using 1 fg of the template; lane 6: amplification of a fragment of 123 bp in length using 1 pg of the template; lane 7: amplification of a fragment of 123 bp in length using 100 fg of the template; lane 8: amplification of a fragment of 123 bp in length using 10 fg of the template; lane 9: amplification of a fragment of 126 bp in length using 1 $\mu$g of the template; lane 10: amplification of a fragment of 126 bp in length using 100 fg of the template; lane 11: amplification of a fragment of 126 bp in length using 10 fg of the template; lane 12: amplification of a fragment of 158 bp in length using 1 pg of the template; lane 13: amplification of a fragment of 158 bp in length using 100 fg of the template; and lane 14: amplification of a fragment of 158 bp in length using 10 fg of the template.

As shown in FIG. 5 and Table 6, it was demonstrated that good results were yielded by lower the reaction temperature depending on the Tm value of the primer when the method of the present invention was carried out using an AT-rich template and a set of AT-rich primers.

(2) The higher-order structure of the primer may influence the reactivity in the method of the present invention. Then, modification of the primer for avoiding the formation of the higher-order structure of the primer and for making the primer readily anneal to the objective template was examined. Primers represented by SEQ ID NOS:136, 137 and 153–158 were used. Specifically, a primer having a nucleotide sequence represented by SEQ ID NOS:136, primers 120I4, 121I5 and 122I6 which are primers having nucleotide sequences represented by SEQ ID NOS:153 to 155 and having an inosine deoxynucleotide at the fourth, fifth or sixth base from the 3'-terminus, a primer having a nucleotide sequence represented by SEQ ID NO:193, and primers 123I4, 124I5 and 125I6 which are primers having nucleotide sequences represented by SEQ ID NOS:156 to 158 and having an inosine deoxynucleotide at the fourth, fifth or sixth base from the 3'-terminus were used. The DNA as the template as prepared in Example 17 was used in this Example. The reaction was carried out as follows. Briefly, 10 $\mu$l of a mixture containing 50 pmol each of the primers, 2 $\mu$l of 0.05% aqueous solution of propylenediamine, 1 ng to 10 ng of the DNA as the template and sterile distilled water was heated at 98° C. for 2 minutes, cooled to 55° C., and incubated at the temperature for 1 minute using a thermal cycler (GeneAmp PCR System 9600, Applied Biosystems).

After annealing, 0.625 mM each of dNTPs, 42.5 mM Tricine-potassium hydroxide buffer (pH 8.5), 5.0 mM magnesium acetate, 0.0125% BSA, 1.25% DMSO, 30 U of *E. coli* RNase H or 5 U of a heat-resistant RNase H from *Thermus thermophilus* (Tth) (Toyobo, hereinafter referred to as Tth RNase H) and 5.5 U of BcaBEST DNA polymerase were added to the mixture to make the final volume to 50 $\mu$l with sterile water. The reaction mixtures were incubated at 55° C. for 1 hour. After reaction, 5 $\mu$l each of the reaction mixtures was subjected to electrophoresis on 3.0% agarose gel. The results are shown in FIG. 6.

Figure 6:
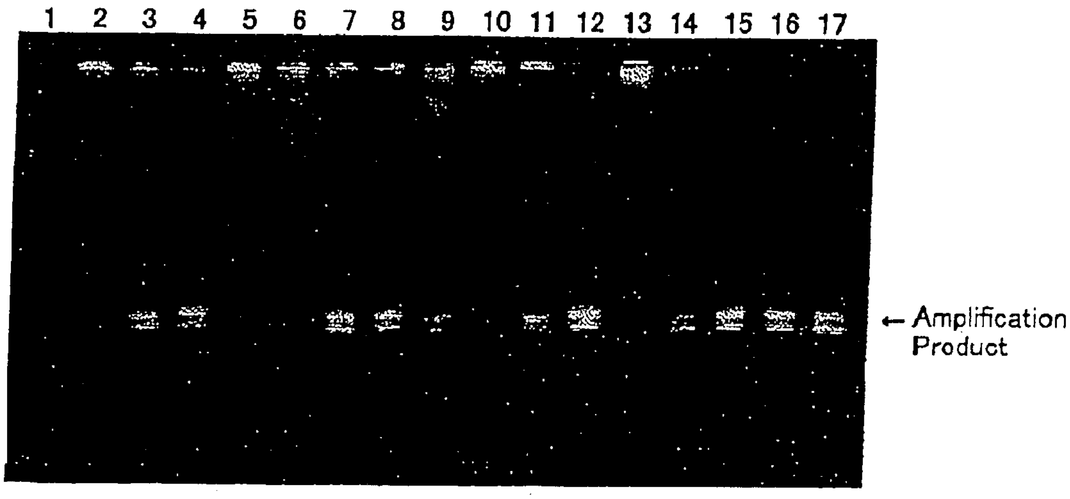
FIG. 6 is a photograph of agarose gel electrophoresis of amplified DNA fragments amplified according to the method of the present invention.

FIG. 6 is a photograph of electrophoresis which shows the effects on chimeric oligonucleotide primers containing inosine deoxynucleotides when *E. coli* RNase H and Tth RNase H were used. Lanes 2 to 9 represent the results obtained using *E. coli* RNase H. Lanes 10 to 17 represent the results obtained using Tth RNase H. Lane 1: molecular weight marker (100 bp ladder); lane 2: a pair of primers represented by SEQ ID NOS:136 and 137, 1 ng of the template; lane 3: a pair of primers 120I4 and 123I4, 1 ng of the template; lane 4: a pair of primers 121I5 and 124I5, 1 ng of the template; lane 5: a pair of primers 122I6 and 125I6, 1 ng of the template; lane 6: a pair of primers represented by SEQ ID NOS:136 and 137, 10 ng of the template; lane 7: a pair of primers 120I4 and 123I4, 10 ng of the template; lane 8: a pair of primers 121I5 and 124I5, 10 ng of the template; lane 9: a pair of primers 122I6 and 125I6, 10 ng of the template; lane 10: a pair of primers represented by SEQ ID NOS:136 and 137, 1 ng of the template; lane 11: a pair of primers 120I4 and 123I4, 1 ng of the template; lane 12: a pair of primers 121I5 and 124I5, 1 ng of the template; lane 13: a pair of primers 1221I6 and 125I6, 1 ng of the template; lane 14: a pair of primers represented by SEQ ID NOS:136 and 137, 10 ng of the template; lane 15: a pair of primers 120I4 and 123I4, 10 ng of the template; lane 16: a pair of primers 121I5 and 124I5, 10 ng of the template; and lane 17: a pair of primers 122I6 and 125I6, 10 ng of the template.

As shown in FIG. 6, when primers having inosines being incorporated at fourth or fifth base from the 3'-termini of the primers were use d , the amplification products of inter est were observed using either of *E. coli* RNase H and the h eat-resistant RNase H from *Thermus thermophilus* regardless of the amount of the template. These results demonstrate that the reactivity of the ICAN is improved by incorporating inosine at an appropriate position.

(3) Primers w ere examined for the same purpose as that in (2) above. Oligonucleotide primers 1S and 4S having nucleotide sequences represented by SEQ ID NOS:173 and 174 in which the three bases at the 3'-terminus were $\alpha$-S (or alpha-thio) ribonucleotides, i.e., which had 5'-phosphothioate bonds in the RNA moieties, were synthesized. In addition, oligonucleotide primers 1N3N3 and 4N3N3 having nucleotide sequences represented by SEQ ID NOS:159 and 160 and having ribonucleotides at the three bases from the 3'-terminus and in a portion of the sequence of the deoxyribonucleotide moiety, i.e., ribonucleotides at eleventh to thirteenth bases from the 3'-terminus of the primer, were synthesized. The template DNA as prepared in Example 17 was used. The reaction was carried out as follows. Briefly, 10 $\mu$l of a mixture containing 50 pmol each of the primers, 2 $\mu$l of 0.05% aqueous solution of propylenediamine, 10 ng of the DNA as the template and sterile water was heated at 98° C. for 2 minutes using a thermal cycler, and then placed on ice for cooling.

After annealing, 40 $\mu$l of a mixture containing 0.625 mM each of dNTPs, 42.5 mM Tricine-potassium hydroxide buffer (pH 8.5), 5.0 mM magnesium acetate, 0.0125% BSA, 1.25% DMSO, 30 U of *E. coli* RNase H or 5 U of Tth RNase H and 5.5 U of BcaBEST DNA polymerase was added to the mixture to make the final volume to 50 $\mu$l with sterile water. The reaction mixtures were incubated at 55° C. for 1 hour in a thermal cycler.

After reaction, 5 $\mu$l each of the reaction mixtures was subjected to electrophoresis on 3.0% agarose gel. As a result, the amplification product was clearly observed at the expected position using the combination of primers 1S and 4S or 1N3N3 and 4N3N3 regardless of the type of the RNase H used. These results confirmed that modification of a primer at its 3'-terminus with 5'-phophothioate was effective for the method of the present invention. Additionally, it was confirmed that substitution with a ribonucleotide at an appropriate internal position in addition to the 3'-terminus of a primer was effective for improving the reactivity of the method of the present invention.

EXAMPLE 20

Use of a DNA polymerase having RNase H activity in the presence of a specific metal ion in the method of the present invention was examined. 10 μl of a mixture containing 120 pmol each of the chimeric oligonucleotide primers used in Example 15(1), 2 μl of an annealing solution containing 500 mM potassium chloride and 8 μM spermidine, 1 ng of the DNA as the template used in Example 15(1) and sterile water was heat-denatured at 98° C. for 2 minutes, and then rapidly cooled on ice to anneal the primers to the template. After annealing, 40 μl of a mixture containing 0.625 mM each of dNTPs, 42.5 mM Tricine-potassium hydroxide buffer (pH 8.5), 5.0 mM magnesium acetate, 0.0125% bovine serum albumin (BSA), 1.0% dimethyl sulfoxide (DMSO) and 11 U of BcaBEST DNA polymerase, and manganese chloride (Nacalai Tesque) at a final concentration of 0.5, 2.5, 5.0 or 10 mM were added to the mixture to make the final volume to 50 μl with sterile water. The reaction mixtures were incubated at 60° C. for 1 hour. In addition, a mixture without the addition of manganese chloride, and a mixture to which 30 U of *E. coli* RNase H was added but manganese chloride was not added were prepared as controls. After reaction, 3 μl each of the reaction mixtures was subjected to electrophoresis on 3.0% agarose gel. The results are shown in FIG. 7.

Figure 7:
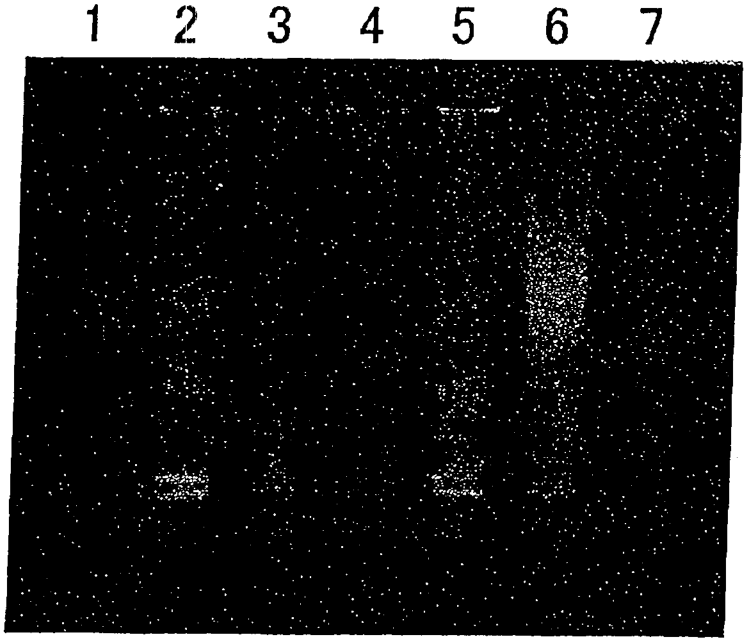
FIG. 7 is a photograph of agarose gel electrophoresis of amplified DNA fragments amplified according to the method of the present invention.

FIG. 7 is a photograph of electrophoresis which shows the results of the ICAN utilizing the RNase H activity of BcaBEST DNA polymerase. Lane 1: molecular weight marker (100 bp ladder); lane 2: without the addition of manganese chloride/with the addition of *E. coli* RNase H; lane 3: without the addition of manganese chloride/without the addition of *E. coli* RNase H; lane 4: with the addition of 0.5 mM manganese chloride/without the addition of *E. coli* RNase H; lane 5: with the addition of 2.5 mM manganese chloride/without the addition of *E. coli* RNase H; lane 6: with the addition of 5.0 mM manganese chloride/without the addition of *E. coli* RNase H; and lane 7: with the addition of 10.0 mM manganese chloride/without the addition of *E. coli* RNase H.

As shown in FIG. 7, the amplification product of interest was observed for a reaction system to which manganese chloride was added at a concentration of 2.5 mM in the absence of *E. coli* RNase H.

EXAMPLE 21

The method of the present invention was examined using a practical biological sample.

(1) Detection was carried out using a hot water-extract prepared from a culture of enterohemorrhagic *Escherichia coli* O-157 (ATCC accession number 43895) as a template. Enterohemorrhagic *Escherichia coli* O-157 was cultured in mEC medium containing novobiocin at 42° C. for 18 hours, and then heated at 95° C. for 10 minutes. Hot water-extracts of O-157 corresponding to 0, 1, 10, $10^2$, $10^3$, $10^4$ or $10^5$ cells were prepared by diluting the extract with sterile water. Vero toxin 2 (VT2) gene was amplified using one of these hot water-extracts of O-157 under the same conditions as those in Example 18(1). In addition, a PCR was carried out using the same template under the conditions as described in Example 18(1) as a control. After reaction, 1 μl (ICAN) or 5 μl (PCR) each of the reaction mixtures was subjected to electrophoresis on 3.0% agarose gel. The results are shown in Table 7 and FIG. 8.

TABLE 7

| Amplification size (bp) | Detection limit (cells) |
|---|---|
| ICAN (total time: 70 minutes) | |
| 135 | $10^2$ |
| 173 | $10^3$ |
| PCR (25 cycles; total time: about 66 minutes) | |
| 135 | $10^3$ |
| PCR (30 cycles; total time: about 80 minutes) | |
| 135 | $10^2$ |

Figure 8:
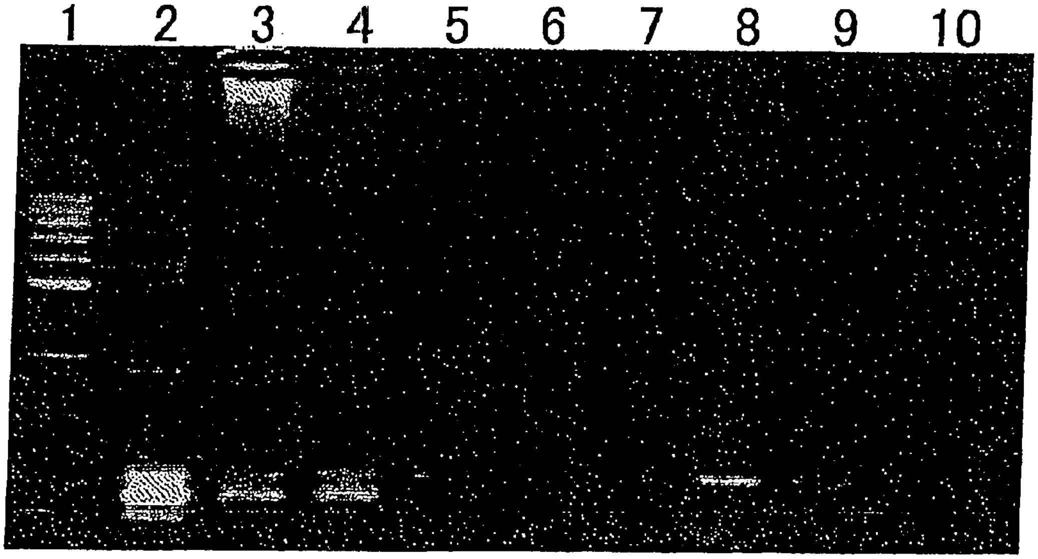
FIG. 8 is a photograph of agarose gel electrophoresis of amplified DNA fragments amplified according to the method of the present invention.

FIG. 8 is a photograph of electrophoresis which shows the detection of *Escherichia coli* O157 using ICAN or PCR. The chain length to be amplified was 135 bp. Lane 1: molecular weight marker (100 bp ladder); lane 2: ICAN for $10^4$ cells; lane 3: ICAN for $10^3$ cells; lane 4: ICAN for $10^2$ cells; lane 5: PCR of 25 cycles for $10^4$ cells; lane 6: PCR of 25 cycles for $10^3$ cells; lane 7: PCR of 25 cycles for $10^2$ cells; lane 8: PCR of 30 cycles for $10^4$ cells; lane 9: PCR of 30 cycles for $10^3$ cells; and lane 10: PCR of 30 cycles for $10^2$ cells.

As shown in Table 7 and FIG. 8, it was confirmed that the detection sensitivity of the detection method of the present invention was equivalent to that of the PCR, and that the method of the present invention required shorter time for detection as compared with that required for the PCR.

(2) λ DNA was detected using the primers represented by SEQ ID NOS:129 and 145 used in Examples 15 and 17. The reaction was carried out as follows. Briefly, 10 μl of a mixture containing 120 pmol each of the primers, 2 μl of an annealing solution containing 500 mM potassium chloride and 8 μM spermidine, 10 fg to 1 ng of λ DNA (Takara Shuzo) and sterile water was prepared. The mixture was heat-denatured at 98° C. for 2 minutes, and then rapidly cooled on ice to anneal the primers to the template.

After annealing, 40 μl of a mixture containing 0.625 mM each of dNTPs, 42.5 mM Tricine-potassium hydroxide buffer (pH 8.5), 5.0 mM magnesium acetate, 0.0125% bovine serum albumin (BSA), 1.25% dimethyl sulfoxide (DMSO), 30 U of *E. coli* RNase H and 11 U of BcaBEST DNA polymerase was added to the mixture to make the final volume to 50 μl with sterile water. The reaction mixtures were incubated at 60° C. for 1 hour. After reaction, 3 μl each of the reaction mixtures was subjected to electrophoresis on 3.0% agarose gel. The results are shown in Table 8.

TABLE 8

| Amplification size (bp) | Detection limit |
|---|---|
| 125 | 1 pg |

As shown in Table 8, it was confirmed that the method of the present invention was effective in detecting λ DNA.

(3) Detection was carried out using a genomic DNA from a bacterium *Flavobacterium* sp. SA-0082 as a template and the primers represented by SEQ ID NOS:150 and 151 used in Example 19(1). The genomic DNA as a template was prepared according to a conventional method from the bacterium of genus *Flavobacterium* cultured as described in WO 97/32010. The reaction was carried out as follows. Briefly, 10 μl of a mixture containing 120 pmol each of the primers, 2 μl of an annealing solution containing 500 mM potassium chloride and 8 μM spermidine, 10 fg to 1 ng of the genomic DNA and sterile water was prepared. The mixture was heat-denatured at 98° C. for 2 minutes, and then rapidly cooled on ice to anneal the primers to the template.

After annealing, 40 μl of a mixture containing 0.625 mM each of dNTPs, 42.5 mM Tricine-potassium hydroxide buffer (pH 8.5), 5.0 mM magnesium acetate, 0.0125% BSA, 1.25% DMSO, 30 U of *E. coli* RNase H and 11 U of BcaBEST DNA polymerase was added to the mixture to make the final volume to 50 μl with sterile water. The reaction mixtures were incubated at 52° C. for 1 hour. After reaction, 3 μl each of the reaction mixtures was subjected to electrophoresis on 3.0% agarose gel. The results are shown in Table 9 and FIG. 9.

TABLE 9

| Amplification size (bp) | Detection limit |
|---|---|
| 91 | 100 fg |

Figure 9:
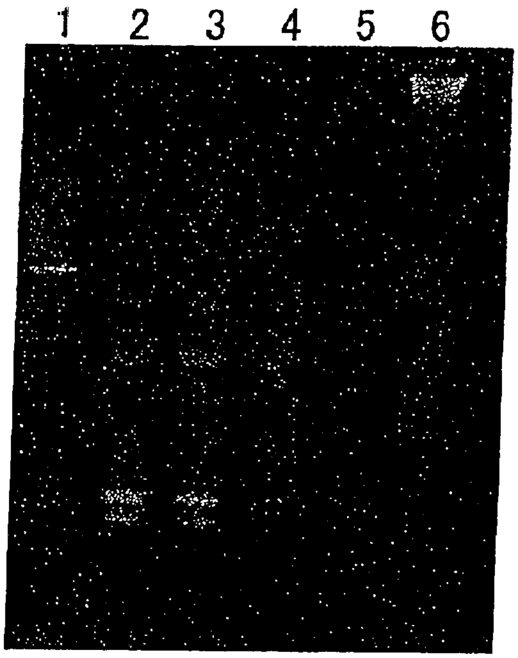
FIG. 9 is a photograph of agarose gel electrophoresis of amplified DNA fragments amplified according to the method of the present invention.

FIG. 9 is a photograph of electrophoresis which shows the detection of a bacterium of genus *Flavobacterium*. Lane 1: molecular weight marker (100 bp ladder); lane 2: 1 ng of the template; lane 3: 10 pg of the template; lane 4: 1 pg of the template; lane 5: 100 fg of the template; and lane 6: 10 fg of the temp late.

As shown in Table 9 and FIG. 9, it was confirmed that the method of the present invention was effective in detecting a bacterium.

EXAMPLE 22

A method for detecting a target nucleic acid in which the amplification method of the present invention and a hybridization method were combined was examined. Enterohemorrhagic *Escherichia coli* O-157 was selected as a target. The DNA as the template was prepared as described in Example 21(1). A region of about 100 bp having a GC content of about 40% was selected as a fragment to be amplified. Primers VT2-IF20 and VT2-IR20-2 having nucleotide sequences represented by SEQ ID NOS:140 and 161 were used as primers. The reaction was carried out as follows. Briefly, 10 μl of a mixture containing 50 pmol each of the primers VT2-IF20 and VT2-IR20-2, an annealing solution containing propylenediamine at a final concentration of 0.01%, one of the hot water-extracts corresponding to 0 to $10^4$ cells and sterile water was prepared. The mixture was heat-denatured at 98° C. for 2 minutes, cooled to 55° C. and incubated at the temperature for 1 minute in Thermal Cycler Personal (Takara Shuzo), and then placed on ice for annealing.

Figure 28:
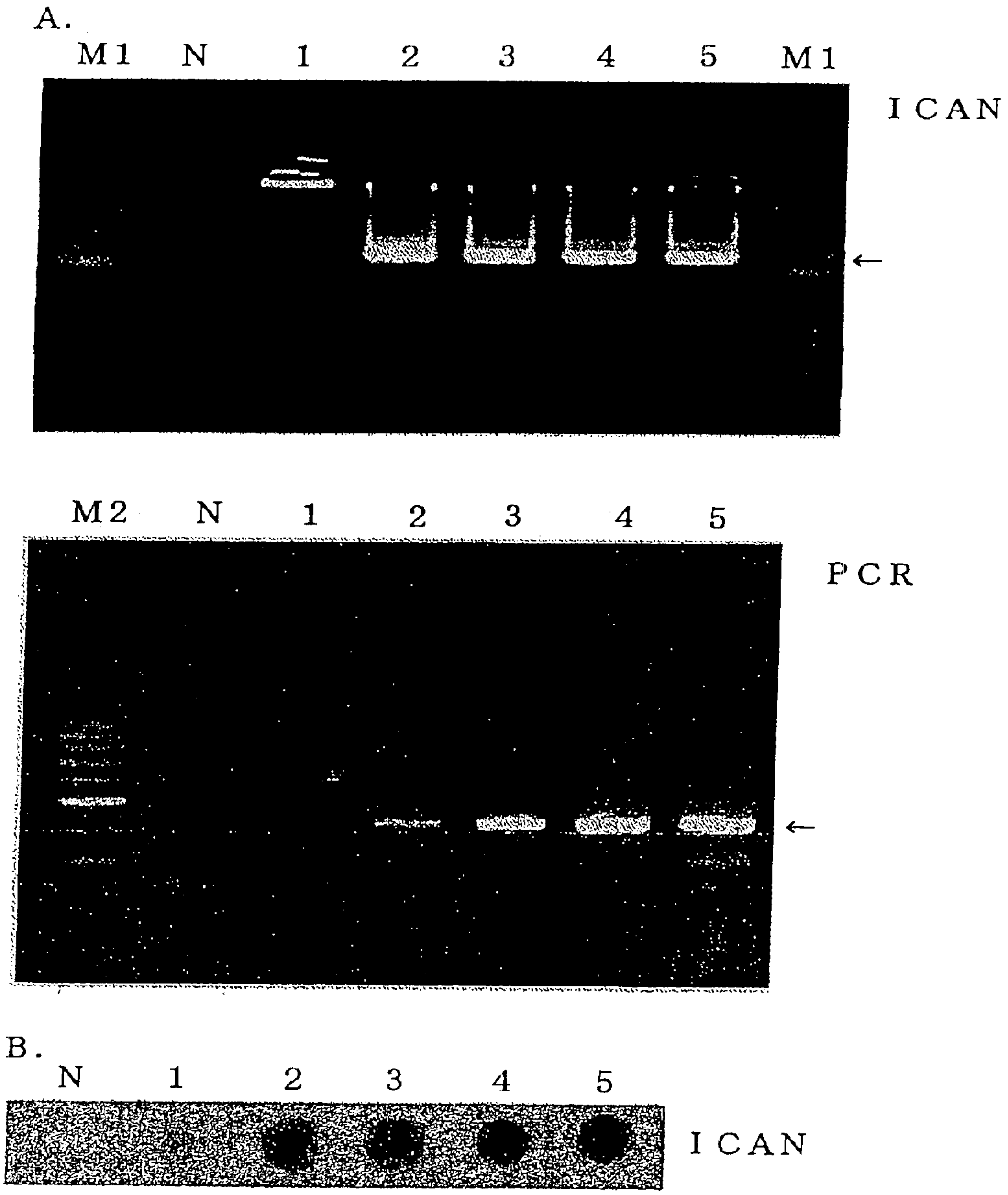
FIG. 28 is a photograph of agarose gel electrophoresis of amplified DNA fragments amplified according to the method of the present invention and the results of dot blot hybridization.

After annealing, at final concentrations, 20 mM HEPES-potassium hydroxide buffer (pH 7.8), 100 mM potassium acetate, 1% dimethyl sulfoxide (DMSO), 0.01% bovine serum albumin (BSA), 4 mM magnesium acetate, 500 μM each of dNTPs, 30 U of *E. coli* RNase H and 5.5 U of BcaBEST DNA polymerase was added to the mixture to make the final volume to 50 μl with sterile water. The reaction mixtures were placed on Thermal Cycler Personal which had been set at 55° C. and incubated at the temperature for 60 minutes. As a control, a PCR was carried out using O-157 Typing Set (Takara Shuzo) according to the manual using Thermal Cycler Personal. The PCR was carried out as follows: 35 cycles of 94° C. for 1 minute, 55° C. for 1 minute and 72° C. for 1 minute. This reaction required about 4 minutes per cycle and a total time of about 145 minutes. The expected size of the amplification product was 404 bp. After reaction, 3 μl each of the reaction mixtures was subjected to electrophoresis on 3% NuSieve 3:1 agarose. The results are shown in FIG. 28A. FIG. 28A shows the results of electrophoresis for the detection of enterohemorrhagic *Escherichia coli* O157 vero toxin II gene using the ICAN or the PCR. Lane M1: molecular weight marker (50–2000 bp); lane M2: molecular weight marker (100 bp ladder); lane N: negative control; lane 1: the template corresponding to 1 cell; lane 2: the template corresponding to 10 cells; lane 3: the template corresponding to $10^2$ cells; lane 4: the template corresponding to $10^3$ cells; and lane 5: the template corresponding to $10^4$ cells. Furthermore, results of comparison between the amplification levels accomplished by the ICAN and the PCR for 1 cell or 10 cells are shown in Table 10.

TABLE 10

| | Number of *E. coli* O-157 cells | | |
|---|---|---|---|
| | 0 | 1 | 10 |
| ICAN | − | + | +++ |
| PCR | − | + | ++ |

−: no amplification
+ to +++ indicate the degree of amplification in three grades.

As shown in FIG. 28A and Table 10, the amplification products of interest were obtained for the reaction systems using a hot water-extract corresponding to 1 cell according to both the detection method of the present invention and the PCR. Dot blot hybridization was further carried out for the amplification product obtained according to the ICAN using an oligonucleotide VT2 having a nucleotide sequence represented by SEQ ID NO:162 labeled with biotin at the 5'-terminus as a probe. Hybridization was carried out under as follows. Briefly, 1 μl of a reaction mixture was denatured at 98° C. for 5 minutes, rapidly cooled on ice, and spotted onto Hybond-N membrane (Amersham Pharmacia Biotech). After exposure to UV, the membrane was placed in a hybridization bag. 10 ml of a hybridization solution containing 0.5 M disodium hydrogenphosphate (pH 7.2), 1 mM ethylenediaminetetraacetic acid and 7% sodium lauryl sulfate was added thereto. Pre-hybridization was then carried out at 42° C. for 30 minutes. 10 μl of the solution of the VT2 probe at a concentration of 100 ng/μl was heat-denatured and added to the pre-hybridization reaction system. After hybridization at 42° C. for 60 minutes, the membrane was washed twice in a solution containing 66.6 mM sodium chloride, 66.6 mM sodium citrate and 0.1% sodium lauryl sulfate at room temperature for 5 minutes, incubated in 6 ml of a washing buffer (0.3 M sodium chloride, 17.3 mM disodium hydrogenphosphate dihydrate, 2.5 mM EDTA, 0.1% sodium lauryl sulfate) to which 2 μl of 5 mg/ml horseradish peroxidase streptoavidin conjugate (PIERCE) was added at 42° C. for 12 minutes, and then washed twice in the washing buffer at room temperature. The membrane was then washed in 10 ml of 0.1 M citrate buffer (pH 5.0) at room temperature and reacted in a mixture of 5 ml of 0.1 M citrate buffer, 5 μl of 3% hydrogen peroxide and 250 μl of a solution of 2 mg/ml tetramethylbenzidine (TMB, Nacalai Tesque) in ethanol in the dark for about 10 minutes. After color development, the reaction was terminated with deionized water. The results are shown in FIG. 28B. FIG. 28B shows the results of dot blot hybridization for detecting a gene for vero toxin II from enterohemorrhagic *Escherichia coli* O-157 by the ICAN. The results were consistent with those obtained for the above-mentioned electrophoresis. Thus, the detection sensitivity of the method of the present invention was equivalent to that of the PCR. The total time required for the amplification reaction using the ICAN of the present invention was 1/2 or shorter as compared with that required for the PCR. Thus, the ICAN of the present invention was confirmed to be effective as a method for detecting a pathogen and the like.

EXAMPLE 23

(1) Combination of a reverse transcription reaction and the method of the preset invention was examined using an RNA from cultured cells as a template. The reaction was carried out as follows. Briefly, RAW264.7 cells (ATCC TIB 71) were suspended in Dulbecco's modified Eagle's medium (Bio Whittaker, 12-604F) containing 10% fetal calf serum (Gibco) at a concentration of $1.5\times10^5$ cells/ml. 5 ml of the suspension was added to each well of a 6-well microtiter plate and the plate was incubated at 37° C. overnight in the presence of 5% $CO_2$. 50 $\mu$l of a 100 $\mu$g/ml solution of lipopolysaccharide (LPS, Sigma) in water and 50 $\mu$l of a 1000 U/$\mu$l solution of interferon-γ (IFN-γ, Genzyme Techne) in water were added to the well. The plate was incubated for additional 4 hours. An RNA was then prepared from the cells using RNeasy Mini Kit (Qiagen) according to the instructions attached to the kit. As a negative control, a group to which LPS or IFN-γ was not added was provided.

A cDNA was prepared by incubating 60 $\mu$l of a mixture containing 3 pg of the thus prepared RNA, 10 mM tris-hydrochloride buffer (pH 8.3), 50 mM KCl, 5 mM $MgCl_2$, 1 mM each of dNTPs, 150 pmol of random 6 mers primer, 60 U of ribonuclease inhibitor (Takara Shuzo) and 15 U of Reverse Transcriptase XL (AMV) (Takara Shuzo, 2620A) at 30° C. for 10 minutes, 42° C. for 1 hour and then 99° C. for 5 minutes for inactivating the enzyme using a thermal cycler (GeneAmp PCR System 9600, Applied Biosystems).

Primers having nucleotide sequences represented by SEQ ID NOS:163 and 164 were synthesized based on the nucleotide sequence of the mRNA for mouse inducible NO synthase (iNOS) (GeneBank accession no. NM-010927). As a control, primers for PCR represented by SEQ ID NOS:165 and 166 were also synthesized.

10 $\mu$l of a mixture containing 50 pmol each of the primers, 2 $\mu$l of an aqueous solution of propylenediamine at a concentration of 0.05%, 1 $\mu$l of the cDNA as a template (corresponding to 50 ng of the RNA) and sterile water was prepared. The mixture was heat-denatured at 98° C. for 2 minutes, cooled to 55° C. and incubated at the temperature for 1 minute in a thermal cycler to anneal the primers to the template.

After annealing, 40 $\mu$l of a mixture containing 0.625 mM each of dNTPs, 42.5 mM Tricine-potassium hydroxide buffer (pH 8.5), 5.0 mM magnesium acetate, 0.0125% bovine serum albumin (BSA), 1.25% dimethyl sulfoxide (DMSO), 15 U of *E. coli* RNase H and 11 U of BcaBEST DNA polymerase was added to the mixture to make the final volume to 50 $\mu$l with sterile water. The reaction mixtures were incubated at 55° C. for 1 hour in a thermal cycler. The reacted samples were stored by freezing at −20° C. until being analyzed. The PCR as a control was carried out as follows. Briefly, 50 $\mu$l of a reaction mixture containing 50 pmol each of the primers, 1 $\mu$l of the cDNA (corresponding to 50 ng of the RNA), 5 $\mu$l of 10×Ex Taq buffer (Takara Shuzo), 1.25 U of TaKaRa Ex Taq DNA polymerase (Takara Shuzo) and 0.2 mM each of dNTPs was reacted in a thermal cycler. The program was as follows: 1 cycle of 94° C. for 2 minutes; 30 cycles of 94° C. for 30 seconds, 55° C. for 30 seconds and 72° C. for 30 seconds; and 1 cycle of 72° C. for 5 minutes. The reacted samples were stored by freezing at −20° C. until being analyzed. After reaction, 5 $\mu$l each of the reaction mixtures was subjected to electrophoresis on 3.0% agarose gel. The results are shown in FIG. 10.

Figure 10:
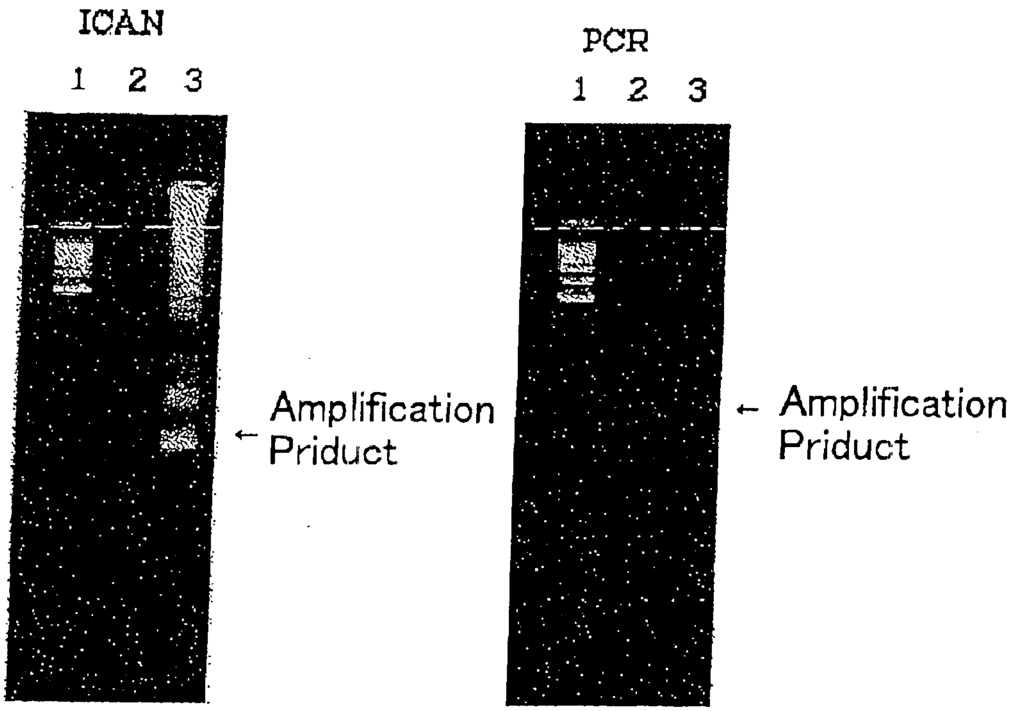
FIG. 10 is a photograph of agarose gel electrophoresis of amplified DNA fragments amplified according to the method of the present invention.

FIG. 10 is a photograph of electrophoresis which shows the comparison between the RT-ICAN and the RT-PCR. Lane 1: molecular weight marker (100 bp ladder); lane 2: negative control group; and lane 3: a group treated with LPS and IFN-γ.

As shown in FIG. 10, the amplification products were observed for both of the method of the present invention and the PCR only when the cDNA prepared from cells treated with LPS and IFN-γ was used as a template. Thus, it was confirmed that, since the method of the present invention required a shorter period of time for reaction as compared with the PCR, the method of the present invention was more effective as a DNA amplification method after reverse transcription.

EXAMPLE 24

*E. coli* RNase H of which the optimal temperature is 37° C. may become inactivated during amplification reaction of the present invention. Then, the effect of addition of *E. coli* RNase H to the reaction mixture during the amplification reaction was examined. An amplified fragment (1071 bp) obtained by a PCR using primers GMO-PCR-F and GMO-PCR-R represented by SEQ ID NOS:167 and 168 from a genomic DNA extracted from recombinant soybeans into which cauliflower mosaic virus 35S promoter and EPSPS gene had been introduced was used as a template DNA. In addition, primers GMO-S1, S2, A1 and A2 having nucleotide sequences represented by SEQ ID NOS:169 to 172 were used. The reaction was carried out as follows. Briefly, 10 $\mu$l of a mixture containing 50 pmol each of the primers, propylenediamine at a final concentration of 0.01%, 1 pg to 10 ng of the DNA as the template and sterile water was prepared. The mixture was heat-denatured at 98° C. for 2 minutes and cooled to 55° C. for annealing.

After annealing, at final concentrations, 500 $\mu$M each of dNTPs, 34 mM Tricine-potassium hydroxide buffer (pH 8.7), 4.0 mM magnesium acetate, 0.01% bovine serum albumin (BSA), 1% dimethyl sulfoxide (DMSO), 30 U of *E. coli* RNase H and 5.5 U of BcaBEST DNA polymerase were added to the mixture to make the final volume to 50 $\mu$l with sterile water. The reaction mixtures were incubated at 55° C. for 25 minutes in a thermal cycler. 30 U of *E. coli* RNase H was further added thereto 25 minutes after the initiation of the reaction. The mixture was incubated at 55° C. for 30 minutes. As a control, a reaction was carried out by incubating the mixture at 55° C. for 55 minutes. After reaction, 3 $\mu$l each of the reaction mixtures was subjected to electrophoresis on 3% agarose. As a result, it was confirmed that the amplification efficiency was improved by the addition of *E. coli* RNase H during the reaction regardless of the concentration of the template DNA for either of the combinations of the primers, S1/A1, S1/A2, S2/A1 and S2/A2.

EXAMPLE 25

The combination of a method for amplifying or duplicating a nucleic acid to be used as a template in the present invention and the method of the present invention was examined. The reaction was carried out as follows. Briefly, in vitro transcription was carried out using a plasmid containing the chrysanthemum viroid gene as prepared in Example 18(3) which was duplicated in *Escherichia coli* as a template and T7 RNA polymerase (Takara Shuzo) to obtain a fragment duplicated from an RNA. A cDNA was synthesized using primers having nucleotide sequences represented by SEQ ID NOS:146 and 147 and cDNA synthesis kit (Takara Shuzo). An amplification reaction was carried out as described in Example 18(3) using the cDNA fragment or the duplicated plasmid as a template. As a result, it was confirmed that both a nucleic acid duplicated in a form of a plasmid and a nucleic acid in a form of a cDNA duplicated from an RNA using an RNA polymerase can be used as templates for the method of the present invention.

EXAMPLE 26

(1) Synthesis of Primer

Oligonucleotide primers NS1 and NS2 represented by SEQ ID NOS:175 and 176 were synthesized on the basis of the nucleotide sequence of the mRNA for mouse inducible NO synthase (iNOS).

Figure 11:
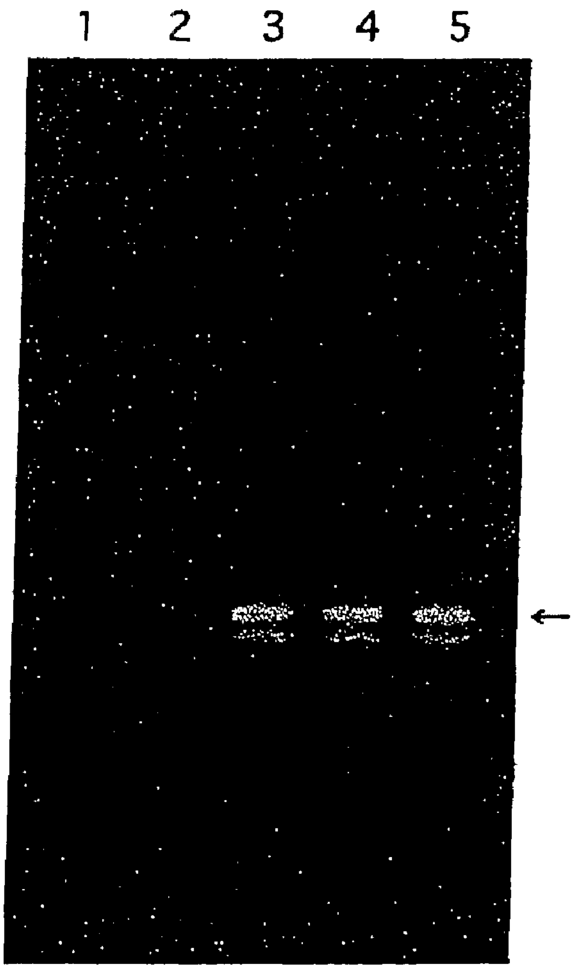
FIG. 11 is a photograph of agarose gel electrophoresis of amplified DNA fragments amplified according to the method of the present invention.

(2) Amplification of DNA Fragment According to ICAN Using PCR Product as Template 10 μl of a mixture containing 50 pmol each of the synthetic oligonucleotide primers, 2 μl of a 0.05% aqueous solution of propylenediamine and 10 fg to 10 pg of the template was heated at 98° C. for 2 minutes and then 60° C. for 2 minutes using a thermal cycler (GeneAmp PCR System 9600, Applied Biosystems) to anneal the primers to the template. iNOS cDNA (741 bp) amplified using primers NS-PCR1 and NS-PCR2 represented by SEQ ID NOS:221 and 222, which was then purified using Suprec02 (Takara Shuzo), was used as the DNA as the template. 40 μl of a reaction mixture containing 0.625 mM each of dNTPs, 40 mM HEPES-potassium hydroxide buffer (pH 7.8), 125 mM potassium acetate, 5.0 mM magnesium acetate, 0.0125% bovine serum albumin, 1.25% dimethyl sulfoxide, 0.0156 μg of Pfu RNase H and 0.66 U of BcaBEST DNA polymerase was added to the heated solution. The mixtures were at incubated at 60° C. for 1 hour in a thermal cycler. 5 μl each of the reaction mixtures was analyzed by electrophoresis on 3.0% agarose gel. The results are shown in FIG. 11. FIG. 11 represents the results of the ICAN using Pfu RNase H. Lane 1: molecular weight marker (100 bp); lane 2: 10 fg of the template; lane 3: 100 fg of the template; lane 4: 1 pg of the template; and lane 5: 10 μg of the template.

As shown in FIG. 11, the amplification product of interest was observed using 100 fg of the template.

EXAMPLE 27

(1) Preparation of RNA

RAW264.7 cells (ATCC TIB 71) were suspended in Dulbecco's modified Eagle's medium (Bio Whittaker) containing 10% fetal calf serum (Gibco) at a concentration of $1.5 \times 10^5$ cells/ml. 5 ml of the suspension was added to each well of a 6-well microtiter plate and the plate was incubated at 37° C. overnight in the presence of 5% $CO_2$. 50 μl of a 100 μg/ml solution of lipopolysaccharide (LPS, Sigma) in water and 50 μl of a 1000 U/ml solution of interferon-γ (IFN-γ, Genzyme Techne) in water were added to the well. The plate was incubated for additional 4 hours. An RNA was then prepared from the cells using RNeasy Mini Kit (Qiagen, 74104) according to the instructions attached to the kit. As a negative control, a group to which LPS or IFN-γ was not added was provided.

A cDNA was prepared by incubating 60 μl of a mixture containing 3 pg of the thus prepared RNA, 10 mM tris-hydrochloride buffer (pH 8.3), 50 mM KCl, 5 mM $MgCl_2$, 1 mM each of dNTPs, 150 pmol of random 6 mers, 60 U of Ribonuclease Inhibitor (Takara Shuzo) and 15 U of Reverse Transcriptase XL (AMV) (Takara Shuzo) at 30° C. for 10 minutes, 42° C. for 1 hour and then 99° C. for 5 minutes for inactivating the enzyme using a thermal cycler (GeneAmp PCR System 9600, Applied Biosystems).

Primers NS5 and NS6 having nucleotide sequences represented by SEQ ID NOS:181 and 182 were synthesized based on the nucleotide sequence of the mRNA for mouse inducible NO synthase (iNOS). Furthermore, primers NS3 and NS4 for PCR represented by SEQ ID NOS:177 and 178 were also synthesized.

50 μl of a mixture containing 50 pmol each of the primers NS5 and NS6, 1 μl of the cDNA solution synthesized as described above (corresponding to 50 ng of the RNA) or a 10-, 100-, 1000- or 10000-fold dilution with water thereof as a template, 0.5 mM each of dNTPs, 32 mM HEPES-potassium hydroxide buffer (pH 7.8), 100 mM potassium acetate, 4.0 mM magnesium acetate, 0.01% bovine serum albumin, 1% dimethyl sulfoxide, 0.0156 μg of Pfu RNase H and 0.66 U of BcaBEST DNA polymerase was incubated at 60° C. for 1 hour in a thermal cycler. The reacted samples were stored by freezing at −20° C. until being analyzed.

On the other hand, a PCR was carried out as a control. 50 μl of a reaction system containing 50 pmol each of the primers NS3 and NS4, 1 μl of the cDNA solution (corresponding to 50 ng of the RNA) or a 10-, 100-, 1000- or 10000-fold dilution with water thereof, 5 μl of 10×Ex Taq buffer (Takara Shuzo), 1.25 U of TaKaRa Ex Taq polymerase (Takara Shuzo) and 0.2 mM each of dNTPs was reacted using a thermal cycler. The program was as follows: 1 cycle of 94° C. for 2 minutes; 35 cycles of 94° C. for 30 seconds, 55° C. for 30 seconds and 72° C. for 30 seconds; and 1 cycle of 72° C. for 5 minutes. The reacted samples were stored by freezing at −20° C. until being analyzed.

Figure 12:
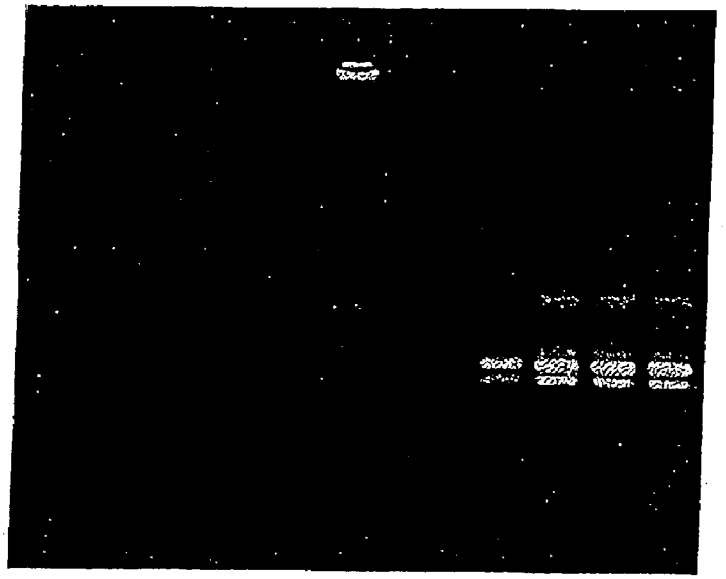
FIG. 12 is a photograph of agarose gel electrophoresis of amplified DNA fragments amplified according to the method of the present invention.
Figure 12:
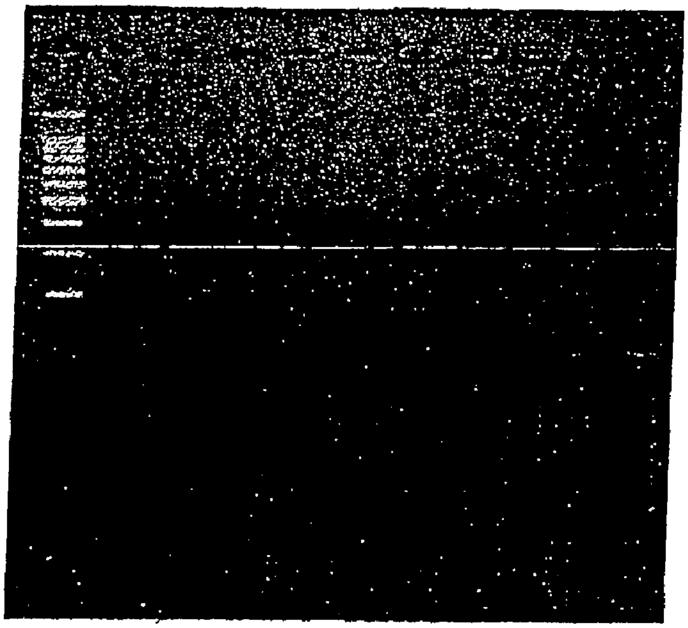

5 μl each of the reaction mixtures (ICAN or PCR) was analyzed by electrophoresis on 3.0% agarose gel. The results are shown in FIG. 12. FIG. 12 shows the results of the detection of iNOS gene according to the ICAN using Pfu RNase H or the PCR. Lane 1: a lane for 100 bp DNA ladder marker; lane 2: the 10000-fold dilution of the negative control cDNA; lane 3: the 1000-fold dilution of the negative control cDNA; lane 4: the 100-fold dilution of the negative control cDNA; lane 5: the 10-fold dilution of the negative control cDNA; lane 6: the original solution of the negative control cDNA; lane 7: the 10000-fold dilution of the cDNA from the group with the addition of LPS and IFN-γ; lane 8: the 1000-fold dilution of the cDNA from the group with the addition of LPS and IFN-γ; lane 9: the 100-fold dilution of the cDNA from the group with the addition of LPS and IFN-γ; lane 10: the 10-fold dilution of the cDNA from the group with the addition of LPS and IFN-γ; and lane 11: the original solution of the cDNA from the group with the addition of LPS and IFN-γ.

As shown in FIG. 12, the amplification products were observed for both of the ICAN and the PCR only when the cDNA prepared from cells treated with LPS and IFN-γ was used as a template. For the ICAN, the increase in amplification product was observed using the 1000-fold dilution of the cDNA. For the PCR, the increase in amplification product was observed using the 100-fold dilution of the cDNA.

EXAMPLE 28

(1) Oligonucleotide primers 4 and 5 represented by SEQ ID NOS:179 and 180 were synthesized based on the nucleotide sequence of λ DNA. The oligonucleotide primer 4 is a sense primer having 75% of a GC content. The oligonucleotide primer 5 is an antisense primer having 80% of a GC content.

10 $\mu$l of a reaction system containing 120 pmol each of the primers 4 and 5, 2 $\mu$l of a 0.05% propylenediamine solution and 10 ng of a template was heat-denatured at 98° C. for 2 minutes, and then rapidly cooled on ice to anneal the primers to the template. The PCR product (1005 bp) purified using Suprec02 as described in Example 15 was used as the template.

Figure 13:
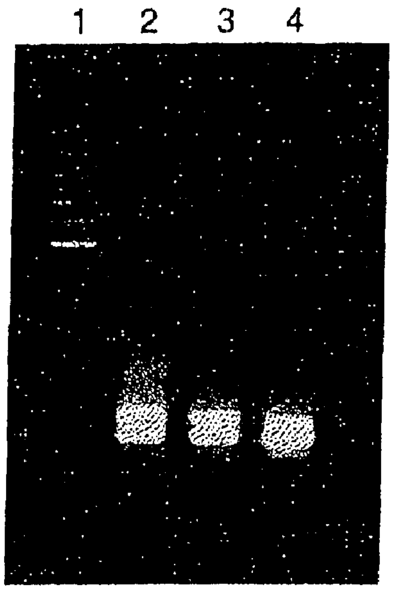
FIG. 13 is a photograph of agarose gel electrophoresis of amplified DNA fragments amplified according to the method of the present invention.

(2) After annealing, 40 $\mu$l of a mixture containing 0.625 mM each of dNTPs, 42.5 mM Bicine-potassium hydroxide buffer (pH 8.3), 5.0 mM magnesium acetate, 0.0125% bovine serum albumin, 1.25% dimethyl sulfoxide, 0.5 $\mu$l of *Thermotoga maritima* RNase HII (0.58 $\mu$g/ml) and 2.2 U of BcaBEST DNA polymerase was added to the mixture to carry out the ICAN at 60, 65 or 70° C. for 1 hour. 3 $\mu$l each of the reaction mixtures after the ICAN was confirmed by electrophoresis on 3.0% agarose gel. The results are shown in FIG. 13. FIG. 13 shows the results of the ICAN using *Thermotoga maritima* RNase HII. Lane 1: molecular weight marker (100 bp); lane 2: reaction temperature of 60° C.; lane 3: reaction temperature of 65° C.; and lane 4: reaction temperature of 70° C.

As shown in FIG. 13, the amplification products of interest were observed for the respective reaction temperatures.

EXAMPLE 29

Figure 14:
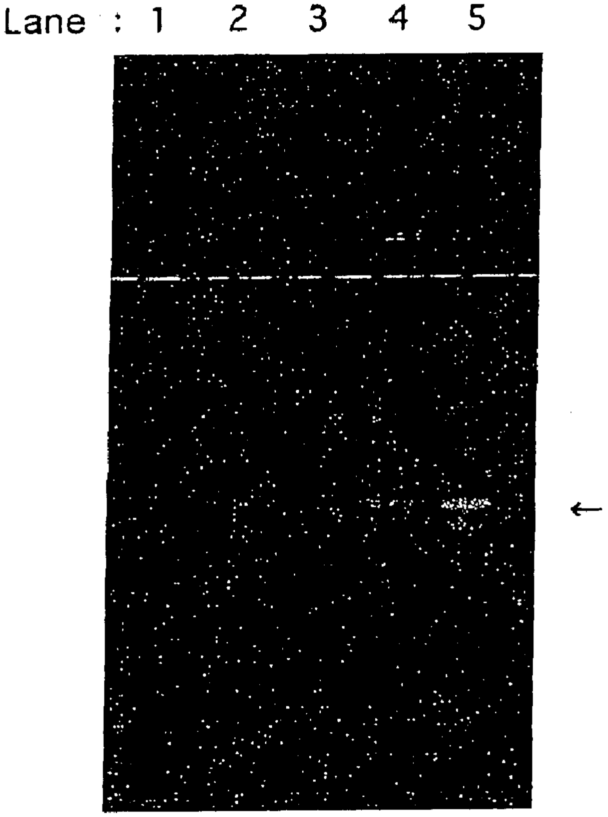
FIG. 14 is a photograph of agarose gel electrophoresis of amplified DNA fragments amplified according to the method of the present invention.

(1) Amplification of a DNA fragment according to the ICAN using a PCR product as a template (alkali-denatured) was examined. 1 $\mu$l of a solution containing 10 fg to 10 pg of a template and 1 $\mu$l of 0.4 N NaOH were mixed together. The mixture was incubated at 37° C. for 5 minutes to denature the template. The PCR-amplified iNOS cDNA (741 bp) purified using Suprec02 (Takara Shuzo) as described in Example 26 was used as a template. Each of the denatured templates was neutralized using 1 $\mu$l of 0.4 N HCl. 47 $\mu$l of a reaction mixture containing 50 pmol each of the primers NS1 and NS2, 0.5 mM each of dNTPs, 32 mM HEPES-potassium hydroxide buffer (pH 7.8), 100 mM potassium acetate, 4.0 mM magnesium acetate, 0.01% bovine serum albumin, 1.0% dimethyl sulfoxide, 0.0156 $\mu$g of Pfu RNase H and 0.66 U of BcaBEST DNA polymerase was then added thereto. The mixture was incubated at 60° C. for 1 hour in a thermal cycler. 5 $\mu$l each of the reaction mixtures was analyzed by electrophoresis on 3.0% agarose gel. The results are shown in FIG. 14. FIG. 14 shows the results of the ICAN using an alkali-denatured template. Lane 1: molecular weight marker (100 bp); lane 2: 10 fg of the template; lane 3: 100 fg of the template; lane 4: 1 pg of the template; and lane 5: 10 pg of the template.

As shown in FIG. 14, the amplification product was clearly increased using 1 pg of the template.

EXAMPLE 30

(1) Amplification of a DNA fragment according to the ICAN without denaturing a template was examined. Primers NS5 and NS6 represented by SEQ ID NOS:181 and 182 were used as primers. The template as prepared in Example 26 was used as a template DNA.

Figure 15:
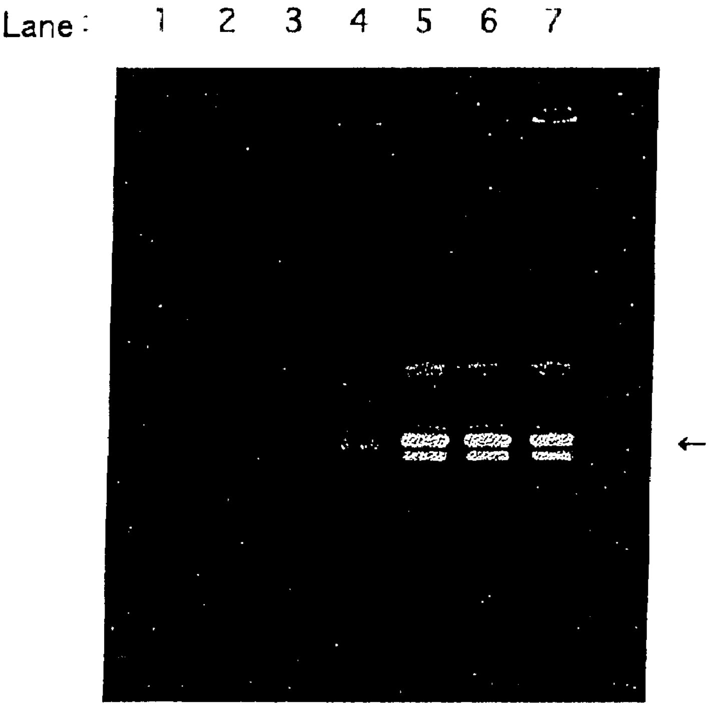
FIG. 15 is a photograph of agarose gel electrophoresis of amplified DNA fragments amplified according to the method of the present invention.

50 $\mu$l of a reaction mixture containing 10 fg to 100 pg of the template or water for a negative control, 50 pmol each of the primers NS5 and NS6, 0.5 mM each of dNTPs, 32 mM HEPES-potassium hydroxide buffer (pH 7.8), 100 mM potassium acetate, 4.0 mM magnesium acetate, 0.01% bovine serum albumin, 1.0% dimethyl sulfoxide, 0.0156 $\mu$g of Pfu RNase H and 1 U of BcaBEST DNA polymerase (Takara Shuzo) was incubated at 60° C. for 1 hour in a thermal cycler. After reaction, 5 $\mu$l each of the reaction mixture was analyzed by electrophoresis on 3.0% agarose gel. A photograph of the electrophoresis is shown in FIG. 15. FIG. 15 is a photograph of electrophoresis for the amplification method of the present invention without denaturing a template DNA. Lane 1: 100 bp DNA ladder marker; lane 2: negative control (water); lane 3: 10 fg of the template; lane 4: 100 fg of the template; lane 5: 1 pg of the template; lane 6: 10 pg of the template; and lane 7: 100 pg of the template.

As shown in FIG. 15, the amplification product of interest was observed using 1 pg of the template.

EXAMPLE 31

(1) Primers pDON-AI-1 and pDON-AI-2 represented by SEQ ID NOS:183 and 184 were synthesized based the nucleotide sequence of the packaging region in a vector plasmid pDON-AI DNA (Takara Shuzo).

(2) Amplification of DNA Fragment According to ICAN without Denaturing Template

Figure 16:
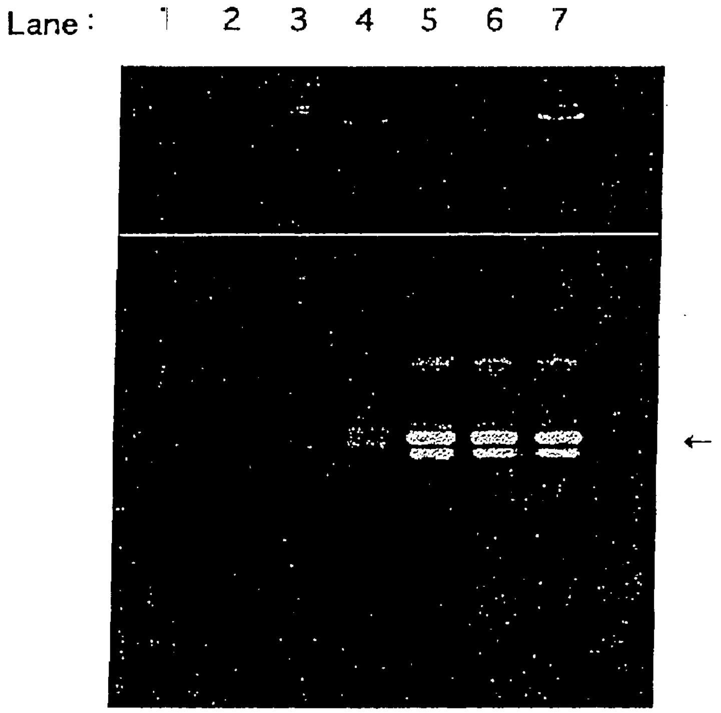
FIG. 16 is a photograph of agarose gel electrophoresis of amplified DNA fragments amplified according to the method of the present invention.

50 $\mu$l of a reaction mixture containing 1 $\mu$l of a solution containing 10 fg to 1 ng of PDON-AI DNA or water for a negative control, 50 pmol each of the primers, 0.5 mM each of dNTPs, 32 mM HEPES-potassium hydroxide buffer (pH 7.8), 100 mM potassium acetate, 4.0 mM magnesium acetate, 0.01% bovine serum albumin, 1.0% dimethyl sulfoxide, 0.0156 $\mu$g of Pfu RNase H as prepared in Referential Example 4 and 1 U of BcaBEST DNA polymerase was incubated at 60° C. for 1 hour in a thermal cycler. 5 $\mu$l each of the reaction mixtures was analyzed by electrophoresis on 3.0% agarose gel. The results are shown in FIG. 16. FIG. 16 is a photograph of electrophoresis for the method of the present invention using a circular double-stranded DNA as a template without denaturation. Lane 1: 100 bp DNA ladder marker; lane 2: negative control (water); lane 3: 10 fg of the template; lane 4: 100 fg of the template; lane 5: 1 pg of the template; lane 6: 10 pg of the template; lane 7: 100 pg of the template; and lane 8: 1 ng of the template.

As shown in FIG. 16, it was confirmed that the amplification product of interest was obtained using 10 fg of the template.

EXAMPLE 32

Detection of human papilloma virus 16 gene utilizing the method of the present invention was examined. A DNA from cells infected with human papilloma virus 16, CaSki cells (Dainippon Pharmaceutical; containing 500 copies of human papilloma virus 16 in a cell), was used as a template. Primers HPV16 S3 and HPV16 A2 having nucleotide sequences represented by SEQ ID NOS:185 and 186 were used as primers for detecting HPV16. The expected size of the amplification product obtained using the primer pair was about 120 bp. The reaction was carried out as follows.

10 $\mu$l of a mixture containing 1 pg, 3 pg, 30 pg, 100 pg, 300 pg, 1 ng, 3 ng or 10 ng of the template DNA, 50 pmol each of the primers HPV16 S3 and HPV16 A2 and propylenediamine at a final concentration of 0.01% was prepared. The mixtures were incubated at 98° C. for 2 minutes and at 55° C. for 1 minute in Thermal Cycler Personal, and then placed on ice. At final concentrations, 20 mM HEPES-potassium hydroxide buffer (pH 7.8), 100 mM potassium acetate, 1% dimethyl sulfoxide, 0.01% bovine serum albumin, 4 mM magnesium acetate, 500 $\mu$M each of dNTPs, 30 U of *E. coli* RNase H and 5.5 U of BcaBEST DNA polymerase were added to the mixture to make the final volume to 50 $\mu$l. The reaction mixtures were placed in a thermal cycler which had been set at 55° C. and reacted for 60 minutes. As a control, a PCR was carried out using Human Papillomavirus Primers HPVp16 (forward, reverse) (Takara Shuzo) according to the manual in Thermal Cycler Personal. The expected size of the amplification product was 140 bp.

Figure 17:
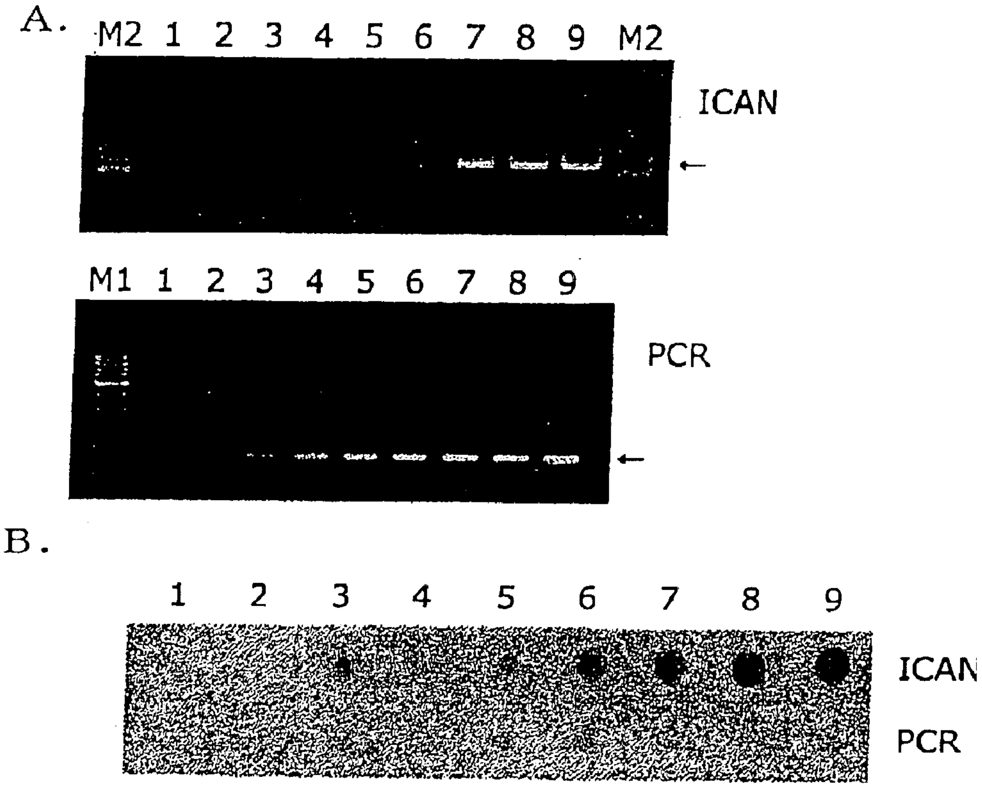
FIG. 17 is a photograph of agarose gel electrophoresis of amplified DNA fragments amplified according to the method of the present invention.

After reaction, 3 µl each of the reaction mixtures was subjected to electrophoresis on 4% NuSieve 3:1 agarose. The results are shown in FIG. 17A. FIG. 17A shows the results of the detection of HPV16 gene utilizing the ICAN and the PCR. Lane M1: molecular weight marker (100 bp ladder); lane M2: molecular weight marker (50–2000 bp); lane 1: no template; lane 2: 1 pg of the template; lane 3: 3 pg of the template; lane 4: 30 pg of the template; lane 5: 100 pg of the template; lane 6: 300 pg of the template; lane 7: 1 ng of the template; lane 8: 3 ng of the template; and lane 9: 10 ng of the template.

As shown in FIG. 17A, it was confirmed that the amplification products of interest were obtained using 3 pg of the template DNA for the ICAN and 1 pg of the template DNA for the PCR, respectively.

Furthermore, dot blot hybridization for the reaction products was carried out using an oligonucleotide HPV16 probe having a nucleotide sequence represented by SEQ ID NO:187. Hybridization was carried out as described in Example 22. The results are shown in FIG. 17B. FIG. 17B shows the results of dot blot hybridization detection of HPV16 gene according to the PCR and the ICAN. Lane 1: no template; lane 2: 1 pg of the template; lane 3: 3 pg of the template; lane 4: 30 pg of the template; lane 5: 100 pg of the template; lane 6: 300 pg of the template; lane 7: 1 ng of the template; lane 8: 3 ng of the template; and lane 9: 10 ng of the template.

As shown in FIG. 17B, the detection sensitivities of the ICAN and the PCR were almost equivalent. Thus, it was confirmed that these methods were effective for detecting a virus or the like.

EXAMPLE 33

Figure 18:
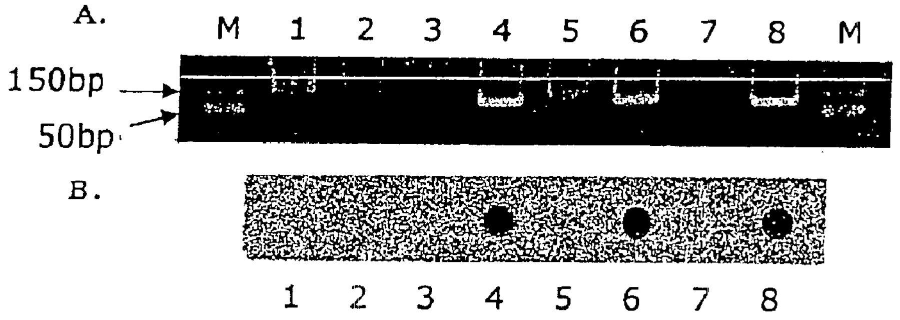
FIG. 18 is a photograph of agarose gel electrophoresis of amplified DNA fragments amplified according to the method of the present invention.

Detection of human papilloma virus 16 gene from a clinical specimen DNA sample was examined. DNAs prepared according to a conventional method from 6 clinical specimens obtained with informed consent were used as templates. The types of the infecting HPVs in the samples prepared from these clinical specimens had been proved by the PCR. The primers HPV16 S3 and HPV16 A2 as described in Example 32 were used as primers for detection. The concentrations of the DNA samples from the clinical specimens to be used as templates were adjusted to 100 ng/µl with TE buffer. The composition of the reaction mixture and the reaction conditions as described in Example 32 were used except for the amount of the template. In addition, similar reactions were carried out using a reaction mixture without the addition of the template DNA as a negative control and a reaction mixture containing 500 pg of the DNA from CaSki cells infected with HPV 16 as a positive control. After reaction, 3 µl each of the reaction mixtures was subjected to electrophoresis on 4% NuSieve 3:1 agarose. The results are shown in FIG. 18A. FIG. 18A shows the results of the detection of HPV16 gene from clinical specimens. Lane M: molecular weight marker; lanes 1 to 6: clinical specimens; lane 7: negative control; and lane 8: positive control.

As shown in FIG. 18A, the amplification products of about 120 bp were observed according to the ICAN for the samples which had been proved to be infected with HPV16 by the conventional PCR. No amplification was observed for samples infected with other types of HPVs or non-infected samples.

Furthermore, dot blot hybridization for the amplification products was carried out as described in Example 22. The results are shown in FIG. 18B and Table 11. FIG. 18B shows the results of dot blot hybridization detection of HPV16 gene from the clinical specimens. Lanes 1 to 6: clinical specimens; lane 7: negative control; and lane 8: positive control.

As shown in FIG. 18B, results consistent with those obtained by the electrophoresis were obtained, confirming that similar results with those of the PCR could be obtained by using electrophoresis as well as dot blot hybridization. Thus, it was confirmed that HPV16 could be detected from practical clinical specimens according to the method of the present invention and that the method was effective for detecting a virus or the like.

TABLE 11

| Sample | No.3 | No.4 | No.6 | No.7 | No.8 | No.9 | No template | Positive control |
|---|---|---|---|---|---|---|---|---|
| Typing by PCR | non-infected | non-infected | Type 18 | Type 16 | Type 67 | Type 16 | + | + |
| ICAN amplification using HPV16 detection primer | − | − | − | + | − | + | − | + |

−: no amplification;
+: amplification observed.

EXAMPLE 34

Detection of HCV from clinical specimens was examined. Specimen samples were prepared from 300 µl each of 5 serum specimens from patients with HCV obtained with informed consent using TRIzol reagent (Life Technologies) according to the instructions attached to the reagent and finally dissolved in 6 µl of injectable water (Otsuka Pharmaceutical) to obtain RNA samples. An RNA similarly extracted from 300 µl of a serum from a healthy individual was used as a negative control. First, 4 µl of a reaction mixture for reverse transcription containing 1×RNA PCR Buffer, 5 mM MgCl$_2$, 1 mM dNTPs, 1 U of AMV Reverse Transcriptase XL, 10 pmol each of primers HCV-F and HCV-R represented by SEQ ID NOS:188 and 189, and 2 µl of one the RNA samples was prepared using RNA PCR kit (AMW) ver 2.1 (Takara Shuzo). The mixtures were warmed at 30° C. for 10 minutes and then reacted at 50° C. for 30 minutes. After reverse transcription, the ICAN was carried out. Primers HCV-F2 and HCV-R1 having nucleotide sequences represented by SEQ ID NOS:190 and 191 were used for the ICAN. The reaction was carried as follows.

10 μl of a mixture containing 50 pmol each of the primers, 3 μl one of the reverse transcription reaction mixtures and propylenediamine at a final concentration of 0.01% was prepared. 3 μl of sterile water was used for a blank. The mixtures were heated at 98° C. for 2 minutes, rapidly cooled to 60° C. and incubated at the temperature for 1 minute in Thermal Cycler Personal, and stored on ice.

After annealing, at final concentrations, 20 mM HEPES-potassium hydroxide buffer (pH 7.8), 100 mM potassium acetate, 1% dimethyl sulfoxide, 0.01% bovine serum albumin, 4 mM magnesium acetate, 500 μM each of dNTPs, 30 U of *E. coli* RNase H and 5.5 U of BcaBEST DNA polymerase were added to the mixture to make the final volume to 50 μl with sterile water. The reaction mixtures were placed in Thermal Cycler MP which had been set at 60° C. and reacted for 60 minutes. After reaction, 3 μl each of the reaction mixtures was subjected to electrophoresis on 3% NuSieve 3:1 agarose. The results are shown in FIG. 19A. FIG. 19A shows the results of HCV detection from clinical specimens. Lane B: sterile water as a template; lane 1: a sample from a healthy individual; lanes 2 to 6: samples from patients with HCV; and lane M: molecular weight marker (50–2000 bp).

As shown in FIG. 19A, the amplification products of about 107 bp expected from the nucleotide sequence of HCV genome were observed only for the RNA samples from patients with HCV, whereas such an amplification product was not observed for the serum from the healthy individual and the blank. Furthermore, dot blot hybridization for the ICAN-amplified products was carried out as described in Example 22 using a probe for HCV represented by SEQ ID NO:192 biotinated at 5'-terminus. The results are shown in FIG. 19B. The lanes for the samples in FIG. 19B are as those indicated for the photograph of electrophoresis.

Figure 19:
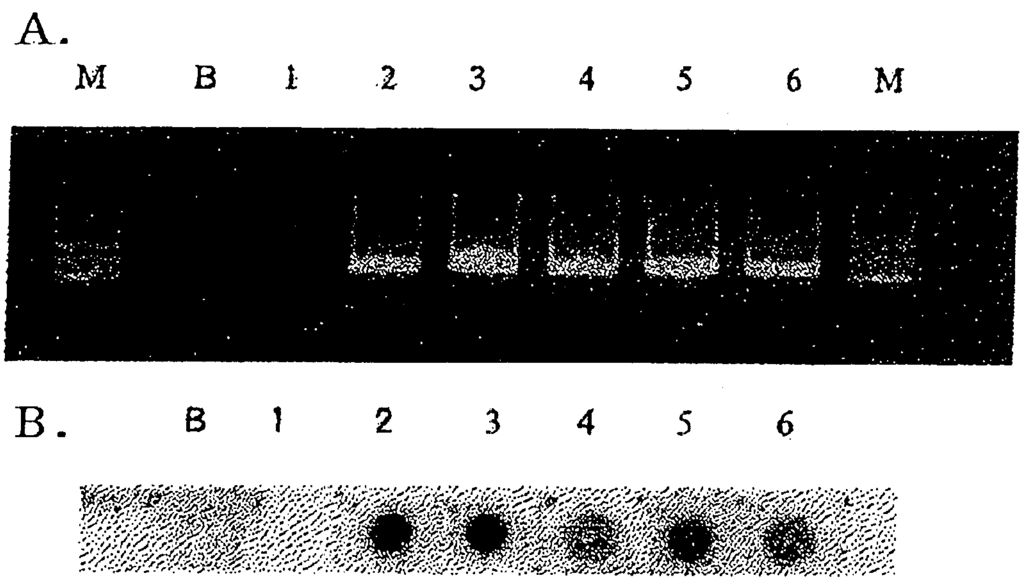
FIG. 19 is a photograph of agarose gel electrophoresis of amplified DNA fragments amplified according to the method of the present invention.

As shown in FIG. 19, it was confirmed that the results from the electrophoresis were consistent with those from the dot blot hybridization. These results confirms that the method of the present invention can be used to detect HCV from practical clinical specimens and is effective for detecting a virus or the like.

EXAMPLE 35

A method for detecting adenovirus was examined.

Primers for amplifying E1A (tumor gene), E1A-1 (sense), E1A-2 (antisense) and E1A-3 (antisense), represented by SEQ ID NOS:193 to 195 were constructed based on the nucleotide sequence of adenovirus (GenBank accession no. J01917). Adenovirus (ATCC accession no. VR-5) was used. A template was prepared as follows. 100 μl of a solution containing adenovirus at a concentration of $8.73\times10^{10}$ PFU/ml was incubated in the presence of SDS at a final concentration of 0.1% and proteinase K at a final concentration of 0.2 mg/ml at 37° C. for 1 hour. The DNA was purified by affinity to silica gel. Adenoviral DNAs corresponding to $10^3$, $10^4$, $10^5$ or $10^6$ PFU prepared by diluting the purified DNA with sterile water were used. The reaction was carried out as follows. Briefly, 10 μl of a reaction system containing 60 pmol each of the primers E1A-1 and E1A-2 (chain length to be amplified: 112 bp) or E1A-1 and E1A-3 (chain length to be amplified: 91 bp), 2 μl of 0.05% propylenediamine and the template was heat-denature at 98° C. for 2 minutes and then rapidly cooled on ice to anneal the primers to the template.

After annealing, 40 μl of a mixture containing 0.625 mM each of dNTPs, 42.5 mM Tricine-potassium hydroxide buffer (pH 8.5), 5.0 mM magnesium acetate, 0.0125% bovine serum albumin, 1.25% dimethyl sulfoxide, 30 U of *E. coli* RNase H and 5.5 U of BcaBEST DNA polymerase was added to the mixture to make the final volume to 50 μl. The reaction mixtures were incubated at 60° C. for 1 hour. As a control, a detection by a PCR was carried out using the same template as the above and primers constructed for PCR-amplifying E1A (tumor gene), E1A-1P (sense), E1A-2P (antisense) and E1A-3P (antisense) having nucleotide sequences represented by SEQ ID NOS:196, 197 and 231. The PCR was carried out as follows. Briefly, 50 μl of a PCR solution containing 60 pmol each of the primers E1A-1P and E1A-2P (chain length to be amplified: 112 bp) or E1A-1P and E1A-3P (chain length to be amplified: 91 bp), 5 μl of 10×Ex Taq buffer (Takara Shuzo), 1.25 U of TaKaRa Ex Taq DNA polymerase (Takara Shuzo) and 0.2 mM each of dNTPs was prepared. The conditions for the PCR were as follows: 30 cycles of 94° C. for 30 seconds, 55° C. for 30 seconds and 72° C. for 30 seconds.

Figure 20:
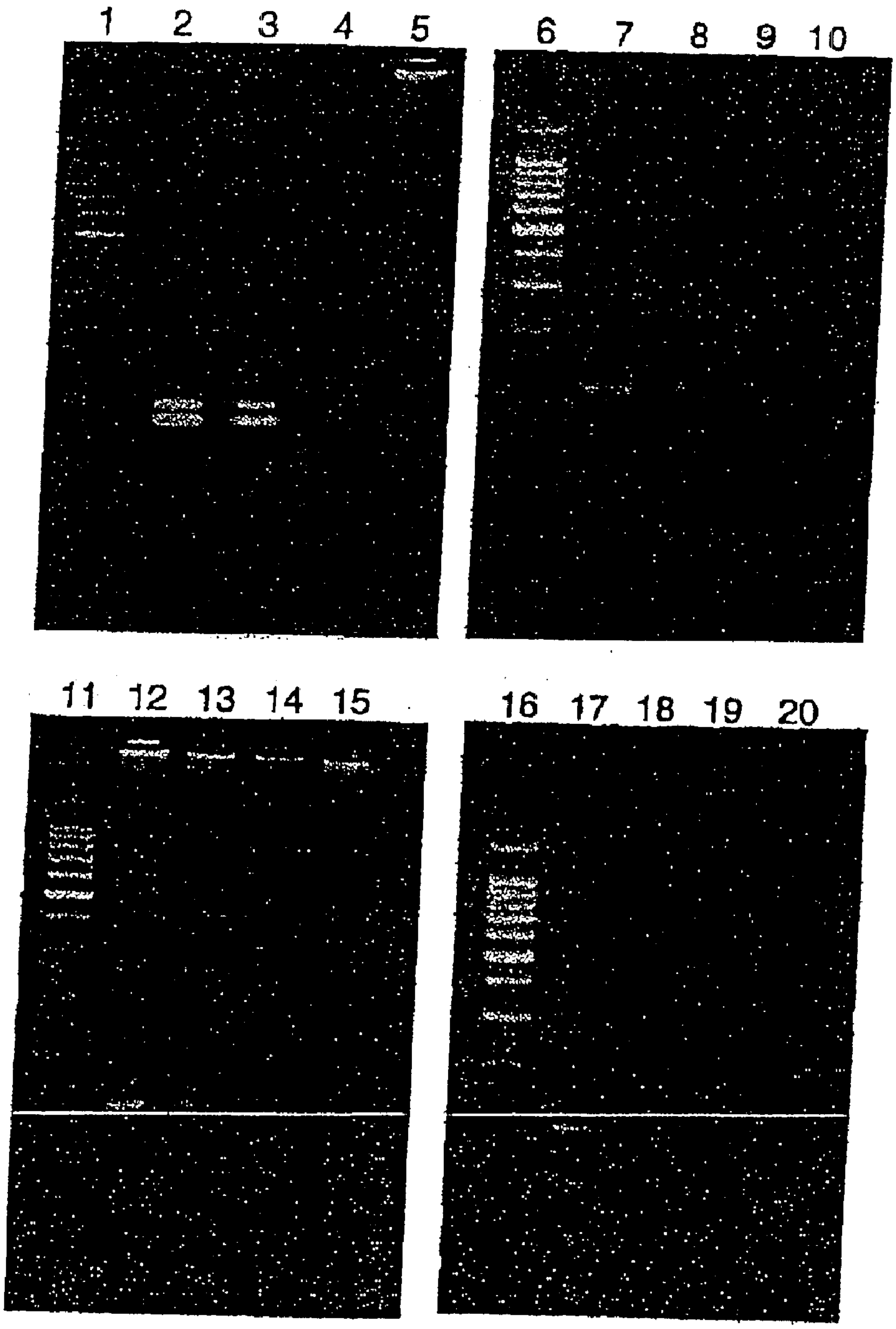
FIG. 20 is a photograph of agarose gel electrophoresis of amplified DNA fragments amplified according to the method of the present invention.

After reaction, 3 μl each of the reaction mixtures of the ICAN and the PCR was subjected to electrophoresis on 3.0% agarose gel. The results are shown in FIG. 20 and Table 12. FIG. 20 shows the results of the detection of viral E1A gene from adenoviral particles. Lanes 1 to 10 show the results obtained using the combination of the primers E1A-1 and E1A-2. Lanes 11 to 20 show the results obtained using the combination of the primers E1A-1 and E1A-3. Lane 1: molecular weight marker (100 bp ladder); lane 2: ICAN using DNA corresponding to $10^6$ PFU; lane 3: ICAN using DNA corresponding to $10^5$ PFU; lane 4: ICAN using DNA corresponding to $10^4$ PFU; lane 5: ICAN using DNA corresponding to $10^3$ PFU; lane 6: molecular weight marker (100 bp ladder); lane 7: PCR using DNA corresponding to $10^6$ PFU; lane 8: PCR using DNA corresponding to $10^5$ PFU; lane 9: PCR using DNA corresponding to $10^4$ PFU; and lane 10: PCR using DNA corresponding to $10^3$ PFU. In addition, lane 11: molecular weight marker (100 bp ladder); lane 12: ICAN using DNA corresponding to $10^6$ PFU; lane 13: ICAN using DNA corresponding to $10^5$ PFU; lane 14: ICAN using DNA corresponding to $10^4$ PFU; lane 15: ICAN using DNA corresponding to $10^3$ PFU; lane 16: molecular weight marker (100 bp ladder); lane 17: PCR using DNA corresponding to $10^6$ PFU; lane 18: PCR using DNA corresponding to $10^5$ PFU; lane 19: PCR using DNA corresponding to $10^4$ PFU; and lane 20: PCR using DNA corresponding to $10^3$ PFU.

TABLE 12

| Amplification size | Detection limit | |
|---|---|---|
| (bp) | ICAN | PCR |
| 112 | $10^4$ | $10^4$ |
| 91 | $10^4$ | $10^4$ |

As shown in FIG. 20 and Table 12, it was confirmed that the detection sensitivity for the detection of adenovirus E1A gene by the ICAN was equivalent to that by the PCR.

EXAMPLE 36

Detection of an integrated viral gene from cells infected with a retrovirus vector was examined. Cells infected with a retrovirus and a genomic DNA were prepared as follows. Briefly, a vector plasmid pDON-AI (Takara Shuzo) was introduced into packaging cells GPE+86 according to the calcium phosphate method. An ecotropic vector was prepared from the culture supernatant of the introduced cells.

Cells infected with a virus vector were prepared by infecting NIH/3T3 cells with the ecotropic vector and culturing the infected cells for 14 days in a medium containing G418. 27 pg of a genomic DNA was obtained according to a conventional method from $4\times10^4$ of the prepared cells infected with the retrovirus. The primers pDON-AI-1 and pDON-AI-2 as described in Example 31(1) were used as primers. The reaction was carried out as follows. Briefly, 10 $\mu$l of a reaction system containing 60 pmol each of the primers, 2 $\mu$l of a 0.25% aqueous solution of propylenediamine and 0.1 ng to 1000 ng of the genomic DNA as a template was heated at 98° C. for 2 minutes and then at 60° C. in a thermal cycler (Takara Shuzo) to anneal the primers to the template.

Figure 21:
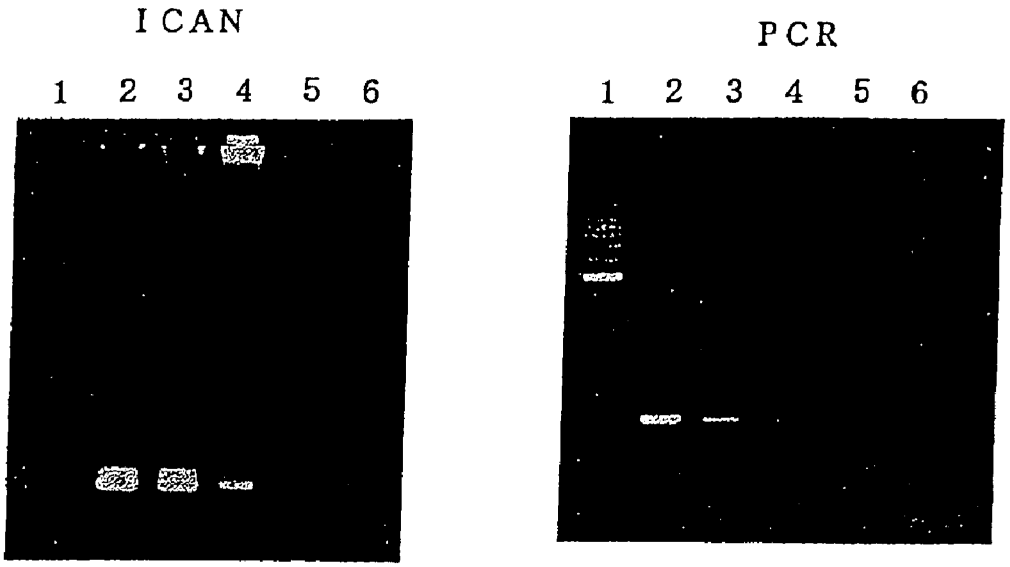
FIG. 21 is a photograph of agarose gel electrophoresis of amplified DNA fragments amplified according to the method of the present invention.

After annealing, 40 $\mu$l of a reaction mixture containing 0.625 mM each of dNTPs, 40 mM HEPES-potassium hydroxide buffer (pH 7.8), 125 mM potassium acetate, 5 mM magnesium acetate, 0.0125% bovine serum albumin, 1.25% dimethyl sulfoxide, 30 U of *E. coli* RNase H and 5.5 U of BcaBEST DNA polymerase was added to the mixture to make the final volume to 50 $\mu$l. The reaction mixtures were incubated at 60° C. for 1 hour in a thermal cycler. After reaction, 5 $\mu$l each of the reaction mixtures was subjected to electrophoresis on 3.0% agarose gel. In addition, a PCR was carried out using primers pDON-AI-3 and pDON-AI-4 represented by SEQ ID NOS:200 and 201 in order to compare the sensitivities of detecting a DNA by the ICAN and the PCR. The PCR was carried out as follows. 50 $\mu$l of a reaction mixture containing 0.1 ng to 100 ng of the template, 60 pmol each of the primers, 5 $\mu$l of 10×Ex Taq buffer, 1.25 U of TaKaRa Ex Taq polymerase and 0.2 mM each of dNTPs was prepared. The mixtures were subjected to reactions using Thermal Cycler Personal as follows: 35 cycles of 94° C. for 30 seconds, 55° C. for 30 seconds and 72° C. for 30 seconds. After reaction, 5 $\mu$l each of the reaction mixtures was subjected to electrophoresis on 3.0% agarose gel. The results are shown in FIG. 21. FIG. 21 shows the results of the detection of an integrated viral gene from cells infected with a retrovirus vector according to the ICAN and the PCR. Lane 1: molecular weight marker (100 bp ladder); lane 2: 1000 ng of the template; lane 3: 100 ng of the template; lane 4: 10 ng of the template; lane 5: 1 ng of the template; and lane 6: 0.1 ng of the template.

As shown in FIG. 21, the amplification products of interest were observed for the ICAN using 1 ng of the template DNA and for the PCR of 35 cycles using 1 ng of the template.

EXAMPLE 37

A method for detecting a target nucleic acid in which the amplification method of the present invention and a hybridization method were combined was examined for the detection of *Escherichia coli* O-157 vero toxin I gene. Vero toxin I gene from enterohemorrhagic *Escherichia coli* O-157 was selected as a target. The template DNA was prepared as described in Example 21(1). A region of about 80 bp having a GC content of about 40% was selected as a region to be amplified. Primers VT1-IF4 and VT1-IR1 having nucleotide sequences represented by SEQ ID NOS:202 and 203 were used as primers. The reaction was carried out as follows. Briefly, 5 $\mu$l of a mixture containing 60 pmol each of the primers VT1-IF4 and VT1-IR1, propylenediamine at a final concentration of 0.01%, one of hot water-extracts corresponding to 0 to $10^5$ cells and sterile water was prepared. The mixtures were heat-denatured at 98° C. for 2 minutes, rapidly cooled to 55° C. and incubated at the temperature for 1 minute in Thermal Cycler Personal, and then placed on ice for annealing.

Figure 22:
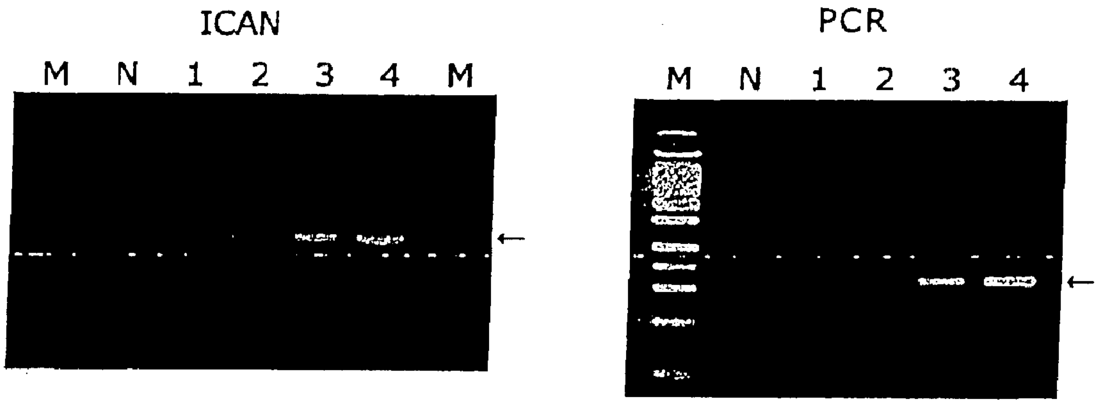
FIG. 22 is a photograph of agarose gel electrophoresis of amplified DNA fragments amplified according to the method of the present invention.

After annealing, at final concentrations, 20 mM HEPES-potassium hydroxide buffer (pH 7.8), 100 mM potassium acetate, 1% dimethyl sulfoxide, 0.01% bovine serum albumin, 4 mM magnesium acetate, 500 $\mu$M each of dNTPs, 15 U of *E. coli* RNase H and 2.75 U of BcaBEST DNA polymerase were added to the mixture to make the final volume to 25 $\mu$l with sterile water. The reaction mixtures were placed in Thermal Cycler Personal which had been set at 55° C. and incubated at the temperature for 60 minutes. As a control, a PCR for the hot water-extract was carried out using O-157 Typing Set (Takara Shuzo) according to the manual in Thermal Cycler Personal. The PCR was carried out as follows: 35 cycles of 94° C. for 1 minute, 55° C. for 1 minute and 72° C. for 1 minute. The total time required for the reaction was about 145 minutes. The expected size of the amplification product was 349 bp. After reaction, 3 $\mu$l each of the reaction mixtures was subjected to electrophoresis on 3% NuSieve 3:1 agarose. The results for the ICAN are shown in FIG. 22. FIG. 22 shows the results of the detection of O-157 vero toxin I gene. Lane M: molecular weight marker (50–2000 bp); lane N: sterile water as template; lane 1: the template corresponding to 1 cell; lane 2: the template corresponding to 10 cells; lane 3: the template corresponding to $10^2$ cells; and lane 4: the template corresponding to $10^3$ cells. Furthermore, the results of the detection by the ICAN and the PCR are shown in Table 13.

TABLE 13

| | Number of *Escherichia coli* 0–157 cells | | |
|---|---|---|---|
| | 0 | 1 | 10 |
| ICAN | − | + | + + + |
| PCR | − | + | + + |

−: no amplification;
+ to + + +: indicate the degree of amplification in three grades.

As shown in Table 13, the amplification products of interest were obtained for the reaction systems in which the hot water-extract corresponding to 1 cell was used for both of the ICAN and the PCR. Furthermore, dot blot hybridization for the amplification products was carried out using an oligonucleotide probe VT1 having a nucleotide sequence represented by SEQ ID NO:204 labeled with biotin at the 5'-terminus. The hybridization was carried out as described in Example 32. The results were consistent with those obtained by the electrophoresis. Thus, it was confirmed that the detection sensitivities of the ICAN and the PCR were equivalent. In addition, the total time required for the amplification reaction using the ICAN of the present invention was 1/2 or shorter as compared with that required for the PCR. Thus, the ICAN of the present invention was confirmed to be effective as a method for detecting a pathogenic bacterium and the like.

EXAMPLE 38

A method for detecting a gene for *botulinum* toxin type A was examined. A DNA prepared from *Clostridium botulinum*, a strain from a food poisoning case, type A-190 was used as a template. This strain is preserved in Department of Hygiene, Kagawa Nutrition University. Primers BotA S2 and BotA A2 having nucleotide sequences represented by SEQ ID NOS:205 and 206 were synthesized as primers for detection. The expected size of the amplification product obtained using the primer pair was about 150 bp. Solutions containing 100 fg, 1 pg, 10 pg or 100 pg of the DNA from type A toxin-producing *Clostridium botulinum* in 1 μl of sterile water to be used as templates were prepared. The reaction was carried out as follows.

10 μl of a mixture containing 50 pmol each of the primers, propylenediamine at a final concentration of 0.01% and 1 μl of one of the DNA solutions as a template was prepared. The mixtures were subjected to the ICAN using the composition of the reaction mixture and the reaction conditions as described in Example 32. As a control, a PCR was carried out in using a primer set for detecting *botulinum* toxin type A gene, BAS-1 and BAS-2 (Takara Shuzo), according to the manual in Thermal Cycler Personal. The expected size of the amplification product was 284 bp.

Figure 23:
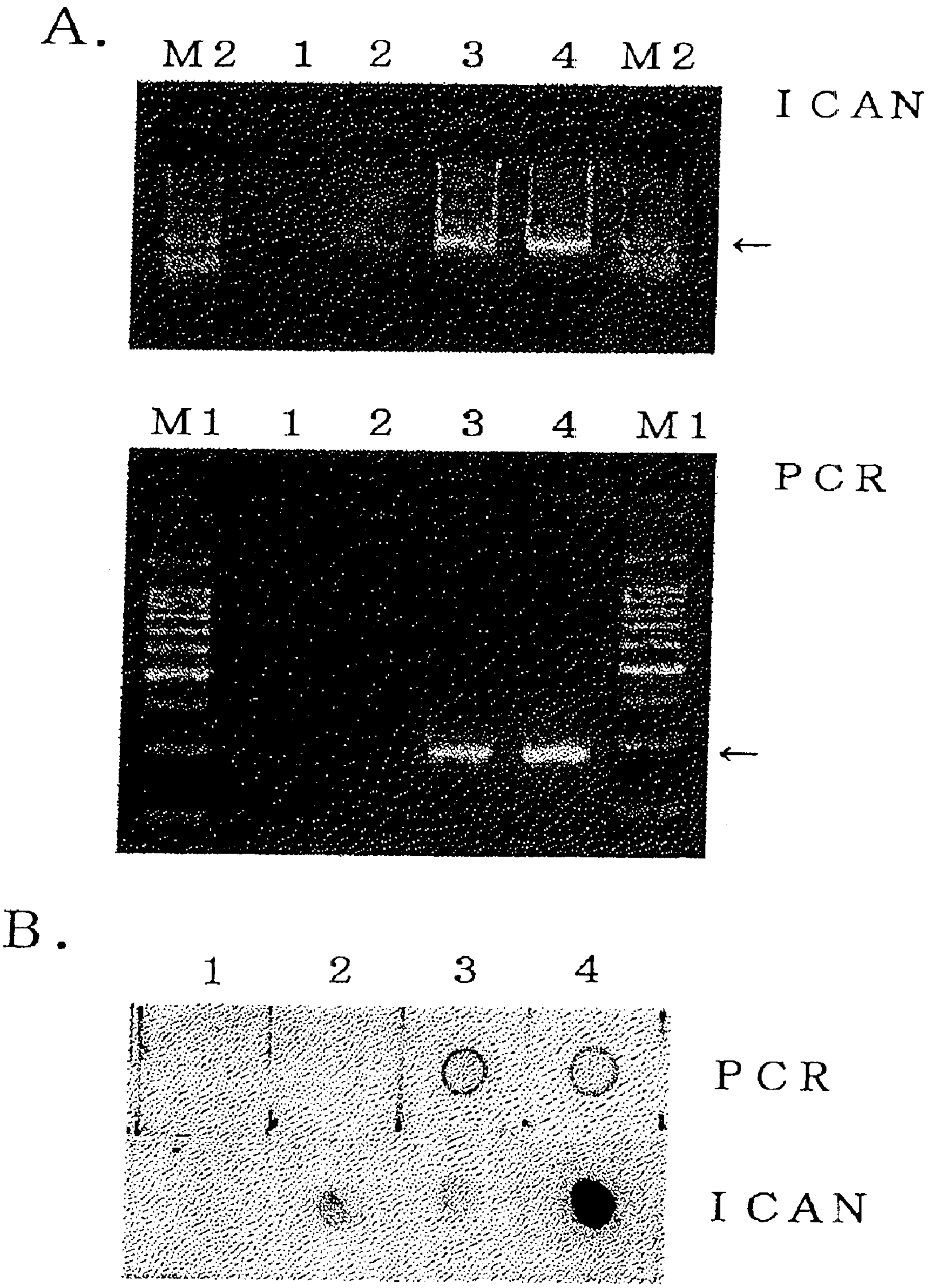
FIG. 23 is a photograph of agarose gel electrophoresis of amplified DNA fragments amplified according to the method of the present invention.

After reaction, 3 μl each of the reaction mixtures was subjected to electrophoresis on 4% NuSieve 3:1 agarose. The results are shown in FIG. 23A. FIG. 23A shows the results of the detection of the gene for *botulinum* toxin type A according to the ICAN and the PCR. Lane M1: molecular weight marker (100 bp ladder); lane M2: molecular weight marker (50–2000 bp marker); lane 1: no template; lane 2: 100 fg of the template; lane 3: 10 pg of the template; and lane 4: 100 pg of the template.

As shown in FIG. 23A, the amplification product of interest was observed for the reaction in which 100 fg of the template DNA was used according to the ICAN. On the other hand, the amplification product of interest was not observed for the reaction in which 100 fg of the template DNA was used according to the PCR. Furthermore, dot blot hybridization for the reaction products was carried out using BotA probe having a nucleotide sequence represented by SEQ ID NO:207. Dot blot hybridization was carried out as described in Example 22. The results are shown in FIG. 23B. As shown in FIG. 23B, the signals were observed using 100 fg of the template for the ICAN and 10 pg of the template for the PCR, respectively. These results were consistent with those of the electrophoresis.

EXAMPLE 39

Detection of chrysanthemum viroid was examined. 10-fold serial dilutions of low molecular weight RNA obtained according to the method for extracting low molecular weight RNAs from chrysanthemum infected with chrysanthemum stunt viroid (CSVd) as described in Example 1 of JP-A 9-140383 were prepared. A reverse transcription reaction was carried out using RNA PCR kit (AMW) ver 2.1 (Takara Shuzo). Specifically, 20 μl of a reaction mixture for reverse transcription containing 1×RNA PCR Buffer, 5 mM $MgCl_2$, 1 mM each of dNTPs, 20 U of RNase Inhibitor, 5 U of AMV Reverse Transcriptase XL, 50 pmol of Random 9 mers, 1 μl of one of the serial dilutions of the RNA was prepared. The mixtures were warmed at 30° C. for 10 minutes, reacted at 55° C. for 30 minutes and then heated at 99° C. for 5 minutes for inactivating the reverse transcriptase. After cooling, the ICAN was carried out. 1 μl of the reverse transcription reaction mixture was used as a template for 50 μl of a reaction mixture for the ICAN. Primers CSVD-F4 and CSVD-R3 having nucleotide sequences represented by SEQ ID NOS:208 and 209 were used as primers in this Example. The reaction was carried out as described in Example 32 except that reaction temperature was 60° C. and that Thermal Cycler MP was used. After reaction, 3 μl each of the reaction mixtures was subjected to electrophoresis on 3% NuSieve 3:1 agarose.

On the other hand, PCR amplification was carried out in a reaction system of 50 μl using 1 μl of the same reverse transcription reaction mixture as a template. Primers F94 and R264 represented by SEQ ID NOS:198 and 199 were used as primers. The reaction was carried out as follows. Briefly, a reaction mixture was prepared using TaKaRa PCR Amplification kit according to the protocol. 10 pmol each of the primers and 1 μl of one of the reverse transcription reaction mixture were added thereto to make the total volume to 50 μl. An amplification reaction was carried out using Thermal Cycler MP. The reaction was carried out as follows: 30 cycles of 94° C. for 30 seconds, 55° C. for 30 seconds and 72° C. for 30 seconds. After reaction, 5 μl each of the reaction mixtures was subjected to electrophoresis on 3% NuSieve 3:1 agarose. The results are shown in Table 14.

TABLE 14

| Dilution rate of RNA as template | $10^2$ | $10^3$ |
|---|---|---|
| RT-ICAN | + + | + |
| RT-PCR | + | − |

−: not amplified;
+: amplified;
+: + amplified well.

As shown in Table 14, the amplification product was observed for the reaction in which the $10^3$-fold-diluted RNA sample was used as a template according to the ICAN. On the other hand, the amplification product was observed for the reaction in which the $10^2$-fold-diluted RNA sample was used as a template according to the PCR.

Furthermore, the ICAN-amplified products and the PCR-amplified products were confirmed to be the products of interest by dot blot hybridization. Dot blot hybridization was carried out using CSVD probe having a nucleotide sequence represented by SEQ ID NO:210 labeled with biotin at the 5'-terminus. Hybridization was carried out as described in Example 22. The results were consistent with those of the electrophoresis. The signals were observed using the $10^3$-fold-diluted RNA sample for the ICAN and the $10^2$-fold-diluted RNA sample for the PCR, respectively, demonstrating that the ICAN was more sensitive than the PCR.

EXAMPLE 40

Detection of a viroid gene from chrysanthemum infected with chrysanthemum dwarfing viroid (CSVd) using Pfu RNase H was examined. 60 μl of a mixture containing 3 μl of one of the 10-fold serial dilutions of the RNA as prepared in Example 39, 10 mM tris-hydrochloride buffer (pH 8.3), 50 mM potassium chloride, 5 mM magnesium chloride, 1 mM each of dNTPs, 150 pmol of Random 6 mers, 60 U of Ribonuclease Inhibitor (Takara Shuzo) and 15 U of Reverse Transcriptase XL (AMV) (Takara Shuzo) was incubated at 30° C. for 10 minutes and at 42° C. for 1 hour and then heated at 99° C. for 5 minutes for inactivating the enzyme using a thermal cycler (GeneAmp PCR System 9600, Applied Biosystems) to prepare a cDNA. Primers Vd1, Vd2, Vd3 and Vd4 represented by SEQ ID NOS:211 to 214 were synthesized based on the nucleotide sequence of the mRNA for the viroid.

50 μl of a mixture containing 50 pmol each of the primers Vd1 and Vd2, 1 μl of the cDNA solution synthesized as described above, a 10-, 100-, 1000- or 10000-fold dilution thereof with water or water for a negative control as a template, 0.5 mM each of dNTPs, 32 mM HEPES-potassium hydroxide buffer (pH 7.8), 100 mM potassium acetate, 4.0 mM magnesium acetate, 0.01% bovine serum albumin, 1% dimethyl sulfoxide, 0.0156 μg of Pfu RNase H and 1 U of BcaBEST DNA polymerase was incubated at 57°

C. for 1 hour in a thermal cycler. The reacted samples were stored by freezing at −20° C. until being analyzed.

A PCR was carried out as a control. Briefly, 50 μl of a reaction system containing 50 pmol each of the primers Vd3 and Vd4, 1 μl of the cDNA solution, a 10-, 100-, 1000- or 10000-fold dilution thereof with water or water for a negative control, 5 μl of 10×Ex Taq buffer, 1.25 U of TaKaRa Ex Taq polymerase and 0.2 mM each of dNTPs was subjected to a reaction in a thermal cycler. The program was as follows: 1 cycle of 94° C. for 2 minute; 35 cycles of 94° C. for 30 seconds, 55° C. for 30 seconds and 72° C. for 30 seconds; and 1 cycle of 72° C. for 5 minutes. The reacted samples were stored by freezing at −20° C. until being analyzed.

Figure 24:
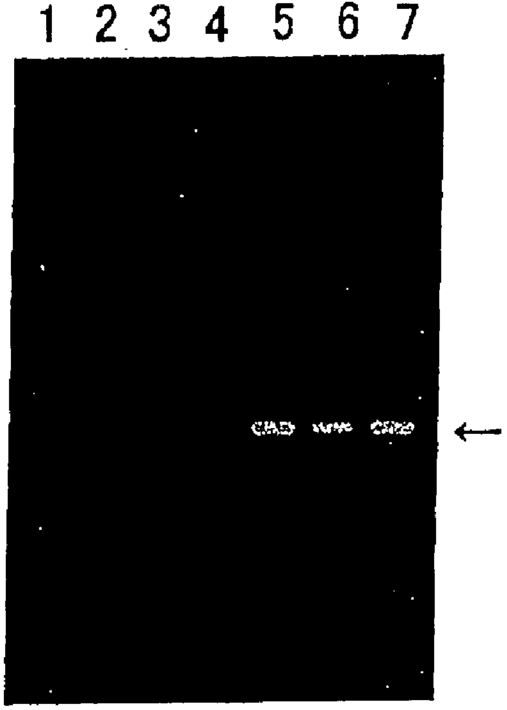
FIG. 24 is a photograph of agarose gel electrophoresis of amplified DNA fragments amplified according to the method of the present invention.
Figure 24:
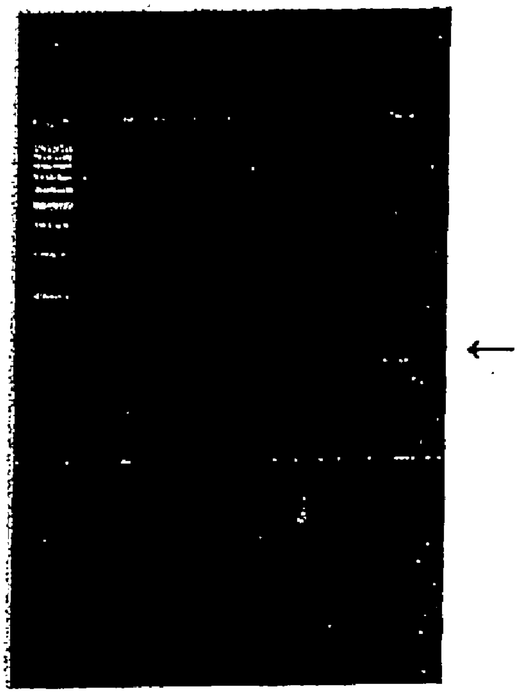

5 μl each of the reaction mixtures of the ICAN and the PCR was subjected to electrophoresis on 3.0% agarose gel. The results are shown in FIG. 24. FIG. 24 shows the results of the detection of a viroid according to the ICAN using Pfu RNase H and the PCR. Lane 1: 100 bp DNA ladder marker; lane 2: negative control; lane 3: 10000-fold dilution of the cDNA; lane 4: 1000-fold dilution of the cDNA; lane 5: 100-fold dilution of the cDNA; lane 6: 10-fold dilution of the cDNA; and lane 7: the original solution of the cDNA.

As shown in FIG. 24, the amplification products of interest were observed using the 100-fold dilution of the cDNA for both of the ICAN and the PCR.

EXAMPLE 41

Detection of K-ras gene was examined.

(1) Detection from Genomic DNA

Primers c-Ki-ras-1 and c-Ki-ras-2 represented by SEQ ID NOS:215 and 216 were constructed based on the nucleotide sequence of human c-Ki-ras.

10 μl of a mixture containing 60 pmol each of the primers, 2 μl of a 0.25% aqueous solution of propylenediamine and 1 ng to 100 ng of human genomic DNA (Clontech) as a template was prepared. The mixtures were heated at 98° C. for 2 minutes and then 53° C. in Thermal Cycler Personal to anneal the primers to the template.

After annealing, 40 μl of a reaction mixture containing 0.625 mM each of dNTPs, 40 mM HEPES-potassium hydroxide buffer (pH 7.8), 125 mM potassium acetate, 5 mM magnesium acetate, 0.0125% bovine serum albumin, 1.25% dimethyl sulfoxide, 30 U of *E. coli* RNase H and 5.5 U of BcaBEST DNA polymerase was added to the mixture to make the final volume to 50 μl. The reaction mixtures were incubated at 53° C. for 1 hour. After reaction, 5 μl each of the reaction mixtures was subjected to electrophoresis on 3.0% agarose gel.

Figure 25:
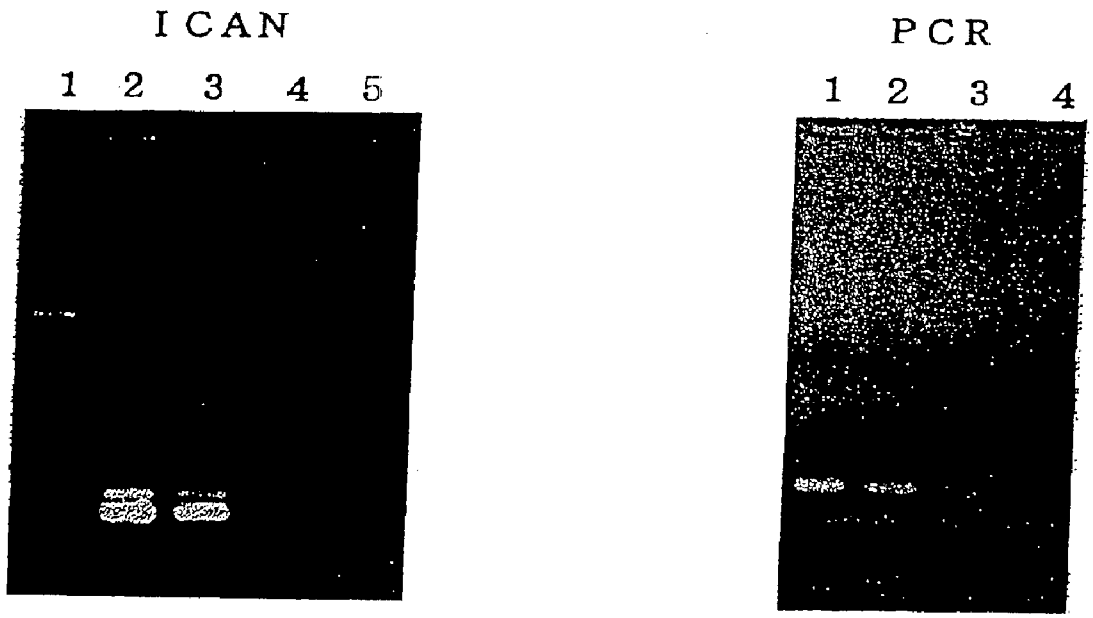
FIG. 25 is a photograph of agarose gel electrophoresis of amplified DNA fragments amplified according to the method of the present invention.

On the other hand, a PCR was carried out as a control. Primers c-Ki-ras-3 and c-Ki-ras-4 represented by SEQ ID NOS:217 and 218 were used as primers. 50 μl of a solution containing 60 pmol each of the primers, 0.1 ng to 100 ng of the template, 5 μl of 10×Ex Taq buffer, 1.25 U of TaKaRa Ex Taq polymerase and 0.2 mM each of dNTPs was prepared. The mixtures were subjected to reactions using Thermal Cycler Personal as follows: 30 or 35 cycles of 94° C. for 30 seconds, 55° C. for 30 seconds and 72° C. for 30 seconds. After reaction, 5 μl each of the reaction mixtures was subjected to electrophoresis on 3.0% agarose gel. The results are shown in FIG. 25. FIG. 25 shows the results of the detection of c-Ki-ras gene from human genomic DNA according to the ICAN and the PCR. For the ICAN, lane 1: molecular weight marker; lane 2: 100 ng of the template; lane 3: 10 ng of the template; lane 4: 1 ng of the template; and lane 5: no template. For the PCR, lane 1: 100 ng of the template; lane 2: 10 ng of the template; lane 3: 1 ng of the template; and lane 4: no template.

Figure 30:
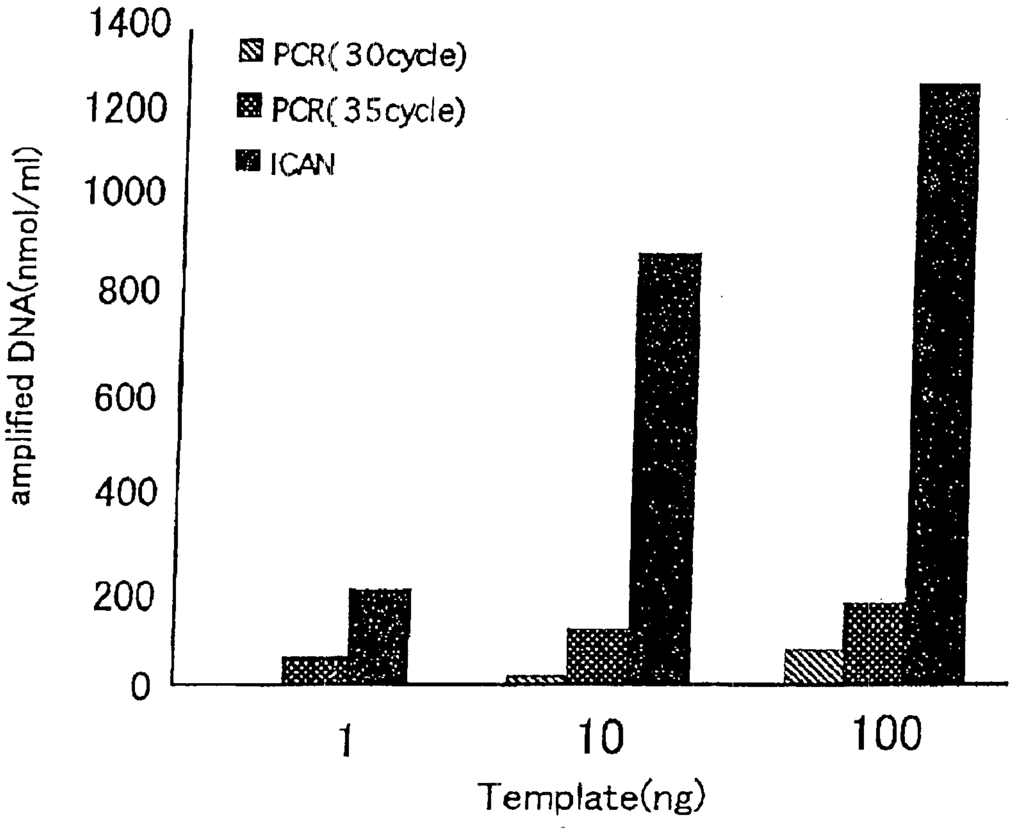
FIG. 30 is a graph which compares the amounts of amplification products amplified according to the method of the present invention and the PCR.

As shown in FIG. 25, the amplification products of interest were observed using 1 ng of the template for the ICAN and 10 ng of the template for the PCR of 30 cycles. The comparative results for the amounts of the amplification products obtained by the ICAN and the PCR using 1 ng to 100 ng of the template are shown in FIG. 30. As shown in FIG. 30, it was confirmed that the amount of the amplification product obtained by the ICAN was greater than that by the PCR.

(2) Detection from Blood Sample

Figure 26:
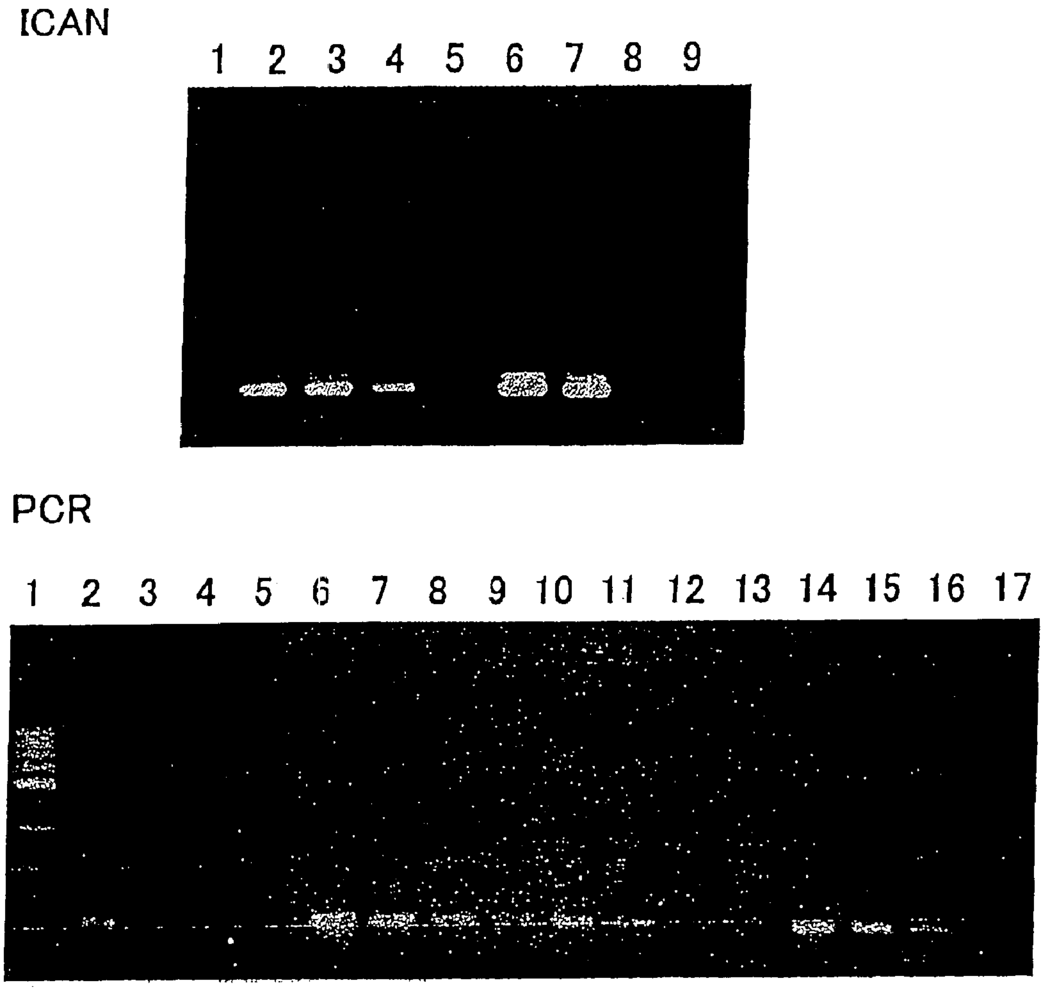
FIG. 26 is a photograph of agarose gel electrophoresis of amplified DNA fragments amplified according to the method of the present invention.

Genomic DNAs were prepared using Dr. GenTLE™ (for Whole Blood) (Takara Shuzo) from 100 μl each of blood samples collected from a healthy individual using sodium citrate or heparin as an anticoagulating agent. Detection of c-Ki-ras gene by the ICAN was carried out as described in (1) above using the prepared DNA corresponding to 0.04 to 5 μl of the blood. Furthermore, detection by PCR using the DNA from 0.04 to 5 μl of the blood sample was carried out as described in (1) above in order to compare the sensitivities for detecting a DNA by the ICAN and the PCR. The results are shown in FIG. 26. FIG. 26 shows the results of the detection of c-Ki-ras gene from blood samples according to the ICAN and the PCR. For the ICAN, lane 1: molecular weight marker; lane 2: 5 μl of citrated blood; lane 3: 1 μl of citrated blood; lane 4: 0.2 μl of citrated blood; lane 5: 0.04 μl of citrated blood; lane 6: 5 μl of heparinized blood; lane 7: 1 μl of heparinized blood; lane 8: 0.2 μl of heparinized blood; and lane 9: 0.04 μl of heparinized blood. For the PCR, lane 1: molecular weight marker; lane 2: 5 μl of citrated blood, 30 cycles; lane 3: 1 μl of citrated blood, 30 cycles; lane 4: 0.2 μl of citrated blood, 30 cycles; lane 5: 0.04 μl of citrated blood, 30 cycles; lane 6: 5 μl of citrated blood, 35 cycles; lane 7: 1 μl of citrated blood, 35 cycles; lane 8: 0.2 μl of citrated blood, 35 cycles; lane 9: 0.04 μl of citrated blood, 35 cycles; lane 10: 5 μl of heparinized blood, 30 cycles; lane 11: 1 μl of heparinized blood, 30 cycles; lane 12: 0.2 μl of heparinized blood, 30 cycles; lane 13: 0.04 μl of heparinized blood, 30 cycles; lane 14: 5 μl of heparinized blood, 35 cycles; lane 15: 1 μl of heparinized blood, 35 cycles; lane 16: 0.2 μl of heparinized blood, 35 cycles; and lane 17: 0.04 μl of heparinized blood, 35 cycles.

As shown in FIG. 26, the amplification products of interest were observed using the genomic DNA corresponding to 0.2 μl of either of the blood samples for the ICAN, and the genomic DNA corresponding to 0.2 μl of either of the blood samples (citrated or heparinized) for the PCR of 30 cycles, respectively.

EXAMPLE 42

Figure 27:
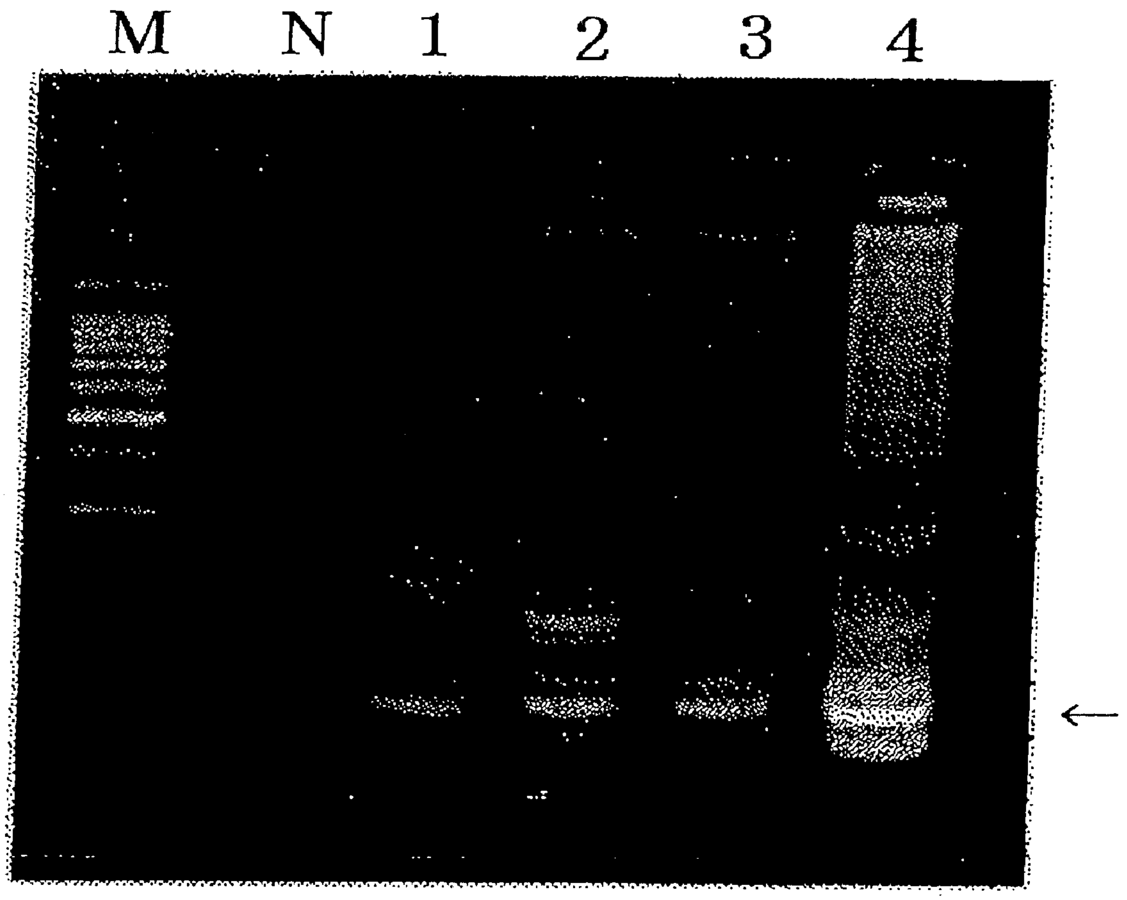
FIG. 27 is a photograph of agarose gel electrophoresis of amplified DNA fragments amplified according to the method of the present invention.

Detection of *Escherichia coli* O-157 vero toxin 2 (VT-2) gene using Bca RNase HIII was examined. Enterohemorrhagic *Escherichia coli* O-157 was cultured in mEC medium containing novobiocin at 42° C. for 18 hours, and then heated at 95° C. for 10 minutes. Dilutions corresponding to 0, 1, 10, $10^2$ or $10^3$ cells in sterile water were prepared and used as templates. Primers VT-2 IF4 and VT-2 IR3 having nucleotide sequences represented by SEQ ID NOS:219 and 220 were synthesized as primers for detection. The expected size of the amplification product obtained using the primer pair was about 146 bp. The reaction was carried out as follows. Briefly, 10 μl of a mixture containing 50 pmol each of the primers, propylenediamine at a final concentration of 0.01% and one of the hot water-extracts was prepared. The mixtures were heated at 98° C. for 2 minutes and incubated at 55° C. for 1 minute in Thermal Cycler Personal, and then placed on ice. At final concentrations, 34 mM Tricine buffer (pH 8.7), 10 mM potassium chloride, 10 mM ammonium sulfate, 1% dimethyl sulfoxide, 0.01% bovine serum albumin, 4 mM magnesium acetate, 500 $\mu$M each of dNTPs, 32 U of Bca RNase HIII as prepared in Referential Example 3(5) and 5.5 U of BcaBEST DNA polymerase were added to the mixture to make the final volume to 50 $\mu$l. The reaction mixtures were placed in a thermal cycler which had been set at 55° C. and reacted at the temperature for 60 minutes. After reaction, 3 $\mu$l each of the reaction mixtures was subjected to electrophoresis on 4% NuSieve 3:1 agarose. The results are shown in FIG. 27. FIG. 27 shows the results of the detection of *Escherichia coli* O-157 vero toxin II (VT2) gene using Bca RNase HIII. Lane M: molecular weight marker (100 bp ladder); lane N: sterile water as template; lane 1: the template corresponding to 1 cell; lane 2: the template corresponding to 10 cells; lane 3: the template corresponding to $10^2$ cells; and lane 4: the template corresponding to $10^3$ cells.

As shown in FIG. 27, VT2 gene was detected using the hot water-extract corresponding to 1 cell according to the ICAN. These results were equivalent to those of the detection reactions according to the ICAN using *E. coli* RNase H and the PCR as described in Example 22. Thus, it was confirmed that the ICAN using a heat-resistant RNase H, Bca RNase HIII, was also effective in detecting a virus, a bacterium and the like.

EXAMPLE 43

Figure 29:
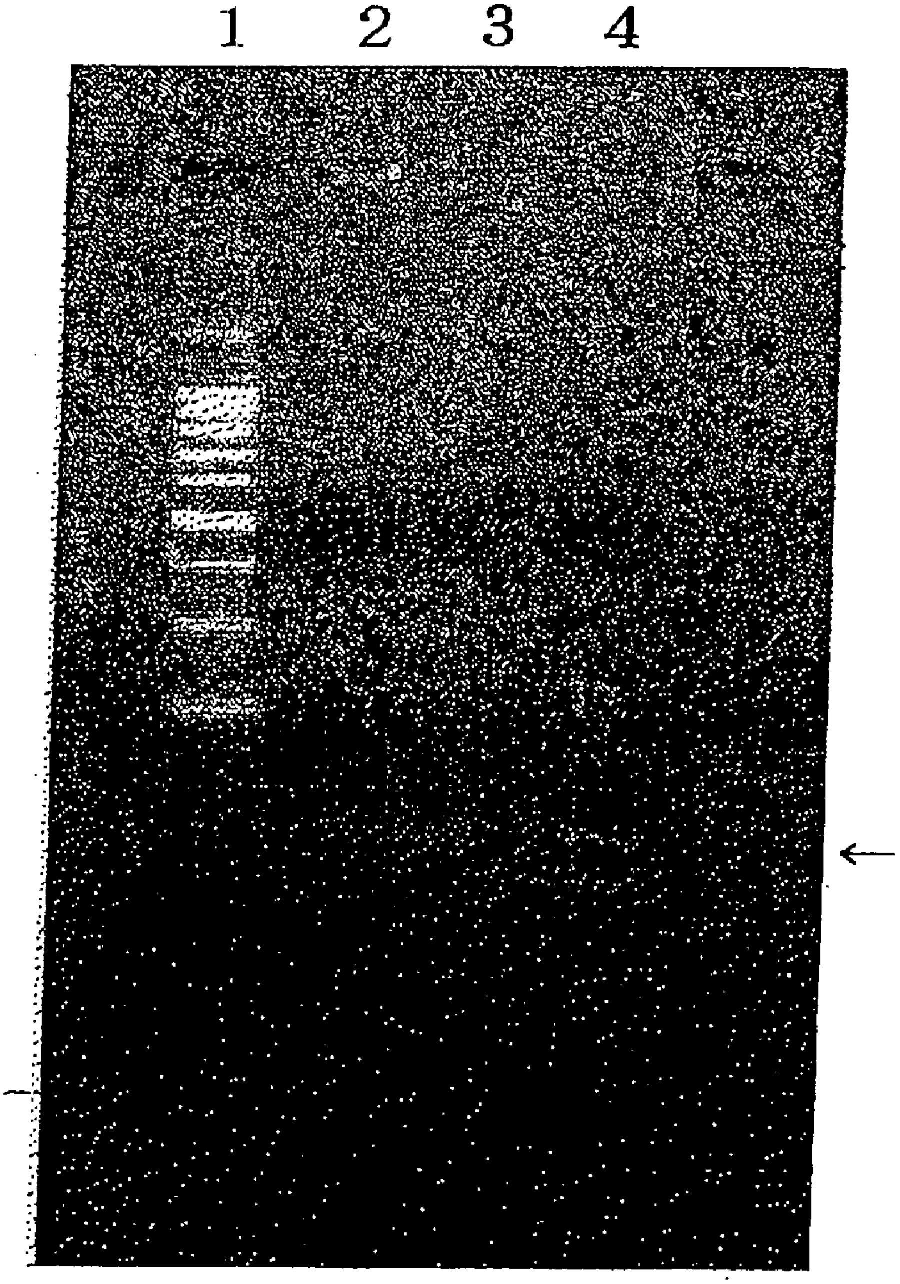
FIG. 29 is a photograph of agarose gel electrophoresis of amplified DNA fragments amplified according to the method of the present invention.

Detection of *Staphylococcus aureus* enterotoxin A gene was examined. Primers SEA-1 and SEA-2 represented by SEQ ID NOS:225 and 226 were synthesized based on the nucleotide sequence of the enterotoxin A gene region of *Staphylococcus aureus*. 50 $\mu$l of a reaction mixture containing 1 $\mu$l of a solution containing 115 pg or 1.15 ng of a genomic DNA from *Staphylococcus aureus* (ATCC accession no. 13565) or 1 $\mu$l of water for a negative control, 50 pmol each of the primers, 0.5 mM each of dNTPs, 32 mM HEPES-potassium hydroxide buffer (pH 7.8), 100 mM potassium acetate, 4.0 mM magnesium acetate, 0.01% bovine serum albumin, 1.0% dimethyl sulfoxide, 0.0156 $\mu$g of Pfu RNase H and 1 U of BcaBEST DNA polymerase was incubated at 58° C. for 1 hour in a thermal cycler. After reaction, 5 $\mu$l each of the reaction mixtures was analyzed by electrophoresis on 3.0% agarose gel. The results are shown in FIG. 29. FIG. 29 shows the results of electrophoresis for the detection of *Staphylococcus aureus* enterotoxin A gene. Lane 1: molecular weight marker (100 bp ladder); lane 2: negative control (sterile water); lane 3: 115 pg of the template; and lane 4: 1.15 ng of the template.

As shown in FIG. 29, the amplification product of interest was observed using about 1.15 ng of the template.

EXAMPLE 44

Detection of hepatitis C virus (HCV) was examined. Primers HCV-F3 and HCV-R1 having nucleotide sequences represented by SEQ ID NOS:227 and 228 were synthesized based on the nucleotide sequence of HCV. A template DNA was prepared as follows. Briefly, 4 $\mu$l of a mixture containing RNA prepared as described in Example 34 from 100 $\mu$l of a serum from a healthy individual or a patient with HCV, 10 mM tris-hydrochloride buffer (pH 8.3), 5 mM $MgCl_2$, 1 mM each of dNTPs, 10 pmol of Random 6 mers primer and 10 U of Reverse Transcriptase XL (Takara Shuzo) was incubated at 30° C. for 10 minutes and at 42° C. for 1 hour and then heated at 99° C. for 5 minutes for inactivating the enzyme using a thermal cycler (Gene Amp PCR System 9600, Applied Biosystems) to prepare a cDNA.

Figure 31:
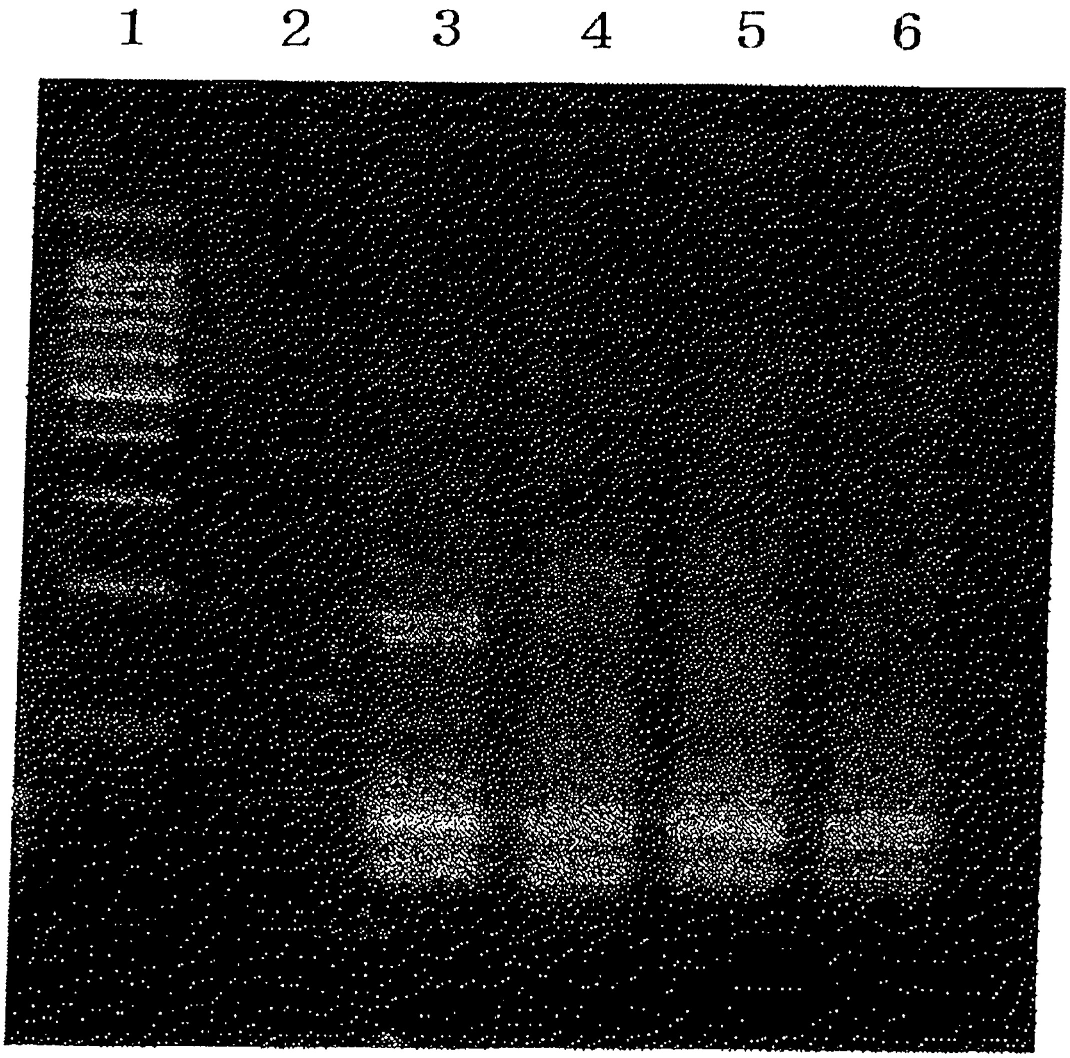
FIG. 31 is a photograph of agarose gel electrophoresis of amplified DNA fragments amplified according to the method of the present invention.

An ICAN was carried out at 55° C. for 1 hour as described in Example 26 except that 1 $\mu$l of the cDNA reaction mixture and 100 pmol each of the primers HCV-F3 and HCV-R1 were used. After reaction, 2.5 $\mu$l each of the reaction mixtures was subjected to electrophoresis on 3.0% agarose gel. The results are shown in FIG. 31. FIG. 31 shows the results of electrophoresis for the detection of hepatitis C virus. Lane 1: molecular weight marker (100 bp); lane 2: the template prepared from a serum from a healthy individual; and lanes 3 to 6: the templates prepared from sera from patients infected with HCV.

As shown in FIG. 31, it was confirmed that HCV could be specifically detected from the serum samples from patients infected with HCV.

EXAMPLE 45

The amplification method of the present invention was examined.

Figure 32:
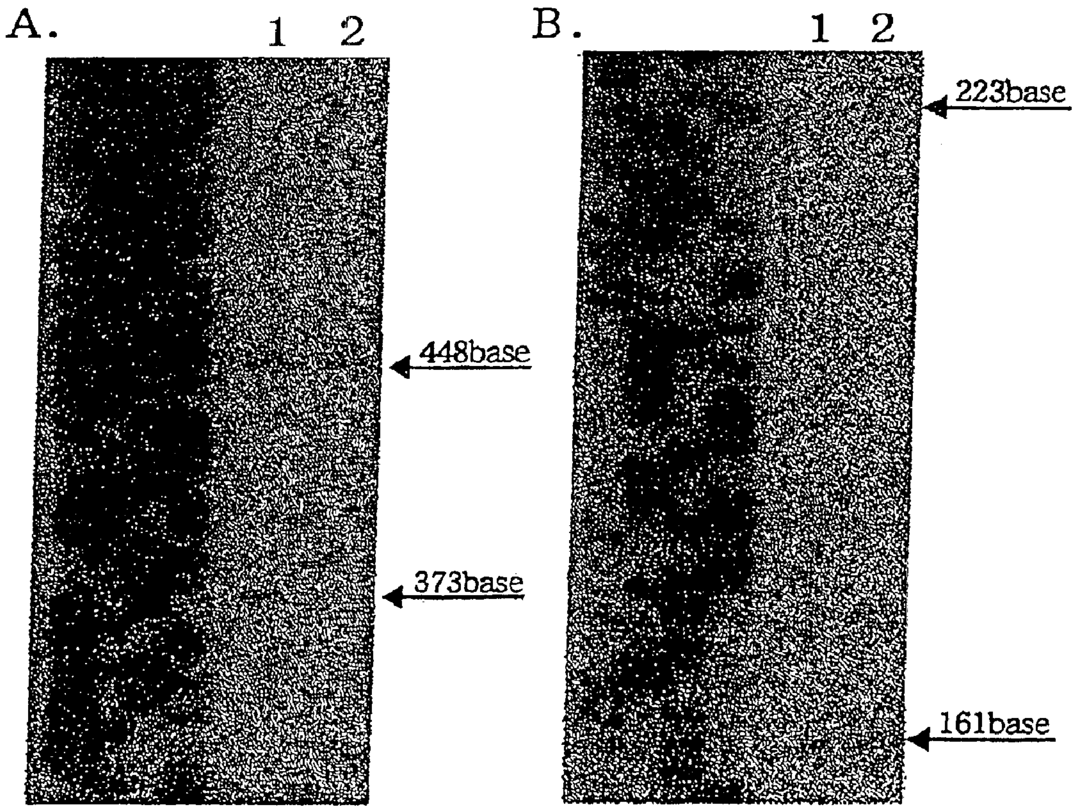
FIG. 32 is a photograph of polyacrylamide gel electrophoresis of amplified DNA fragments amplified according to the method of the present invention.

(1) A PCR was carried out using the pUC19-150 plasmid DNA as prepared in Example 15(2) as a template and primers MCS-F and MCS-R represented by SEQ ID NOS:124 and 125. A PCR-amplified fragment of 534 bp was obtained by purifying the reaction mixture using Microcon-100 (Millipore). A reaction mixture containing 15 ng of the PCR fragment and 30 pmol of a primer MR1 having a nucleotide sequence represented by SEQ ID NO:229 labeled with [$\gamma$-$^{32}$P]ATP by phosphorylation at the 5-terminus and sterile distilled water to 5 $\mu$l and a reaction mixture further containing 30 pmol of a primer MR2 having a nucleotide sequence represented by SEQ ID NO:230 were prepared. The reaction mixtures were heat-denatured at 98° C. for 2 minutes and then cooled to 55° C. 20 $\mu$l of a reaction mixture (42.5 mM Tricine buffer (pH 8.7), 12.5 mM potassium chloride, 12.5 mM ammonium sulfate, 0.0125% BSA, 1.25% DMSO, 5 mM magnesium acetate, 0.625 mM each of dNTPs) containing 1 U of BcaBEST DNA polymerase was added to the reaction mixture. The resulting mixture was reacted at 55° C. for 15 minutes. After reaction, 2.5 $\mu$l of a reaction termination solution (95% formamide, 20 mM EDTA, 0.05% Bromophenol Blue, 0.5% xylene cyanol) was added to 5 $\mu$l of the reaction mixture. The mixture was heat-denatured at 94° C. for 3 minutes. 1.6 $\mu$l each of the reaction mixtures was subjected to electrophoresis on 6% polyacrylamide gel containing 8 M urea and the signals were read using BAS2000 (Fujix) to detect products extended from the primer MR1. The results are shown in FIG. 32A. The sequence ladder in FIG. 32A was prepared by sequencing M13mp18 single strand DNA (Takara Shuzo) using the primer MF2 labeled with [$\gamma$-$^{32}$P]ATP by phosphorylation and used for the determination of the length of the extension product. Lane 1: a combination of the primers MF2 and MR1; and lane 2: MR1.

As shown in FIG. 32A, a band of 448 bp extended from the primer MR1 to the end of the template was detected when the extension reaction was carried out by adding only the primer MR1 to the template. On the other hand, a band of 373 bp bounded by the primers MR1 and MF2 was detected in addition to the above-mentioned band by further adding the primer MF2. Thus, it was confirmed that the extension from the MR1 primer using the PCR-amplified fragment as a template by the action of BcaBEST DNA polymerase was switched due to template switching to the extension using a strand extended from the primer MF2 as a template. Furthermore, template switching was observed when Klenow DNA polymerase was used as a mesophilic DNA polymerase having a strand displacement activity under similar conditions. On the other hand, template switching was not observed when TaKaRa Taq DNA polymerase (Takara Shuzo) or PyroBEST DNA polymerase (Takara Shuzo) without a strand displacement activity was used.

(2) The template switching reaction was examined using a template DNA strand with a primer being annealed thereto. DNA fragments to which the primers MF2 and MR1 could be annealed were prepared as follows. PCRs were carried out using the plasmid pUC19 as a template and primers MCSF and RV (Takara Shuzo) or primers M4 (Takara Shuzo) and MCSR. The reaction mixtures were purified using Microcon-100 to obtain PCR-amplified fragments MSCF-RV (236 bp) and M4-MCSR (271 bp). The region bounded by the primers M4 and RV was commonly present in the two PCR-amplified fragments.

Next, a template-primer (1) in which template DNA strands with primers being annealed thereto were not annealed each other, and a template-primer (2) in which template DNA strands with primers being annealed thereto were annealed each other were prepared as follows.

(1) A reaction mixture containing 30 ng of the fragment MCSF-RV, 40 pmol of the primer MF2 labeled with [γ-$^{32}$P] ATP by phosphorylation at the 5'-terminus, propylenediamine at a final concentration of 0.01% and sterile distilled water to 5 μl, and a mixture containing 30 ng of the fragment M4-MCSR, 40 pmol of the primer MR1, propylenediamine at a final concentration of 0.01% and sterile distilled water to 5 μl were separately heat-denatured at 98° C. for 2 minutes and then cooled to 55° C. 2.5 μl each of the reaction mixtures were mixed together to prepare a template-primer.

(2) A reaction mixture containing 15 ng of the fragment MCSF-RV, 15 ng of the fragment M4-MCSR, 20 pmol of the primer MF2 labeled with [γ-$^{32}$P]ATP by phosphorylation at the 5'-terminus, 20 pmol of the primer MR1, propylenediamine at a final concentration of 0.01% and sterile distilled water to 5 μl was heat-denatured at 98° C. for 2 minutes and then cooled to 55° C. to prepare a template-primer.

20 μl of a reaction mixture (42.5 mM Tricine buffer (pH 8.7), 12.5 mM potassium chloride, 12.5 mM ammonium sulfate, 0.0125% BSA, 1.25% DMSO, 5 mM magnesium acetate, 0.625 mM each of dNTPs) containing 1 U of BcaBEST DNA polymerase was added to 5 μl of the template-primer reaction mixture. The resulting mixture was reacted at 55° C. for 15 minutes. After reaction, 2.5 μl of a reaction termination solution (95% formamide, 20 mM EDTA, 0.05% Bromophenol Blue, 0.5% xylene cyanol) was added to 5 μl of the reaction mixture. The mixture was heat-denatured at 94° C. for 3 minutes. 1.6 μl each of the reaction mixtures was subjected to electrophoresis on 6% polyacrylamide gel containing 8 M urea and the signals were read using BAS2000 (Fujix) to detect products extended from the primer MF2. The results are shown in FIG. 32B. The sequence ladder in FIG. 32B was prepared by sequencing M13mp18 single strand DNA using the primer MR1 labeled with [γ-$^{32}$P]ATP by phosphorylation and used for the determination of the length of the extension product. Lane 1: template DNA strands not being annealed each other; and lane 2: template DNA strands being annealed each other.

As shown in FIG. 32B, only a band of 161 bp extended from the primer MF2 to the end of the template was detected for the template-primer in which template DNA strands with primers being annealed thereto were not annealed each other. On the other hand, a band of 223 bp bounded by the primers MF2 and MR1 in addition to the above-mentioned band was detected for the template-primer in which template DNA strands with primers being annealed thereto were annealed each other. Thus, it was confirmed that a template switching reaction took place if template DNA strands with primers being annealed thereto were annealed each other.

EXAMPLE 46

(1) Detection of *Mycobacterium tuberculosis* was examined using the RNase H derived from *Archaeoglobus fulgidus* (Afu) described in Referential Example 7. Primers MTIS2F (SEQ ID NO:244) and MTIS2R (SEQ ID NO:245) were synthesized on the basis of the nucleotide sequence of the *Mycobacterium tuberculosis* genome registered in GenBank under accession number AL123456. The length of the region bordered by the primer pair including the primer portions is 103 bp. *Mycobacterium tuberculosis* genomic DNA as a template was extracted from dried BCG vaccine (Nippon BCG Seizo) according to a conventional method. Solutions containing 100 pg, 10 pg, 1 pg, 100 fg, 10 fg or 1 fg of the genomic DNA per μl of sterile water were prepared. Reactions were carried out as follows. Briefly, at final concentrations, 32 mM HEPES-potassium hydroxide buffer (pH 7.8), 100 mM potassium acetate, 1% DMSO, 0.01% BSA, 4 mM magnesium acetate, 500 μM each of dNTPs, 50 pmol each of the primers MTIS2F and MTIS2R, 8.75 U of RNase H from Afu, 8 U of BcaBEST DNA polymerase and 1 μl of one of the templates were mixed and the final volume was made to 50 μl with sterile water. The reaction mixtures were placed in Thermal Cycler Personal which had been set at 60° C. and incubated for 60 minutes. After reaction, 3 μl each of the reaction mixtures was subjected to electrophoresis on 3.0% agarose gel.

On the other hand, a PCR was carried out as a control. Primers MTIS PCR-F and MTIS PCR-R as described in Rinsho Byori (the Japanese Journal of Clinical Pathology), 43(9):941–947 (1995) were used as primers. An amplification product of 276 bp is obtained using the primer pair. A reaction mixture of 50 μl was prepared using 10 pmol each of the primers according to the instruction manual attached to Ex Taq DNA polymerase (Takara Shuzo). The reaction mixture was placed in Thermal Cycler and subjected to a reaction of 40 cycles each cycle consisting of 94° C. for 30 seconds, 50° C. for 30 seconds and 72° C. for 30 seconds. After reaction, 3 μl each of the reaction mixtures was subjected to electrophoresis on 3.0% agarose gel.

As a result, the amplification products of interest were observed in either case using 100 fg of the template.

(2) Detection of *Chlamydia trachomatis* was examined using RNase H from Afu or RNase H from *Pyrococcus horikoshii* (Pho). Primers CT2F (SEQ ID NO:246) and CT2R (SEQ ID NO:247) were synthesized on the basis of the nucleotide sequence of the *Chlamydia trachomatis* plasmid registered in GenBank under accession number X06707. The length of the region bordered by the primer pair including the primer portions is 109 bp. A samples as a template DNA was prepared by subjecting a clinical specimen obtained from a patient agreed with the informed concept to phenol-chloroform treatment and ethanol precipitation, and collecting a DNA. Reactions were carried out as follows. Briefly, at final concentrations, 32 mM HEPES-potassium hydroxide buffer (pH 7.8), 100 mM potassium acetate, 1% DMSO, 0.01% BSA, 4 mM magnesium acetate, 500 μM each of dNTPs, 50 pmol each of the primers CT2F and CT2R, 46.4 U of RNase H from Pho or 8.75 U of RNase H from Afu, 8 U of BcaBEST DNA polymerase and 1 μl of the sample were mixed and the final volume was made to 50 μl with sterile water. The reaction mixtures were placed in Thermal Cycler Personal which had been set at 55° C. and incubated for 60 minutes. After reaction, 3 μl each of the reaction mixtures was subjected to electrophoresis on 3.0% agarose gel. As a result, the amplification products of interest was observed. These results demonstrate that *Chlamydia trachomatis* can be detected using RNase H from Afu or Pho in the method of the present invention.

(3) Furthermore, detection using magnetic beads in a commercially available detection instrument was examined. Briefly, an amplification reaction was carried out as described in (1) above using the primer MTIS2R used in (1) above labeled at its 5'-terminus with biotin as a primer and 100 ng of the *Mycobacterium tuberculosis* genomic DNA as a template. The resulting amplified fragment was diluted 30-fold, 300-fold or 3000-fold and subjected to detection using streptoavidin-coated magnetic beads (Pierce) in an automated detection instrument Lumipuls (Fujirebio). Magnetic beads having streptoavidin capable of binding 100 pmol of biotin being immobilized was reacted with the biotinylated amplified fragment for 5 minutes on the first layer of a cuvette. 0.1 N NaOH was then added thereto. Hybridization with a FITC-labeled probe MTISBF was carried out for 5 minutes. After washing, a POD-labeled anti-FITC antibody was added thereto. After reacting for 5 minutes and washing, a luminescent substrate was added thereto. As a result, it was shown that detection can be carried out semi-quantitatively in a short time (20 minutes) using magnetic beads in a conventional automated detection instrument. The detection was carried out by measuring the luminescence level by photocounting. The results are shown in Table 15.

TABLE 15

| Mycobacterium tuberculosis amplicon | Photocounting | S/N ratio |
|---|---|---|
| × 30 | $3.55 \times 10^7$ | 29.6 |
| × 300 | $1.21 \times 10^7$ | 10.0 |
| × 3000 | $0.21 \times 10^7$ | 1.75 |
| 0 | $0.12 \times 10^7$ | — |

The results in Table 15 demonstrate that detection can be carried out with sensitivity equivalent to that of the conventional plate luminescence method.

(4) A hybrid chromatography method was examined as a method for detecting the above-mentioned amplified fragment. Streptoavidin (Nacalai Tesque) was immobilized onto a nitrocellulose membrane. A water-absorptive pad was connected therewith to construct a hybrid chromatography strip. This strip was used to detect the amplified fragment used in (3) above according to a hybrid chromatography method. Detection was carried out by color development using 1-step TMB-Blotting (Pierce). Specifically, a reaction mixture containing the amplified fragment was developed on the nitrocellulose membrane. Then, 0.1 N NaOH solution, FITC-labeled probe, washing solution and color development solution were developed in this order. As a result, a blue band was detected for the amplified fragment derived from a *Mycobacterium tuberculosis*-positive sample. It was demonstrated that this method is useful as a rapid gene examination method because, using this method, results are obtained with naked eyes in 5 to 10 minutes by the method of the present invention.

EXAMPLE 47

Figure 37:
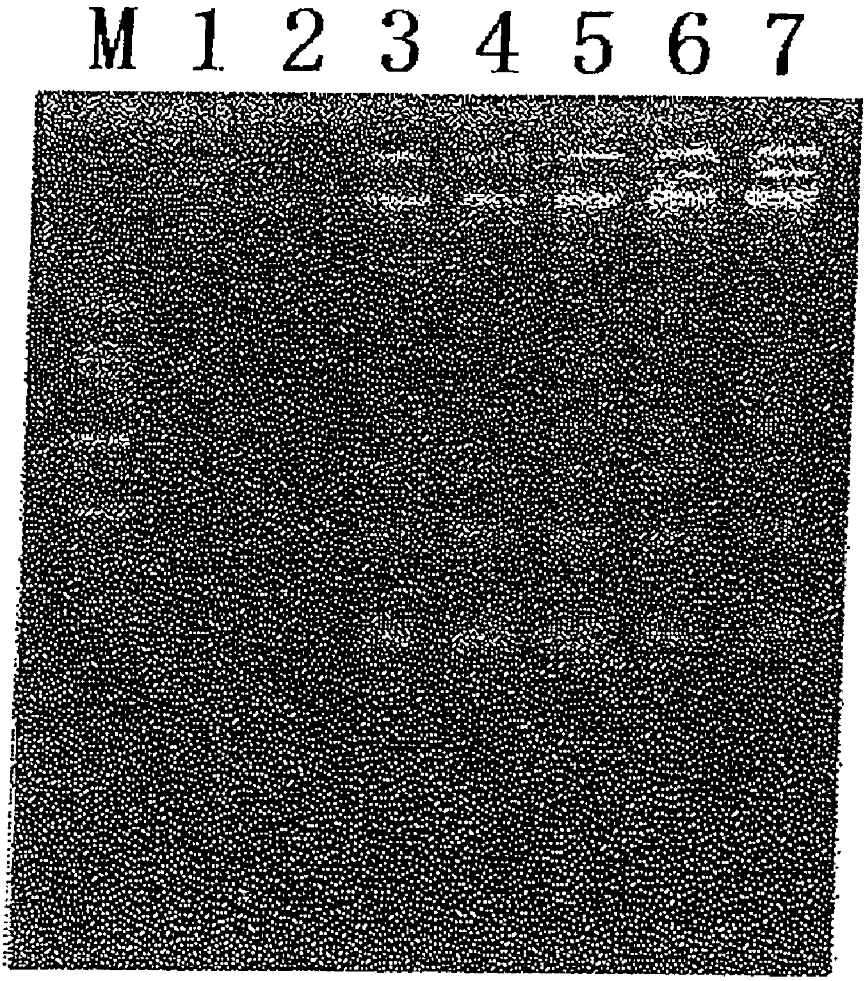
FIG. 37 is a photograph of agarose gel electrophoresis of amplified DNA fragments amplified according to the method of the present invention.

(1) Southern Hybridization Analysis of Amplified Products Containing Laddered Bands In some cases, plural high molecular weight laddered bands other than three bands of interest may be observed in the amplification method of the present invention. The laddered bands were examined. Enterohemorrhagic *E. coli* O-157 was selected as a target. A template DNA, chimeric primers and reaction conditions for ICAN were as described in Example 22. After reaction, 5 μl of the reaction mixture was subjected to electrophoresis on 3% NuSieve 3:1 agarose gel. The results are shown in FIG. 37. In FIG. 37, the lanes represent results for the following: lane M: 100 bp DNA ladder marker; lane 1: negative control; lane 2: the heated extract corresponding to 1 cell; lane 3: the heated extract corresponding to 10 cells; lane 4: the heated extract corresponding to $10^2$ cells; lane 5: the heated extract corresponding to $10^3$ cells; lane 6: the heated extract corresponding to $10^4$ cells; and lane 7: the heated extract corresponding to $10^5$ cells. Ladder bands were observed as shown in FIG. 37.

(2) Analysis of Laddered Amplified Fragments

The nucleotide sequences of the laddered bands obtained in (1) above were analyzed. Briefly, 50 μl of the reaction mixture prepared in (1) was subjected to electrophoresis on 3% agarose gel. After electrophoresis, the laddered bands were excised from the gel. The amplified DNA fragments were then recovered from the gel using EASYTRAP Ver.2 (Takara Shuzo). The recovered amplified fragments were blunt-ended using DNA Blunting kit (Takara Shuzo).

The blunt-ended DNA fragments were ligated with a vector pGEM-3Z (Promega) digested with a restriction enzyme HincII (Takara Shuzo) using DNA ligation Kit (Takara Shuzo) The ligation mixtures were used to transform competent cells of JM109 (Takara Shuzo). After transformation, the cells were cultured on LB agar plate containing 0.1 mM ampicillin, 1 mM IPTG and 0.02% X-gal at 37° C. overnight.

After cultivation, several white colonies were selected from the plates. Colony PCRs were carried out using primers M13-M4 and M13-RV (both from Takara Shuzo) to determine the presence of an insert. Colonies having inserts were cultured with shaking in LB liquid medium containing 0.1 mM ampicillin at 37° C. overnight. After cultivation, plasmids were purified from cells using QIAGEN plasmid mini Kit (Qiagen). The sequences of fragments cloned at the HincII sites of the plasmids were analyzed in both directions using primers M13-M4 and M13-RV according to a conventional method.

As a result, it was demonstrated that the laddered fragment obtained by the method of the present invention has a structure in which the region to be amplified is repeated. Furthermore, it was confirmed that the repetition is in the same direction from 5' to 3'.

(3) The laddered amplified fragments other than three amplified fragments of interest formed in the method of the present invention for detecting *Mycobacterium tuberculosis*, HCV or *Chlamydia trachomatis* were examined. HCV was detected under conditions as described in Example 44. *Mycobacterium tuberculosis* or *Chlamydia trachomatis* was detected under conditions as described in Example 46. The resulting laddered amplified fragments were subcloned and sequenced as described in (2) above. As a result, it was demonstrated that the laddered fragment obtained by the method of the present invention has a structure in which the region to be amplified is repeated. Furthermore, it was confirmed that the repetition is in the same direction from 5' to 3'.

EXAMPLE 48

(1) The detection method of the present invention for *Mycobacterium tuberculosis* was examined. First, primers K-F-1033(60) (SEQ ID NO:248) and K-F-1133(62) (SEQ ID NO:249) were synthesized for amplifying a region with relatively low GC content in the *Mycobacterium tuberculosis* genome. Serial dilutions containing 100 fg to 10 pg of the *Mycobacterium tuberculosis* genomic DNA as described in Example 46(1) were used as templates. The reaction was carried our as follows. Briefly, at final concentrations, 32 mM HEPES-potassium hydroxide buffer (pH 7.8), 100 mM potassium acetate, 1% DMSO, 0.01% BSA, 4 mM magnesium acetate, 500 μM each of dNTPs, 50 pmol each of the primers K-F-1033(60) and K-F-1133(62), 9.375 U of RNase HII from Pfu or 4.375 U of RNase H from Afu, 2.75 U of BcaBEST DNA polymerase and 1 μl of one of the templates were mixed and the final volume was made to 25 μl with sterile water. The reaction mixtures were placed in Thermal Cycler Personal which had been set at 62° C. and incubated for 60 minutes. After reaction, 3 μl each of the reaction mixtures was subjected to electrophoresis on 3.0% agarose gel. As a result, it was demonstrated that the amplification products could be detected using 100 fg to 10 pg of the genomic DNA as a template and either RNase H.

Figure 38:
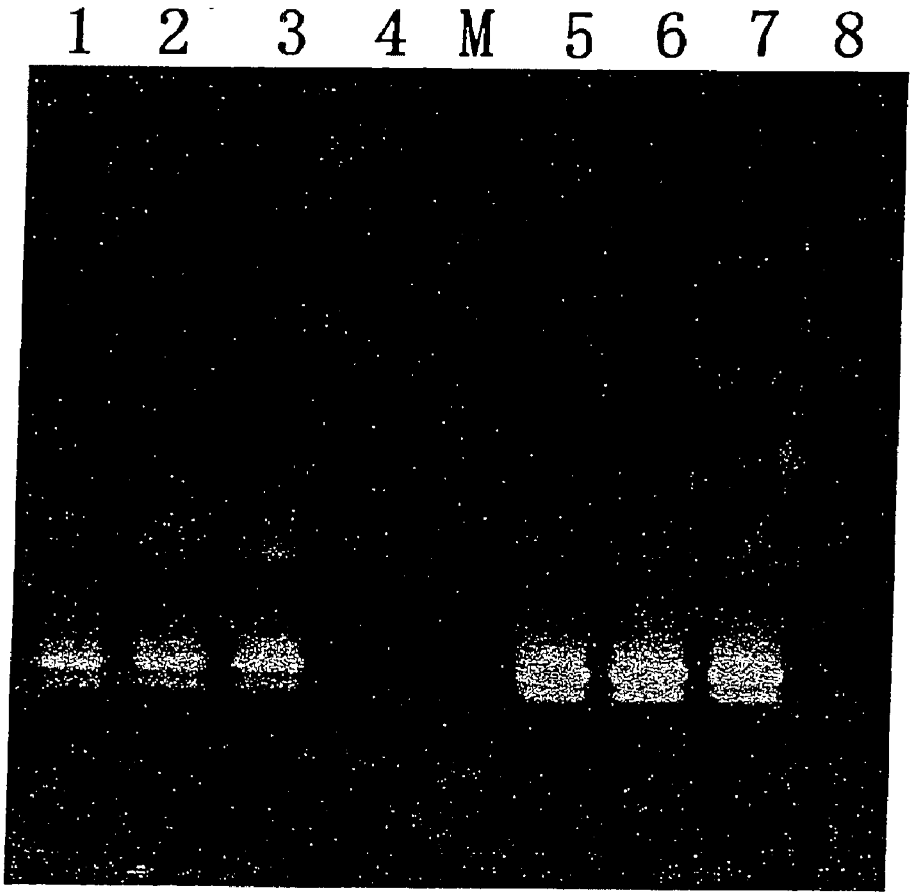
FIG. 38 is a photograph of agarose gel electrophoresis of amplified DNA fragments amplified according to the method of the present invention.

(2) The method as described in (1) above was examined using primers having higher Tm values. First, primers K-F-1033(68) (SEQ ID NO:250) and K-F-1133(68) (SEQ ID NO:251) were synthesized. The amplification reaction was carried out under the same conditions as those described in (1) above except that the reaction temperature was 63° C. After reaction, 3 μl each of the reaction mixtures was subjected to electrophoresis on 3.0% agarose gel. The results are shown in FIG. 38. FIG. 38 illustrates results of electrophoresis of *Mycobacterium tuberculosis* genome amplified using RNase H from Pfu or RNase H from Afu. Lanes 1 to 4 represent results obtained using RNase HII from Pfu and the following amount of template DNA: lane 1: 10 pg; lane 2: 1 pg; lane 3: 100 fg; and lane 4: negative control. Lanes 5 to 8 represent results obtained using RNase HII from Afu and the following amount of template DNA: lane 5: 10 pg; lane 6: 1 pg; lane 7: 100 fg; and lane 8: negative control. Lane M represents 100 bp DNA ladder marker.

As shown in FIG. 38, it was demonstrated that the amplification fragment of interest could be detected using 100 fg of the template DNA and either RNase H. It was shown that more amplification product is obtained when RNase H from Afu is used. In addition, it was shown that more stable detection sensitivity is accomplished when RNase H from Afu is used.

(3) Amplification using a combination of the primers K-F-1033(68) and K-F-1133(68) and a plasmid containing a region to be amplified as a template was examined. First, primers F26 (SEQ ID NO:252) and R1310 (SEQ ID NO:253) were synthesized in order to prepare a plasmid containing a region to be amplified. A PCR was carried out using these primers and BCG vaccine strain. The resulting amplification product was then introduced into pT7-Blue-T vector (Takara Shuzo) to prepare the plasmid. The composition of the reaction mixture was as described in (2) above except that 4 U of Bca DNA polymerase was used. As a result, it was confirmed that detection can be carried out using 1 fg of the template.

(4) The detection sensitivity accomplished when a combination of primers MTIS2F and MTIS2R, which results in the formation of laddered amplified fragments containing the three amplified fragments of interest, was used was compared with that accomplished when a combination of primers K-F-1033(68) and K-F-1133(68), which results in the three amplified fragments of interest, was used. *Mycobacterium tuberculosis* was selected as a target. Reactions were carried out as described in Example 46(2) when the combination of the primers MTIS2F and MTIS2R was used or in (2) above when the combination of the primers K-F-1033(68) and K-F-1133(68) was used. As a result, the same detection sensitivity was observed in either case.

EXAMPLE 49

The amplification method of the present invention that does not comprise denaturation of a genomic DNA as a template was examined.

(1) Primers pDON-AI-68-1 (SEQ ID NO:254) and pDON-AI-68-2 (SEQ ID NO:255) were synthesized in accordance with the nucleotide sequence of the packaging region in a plasmid pDON-AI (Takara Shuzo).

Figure 39:
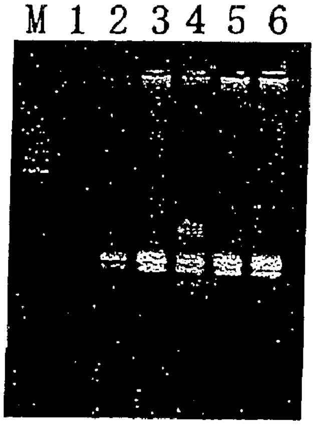
FIG. 39 is a photograph of agarose gel electrophoresis of amplified DNA fragments amplified according to the method of the present invention.

(2) A reaction mixture of a total volume of 50 μl containing 1 μl of a solution containing 10 fg or 1 pg of pDON-AI, 1 μl of a solution containing 1 ng, 10 ng or 100 ng of the genomic DNA derived from NIH/3T3 cells having pDON-AI being incorporated prepared in Example 36, or 1 μl of water as a negative control, 50 pmol each of the primers as described in (1) above, 0.5 mM each of dNTPs, 32 mM HEPES-potassium hydroxide buffer (pH 7.8), 100 mM potassium acetate, 4 mM magnesium acetate, 0.01% BSA, 1% DMSO, 18.5 U of RNase HII from Pfu and 4 U of BcaBEST DNA polymerase was prepared. The reaction mixtures were placed in Thermal Cycler Personal and incubated at 64° C. for 1 hour. After reaction, 5 μl each of the reaction mixtures was subjected to electrophoresis on 3% agarose gel to observe amplification products. The results are shown in FIG. 39. In FIG. 39, the lanes represent results for the following templates: lane M: 100 bp DNA ladder marker; lane 1: negative control; lane 2: 1 ng of genomic DNA having pDON-AI being incorporated; lane 3: 10 ng of genomic DNA having pDON-AI being incorporated; lane 4: 100 ng of genomic DNA having pDON-AI being incorporated; lane 5: 10 fg of pDNA-AI DNA; and lane 6: 1 pg of pDON-AI DNA.

As shown in FIG. 39, amplification of specific DNA fragments was observed for either pDON-AI or the genomic DNA having pDON-AI being incorporated. Thus, it was confirmed that a DNA fragment of interest can be amplified without denaturing the DNA as a template prior to the reaction even if a genomic DNA is used as a template.

EXAMPLE 50

The fidelity (accuracy) of the present invention was compared with that of a PCR utilizing LA technology in which TaKaRa Ex Taq polymerase (Takara Shuzo) was used. First, a plasmid as a template was prepared as follows.

Specifically, the regions each consisting of 300 bp represented by SEQ ID NOS:256 to 259 were amplified by PCR from human proto-oncogene, Wnt-5a gene (GenBank accession no. L20861), ribosomal protein S5 gene (GenBank accession no. XM_009371), human NADH gene (GenBank accession no. NM_000903) and human protocadherin 43 gene (GenBank accession no. AU077347). In this case, the PCRs were carried out using specific primers each having a site for a restriction enzyme SfiI at the 5'-terminus of the primer. After reaction, the amplified fragments were digested with a restriction enzyme SfiI (Takara Shuzo) pUC19 (Takara Shuzo) was digested with restriction enzymes AflIII (NEB) and NdeI (Takara Shuzo) and subjected to agarose gel electrophoresis. A fragment of about 2 kbp was excised from the gel and recovered using EASYTRAP (Takara Shuzo). A DNA having the sequence of SEQ ID NO:260 and a DNA complementary thereto were synthesized using a DNA synthesizer. These DNAs were heat-denatured and then annealed each other to form a double-stranded DNA. This double-stranded DNA has cohesive ends for restriction enzymes AflIII and NdeI at its termini. The double-stranded synthetic DNA was inserted into the fragment obtained by digesting pUC19 with restriction enzymes AflIII and NdeI using DNA Ligation kit ver. 2 (Takara Shuzo). The resulting plasmid was designated as pIC62. pIC62 has sequences to which primers ICAN2 (SEQ ID NO:261) and ICAN6 (SEQ ID NO:262) anneal as well as a site for a restriction enzyme SfiI. The plasmid pIC62 was digested with the restriction enzyme SfiI. The above-mentioned PCR-amplified fragment digested with the restriction enzyme SfiI was ligated with the plasmid using Ligation kit ver. 2 (Takara Shuzo). The ligation mixture was used to transform *Escherichia coli* JM109 (Takara Shuzo). The resulting transformants were cultured, plasmids having the about 300-bp DNAs being inserted were obtained, and the sequences of the inserted DNAs were determined. The plasmids were then used as templates in this Example.

(2) ICAN amplification products were prepared as follows. Briefly, a solution of 10 $\mu$l containing 10 ng of one of the plasmids as a template, 50 pmol each of chimeric primers ICAN2 (SEQ ID NO:261) and ICAN6 (SEQ ID NO:262) and 0.01% propylenediamine was prepared. The solution was denatured at 98° C. for 2 minutes and incubated at 60° C. for 1 minute in Thermal Cycler Personal, and then transferred onto ice. Next, at final concentrations, 20 mM HEPES-potassium hydroxide buffer (pH 7.8), 100 mM potassium acetate, 1% DMSO, 0.01% BSA, 4 mM magnesium acetate, 500 $\mu$M each of dNTPs, 30 U of RNase H from *E. coli* and 5.5 U of BcaBEST DNA polymerase were added thereto and the final volume was made to 50 $\mu$l with sterile water. The reaction mixtures were placed in Thermal Cycler Personal which had been set at 60° C. and incubated for 60 minutes. After reaction, the reaction mixtures were subjected to electrophoresis on 2% SeaKem GTG agarose gel (Takara Shuzo) After electrophoresis, bands for the amplification products of interest were recovered by excision from the agarose gel, recovery using SUPREC-10 (Takara Shuzo), treatment with phenol-chloroform and ethanol precipitation.

(3) PCR amplification products were prepared as follows using TaKaRa Ex Taq DNA polymerase. Briefly, a reaction mixture was prepared using 10 ng of the above-mentioned plasmid as a template as well as 10 pmol each of DNA primers ICAN2 (SEQ ID NO:263) and ICAN6 (SEQ ID NO:264) according to the instruction manual attached to TaKaRa Ex Taq DNA polymerase (Takara Shuzo). The reaction mixture was placed in Thermal Cycler and subjected to a reaction of 30 cycles, each cycle consisting of 94° C. for 30 seconds, 55° C. for 30 seconds and 72° C. for 30 seconds. After reaction, the reaction mixture was subjected to agarose gel electrophoresis as described in (2) above. The amplification products of interest were recovered by excision from the agarose gel, recovery using Microcon-100 (Takara Shuzo), treatment with phenol-chloroform and ethanol precipitation.

(4) The amplification products obtained in (2) and (3) above were subcloned as follows. Briefly, the ICAN amplification products and the PCR amplification products were introduced into a vector pT7 Blue (Takara Shuzo) using Perfectly Blunt Cloning kit (Takara Shuzo) according to the instruction manual. The ligation mixture was used to transform NovaBlue Singles Competent Cell (Takara Shuzo). For each clone, 10 colonies were selected from the resulting transformants and cultured to obtain plasmids each having about 0.4-kb DNA being inserted. The fragments inserted in the plasmids were sequenced using T7 promoter primer (Takara Shuzo) and M3 primer (Takara Shuzo).

A total of about 16,000 bases were analyzed by sequencing as described above. As a result, one mutation was found in about 25,000 bases for both of the fragments amplified according to the method of the present invention and the fragments amplified by PCR using TaKaRa Ex Taq DNA polymerase. Thus, it was confirmed that the fidelity (accuracy) of the method of the present invention is equivalent to that of LA-PCR whose fidelity is high.

EXAMPLE 51

(1) Preparation of Template for ICAN Reaction by PCR

A double-stranded cDNA was prepared from polyA+ RNA derived from mouse brain (OriGene) using cDNA synthesis kit (Takara Shuzo). PCR fragments were amplified using the double-stranded cDNA as a template and combinations of the primers having nucleotide sequences of SEQ ID NOS:265–278. The fragments were introduced into pT7 Blue T-vector (Takara Shuzo) by TA cloning to obtain plasmid clones. A reaction mixture of total volume of 50 $\mu$l containing 1 $\mu$l (1 ng) of one the plasmid clones, 10 pmol each of primers MCS-F (SEQ ID NO:279) and MCS-R (SEQ ID NO:280), 1.25 U of Ex Taq (Takara Shuzo), 5 $\mu$l of 10×Ex Taq buffer (Takara Shuzo) and 0.2 mM each of dNTPs was subjected to the following reaction using TaKaRa PCR Thermal Cycler Personal (Takara Shuzo): 94° C. for 2 minutes; 30 cycles of 94° C. for 30 seconds, 55° C. for 30 seconds and 72° C. for 1 minute. The resulting amplified DNA fragment was used as a template for an ICAN reaction.

(2) Amplification of DNA Fragment by ICAN Using PCR Product as Template

An ICAN reaction was carried out using Aminoallyl dUTP (Sigma) in order to introduce an amino group into an ICAN amplification product. The ratio of amino group introduced into an ICAN amplification product was examined by changing the ratio of the amount of dTTP to the amount of Aminoallyl dUTP in the ICAN reaction as follows: 10:0, 9:1, 8:2, 7:3 and 6:4. The reaction was carried out as follows.

First, a solution of total volume of 10 $\mu$l containing 1 $\mu$l of the PCR reaction mixture prepared in (1) above, 50 pmol each of primers MF2N3(24) (SEQ ID NO:281) and MR1N3 (24) (SEQ ID NO:282) and 2 $\mu$l of 0.05% aqueous solution of propylenediamine was heated at 98° C. for 2 minutes followed by 65° C. for 30 seconds in TaKaRa PCR Thermal Cycler Personal and rapidly cooled on ice to anneal the primers to the template. A reaction mixture of total volume of 40 $\mu$l containing 0.625 mM each of DATP, dCTP and dGTP, 0.625 mM of a dTTP+Aminoallyl dUTP mixture, 32 mM HEPES-potassium hydroxide buffer (pH 7.8), 5.0 mM magnesium acetate, 0.6 U of RNase H from *E. coli* (Takara Shuzo) and 2.75 U of BcaBEST DNA polymerase was added to the heated solution. The resulting mixture was incubated in Thermal Cycler at 65° C. for 1 hour.

50 $\mu$l of isopropanol and 5 $\mu$l of 3 M sodium acetate solution (pH 5.2) were added to the reaction mixture of 50

μl. The resulting mixture was cooled at −80° C. for 20 minutes and then centrifuged to remove a supernatant. 200 μl of 70% ethanol solution was added thereto. The supernatant was removed by centrifugation. The precipitate was air-dried. The resulting DNA was redissolve in water. $OD_{260/280}$ was measured to determined the amount of the product.

(3) Confirmation of Introduction of Aminoallyl dUTP into ICAN Amplification Product Introduction of an amino group into an ICAN product was confirmed by fluorescence-label the amino group in the ICAN product using 5-carboxyfluorecein succinimidil ester (Molecular Probe). The above-mentioned DNA solution was diluted to make the concentration to 2 μg/50 μl. 20 μl of 1 M sodium carbonate buffer (pH 9.0) was added thereto. Then, 4 μl of a solution of FITC (Nacalai Tesque) in N,N-dimethylformamide at a concentration of 10 mM was further added. The resulting mixture was reacted at 20° C. for 16 hours. After removing excess FITC using a commercially available spin column, 10 μl of the reaction mixture was applied onto 2.0% agarose gel and electrophoresed. After electrophoresis, fluorescent dye was detected using FM-BIO. Furthermore, the ICAN-amplified fragment was detected by staining with EtBr. As a result, it was confirmed that an amino group can be introduced into an ICAN amplification product by conducting an ICAN using Aminoallyl dUTP. It was also confirmed that the detection sensitivity can be further increased by using a modified nucleotide having a functional group and fluorescent label for an amplification product in combination.

(4) The amplification method of the present invention was examined using deoxyUTP. *Mycobacterium tuberculosis* was selected as a target. First, primers MTIS2F-16 (SEQ ID NO:283) and MTIS2R-ACC (SEQ ID NO:284) were synthesized in accordance with the nucleotide sequence of *Mycobacterium tuberculosis* genome registered in GenBank under accession no. AL123456. The length of the region to be amplified using this primer pair including the primer portions is 98 bp. A template was prepared as follows. Briefly, a product obtained by PCR-amplifying the *Mycobacterium tuberculosis* genome using primers MTIS-PCR-F-2 (SEQ ID NO:285) and MTIS-PCR-R-2 (SEQ ID NO:286) was inserted into pT7 Blue T-Vector (Takara Shuzo) using DNA Ligation kit Ver. 2. The ligated plasmid was used to transform *Escherichia coli* JM109. The resulting transformants were cultured to obtain a plasmid having an about 400-bp DNA being introduced. A solution containing $10^3$ copies of the plasmid per μl was prepared based on the concentration determined by measuring OD260.

At final concentrations, 32 mM HEPES-potassium hydroxide buffer (pH 7.8), 100 mM potassium acetate, 1% DMSO, 0.01% BSA, 4 mM magnesium acetate, 500 μM each of dATP, dCTP, dGTP and a dTTP/dUTP mixture (500/0, 400/100, 300/200, 200/300, 100/400 or 0/500 μM), 50 pmol each of the primers MTIS 2F-16 and MTIS 2R-AAC, 8.75 U of RNase H from Afu, 8 U of BcaBEST DNA polymerase and 1 μl of the template (103 copies) were mixed and the final volume was made to 50 μl with sterile water. The reaction mixtures were placed in Thermal Cycler Personal which had been set at 60° C. and incubated for 60 minutes. After reaction, 3 μl each of the reaction mixtures was subjected to electrophoresis on 3% agarose gel.

As a result, the amplification product of interest was observed for each of the dTTP/dUTP ratios. Based on these results, it was confirmed that a modified nucleotide can be used as a substrate in the method of the present invention.

EXAMPLE 52

Application of the method of the present invention to a one-step amplification method was examined. HCV was selected as a target.

(1) Preparation of Transcript RNA

A transcript RNA as a template was prepared. At first, HCV RNA was prepared from 300 μl of a serum derived from a patient with hepatitis C virus agreed with the informed concept using TRIzol reagent (Life Technologies) according to the instructions attached to the reagent and finally dissolved in 20 μl of injectable water (Otsuka Pharmaceutical) to obtain an RNA sample. An RT-PCR was carried out using the RNA sample above as a template. The reaction was carried out as follows. A reaction mixture of 50 μl was prepared using 2 μl of the RNA sample and 20 pmol each of primers SP6-HCV-F (SEQ ID NO:287) and T7-HCV-R (SEQ ID NO:288) according to a manual attached to One-Step RNA PCR kit (Takara Shuzo). The reaction mixture was placed in Thermal Cycler Personal and subjected to the following reaction: 50° C. for 15 minutes; 94° C. for 2 minutes; and 40 cycles of 94° C. for 30 seconds, 60° C. for 30 seconds and 72° C. for 30 seconds. After reaction, the reaction mixture was subjected to electrophoresis on 2% SeaPlaque GTG agarose gel. A 350-bp amplification product of interest was excised from the gel. The DNA was then recovered using EASYTRAP Ver. 2 according to the instructions attached to the kit. A transcript RNA was synthesized using the recovered DNA as a template and Competitive RNA Transcription kit (Takara Shuzo) according to the instructions attached to the kit. The transcript RNA was used as a template for examination of a one-step RT-ICAN.

(2) Examination of One-Step RT-ICAN

The concentration of the transcript RNA prepared in (1) above was determined based on the $OD26_0$ value and dilutions containing $10^4$, $10^5$, $10^6$ or $10^7$ copies per μl were prepared. A reaction mixture of 50 μl was prepared by adding thereto, at final concentrations, 32 mM HEPES-potassium hydroxide buffer (pH 7.8), 100 mM potassium acetate, 1% DMSO, 0.01% BSA, 4 mM magnesium acetate, 500 μM each of dNTPs, 50 pmol each of the primers HCV-A S (SEQ ID NO:289) and HCV-AA (SEQ ID NO:290), 30 U of RNase H from Pfu, 8 U of BcaBEST DNA polymerase, 20 U of RNase inhibitor, 0, 1, 2.5, 3 or 5 U of AMV RTase XL (Takara Shuzo) and 1 μl of one of the dilutions containing varying copies of the transcript RNA. The reaction mixtures were placed in Thermal Cycler Personal which had been set at 60° C. and incubated for 60 minutes. After reaction, 2 μl each of the reaction mixtures was subjected to electrophoresis on 3% agarose gel.

As a result, no amplification product of interest was observed using each of the dilutions of the template when AMV RTase was not added. On the other hand, the amplification product of interest was observed using the dilution containing $10^7$ copies (1 U of AMV RTase XL added), $10^6$ copies (2.5 U of AMV RTase XL added), $10^6$ copies (3 U of AMV RTase XL added) or $10^6$ copies (5 U of AMV RTase XL added). When the reaction was carried out at a temperature of 57° C., the amplification product of interest was observed using the dilution containing $10^5$ copies and 2.5 U of AMV RTase XL. Furthermore, when 1 U of BcaBEST DNA polymerase and 10 U of RNase H from Pfu were used, the amplification product of interest was observed using the dilution containing $10^6$ copies even if no AMV RTase was added.

Sequence Listing Free Text

SEQ ID No:1: Synthetic DNA corresponding to a portion of human transferrin receptor-encoding sequence used as a template SEQ ID NO:2: Designed oligonucleotide primer to amplify a portion of human transferrin receptor-encoding sequence SEQ ID NO:3: Designed oligonucleotide primer to amplify a portion of human transferrin receptor-encoding sequence SEQ ID No:4: Designed chimeric oligonucleotide primer to amplify a portion of human transferrin receptor-encoding sequence. "nucleotide 21 is ribonucleotide-other nucleotides are deoxyribonucleotides"

SEQ ID No:5: Designed chimeric oligonucleotide primer to amplify a portion of human transferrin receptor-encoding sequence. "nucleotide 21 is ribonucleotide-other nucleotides are deoxyribonucleotides"

SEQ ID No:6: Designed chimeric oligonucleotide primer to amplify a portion of human transferrin receptor-encoding sequence. "nucleotide 22 is ribonucleotide-other nucleotides are deoxyribonucleotides"

SEQ ID No:7: Designed chimeric oligonucleotide primer to amplify a portion of human transferrin receptor-encoding sequence. "nucleotide 22 is ribonucleotide-other nucleotides are deoxyribonucleotides"

SEQ ID No:8: Designed chimeric oligonucleotide encoding sequence. "nucleotides 21 to 22 are ribonucleotides-other nucleotides are deoxyribonucleotides"

SEQ ID No:9: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:10: Designed chimeric oligonucleotide primer to amplify a portion of human transferrin receptor-encoding sequence. "nucleotides 19 to 20 are ribonucleotides-other nucleotides are deoxyribonucleotides"

SEQ ID No:11: Designed chimeric oligonucleotide primer to amplify a portion of human transferrin receptor-encoding sequence. "nucleotides 19 to 20 are ribonucleotides-other nucleotides are deoxyribonucleotides"

SEQ ID No:12: Designed oligonucleotide used as a probe for detecting an amplified portion of human transferrin receptor-encoding sequence SEQ ID No:13: Designed chimeric oligonucleotide primer designated as pUC19 upper (2) NN to amplify a portion of plasmid pUC19. "nucleotides 24 to 25 are ribonucleotides-other nucleotides are deoxyribonucleotides"

SEQ ID No:14: Designed chimeric oligonucleotide primer designated as pUC19 lower NN to amplify a portion of plasmid pUC19. "nucleotides 24 to 25 are ribonucleotides-other nucleotides are deoxyribonucleotides"

SEQ ID No:15: Designed chimeric oligonucleotide primer to amplify a portion of plasmid pUC19. "nucleotides 24 to 25 are ribonucleotides-other nucleotides are deoxyribonucleotides"

SEQ ID No:16: Designed chimeric oligonucleotide primer designated as pUC19 lower 542 to amplify a portion of plasmid pUC19. "nucleotides 24 to 25 are ribonucleotides-other nucleotides are deoxyribonucleotides"

SEQ ID No:17: Designed chimeric oligonucleotide primer to amplify a portion of plasmid pUC19. "nucleotides 24 to 25 are ribonucleotides-other nucleotides are deoxyribonucleotides"

SEQ ID No:18: Designed oligonucleotide primer designated as pUC19 upper 150 to amplify a portion of plasmid pUC19. "nucleotides 23 to 25 are ribonucleotides-other nucleotides are deoxyribonucleotides"

SEQ ID No:19: Designed chimeric oligonucleotide primer designated as pUC19 lower NN to amplify a portion of plasmid pUC19. "nucleotides 23 to 25 are ribonucleotides-other nucleotides are deoxyribonucleotides"

SEQ ID No:20: Designed chimeric oligonucleotide primer designated as pUC19 upper 249 to amplify a portion of plasmid pUC19. "nucleotides 23 to 25 are ribonucleotides-other nucleotides are deoxyribonucleotides"

SEQ ID No:21: Designed chimeric oligonucleotide primer to amplify a portion of human transferrin receptor-encoding sequence. "nucleotides 20 to 22 are ribonucleotides-other nucleotides are deoxyribonucleotides"

SEQ ID No:22: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:23: Designed chimeric oligonucleotide primer designated as pUC19 upper (2) NN to amplify a portion of plasmid pUC19. "nucleotides 24 to 25 are ribonucleotides-other nucleotides are deoxyribonucleotides"

SEQ ID No:24: Designed chimeric oligonucleotide primer designated as pUC19 upper (2) NN to amplify a portion of plasmid pUC19. "nucleotides 24 to 25 are ribonucleotides-other nucleotides are deoxyribonucleotides"

SEQ ID No:25: Designed chimeric oligonucleotide primer designated as pUC19 upper (2) NN to amplify a portion of plasmid pUC19. "nucleotides 24 to 25 are ribonucleotides-other nucleotides are deoxyribonucleotides"

SEQ ID No:26: Designed chimeric oligonucleotide primer designated as pUC19 upper (2) NN to amplify a portion of plasmid pUC19. "nucleotides 24 to 25 are ribonucleotides-other nucleotides are deoxyribonucleotides"

SEQ ID No:27: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:28: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:29: Designed chimeric oligonucleotide primer designated as MF2N3(24) to amplify a portion of plasmid pUC19-249 or plasmid pUC19-911. "nucleotides 22 to 24 are ribonucleotides-other nucleotides are deoxyribonucleotides"

SEQ ID No:30: Designed oligonucleotide primer designated as MR1N3(24) to amplify a portion of plasmid pUC19-249 or plasmid pUC19-911. "nucleotides 22 to 24 are ribonucleotides-other nucleotides are deoxyribonucleotides"

SEQ ID No:31: Designed chimeric oligonucleotide primer designated as pUC19 upper 249 to amplify a portion of plasmid pUC19. "nucleotides 24 to 25 are ribonucleotides-other nucleotides are deoxyribonucleotides"

SEQ ID No:32: Designed oligonucleotide primer designated as pUC19 upper 150 to amplify a portion of plasmid pUC19

SEQ ID No:33: Designed oligonucleotide primer designated as pUC19 upper 249 to amplify a portion of plasmid pUC19

SEQ ID No:34: Designed oligonucleotide primer designated as pUC19 lower NN to amplify a portion of plasmid pUC19

SEQ ID No:35: Designed chimeric oligonucleotide primer to amplify a portion of plasmid pUC19. "nucleotides 28 to 30 are ribonucleotides-other nucleotides are deoxyribonucleotides"

SEQ ID No:36: Designed chimeric oligonucleotide primer designated as MR1N3 to amplify a portion of plasmid pUC19. "nucleotides 28 to 30 are ribonucleotides-other nucleotides are deoxyribonucleotides"

SEQ ID No:37: Designed oligonucleotide primer to amplify a portion of plasmid pUC19

SEQ ID No:38: Designed oligonucleotide primer designated as MR1N3 to amplify a portion of plasmid pUC19

SEQ ID No:39: Synthetic RNA used as a probe for detecting an amplified portion of plasmid pUC19

SEQ ID No:40: Designed chimeric oligonucleotide primer designated as pUC19 upper 150 to amplify a portion of plasmid pUC19. "nucleotides 24 to 25 are ribonucleotides-other nucleotides are deoxyribonucleotides"

SEQ ID No:41: Designed chimeric oligonucleotide primer designated as MR1N3 to amplify a portion of plasmid pUC19. "nucleotides 28 to 30 are ribonucleotides-other nucleotides are deoxyribonucleotides"

SEQ ID No:42: Designed oligonucleotide primer designated as M13M4

SEQ ID No:43: Designed chimeric oligonucleotide primer to amplify a portion of vero toxin 1-encoding sequence from hemorrhagic *Escherichia coli* O-157. "nucleotides 16 to 18 are ribonucleotides-other nucleotides are deoxyribonucleotides"

SEQ ID No:44: Designed chimeric oligonucleotide primer to amplify a portion of vero toxin 1-encoding sequence from hemorrhagic *Escherichia coli* O-157. "nucleotides 15 to 17 are ribonucleotides-other nucleotides are deoxyribonucleotides"

SEQ ID No:45: Designed chimeric oligonucleotide primer to amplify a portion of vero toxin 2-encoding sequence from hemorrhagic *Escherichia coli* O-157. "nucleotides 16 to 18 are ribonucleotides-other nucleotides are deoxyribonucleotides"

SEQ ID No:46: Designed chimeric oligonucleotide primer to amplify a portion of vero toxin 2-encoding sequence from hemorrhagic *Escherichia coli* O-157. "nucleotides 16 to 18 are ribonucleotides-other nucleotides are deoxyribonucleotides"

SEQ ID No:47: Designed oligonucleotide primer designated as MCR-F to amplify a long DNA fragment SEQ ID No:48: Designed oligonucleotide primer designated as MCR-R to amplify a long DNA fragment SEQ ID No:49: Designed chimeric oligonucleotide primer designated as MF2N3(24) to amplify a long DNA fragment. "nucleotides 22 to 24 are ribonucleotides-other nucleotides are deoxyribonucleotides"

SEQ ID No:50: Designed chimeric oligonucleotide primer designated as MR1N3(24) to amplify a long DNA fragment. "nucleotides 22 to 24 are ribonucleotides-other nucleotides are deoxyribonucleotides"

SEQ ID No:51: Designed oligonucleotide primer to amplify a portion of bacteriophage lambda DNA SEQ ID No:52: Designed oligonucleotide primer to amplify a portion of bacteriophage lambda DNA SEQ ID No:53: Designed chimeric oligonucleotide primer to amplify a portion of bacteriophage lambda DNA. "nucleotides 16 to 17 are ribonucleotides-other nucleotides are deoxyribonucleotides"

SEQ ID No:54: Designed chimeric oligonucleotide primer to amplify a portion of bacteriophage lambda DNA. "nucleotides 16 to 17 are ribonucleotides-other nucleotides are deoxyribonucleotides"

SEQ ID No:55: Designed oligonucleotide primer to amplify a portion of bacteriophage lambda DNA SEQ ID No:56: Designed oligonucleotide primer to amplify a portion of bacteriophage lambda DNA SEQ ID No:57: Designed oligonucleotide primer to amplify a portion of bacteriophage lambda DNA SEQ ID No:58: Designed oligonucleotide primer designated as R1-S1 to amplify a portion of bacteriophage lambda DNA SEQ ID No:59: Designed oligonucleotide primer designated as R1-A3 to amplify a portion of bacteriophage lambda DNA SEQ ID No:60: Designed oligonucleotide primer designated as R2-S1 to amplify a portion of bacteriophage lambda DNA SEQ ID No:61: Designed oligonucleotide primer designated as R2-A3 to amplify a portion of bacteriophage lambda DNA SEQ ID No:62: Designed oligonucleotide primer designated as R3-S1 to amplify a portion of bacteriophage lambda DNA SEQ ID No:63: Designed oligonucleotide primer designated as R3-A3 to amplify a portion of bacteriophage lambda DNA SEQ ID No:64: Designed chimeric oligonucleotide primer designated as M13RV-2N 17 mer. "nucleotides 16 to 17 are ribonucleotides-other nucleotides are deoxyribonucleotides"

SEQ ID No:65: Designed chimeric oligonucleotide primer designated as M13RV-2N 20 mer. "nucleotides 19 to 20 are ribonucleotides-other nucleotides are deoxyribonucleotides"

SEQ ID No:66: Designed oligonucleotide primer to amplify a portion of CDC2-related protein kinase PISSLRE gene SEQ ID No:67: Designed oligonucleotide primer to amplify a portion of CDC2-related protein kinase PISSLRE gene SEQ ID No:68: Designed oligonucleotide primer to amplify a portion of Type II cytoskeltal 11 keratin gene SEQ ID No:69: Designed oligonucleotide primer to amplify a portion of Type II cytoskeltal 11 keratin gene SEQ ID No:70: Designed oligonucleotide primer to amplify a portion of bacteriophage lambda DNA SEQ ID No:71: Designed oligonucleotide primer to amplify a portion of bacteriophage lambda DNA SEQ ID No:72: Designed oligonucleotide primer to amplify a portion of bacteriophage lambda DNA SEQ ID No:73: Designed oligonucleotide primer to amplify a portion of bacteriophage lambda DNA SEQ ID No:74: Designed oligonucleotide primer designated as MF2N3(24) to amplify a portion of plasmid pUC19-249 or plasmid pUC19-911

SEQ ID No:75: Designed oligonucleotide primer designated as MR1N3(24) to amplify a portion of plasmid pUC19-249 or plasmid pUC19-911

SEQ ID No:76: Designed chimeric oligonucleotide primer designated as M13M4-3N 20 mer. "nucleotides 18 to 20 are ribonucleotides-other nucleotides are deoxyribonucleotides"

SEQ ID No:77: Designed chimeric oligonucleotide primer designated as M13RV-3N 20 mer. "nucleotides 18 to 20 are ribonucleotides-other nucleotides are deoxyribonucleotides"

SEQ ID No:78: Designed chimeric oligonucleotide primer designated as M13M4-3N 24 mer. "nucleotides 22 to 24 are ribonucleotides-other nucleotides are deoxyribonucleotides"

SEQ ID No:79: Designed oligonucleotide primer designated as M13RV-3N 24 mer. "nucleotides 22 to 24 are ribonucleotides-other nucleotides are deoxyribonucleotides"

SEQ ID No:80: Designed oligonucleotide primer designated as 5' ID to amplify a portion of cyclin A DNA SEQ ID No:81: Designed oligonucleotide primer designated as 3' ID to amplify a portion of cyclin A DNA SEQ ID No:82: Designed oligonucleotide primer designated as M13RV-2N 16 mer. "nucleotides 15 to 16 are ribonucleotides-other nucleotides are deoxyribonucleotides"

SEQ ID No:83: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:84: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:85: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:86: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:87: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:88: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:89: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:90: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:91: Designed chimeric oligonucleotide primer to amplify a portion of human transferrin receptor-encoding sequence. "nucleotides 21 t o 22 are ribonucleotides-other nucleotides are deoxyribonucleotides"

SEQ ID No:92: Designed chimeric oligonucleotide primer to amplify a portion of human transferrin receptor-encoding sequence. "nucleotides 21 to 22 are ribonucleotides-other nucleotides are deoxyribonucleotides"

SEQ ID No: 93: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:94: Designed chimeric oligonucleotide primer to amplify a portion of human transferrin receptor-encoding sequence. "nucleotides 21 to 22 are ribonucleotides-other nucleotides are deoxyribonucleotides"

SEQ ID No:95: Designed oligonucleotide primer to amplify a portion of human transferrin receptor-encoding sequence SEQ ID No:96: Designed oligonucleotide primer to amplify a portion of human transferrin receptor-encoding sequence SEQ ID NO:97: PCR primer BsuII-3 for cloning a gene encoding a polypeptide having a RNaseHII activity from *Bacillus caldotenax.*

SEQ ID NO:98: PCR primer BsuII-6 for cloning a gene encoding a polypeptide having a RNaseHII activity from *Bacillus caldotenax.*

SEQ ID NO:99: PCR primer RNII-S1 for cloning a gene encoding a polypeptide having a RNaseHII activity from *Bacillus caldotenax.*

SEQ ID NO:100: PCR primer RNII-S2 for cloning a gene encoding a polypeptide having a RNaseHII activity from *Bacillus caldotenax.*

SEQ ID NO:101: PCR primer RNII-S5 for cloning a gene encoding a polypeptide having a RNaseHII activity from *Bacillus caldotenax.*

SEQ ID NO:102: PCR primer RNII-56 for cloning a gene encoding a polypeptide having a RNaseHII activity from *Bacillus caldotenax.*

SEQ ID NO:103: PCR primer RNII-Nde for cloning a gene encoding a polypeptide having a RNaseHII activity from *Bacillus caldotenax.*

SEQ ID NO:104: Nucleotide sequence of ORF in RNase-HII gene from *Bucillus caldotenax.*

SEQ ID NO:105: Amino acid sequence of RNaseHII from *Bacillus caldotenax.*

SEQ ID NO:106: PCR primer BsuIII-1 for cloning a gene encoding a polypeptide having a RNaseHIII activity from *Bacillus caldotenax.*

SEQ ID NO:107: PCR primer BsuIII-3 for cloning a gene encoding a polypeptide having a RNaseHIII activity from *Bacillus caldotenax.*

SEQ ID NO:108: PCR primer BsuIII-6 for cloning a gene encoding a polypeptide having a RNaseHIII activity from *Bacillus caldotenax.*

SEQ ID NO:109: PCR primer BsuIII-8 for cloning a gene encoding a polypeptide having a RNaseHIII activity from *Bacillus caldotenax.*

SEQ ID NO:110: PCR primer RNIII-S3 for cloning a gene encoding a polypeptide having a RNaseHIII activity from *Bacillus caldotenax.*

SEQ ID NO:111: PCR primer BcaRNIII-3 for cloning a gene encoding a polypeptide having a RNaseHIII activity from *Bacillus caldotenax.*

SEQ ID NO:112: Nucleotide sequence of ORF in RNase-HIII from *Bacillus caldotenax.*

SEQ ID NO:113: Amino acid sequence of RNaseHIII from *Bacillus caldotenax.*

SEQ ID NO:114: PCR primer BcaRNIIINde for amplifying a gene encoding a polypeptide having a RNaseHIII activity from *Bacillus caldotenax.*

SEQ ID NO:115: Nucleotide sequence conserving between PH1650 and a portion of *Pyrococcus furiosus* genome sequence.

SEQ ID NO:116: PCR primer 165ONde for cloning a gene encoding a polypeptide having a RNaseHII activity from *Pyrococcus furiosus.*

SEQ ID NO:117: PCR primer 1650Bam for cloning a gene encoding a polypeptide having a RNaseHII activity from *Pyrococcus furiosus.*

SEQ ID NO:118: Nucleotide sequence of ORF in RNase-HII from *Pyrococcus furiosus.*

SEQ ID NO:119: Amino acid sequence of RNaseHII from *Pyrococcus furiosus.*

SEQ ID NO:120: PCR primer 915-F1 for cloning a gene encoding a polypeptide having a RNaseHII activity from *Thermotoga maritima.*

SEQ ID NO:121: PCR primer 915-F2 for cloning a gene encoding a polypeptide having a RNaseHII activity from *Thermotoga maritima.*

SEQ ID NO:122: PCR primer 915-R1 for cloning a gene encoding a polypeptide having a RNaseHII activity from *Thermotoga maritima.*

SEQ ID NO:123: PCR primer 915-R2 for cloning a gene encoding a polypeptide having a RNaseHII activity from *Thermotoga maritima.*

SEQ ID NO:124: Designed oligonucleotide primer designated as MCR-F to amplify a long DNA fragment SEQ ID NO:125: Designed oligonucleotide primer designated as MCR-R to amplify a long DNA fragment SEQ ID NO:126: Designed chimeric oligonucleotide primer designated as MF2N3(24) to amplify a long DNA fragment. "nucleotides 22 to 24 are ribonucleotides-other nucleotides are deoxyribonucleotides"

SEQ ID NO:127: Designed chimeric oligonucleotide primer designated as MR1N3(24) to amplify a long DNA fragment. "nucleotides 22 to 24 are ribonucleotides-other nucleotides are deoxyribonucleotides"

SEQ ID NO:128: Designed oligonucleotide primer to amplify a portion of lambda DNA. "nucleotides 18 to 20 are ribonucleotides-other nucleotides are deoxyribonucleotides"

SEQ ID NO:129: Designed chimeric oligonucleotide primer to amplify a portion of lambda DNA. "nucleotides 18 to 20 are ribonucleotides-other nucleotides are deoxyribonucleotides"

SEQ ID NO:130: Designed oligonucleotide primer to amplify a portion of lambda DNA SEQ ID NO:131: Designed oligonucleotide primer to amplify a portion of lambda DNA SEQ ID NO:132: Designed chimeric oligonucleotide primer to amplify a portion of *Flavobacterium* species DNA. "nucleotides 18 to 20 are ribonucleotides-other nucleotides are deoxyribonucleotides"

SEQ ID NO:133: Designed chimeric oligonucleotide primer to amplify a portion of *Flavobacterium* species DNA. "nucleotides 18 to 20 are ribonucleotides-other nucleotides are deoxyribonucleotides"

SEQ ID NO:134: Designed oligonucleotide primer to amplify a portion of *Flavobacterium* species DNA.

SEQ ID NO:135: Designed oligonucleotide primer to amplify a portion of *Flavobacterium* species DNA.

SEQ ID NO:136: Designed chimeric oligonucleotide primer to amplify a portion of vero toxin 2-encoding sequence from hemorrhagic *Escherichia coli* O-157. "nucleotides 19 to 21 are ribonucleotides-other nucleotides are deoxyribonucleotides"

SEQ ID NO:137: Designed chimeric oligonucleotide primer to amplify a portion of vero toxin 2-encoding sequence from hemorrhagic *Escherichia coli* O-157. "nucleotides 18 to 20 are ribonucleotides-other nucleotides are deoxyribonucleotides"

SEQ ID NO:138: Designed oligonucleotide primer to amplify a portion of vero toxin 2-encoding sequence from hemorrhagic *Escherichia coli* O-157.

SEQ ID NO:139: Designed oligonucleotide primer to amplify a portion of vero toxin 2-encoding sequence from hemorrhagic *Escherichia coli* O-157.

SEQ ID NO:140: Designed chimeric oligonucleotide primer to amplify a portion of vero toxin 2-encoding sequence from hemorrhagic *Escherichia coli* O-157. "nucleotides 18 to 20 are ribonucleotides-other nucleotides are deoxyribonucleotides"

SEQ ID NO:141: Designed chimeric oligonucleotide primer to amplify a portion of vero toxin 2-encoding sequence from hemorrhagic *Escherichia coli* O-157. "nucleotides 18 to 20 are ribonucleotides-other nucleotides are deoxyribonucleotides"

SEQ ID NO:142: Designed chimeric oligonucleotide primer to amplify a portion of vero toxin 2-encoding sequence from hemorrhagic *Escherichia coli* O-157. "nucleotides 18 to 20 are ribonucleotides-other nucleotides are deoxyribonucleotides"

SEQ ID NO:143: Designed oligonucleotide primer to amplify a portion of vero toxin 2-encoding sequence from hemorrhagic *Escherichia coli* O-157.

SEQ ID NO:144: Designed oligonucleotide primer to amplify a portion of vero toxin 2-encoding sequence from hemorrhagic *Escherichia coli* O-157.

SEQ ID NO:145: Designed chimeric oligonucleotide primer to amplify a portion of lambda DNA. "nucleotides 18 to 20 are ribonucleotides-other nucleotides are deoxyribonucleotides"

SEQ ID NO:146: Designed oligonucleotide primer to amplify a portion of viroid CSVd.

SEQ ID NO:147: Designed oligonucleotide primer to amplify a portion of viroid CSVd.

SEQ ID NO:148: Designed chimeric oligonucleotide primer to amplify a portion of viroid CSVd. "nucleotides 16 to 18 are ribonucleotides-other nucleotides are deoxyribonucleotides"

SEQ ID NO:149: Designed chimeric oligonucleotide primer to amplify a portion of viroid CSVd. "nucleotides 18 to 20 are ribonucleotides-other nucleotides are deoxyribonucleotides"

SEQ ID NO:150: Designed chimeric oligonucleotide primer to amplify a portion of *Flavobacterium* species DNA. "nucleotides 18 to 20 are ribonucleotides-other nucleotides are deoxyribonucleotides"

SEQ ID NO:151: Designed chimeric oligonucleotide primer to amplify a portion of *Flavobacterium* species DNA. "nucleotides 18 to 20 are ribonucleotides-other nucleotides are deoxyribonucleotides"

SEQ ID NO:152: Designed chimeric oligonucleotide primer to amplify a portion of *Flavobacterium* species DNA. "nucleotides 18 to 20 are ribonucleotides-other nucleotides are deoxyribonucleotides"

SEQ ID NO:153: Designed chimeric oligonucleotide primer to amplify a portion of vero toxin 2-encoding sequence from hemorrhagic *Escherichia coli* O-157. "nucleotides 19 to 21 are ribonucleotides-nucloetide 18 is inosine-other nucleotides are deoxyribonucleotides"

SEQ ID NO:154: Designed chimeric oligonucleotide primer to amplify a portion of vero toxin 2-encoding sequence from hemorrhagic *Escherichia coli* O-157. "nucleotides 19 to 21 are ribonucleotides-nucleotide 17 is inosine other nucleotides are deoxyribonucleotides"

SEQ ID NO:155: Designed chimeric oligonucleotide primer to amplify a portion of vero toxin 2-encoding sequence from hemorrhagic *Escherichia coli* O-157. "nucleotides 19 to 21 are ribonucleotides-nucleotide 16 is inosine-other nucleotides are deoxyribonucleotides"

SEQ ID NO:156: Designed chimeric oligonucleotide primer to amplify a portion of vero toxin 2-encoding sequence from hemorrhagic *Escherichia coli* O-157. "nucleotides 18 to 20 are ribonucleotides-nucleotide 17 is inosine-other nucleotides are deoxyribonucleotides"

SEQ ID NO:157: Designed chimeric oligonucleotide primer to amplify a portion of vero toxin 2-encoding sequence from hemorrhagic *Escherichia coli* O-157. "nucleotides 18 to 20 are ribonucleotides-nucleotide 16 is inosine-other nucleotides are deoxyribonucleotides"

SEQ ID NO:158: Designed chimeric oligonucleotide primer to amplify a portion of vero toxin 2-encoding sequence from hemorrhagic *Escherichia coli* O-157. "nucleotides 18 to 20 are ribonucleotides-nucleotide 15 is inosine-other nucleotides are deoxyribonucleotides"

SEQ ID NO:159: Designed chimeric oligonucleotide primer to amplify a portion of vero toxin 2-encoding sequence from hemorrhagic *Escherichia coli* O-157. "nucleotides 9 to 11 and 19 to 21 are ribonucleotides-other nucleotides are deoxyribonucleotides"

SEQ ID NO:160: Designed chimeric oligonucleotide primer to amplify a portion of vero toxin 2-encoding sequence from hemorrhagic *Escherichia coli* O-157. "nucleotides 8 to 10 and 18 to 20 are ribonucleotides-other nucleotides are deoxyribonucleotides"

SEQ ID NO:161: Designed chimeric oligonucleotide primer to amplify a portion of vero toxin 2-encoding sequence from hemorrhagic *Escherichia coli* O-157. "nucleotides 18 to 20 are ribonucleotides-other nucleotides are deoxyribonucleotides"

SEQ ID NO:162: Designed oligonucleotide probe to detect a DNA fragment amplifying a portion of vero toxin 2-encoding sequence from hemorrhagic *Escherichia coli* O-157.

SEQ ID NO:163: Designed chimeric oligonucleotide primer to amplify a portion of iNOS-encoding sequence from mouse. "nucleotides 18 to 20 are ribonucleotides-other nucleotides are deoxyribonucleotides"

SEQ ID NO:164: Designed chimeric oligonucleotide primer to amplify a portion of iNOS-encoding sequence from mouse. "nucleotides 17 to 19 are ribonucleotides-other nucleotides are deoxyribonucleotides"

SEQ ID NO:165: Designed oligonucleotide primer to amplify a portion of INOS-encoding sequence from mouse.

SEQ ID NO:166: Designed oligonucleotide primer to amplify a portion of iNOS-encoding sequence from mouse SEQ ID NO:167: Designed oligonucleotide primer designated as GMO-PCR-F 20 mer SEQ ID NO:168: Designed oligonucleotide primer designated as GMO-PCR-R 20 mer SEQ ID NO:169: Designed chimeric oligonucleotide primer designated as GMO-S1 20 mer. "nucleotides 19 to 20 are ribonucleotides-other nucleotides are deoxyribonucleotides"

SEQ ID NO:170: Designed oligonucleotide primer designated as GMO-S2 20 mer. "nucleotides 19 to 20 are ribonucleotides-other nucleotides are deoxyribonucleotides"

SEQ ID NO:171: Designed oligonucleotide primer designated as GMO-A1 20 mer. "nucleotides 19 to 20 are ribonucleotides-other nucleotides are deoxyribonucleotides"

SEQ ID NO:172: Designed oligonucleotide primer designated as GMO-A2 20 mer. "nucleotides 19 to 20 are ribonucleotides-other nucleotides are deoxyribonucleotides"

SEQ ID NO:173: Designed chimeric oligonucleotide primer to amplify a portion of vero toxin 2-encoding sequence from hemorrhagic *Escherichia coli* O-157. "nucleotides 18 to 20 are (alpha-thio)ribonucleotides-other nucleotides are deoxyribonucleotides"

SEQ ID NO:174: Designed chimeric oligonucleotide primer to amplify a portion of vero toxin 2-encoding sequence from hemorrhagic *Escherichia coli* O-157. "nucleotides 18 to 20 are (alpha-thio)ribonucleotides-other nucleotides are deoxyribonucleotides"

SEQ ID NO:175: Designed chimeric oligonucleotide primer to amplify a portion of INOS-encoding sequence from mouse. "nucleotides 20 to 22 are ribonucleotides-other nucleotides are deoxyribonucleotides"

SEQ ID NO:176: Designed chimeric oligonucleotide primer to amplify a portion of INOS-encoding sequence from mouse. "nucleotides 20 to 22 are ribonucleotides-other nucleotides are deoxyribonucleotides"

SEQ ID NO:177: Designed oligonucleotide primer to amplify a portion of INOS-encoding sequence from mouse.

SEQ ID NO:178: Designed oligonucleotide primer to amplify a portion of INOS-encoding sequence from mouse.

SEQ ID NO:179: Designed chimeric oligonucleotide primer to amplify a portion of lambda DNA."nucleotides 18 to 20 are ribonucleotides-other nucleotides are deoxyribonucleotides"

SEQ ID NO:180: Designed chimeric oligonucleotide primer to amplify a portion of lambda DNA."nucleotides 19 to 21 are ribonucleotides-other nucleotides are deoxyribonucleotides"

SEQ ID NO:181: Designed chimeric oligonucleotide primer to amplify a portion of INOS-encoding sequence from mouse. "nucleotides 21 to 23 are ribonucleotides-other nucleotides are deoxyribonucleotides"

SEQ ID NO:182: Designed chimeric oligonucleotide primer to amplify a portion of INOS-encoding sequence from mouse. "nucleotides 20 to 22 are ribonucleotides-other nucleotides are deoxyribonucleotides"

SEQ ID NO:183: Designed chimeric oligonucleotide primer to amplify a portion of pDON-AI DNA."nucleotides 17 to 19 are ribonucleotides-other nucleotides are deoxyribonucleotides"

SEQ ID NO:184: Designed chimeric oligonucleotide primer to amplify a portion of pDON-AI DNA."nucleotides 19 to 21 are ribonucleotides-other nucleotides are deoxyribonucleotides"

SEQ ID NO:185: Designed chimeric oligonucleotide primer to amplify a portion of HPV DNA. "nucleotides 19 to 21 are ribonucleotides-other nucleotides are deoxyribonucleotides"

SEQ ID NO:186: Designed chimeric oligonucleotide primer to amplify a portion of HPV DNA. "nucleotides 19 to 21 are ribonucleotides-other nucleotides are deoxyribonucleotides"

SEQ ID NO:187: Designed oligonucleotide probe to detect a DNA fragment amplifying a portion of HPV DNA.

SEQ ID NO:188: Designed oligonucleotide primer to amplify a portion of HCV.

SEQ ID NO:189: Designed oligonucleotide primer to amplify a portion of HCV.

SEQ ID NO:190: Designed chimeric oligonucleotide primer to amplify a portion of HCV."nucleotides 19 to 21 are ribonucleotides-other nucleotides are deoxyribonucleotides"

SEQ ID NO:191: Designed chimeric oligonucleotide primer to amplify a portion of HCV. "nucleotides 16 to 18 are ribonucleotides-other nucleotides are deoxyribonucleotides"

SEQ ID NO:192: Designed oligonucleotide probe to detect a DNA fragment amplifying portion of HCV.

SEQ ID NO:193: Designed chimeric oligonucleotide primer to amplify a portion of adenovirus. "nucleotides 19 to 21 are ribonucleotides-other nucleotides are deoxyribonucleotides"

SEQ ID NO:194: Designed chimeric oligonucleotide primer to amplify a portion of adenovirus. "nucleotides 19 to 21 are ribonucleotides-other nucleotides are deoxyribonucleotides"

SEQ ID NO:195: Designed chimeric oligonucleotide primer to amplify a portion of adenovirus. "nucleotides 19 to 21 are ribonucleotides-other nucleotides are deoxyribonucleotides"

SEQ ID NO:196: Designed oligonucleotide primer to amplify a portion of adenovirus SEQ ID NO:197: Designed oligonucleotide primer to amplify a portion of adenovirus.

SEQ ID NO:198: Designed oligonucleotide primer to amplify a portion of viroid CSVd.

SEQ ID NO:199: Designed oligonucleotide primer to amplify a portion of viroid CSVd.

SEQ ID NO:200: Designed oligonucleotide primer to amplify a portion of pDON-AI DNA.

SEQ ID NO:201: Designed oligonucleotide primer to amplify a portion of pDON-AI DNA.

SEQ ID NO:202: Designed chimeric oligonucleotide primer to amplify a portion of verotoxin-1 encoding sequence from hemorrhagic *Escherichia coli* O-157. "nucleotides 18 to 20 are ribonucleotides-other nucleotides are deoxyribonucleotides"

SEQ ID NO:203: Designed chimeric oligonucleotide primer to amplify a portion of verotoxin-1 encoding sequence from hemorrhagic *Escherichia coli* O-157. "nucleotides 18 to 20 are ribonucleotides-other nucleotides are deoxyribonucleotides"

SEQ ID NO:204: Designed oligonucleotide probe to detect a DNA fragment amplifying a portion of verotoxin-1 encoding sequence from hemorrhagic *Escherichia coli* O-157.

SEQ ID NO:205: Designed chimeric oligonucleotide primer to amplify a portion of *botulinum* toxin A encoding sequence from *Clostridium botulinum*. "nucleotides 19 to 21 are ribonucleotides-other nucleotides are deoxyribonucleotides"

SEQ ID NO:206: Designed chimeric oligonucleotide primer to amplify a portion of *botulinum* toxin A encoding sequence from *Clostridium botulinum*. "nucleotides 21 to 23 are ribonucleotides-other nucleotides are deoxyribonucleotides"

SEQ ID NO:207: Designed oligonucleotide probe to detect a DNA fragment amplifying a portion of *botulinum* toxin A encoding sequence from *Clostridium botulinum.*

SEQ ID NO:208: Designed chimeric oligonucleotide primer to amplify a portion of viroid CSVd. "nucleotides 19 to 21 are ribonucleotides-other nucleotides are deoxyribonucleotides"

SEQ ID NO:209: Designed chimeric oligonucleotide primer to amplify a portion of viroid CSVd. "nucleotides 18 to 20 are ribonucleotides-other nucleotides are deoxyribonucleotides"

SEQ ID NO:210: Designed oligonucleotide probe to detect a DNA fragment amplifying a portion of viroid CSVd.

SEQ ID NO:211: Designed chimeric oligonucleotide primer to amplify a portion of viroid CSVd."nucleotides 19 to 21 are ribonucleotides-other nucleotides are deoxyribonucleotides"

SEQ ID NO:212: Designed chimeric oligonucleotide primer to amplify a portion of viroid CSVd. "nucleotides 19 to 21 are ribonucleotides-other nucleotides are deoxyribonucleotides"

SEQ ID NO:213: Designed oligonucleotide primer to amplify a portion of viroid CSVd.

SEQ ID NO:214: Designed oligonucleotide primer to amplify a portion of viroid CSVd.

SEQ ID NO:215: Designed chimeric oligonucleotide primer to amplify a portion of c-ki-ras oncogene."nucleotides 18 to 20 are ribonucleotides-other nucleotides are deoxyribonucleotides"

SEQ ID NO:216: Designed chimeric oligonucleotide primer to amplify a portion of c-ki-ras oncogene. "nucleotides 18 to 20 are ribonucleotides-other nucleotides are deoxyribonucleotides"

SEQ ID NO:217: Designed oligonucleotide primer to amplify a portion of c-ki-ras oncogene.

SEQ ID NO:218: Designed oligonucleotide primer to amplify a portion of c-ki-ras oncogene.

SEQ ID NO:219: Designed chimeric oligonucleotide primer to amplify a portion of verotoxin-1 encoding sequence from hemorrhagic *Escherichia coli* O-157. "nucleotides 18 to 20 are ribonucleotides-other nucleotides are deoxyribonucleotides"

SEQ ID NO:220: Designed chimeric oligonucleotide primer to amplify a portion of verotoxin-1 encoding sequence from hemorrhagic *Escherichia coli* O-157. "nucleotides 18 to 20 are ribonucleotides-other nucleotides are deoxyribonucleotides"

SEQ ID NO:221: Designed oligonucleotide primer to amplify a portion of INOS-encoding sequence from mouse.

SEQ ID NO:222: Designed oligonucleotide primer to amplify a portion of INOS-encoding sequence from mouse.

SEQ ID NO:223: Designed oligonucleotide primer designated as pUC19 upper 150 to amplify a portion of plasmid pUC19.

SEQ ID NO:224: Designed oligonucleotide primer designated as pUC19 lower NN to amplify a portion of plasmid pUC19.

SEQ ID NO:225: Designed chimeric oligonucleotide primer designated as SEA-1 to amplify a portion of *Staphylococcus aureus*. "nucleotides 19 to 21 are ribonucleotides-other nucleotides are deoxyribonucleotides"

SEQ ID NO:226: Designed chimeric oligonucleotide primer designated as SEA-2 to amplify a portion of *Staphylococcus aureus*. "nucleotides 19 to 21 are ribonucleotides-other nucleotides are deoxyribonucleotides"

SEQ ID NO:227: Designed chimeric oligonucleotide primer designated as HCV-F3 to amplify a portion of HCV. "nucleotides 17 to 19 are ribonucleotides-other nucleotides are deoxyribonucleotides"

SEQ ID NO:228: Designed chimeric oligonucleotide primer designated as HCV-R2 to amplify a portion of HCV. "nucleotides 16 to 18 are ribonucleotides-other nucleotides are deoxyribonucleotides"

SEQ ID NO:229: Designed oligonucleotide primer designated as MF2 to amplify a portion of pUC19 plasmid DNA.

SEQ ID NO:230: Designed oligonucleotide primer designated as MR1 to amplify a portion of pUC19 plasmid DNA.

SEQ ID NO:231: Designed oligonucleotide primer to amplify a portion of adenovirus.

SEQ ID NO:232: Nucleotide sequence of ORF in RNase-HII gene from *Thermotoga maritima.*

SEQ ID NO:233: Amino acid sequence of RNaseHII from *Thermotoga maritima.*

SEQ ID NO:234: Nucleotide sequence of PH1650 from *Pyrococcus horikoshii.*

SEQ ID NO:235: PCR primer PhoNde for cloning a gene encoding a polypeptide having a RNaseHII activity from *Pyrococcus horikoshii.*

SEQ ID NO:236: PCR primer PhoBam for cloning a gene encoding a polypeptide having a RNaseHII activity from *Pyrococcus horikoshii*

SEQ ID NO:237: Nucleotide sequence of ORF in RNase-HII gene from *Pyrococcus horikoshii.*

SEQ ID NO:238: Amino acid sequence of RNaseHII from *Pyrococcus horikoshii.*

SEQ ID NO:239: Nucleotide sequence of AF0621 from *Archaeoglobus fulgidus.*

SEQ ID NO:240: PCR primer AfuNde for cloning a gene encoding a polypeptide having a RNaseHII activity from *Archaeoglobus fulgidus*

SEQ ID NO:241: PCR primer AfuBam for cloning a gene encoding a polypeptide having a RNaseHII activity from *Archaeoglobus fulgidus*

SEQ ID NO:242: Nucleotide sequence of ORF in RNase-HII gene from *Archaeoglobus fulgidus.*

SEQ ID NO:243: Amino acid sequence of RNaseHII from *Archaeoglobus fulgidus.*

SEQ ID NO:244: Designed chimeric oligonucleotide primer designated as MTIS2F to amplify a portion of *Mycobacterium tuberculosis* DNA. "nucleotides 16 to 18 are ribonucleotides-other nucleotides are deoxyribonucleotides."

SEQ ID NO:245: Designed chimeric oligonucleotide primer designated as MTIS2R to amplify a portion of *Mycobacterium tuberculosis* DNA. "nucleotides 19 to 21 are ribonucleotides-other nucleotides are deoxyribonucleotides."

SEQ ID NO:246: Designed chimeric oligonucleotide primer designated as CT2F to amplify a portion of *Chlamydia trachomatis* cryptic plasmid DNA. "nucleotides 18 to 20 are ribonucleotides-other nucleotides are deoxyribonucleotides."

SEQ ID NO:247: Designed chimeric oligonucleotide primer designated as CT2R to amplify a portion of *Chlamydia trachomatis* cryptic plasmid DNA. "nucleotides 16 to 18 are ribonucleotides-other nucleotides are deoxyribonucleotides."

SEQ ID NO:248: Designed chimeric oligonucleotide primer designated as K-F-1033(60) to amplify a portion of *Mycobacterium tuberculosis* DNA. "nucleotides 17 to 19 are ribonucleotides-other nucleotides are deoxyribonucleotides."

SEQ ID NO:249: Designed chimeric oligonucleotide primer designated as K-R-1133(62) to amplify a portion of *Mycobacterium tuberculosis* DNA. "nucleotides 18 to 20 are ribonucleotides-other nucleotides are deoxyribonucleotides."

SEQ ID NO:250: Designed chimeric oligonucleotide primer designated as K-F-1033(68) to amplify a portion of *Mycobacterium tuberculosis* DNA. "nucleotides 20 to 22 are ribonucleotides-other nucleotides are deoxyribonucleotides."

SEQ ID NO:251: Designed chimeric oligonucleotide primer designated as K-R-1133(68) to amplify a portion of *Mycobacterium tuberculosis* DNA. "nucleotides 20 to 22 are ribonucleotides-other nucleotides are deoxyribonucleotides."

SEQ ID NO:252: Designed oligonucleotide primer designated as F26 to amplify a portion of *Mycobacterium tuberculosis* DNA.

SEQ ID NO:253: Designed oligonucleotide primer designated as R1310 to amplify a portion of *Mycobacterium tuberculosis* DNA.

SEQ ID NO:254: Designed chimeric oligonucleotide primer designated as pDON-AI-68-1 to amplify a portion of pDON-AI. "nucleotides 20 to 22 are ribonucleotides-other nucleotides are deoxyribonucleotides."

SEQ ID NO:255: Designed chimeric oligonucleotide primer designated as pDON-AI-68-2 to amplify a portion of pDON-AI. "nucleotides 21 to 23 are ribonucleotides-other nucleotides are deoxyribonucleotides."

SEQ ID NO:256: Nucleotide sequence of *Homo sapiens* proto-oncogene Wn t-5a

SEQ ID NO:257: Nucleotide sequence of *Homo sapiens* ribosomal protein S5

SEQ ID NO:258: Nucleotide sequence of *Homo sapiens* diaphorase

SEQ ID NO:259: Nucleotide sequence of Human protocadherin

SEQ ID NO:260: Designed oligonucleotide for making of pIC62.

SEQ ID NO:261: Designed chimeric oligonucleotide primer designated as ICAN2. "nucleotides 19 to 20 are ribonucleotides-other nucleotides are deoxyribonucleotides."

SEQ ID NO:262: Designed chimeric oligonucleotide primer designated as ICAN6. "nucleotides 19 to 20 are ribonucleotides-other nucleotides are deoxyribonucleotides."

SEQ ID NO:263: Designed oliqonucleotide primer designated as ICAN2 DNA.

SEQ ID NO:264: Designed oligonucleotide primer designated as ICAN6 DNA.

SEQ ID NO:265: Designed oligonucleotide primer to amplify a portion of ribosomal protein S18-encoding sequence from mouse.

SEQ ID NO:266: Designed oligonucleotide primer to amplify a portion of ribosomal protein S18-encoding sequence from mouse.

SEQ ID NO:267: Designed oligonucleotide primer to amplify a portion of transferrin receptor (TFR)-encoding sequence from mouse.

SEQ ID NO:268: Designed oligonucleotide primer to amplify a portion of transferrin receptor (TFR)-encoding sequence from mouse.

SEQ ID NO:269: Designed oligonucleotide primer to amplify a portion of stromal cell derived factor 4 (Sdf4)-encoding sequence from mouse.

SEQ ID NO:270: Designed oligonucleotide primer to amplify a portion of stromal cell derived factor 4 (Sdf4)-encoding sequence from mouse.

SEQ ID NO:271: Designed oligonucleotide primer to amplify a portion of cytoplasmic beta-actin encoding sequence from mouse.

SEQ ID NO:272: Designed oligonucleotide primer to amplify a portion of cytoplasmic beta-actin encoding sequence from mouse.

SEQ ID NO:273: Designed oligonucleotide primer to amplify a portion of ornithine decarboxylase-encoding sequence from mouse.

SEQ ID NO:274: Designed oligonucleotide primer to amplify a portion of ornithine decarboxylase-encoding sequence from mouse.

SEQ ID NO:275: Designed oligonucleotide primer to amplify a portion of hypoxanthine guanine phosphoribosyl transferase (HPRT)-encoding sequence from mouse.

SEQ ID NO:276: Designed oligonucleotide primer to amplify a portion of hypoxanthine guanine phosphoribosyl transferase (HPRT)-encoding sequence from mouse.

SEQ ID NO:277: Designed oligonucleotide primer to amplify a portion of tyrosine 3-monooxygenase encoding sequence from mouse.

SEQ ID NO:278: Designed oligonucleotide primer to amplify a portion of tyrosine 3-monooxygenase encoding sequence from mouse.

SEQ ID NO:279: Designed oligonucleotide primer designated as MCS-F.

SEQ ID NO:280: Designed oligonucleotide primer designated as MCS-R

SEQ ID NO:281: Designed chimeric oligonucleotide primer designated as MF2N3(24). "nucleotides 22 to 24 are ribonucleoitdes-other nucleotides are deoxyribonucleotides"

SEQ ID NO:282: Designed chimeric oligonucleotide primer designated as MR1N3(24). "nucleotides 22 to 24 are ribonucleoitdes-other nucleotides are deoxyribonucleotides"

SEQ ID NO:283: Designed chimeric oligonucleotide primer designated as MTIS2F-16 to amplify a portion of *Mycobacterium tuberculosis* DNA. "nucleotides 14 to 16 are ribonucleotides-other nucleotides are deoxyribonucleotides."

SEQ ID NO:284: Designed chimeric oligonucleotide primer designated as MTIS2R-ACC to amplify a portion of *Mycobacterium tuberculosis* DNA. "nucleotides 18 to 20 are ribonucleotides-other nucleotides are deoxyribonucleotides."

SEQ ID NO:285: Designed oligonucleotide primer designated as MTIS-PCR-F-2 to amplify a portion of *Mycobacterium tuberculosis* DNA SEQ ID NO:286: Designed oligonucleotide primer designated as MTIS-PCR-R-2 to amplify a portion of *Mycobacterium tuberculosis* DNA SEQ ID NO:287: Designed oligonucleotide primer designated as SP6-HCV-F to amplify a portion of HCV SEQ ID NO:288: Designed oligonucleotide primer designated as SP6-HCV-R to amplify a portion of HCV SEQ ID NO:289: Designed chimeric oligonucleotide primer designated as HCV-A S to amplify a portion of HCV. "nucleotides 18 to 20 are ribonucleotides-other nucleotides are deoxyribonucleotides."

SEQ ID NO:290: Designed chimeric oligonucleotide primer designated as HCV-A A to amplify a portion of HCV. "nucleotides 18 to 20 are ribonucleotides-other nucleotides are deoxyribonucleotides.

What is claimed is:

1. A method for amplifying a nucleic acid, characterized in that the method comprises:

(a) preparing a reaction mixture by mixing a nucleic acid as a template, a deoxyribonucleotide triphosphate, a DNA polymerase having a strand displacement activity, at least one primer and an endonuclease that cleaves an extended strand generated from the primer, wherein the primer is a chimeric oligonucleotide primer that is substantially complementary to the nucleotide sequence of the nucleic acid as the template and contains a ribonucleotide as well as at least one selected from the group consisting of a deoxyribonucleotide and a nucleotide analog, the ribonucleotide being positioned at the 3'-terminus or on the 3'-terminal side of the primer; and (b) incubating the reaction mixture for a sufficient time to generate a reaction product under conditions where specific annealing of the primer to the nucleic acid as the template, an extended strand synthesis reaction and a strand displacement reaction by the DNA polymerase, and a reaction of cleaving the extended strand by the endonuclease take place.

2. The method according to claim 1, wherein the reaction mixture is incubated isothermally.

3. The method according to claim 1, wherein the reaction mixture further contains another chimeric oligonucleotide primer having a sequence substantially homologous to the nucleotide sequence of the nucleic acid as the template.

4. The method according to claim 1, wherein the DNA polymerase is selected from the group consisting of Klenow fragment of DNA polymerase I from *Escherichia coli*, Bst DNA polymerase lacking 5'→3' exonuclease from *Bacillus stearothermophilus* and Bca DNA polymerase lacking 5'→3' exonuclease from *Bacillus caldotenax*.

5. The method according to claim 1, wherein the endonuclease is an endoribonuclease.

6. The method according to claim 5, wherein the endoribonuclease is RNase H.

7. The method according to claim 6, wherein the RNase H is selected from the group consisting of an RNase H from *Escherichia coli*, an RNase H from a bacterium of genus *Thermotoga*, an RNase H from a bacterium of genus *Thermus*, an RNase H from a bacterium of genus *Pyrococcus*, an RNase H from a bacterium of genus *Archaeoglobus* and an RNase H from a bacterium of genus *Bacillus*.

8. The method according to claim 1, wherein the DNA polymerase having a strand displacement activity is Bca DNA polymerase lacking 5'→3' exonuclease from *Bacillus caldotenax* and the RNase H as an endonuclease is selected from the group consisting of an RNase H from *Escherichia coli*, an RNase H from a bacterium of genus *Pyrococcus* and an RNase H from a bacterium of genus *Archaeoglobus*.

9. The method according to claim 8, wherein the RNase H is type I RNase H from *Escherichia coli*, or type II RNase H from a bacterium of genus *Pyrococcus* or a bacterium of genus *Archaeoglobus*.

10. The method according to claim 1, wherein a DNA polymerase having an endonuclease activity is used.

11. The method according to claim 10, wherein the DNA polymerase is Bca DNA polymerase lacking 5→3' exonuclease from *Bacillus caldotenax* and the Bca DNA polymerase is used in the presence of a substance that allows the endonuclease activity of the Bca DNA polymerase to express.

12. The method according to claim 11, wherein the substance that allows the endonuclease activity of the DNA polymerase to express is a manganese ion.

13. The method according to claim 1, wherein the amplification reaction is conducted in the presence of a substance that inhibits the reverse transcription activity of the DNA polymerase.

14. The method according to claim 13, wherein the substance that inhibits the reverse transcription activity of the DNA polymerase is phosphonoformic acid.

15. The method according to claim 1, wherein the chimeric oligonucleotide primer contains two or more successive ribonucleotide residues.

16. The method according to claim 1, wherein the chimeric oligonucleotide primer contains one or more modified ribonucleotide.

17. The method according to claim 16, wherein the chimeric oligonucleotide primer contains an (α-S) ribonucleotide in which the oxygen atom bound to the phosphorous atom at the a-position of the ribonucleotide is replaced by a sulfur atom.

18. The method according to claim 1, wherein a chimeric oligonucleotide primer represented by general formula below is used:

5'-dNa-Nb-dNc-3' General formula:

wherein a is an integer of 11 or more; b is an integer of 1 or more; c is 0 or an integer of 1 or more; dN is an deoxyribonucleotide and/or nucleotide analog; N is an unmodified ribonucleotide and/or modified ribonucleotide, wherein some of dNs in dNa may be replaced by Ns, and the nucleotide at the 3'-terminus may be modified such that extension from the 3'-terminus by the action of the DNA polymerase does not take place.

19. The method according to claim 18, wherein c is 0.

20. The method according to claim 18, wherein the nucleotide analog is deoxyriboinosine nucleotide or deoxyribouracil nucleotide, and the modified ribonucleotide is (α-S) ribonucleotide.

21. The method according to claim 18, wherein the nucleic acid amplification reaction is conducted at a temperature suitable for the chimeric oligonucleotide primer as defined in claim 18.

22. The method according to claim 1, wherein the chimeric oligonucleotide primer is at least one chimeric oligonucleotide primer selected from the group consisting of:

a) a chimeric oligonucleotide primer for detecting enterohemorrhagic *Escherichia coli* having a nucleotide sequence selected from the group consisting of SEQ ID NOS: 43 to 46, 136, 137, 140–142, 153–161, 173, 174, 202, 203, 219 and 220;

b) a chimeric oligonucleotide primer for detecting a viroid having a nucleotide sequence selected from the group consisting of SEQ ID NOS: 148, 149, 208, 209, 211, 212;

c) a chimeric oligonucleotide primer for detecting *Clostridium botulinum* having a nucleotide sequence represented by SEQ ID NO: 205 or 206;

d) a chimeric oligonucleotide primer for detecting papilloma virus having a nucleotide sequence represented by SEQ ID NO: 185 or 186;

e) a chimeric oligonucleotide primer for detecting hepatitis C virus having a nucleotide sequence selected from the group consisting of SEQ ID NOS: 190, 191, 227, 228, 289 and 290;

f) a chimeric oligonucleotide primer for detecting *Staphylococcus aureus* having a nucleotide sequence represented by SEQ ID NO: 225 or 226;

g) a chimeric oligonucleotide primer for detecting *Mycobacterium tuberculosis* having a nucleotide sequence selected from the group consisting of SEQ ID NOS: 244, 245, 248 to 251, 283, 284; and h) a chimeric oligonucleotide primer for detecting *Chlamydia* having a nucleotide sequence selected from the group consisting of SEQ ID NOS: 246 and 247.

23. The method according to claim 1, which is conducted in a buffer that contains a buffering component selected from the group consisting of Tricine, a phosphate, tris, Bicine and HEPES.

24. The method according claim 1, wherein the nucleic acid as the template is a single-stranded DNA or a double-stranded DNA.

25. The method according to claim 24, which is conducted after converting a double-stranded DNA as the template into single-stranded DNAs.

26. The method according to claim 24, wherein the nucleic acid as the template is a cDNA obtained from an RNA by a reverse transcription reaction.

27. The method according to claim 26, which is conducted after synthesizing a cDNA by a reverse transcription reaction using an RNA as a template.

28. The method according to claim 27, wherein a primer selected from the group consisting of an oligo-dT primer, a random primer and a specific primer is used as a primer for the reverse transcription reaction.

29. The method according to claim 27, wherein a chimeric oligonucleotide primer is used as a primer for the reverse transcription reaction.

30. The method according to claim 27, wherein a DNA polymerase having a reverse transcriptase activity is used as a reverse transcriptase.

31. The method according to claim 27, wherein the reverse transcription reaction and the nucleic acid amplification reaction are conducted using one DNA polymerase having a reverse transcriptase activity and a strand displacement activity.

32. The method according to claim 31, wherein the DNA polymerase is Bst DNA polymerase lacking 5'→3' exonuclease from *Bacillus stearothermophilus* or Bca DNA polymerase lacking 5'→3' exonuclease from *Bacillus caldotenax*.

33. The method according to claim 26, wherein the RNA as the template in the reverse transcription reaction is an RNA amplified by an additional nucleic acid amplification reaction.

34. The method according to claim 33, which is conducted after synthesizing an amplified RNA fragment by an additional nucleic acid amplification reaction using an RNA as a template.

35. The method according to claim 33, wherein the additional nucleic acid amplification reaction is selected from the group consisting of the transcription-based amplification system (TAS) method, the self-sustained sequence replication (3SR) method, the nucleic acid sequence-based amplification (NASBA) method, the transcription-mediated amplification (TMA) method and the Qβ replicase method.

36. The method according to claim 24, wherein the nucleic acid as the template is a DNA obtained by an additional nucleic acid amplification reaction.

37. The method according to claim 36, which is conducted after synthesizing an amplified DNA fragment by an additional nucleic acid amplification reaction using an DNAAs a template.

38. The method according to claim 36, wherein the additional nucleic acid amplification reaction is selected from the group consisting of the polymerase chain reaction (PCR) method, the ligase chain reaction (LCR) method and the strand displacement amplification (SDA) method.

39. The method according to claim 33, wherein a random primer or a degenerate primer is used for the additional nucleic acid amplification reaction.

40. The method according to claim 39, wherein the random primer or the degenerate primer is a primer having a random sequence or a degenerate sequence at least at the 3'-terminus or on the 3'-terminal side.

41. The method according to claim 36, wherein a random primer or a degenerate primer is used for the additional nucleic acid amplification reaction.

42. The method according to claim 41, wherein the random primer or the degenerate primer is a primer having a random sequence or a degenerate sequence at least at the 3'-terminus or on the 3'-terminal side.

43. The method according to claim 1, wherein the length of the region of the nucleic acid to be amplified is 200 bp or shorter.

44. The method according to claim 1, which comprises annealing the nucleic acid as the template to the chimeric oligonucleotide primer that is substantially complementary to the nucleotide sequence of the nucleic acid in an annealing solution containing a substance that enhances the annealing of the nucleic acid to the primer.

45. The method according to claim 44, wherein the annealing solution contains spermidine and/or propylenediamine.

46. The method according to claim 44, wherein the annealing is conducted by incubating the annealing solution containing the nucleic acid as the template and the chimeric oligonucleotide primer that is substantially complementary to the nucleotide sequence of the nucleic acid at 90° C. or above and then cooling the solution to a temperature at which the amplification reaction is conducted or below.

47. The method according to claim 1, wherein the nucleic acid amplification reaction is conducted in the presence of a deoxyribonucleotide triphosphate analog.

48. The method according to claim 47, wherein the deoxyribonucleotide triphosphate analog is deoxyuridine triphosphate or a derivative thereof.

49. The method according to claim 1, wherein a template switching reaction is effected.

50. The method according to claim 1, which further comprises a step of duplicating a DNA or an RNA containing a sequence to be amplified to prepare a nucleic acid as a template prior to step (a), wherein the duplicated nucleic acid is used in step (a) as a nucleic acid as a template.

51. A method for producing a nucleic acid in large quantities, characterized in that the method comprises:

(a) amplifying a nucleic acid by the method defined by claim 1; and (b) collecting the nucleic acid amplified in step (a).

52. A method for detecting a target nucleic acid in a sample, characterized in that the method comprises:

(a) amplifying a target nucleic acid by the method defined by claim 1; and (b) detecting the target nucleic acid amplified in step (a).

53. The method according to claim 52, which comprises detecting the amplified nucleic acid using a probe for detection.

54. The method according to claim 53, wherein the probe for detection is a probe that has been labeled with a labeling substance.

55. The method according to claim 54, wherein the probe is an RNA probe labeled with two or more fluorescent substances positioned at a distance that results in a quenching state.

56. The method according to claim 53, wherein the probe is a probe which hybridizes to a region amplified using at least one chimeric oligonucleotide primer selected from the group consisting of:

a) a chimeric oligonucleotide primer for detecting enterohemorrhagic *Escherichia coli* having a nucleotide sequence selected from the group consisting of SEQ ID NOS: 43 to 46, 136, 137, 140–142, 153–161, 173, 174, 202, 203, 219 and 220;

b) a chimeric oligonucleotide primer for detecting a viroid having a nucleotide sequence selected from the group consisting of SEQ ID NOS: 148, 149, 208, 209, 211 and 212;

c) a chimeric oligonucleotide primer for detecting *Clostridium botulinum* having a nucleotide sequence represented by SEQ ID NO: 205 or 206;

d) a chimeric oligonucleotide primer for detecting papilloma virus having a nucleotide sequence represented by SEQ ID NO: 185 or 186;

e) a chimeric oligonucleotide primer for detecting hepatitis C virus having a nucleotide sequence selected from the group consisting of SEQ ID NOS: 190, 191, 227, 228, 289 and 290;

f) a chimeric oligonucleotide primer for detecting *Staphylococcus aureus* having a nucleotide sequence represented by SEQ ID NO: 225 or 226;

g) a chimeric oligonucleotide primer for detecting *Mycobacterium tuberculosis* having a nucleotide sequence selected from the group consisting of SEQ ID NOS: 244, 245, 248 to 251, 283, 284; and h) a chimeric oligonucleotide primer for detecting *Chlamydia* having a nucleotide sequence selected from the group consisting of SEQ ID NOS: 246 or 247.

57. A method for determining a nucleotide sequence of a nucleic acid, characterized in that the method comprises:

(a) amplifying a nucleic acid by the method defined by claim 1; and (b) determining the nucleotide sequence of the nucleic acid amplified in step (a).

58. A method for preparing a single-stranded nucleic acid, the method comprising generating a single-stranded nucleic acid using the method defined by claim 1.

59. The method according to claim 58, wherein at least two primers at different concentrations are used.

60. A method for amplifying a nucleotide sequence, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template, wherein the primer is a chimeric oligonucleotide primer containing a deoxyribonucleotide and a ribonucleotide, the ribonucleotide being positioned at the 3'-terminus or on the 3'-terminal side of the primer;

(b) cleaving the primer-extended strand of a double-stranded nucleic acid obtained in step (a) with an endonuclease at a site that contains the ribonucleotide; and (c) extending a nucleotide sequence that is complementary to the template using a DNA polymerase having a strand displacement activity from the 3'-terminus of the primer portion of the double-stranded nucleic acid in which the primer-extended strand is cleaved obtained in step (b) to effect a strand displacement.

61. A method for amplifying a nucleotide sequence using at least two primers, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template, wherein the primer is a chimeric oligonucleotide primer containing a deoxyribonucleotide and a ribonucleotide, the ribonucleotide being positioned at the 3'-terminus or on the 3'-terminal side of the primer;

(b) cleaving the primer-extended strand of a double-stranded nucleic acid obtained in step (a) with an endonuclease at a site that contains the ribonucleotide;

(c) extending a nucleotide sequence that is complementary to the template using a DNA polymerase having a strand displacement activity from the 3'-terminus of the primer portion of the double-stranded nucleic acid in which the primer-extended strand is cleaved obtained in step (b) to effect a strand displacement, wherein a double-stranded nucleic acid containing a regenerated primer-extended strand is reused in step (b);

(d) treating a released displaced strand obtained in step (c) as a template with at least one primer that is different from that used in step (a) and a DNA polymerase to synthesize a primer-extended strand that is complementary to the displaced strand, wherein the primer that is different from that used in step (a) is a chimeric oligonucleotide primer that is substantially complementary to the nucleotide sequence of the displaced strand and contains a deoxyribonucleotide and a ribonucleotide, the ribonucleotide being positioned at the 3'-terminus or on the 3'-terminal side of the primer;

(e) cleaving the primer-extended strand of a double-stranded nucleic acid obtained in step (d) with an endonuclease at a site that contains the ribonucleotide; and (f) extending a nucleotide sequence that is complementary to the template using a DNA polymerase having a strand displacement activity from the 3'-terminus of the primer portion of the double-stranded nucleic acid in which the primer-extended strand is cleaved obtained in step (e) to effect a strand displacement, wherein a double-stranded nucleic acid containing a regenerated primer-extended strand is reused in step (e).

62. A method for amplifying a nucleic acid, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template and synthesize a double-stranded nucleic acid, wherein the primer is a chimeric oligonucleotide primer containing a ribonucleotide as well as at least one selected from the group consisting of a deoxyribonucleotide and a nucleotide analog, the ribonucleotide being positioned at the 3'-terminus or on the 3'-terminal side of the primer;

(b) extending a nucleic acid that is complementary to the double-stranded nucleic acid as a template obtained in the previous step using a DNA polymerase having a strand displacement activity in the presence of an RNase H to effect a strand displacement and synthesize a displaced strand and a double-stranded nucleic acid; and (c) reusing in step (b) the double-stranded nucleic acid obtained in step (b) as a template.

63. The method according to claim 62, wherein the DNA polymerase in step (a) is different from the DNA polymerase having a strand displacement activity in step (b).

64. A method for amplifying a nucleic acid using at least two primers, characterized in that the method comprises:

(a) treating a nucleic acid as a template with at least one primer that is substantially complementary to the nucleotide sequence of the nucleic acid and a DNA polymerase to synthesize a primer-extended strand that is complementary to the template, wherein the primer is a chimeric oligonucleotide primer containing a ribonucleotide as well as at least one selected from the group consisting of a deoxyribonucleotide and a nucleotide analog, the ribonucleotide being positioned at the 3'-terminus or on the 3'-terminal side of the primer;

(b) extending a nucleic acid that is complementary to the double-stranded nucleic acid as a template obtained in the previous step using a DNA polymerase having a strand displacement activity in the presence of an RNase H to effect a strand displacement and synthesize a displaced strand and a double-stranded nucleic acid;

(c) reusing in step (b) the double-stranded nucleic acid obtained in step (b) as a template;

(d) treating a displaced strand obtained in step (b) as a template with at least one primer that is different from that used in step (a) and a DNA polymerase to synthesize a primer-extended strand that is complementary to the displaced strand, wherein the primer that is different from that used in step (a) is a chimeric oligonucleotide primer that is substantially complementary to the nucleotide sequence of the displaced strand and contains a ribonucleotide as well as at least one selected from the group consisting of a deoxyribonucleotide and a nucleotide analog, the ribonucleotide being positioned at the 3'-terminus or on the 3'-terminal side of the primer;

(e) extending a nucleic acid that is complementary to the double-stranded nucleic acid as a template obtained in the previous step using a DNA polymerase having a strand displacement activity in the presence of an RNase H to effect a strand displacement and synthesize a displaced strand and a double-stranded nucleic acid; and (f) reusing in step (e) the double-stranded nucleic acid obtained in step (e) as a template.

65. The method according to claim 64, wherein the DNA polymerase in step (a) and (d) is different from the DNA polymerase having a strand displacement activity in steps (b) and (f).

66. A method for amplifying a nucleic acid, characterized in that the method comprises:

(a) treating a double-stranded nucleic acid as a template with two primers that are substantially complementary to the nucleotide sequences of the respective strands of the double-stranded nucleic acid and a DNA polymerase having a strand displacement activity to synthesize primer-extended strands that are complementary to the template and obtain a double-stranded nucleic acid consisting of the synthesized primer-extended strands being annealed each other, wherein each primer is a chimeric oligonucleotide primer containing a ribonucleotide as well as at least one selected from the group consisting of a deoxyribonucleotide and a nucleotide analog, the ribonucleotide being positioned at the 3'-terminus or on the 3'-terminal side of the primer;

(b) cleaving the sites that contain the ribonucleotide of the double-stranded nucleic acid consisting of the primer-extended strands obtained in step (a) with the endonuclease; and (c) extending nucleic acids that are complementary to the template using a DNA polymerase having a strand displacement activity from the 3'-termini of the respective primer portions of the double-stranded nucleic acid in which the primer-extended strands are cleaved obtained in step (b) to effect strand displacements and obtain a double-stranded nucleic acid consisting of the template and the primer-extended strand.

67. A method for amplifying a nucleic acid, characterized in that the method comprises:

(a) treating a double-stranded nucleic acid as a template with two primers that are substantially complementary to the nucleotide sequences of the respective strands of the double-stranded nucleic acid and a DNA polymerase having a strand displacement activity to synthesize primer-extended strands that are complementary to the template and obtain a double-stranded nucleic acid consisting of the synthesized primer-extended strands being annealed each other, wherein each primer is a chimeric oligonucleotide primer containing a ribonucleotide as well as at least one selected from the group consisting of a deoxyribonucleotide and a nucleotide analog, the ribonucleotide being positioned at the 3'-terminus or on the 3'-terminal side of the primer;

(b) cleaving the sites that contain the ribonucleotide of the double-stranded nucleic acid consisting of the primer-extended strands obtained in step (a) with the endonuclease; and (c) extending nucleic acids that are complementary to the template using a DNA polymerase having a strand displacement activity from the 3'-termini of the respective primer portions of the double-stranded nucleic acid in which the primer-extended strands are cleaved obtained in step (b) to effect strand displacements and obtain a double-stranded nucleic acid consisting of the primer-extended strands being annealed each other.

68. A method for amplifying a nucleic acid, characterized in that the method comprises:

(a) treating a double-stranded nucleic acid as a template with two primers that are substantially complementary to the nucleotide sequences of the respective strands of the double-stranded nucleic acid and a DNA polymerase having a strand displacement activity to synthesize primer-extended strands that are complementary to the template and obtain a double-stranded nucleic acid consisting of the synthesized primer-extended strands being annealed each other, wherein each primer is a chimeric oligonucleotide primer containing a ribonucleotide as well as at least one selected from the group consisting of a deoxyribonucleotide and a nucleotide analog, the ribonucleotide being positioned at the 3'-terminus or on the 3'-terminal side of the primer;

(b) cleaving the sites that contain the ribonucleotide of the double-stranded nucleic acid consisting of the primer-extended strands obtained in step (a) with the endonuclease;

(c) extending nucleic acids that are complementary to the template using a DNA polymerase having a strand displacement activity from the 3'-termini of the respective primer portions of the double-stranded nucleic acid in which the primer-extended strands are cleaved obtained in step (b) to effect strand displacements and obtain a double-stranded nucleic acid consisting of the primer-extended strands being annealed each other and a double-stranded nucleic acid consisting of the templates being annealed each other to which the two primers in step (a) are annealed;

(d) extending nucleic acids that are complementary to the template using a DNA polymerase having a strand displacement activity from the 3'-termini of the respective primer portions of the double-stranded nucleic acid to which the two primers are annealed obtained in step (c) to effect strand displacements and obtain a double-stranded nucleic acid consisting of the primer-extended strands being annealed each other and a double-stranded nucleic acid consisting of the templates being annealed each other to which the two primers in step (a) are annealed; and (e) reusing in step (d) the double-stranded nucleic acid to which the two primers are annealed obtained in step (d).

69. A method for amplifying a nucleic acid, characterized in that the method comprises:

(a) treating a double-stranded nucleic acid as a template with two primers that are substantially complementary to the nucleotide sequences of the respective strands of the double-stranded nucleic acid and a DNA polymerase having a strand displacement activity to synthesize primer-extended strands that are complementary to the template and obtain a double-stranded nucleic acid consisting of the synthesized primer-extended strands being annealed each other, wherein each primer is a chimeric oligonucleotide primer containing a ribonucleotide as well as at least one selected from the group consisting of a deoxyribonucleotide and a nucleotide analog, the ribonucleotide being positioned at the 3'-terminus or on the 3'-terminal side of the primer;

(b) cleaving the sites that contain the ribonucleotide of the double-stranded nucleic acid consisting of the primer-extended strands obtained in step (a) with the endonuclease;

(c) extending nucleic acids that are complementary to the template using a DNA polymerase having a strand displacement activity from the 3'-termini of the respective primer portions of the double-stranded nucleic acid in which the primer-extended strands are cleaved obtained in step (b) to effect strand displacements and obtain a double-stranded nucleic acid consisting of the primer-extended strands being annealed each other and a double-stranded nucleic acid consisting of the templates being annealed each other to which the two primers in step (a) are annealed;

(d) extending nucleic acids that are complementary to the template using a DNA polymerase having a strand displacement activity from the 3'-termini of the respective primer portions of the double-stranded nucleic acid to which the two primers are annealed obtained in step (c) to effect strand displacements and obtain a double-stranded nucleic acid consisting of the template and the primer-extended strand;

(e) cleaving the sites that contain the ribonucleotide of the double-stranded nucleic acid consisting of the template and the primer-extended strand obtained in step (d) with the endonuclease; and (f) extending a nucleic acid that is complementary to the template using a DNA polymerase having a strand displacement activity from the 3'-terminus of the primer portion of the double-stranded nucleic acid in which the primer-extended strand is cleaved obtained in step (e) to synthesize a displaced strand.

70. The method according to claim 60, wherein step (b) and step (c) are sequentially repeated.

71. The method according to claim 60, wherein the DNA polymerase in step (a) is different from the DNA polymerase having a strand displacement activity in step (c).

72. The method according to claim 61, wherein one DNA polymerase having a strand displacement activity is used.

* * * * *

SEQUENCE LISTING

<160> NUMBER OF SEQ ID NOS: 290

<210> SEQ ID NO 1
<211> LENGTH: 99
<212> TYPE: DNA
<213> ORGANISM: Artificial
<220> FEATURE:
<223> OTHER INFORMATION: Synthetic DNA corresponding to a portion of human transferrin receptor-encoding sequence used as a template

<400> SEQUENCE: 1
ggacagcaac tgggccagca aagttgagaa actcacttta gagaattctg ctttcccttt 60
ccttgcatat tctgagcagt ttctttctgt ttttgcgag 99

<210> SEQ ID NO 2
<211> LENGTH: 22
<212> TYPE: DNA
<213> ORGANISM: Artificial
<220> FEATURE:
<223> OTHER INFORMATION: Designed oligonucleotide primer to amplify a portion of human transferrin receptor-encoding sequence

<400> SEQUENCE: 2
cagcaactgg gccagcaaag tt 22

<210> SEQ ID NO 3
<211> LENGTH: 22
<212> TYPE: DNA
<213> ORGANISM: Artificial
<220> FEATURE:
<223> OTHER INFORMATION: Designed oligonucleotide primer to amplify a portion of human transferrin receptor-encoding sequence

<400> SEQUENCE: 3
gcaaaaacag aaagaaactg ct 22

<210> SEQ ID NO 4
<211> LENGTH: 22
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. “nucleotide 21 is ribonucleotide-other nucleotides are deoxyribonucleotides”

<400> SEQUENCE: 4
cagcaactgg gccagcaaag ut 22

<210> SEQ ID NO 5
<211> LENGTH: 22
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. nucleotide 21 is ribonucleotide-other nucleotides are deoxyribonucleotides“

<400> SEQUENCE: 5
gcaaaaacag aaagaaactg ct 22

<210> SEQ ID NO 6
<211> LENGTH: 22
<212> TYPE: DNA

-continued

```
<213> ORGANISM: Artificial
<220> FEATURE:
<223> OTHER INFORMATION: Designed chimeric oligonucleotide primer to
      amplify a portion of human transferrin receptor-encoding sequence.
      "nucleotide 22 is ribonucleotide-other nucleotides are
       deoxyribonucleotides"

<400> SEQUENCE: 6

cagcaactgg gccagcaaag tu                                              22


<210> SEQ ID NO 7
<211> LENGTH: 22
<212> TYPE: DNA
<213> ORGANISM: Artificial
<220> FEATURE:
<223> OTHER INFORMATION: Designed chimeric oligonucleotide primer to
      amplify a portion of human transferrin receptor-encoding sequence.
      nucleotides 21 to 22 are ribonucleotides-other nucleotides are
      deoxyribonucleotides"

<400> SEQUENCE: 7

gcaaaaacag aaagaaactg cu                                              22


<210> SEQ ID NO 8
<211> LENGTH: 22
<212> TYPE: DNA
<213> ORGANISM: Artificial
<220> FEATURE:
<223> OTHER INFORMATION: Designed chimeric oligonucleotide primer to
      amplify a portion of human transferrin receptor-encoding sequence.
      nucleotides 21 to 22 are ribonucleotides-other nucleotides are
      deoxyribonucleotides"

<400> SEQUENCE: 8

cagcaactgg gccagcaaag uu                                              22


<210> SEQ ID NO 9
<211> LENGTH: 22
<212> TYPE: DNA
<213> ORGANISM: Artificial
<220> FEATURE:
<223> OTHER INFORMATION: Designed chimeric oligonucleotide primer
      to amplify a portion of human transferrin receptor-encoding
      sequence. "nucleo 22 are ribonucleotides-other nucleotides are
      deoxyribonucleotides"

<400> SEQUENCE: 9

gcaaaaacag aaagaaactg cu                                              22


<210> SEQ ID NO 10
<211> LENGTH: 22
<212> TYPE: DNA
<213> ORGANISM: Artificial
<220> FEATURE:
<223> OTHER INFORMATION: Designed chimeric oligonucleotide primer to
      amplify a portion of human transferrin receptor-encoding sequence.
      "nucleotides 19 to 20 are ribonucleotides-other nucleotides are
      deoxyribonucleotides"

<400> SEQUENCE: 10

cagcaactgg gccagcaaag tt                                              22


<210> SEQ ID NO 11
<211> LENGTH: 22
<212> TYPE: DNA
<213> ORGANISM: Artificial
<220> FEATURE:
<223> OTHER INFORMATION: Designed chimeric oligonucleotide primer to
      amplify a portion of human transferrin receptor-encoding sequence.
```

-continued

"nucleotides 19 to 20 are ribonucleotides-other nucleotides are deoxyribonucleotides"

<400> SEQUENCE: 11
gcaaaaacag aaagaaacug ct 22

<210> SEQ ID NO 12
<211> LENGTH: 26
<212> TYPE: DNA
<213> ORGANISM: Artificial
<220> FEATURE:
<223> OTHER INFORMATION: Designed oligonucleotide used as a probe for detecting an amplified portion of human transferrin receptor -encoding sequence

<400> SEQUENCE: 12
tgctttccct ttccttgcat attctg 26

<210> SEQ ID NO 13
<211> LENGTH: 25
<212> TYPE: DNA
<213> ORGANISM: Artificial
<220> FEATURE:
<223> OTHER INFORMATION: Designed chimeric oligonucleotide primer designated as pUC19 upper(2)NN to amplify a portion of plasmid pUC19. "nucleotides 24 to 25 are ribonucleotides-other nucleotides are deoxyribonucleotides"

<400> SEQUENCE: 13
attgcttaat cagtgaggca cctau 25

<210> SEQ ID NO 14
<211> LENGTH: 25
<212> TYPE: DNA
<213> ORGANISM: Artificial
<220> FEATURE:
<223> OTHER INFORMATION: Designed chimeric oligonucleotide primer designated as pUC19 lower NN to amplify a portion of plasmid pUC19. "nucleotides 24 to 25 are ribonucleotides-other nucleotides are deoxyribonucleotides"

<400> SEQUENCE: 14
gataacactg cggccaactt actuc 25

<210> SEQ ID NO 15
<211> LENGTH: 25
<212> TYPE: DNA
<213> ORGANISM: Artificial
<220> FEATURE:
<223> OTHER INFORMATION: Designed chimeric oligonucleotide primer to amplify a portion of plasmid pUC19. "nucleotides 24 to 25 are ribonucleotides-other nucleotides are deoxyribonucleotides"

<400> SEQUENCE: 15
actggcgaac tacttactct agcuu 25

<210> SEQ ID NO 16
<211> LENGTH: 26
<212> TYPE: DNA
<213> ORGANISM: Artificial
<220> FEATURE:
<223> OTHER INFORMATION: Designed chimeric oligonucleotide primer designated as pUC19 lower 542 to amplify a portion of plasmid pUC19. "nucleotides 24 to 25 are ribonucleotides-other nucleotides are deoxyribonucleotides"

<400> SEQUENCE: 16
agtcaccaga aaagcatctt acggau 26

-continued

<210> SEQ ID NO 17
<211> LENGTH: 25
<212> TYPE: DNA
<213> ORGANISM: Artificial
<220> FEATURE:
<223> OTHER INFORMATION: Designed chimeric oligonucleotide primer to amplify a portion of plasmid pUC19. "nucleotides 24 to 25 are ribonucleotides-other nucleotides are deoxyribonucleotides"

<400> SEQUENCE: 17
gctcatgaga caataaccct gataa 25

<210> SEQ ID NO 18
<211> LENGTH: 25
<212> TYPE: DNA
<213> ORGANISM: Artificial
<220> FEATURE:
<223> OTHER INFORMATION: Designed oligonucleotide primer designated as pUC19 upper 150 to amplify a portion of plasmid pUC19. "nucleotides 23 to 25 are ribonucleotides-other nucleotides are deoxyribonucleotides"

<400> SEQUENCE: 18
ggtgtcacgc tcgtcgtttg gtaug 25

<210> SEQ ID NO 19
<211> LENGTH: 25
<212> TYPE: DNA
<213> ORGANISM: Artificial
<220> FEATURE:
<223> OTHER INFORMATION: Designed chimeric oligonucleotide primer designated as pUC19 lower NN to amplify a portion of plasmid pUC19. "nucleotides 23 to 25 are ribonucleotides-other nucleotides are deoxyribonucleotides"

<400> SEQUENCE: 19
gataacactg cggccaactt acuuc 25

<210> SEQ ID NO 20
<211> LENGTH: 25
<212> TYPE: DNA
<213> ORGANISM: Artificial
<220> FEATURE:
<223> OTHER INFORMATION: Designed chimeric oligonucleotide primer designated as pUC19 upper 249 to amplify a portion of plasmid pUC19. "nucleotides 23 to 25 are ribonucleotides-other nucleotides are deoxyribonucleotides"

<400> SEQUENCE: 20
cgcctccatc cagtctatta atugu 25

<210> SEQ ID NO 21
<211> LENGTH: 22
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. "nucleotides 20 to 22 are ribonucleotides-other nucleotides are deoxyribonucleotides"

<400> SEQUENCE: 21
ctgattgaga ggattcctga gu 22

<210> SEQ ID NO 22
<211> LENGTH: 22
<212> TYPE: DNA

-continued

```
<213> ORGANISM: Artificial
<220> FEATURE:
<223> OTHER INFORMATION: Designed chimeric oligonucleotide primer to
      amplify a portion of human transferrin receptor-encoding sequence.
      "nucleotides 21 to 22 are ribonucleotides-other nucleotides
      are deoxyribonucleotides"

<400> SEQUENCE: 22

tagggagaga ggaagtgata cu                                              22


<210> SEQ ID NO 23
<211> LENGTH: 25
<212> TYPE: DNA
<213> ORGANISM: Artificial
<220> FEATURE:
<223> OTHER INFORMATION: Designed chimeric oligonucleotide primer
      designated as pUC19 upper(2)NN to amplify a portion of plasmid
      pUC19. "nucleotides 24 to 25 are ribonucleotides-other nucleotides
      are deoxyribonucleotides"

<400> SEQUENCE: 23

attgcttaat cagtgaggca cctau                                           25


<210> SEQ ID NO 24
<211> LENGTH: 25
<212> TYPE: DNA
<213> ORGANISM: Artificial
<220> FEATURE:
<223> OTHER INFORMATION: Designed chimeric oligonucleotide primer
      designated as pUC19 upper(2)NN to amplify a portion of plasmid
      pUC19. "nucleotides 24 to 25 are ribonucleotides-other nucleotides
      are deoxyribonucleotides"

<400> SEQUENCE: 24

attgcttaat cagtgaggca cctaa                                           25


<210> SEQ ID NO 25
<211> LENGTH: 25
<212> TYPE: DNA
<213> ORGANISM: Artificial
<220> FEATURE:
<223> OTHER INFORMATION: Designed chimeric oligonucleotide primer
      designated as pUC19 upper(2)NN to amplify a portion of plasmid
      pUC19. "nucleotides 24 to 25 are ribonucleotides-other nucleotides
      are deoxyribonucleotides"

<400> SEQUENCE: 25

attgcttaat cagtgaggca cctac                                           25


<210> SEQ ID NO 26
<211> LENGTH: 25
<212> TYPE: DNA
<213> ORGANISM: Artificial
<220> FEATURE:
<223> OTHER INFORMATION: Designed chimeric oligonucleotide primer
      designated as pUC19 upper(2)NN to amplify a portion of plasmid
      pUC19. "nucleotides 24 to 25 are ribonucleotides-other nucleotides
      are deoxyribonucleotides"

<400> SEQUENCE: 26

attgcttaat cagtgaggca cctag                                           25


<210> SEQ ID NO 27
<211> LENGTH: 22
<212> TYPE: DNA
<213> ORGANISM: Artificial
<220> FEATURE:
<223> OTHER INFORMATION: Designed chimeric oligonucleotide primer to
      amplify a portion of human transferrin receptor-encoding sequence.
```

-continued

"nucleotides 21 to 22 are ribonucleotides-other nucleotides are deoxyribonucleotides"

<400> SEQUENCE: 27
ctgattgaga ggattcctga gu 22

<210> SEQ ID NO 28
<211> LENGTH: 22
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. "nucleotides 21 to 22 are ribonucleotides-other nucleotides are deoxyribonucleotides"

<400> SEQUENCE: 28
tagggagaga ggaagtgata cu 22

<210> SEQ ID NO 29
<211> LENGTH: 24
<212> TYPE: DNA
<213> ORGANISM: Artificial
<220> FEATURE:
<223> OTHER INFORMATION: Designed chimeric oligonucleotide primer designated as MF2N3(24) to amplify a portion of plasmid pUC19-24 9 or plasmid pUC19-911. "nucleotides 22 to 24 are ribonucleotides -other nucleotides are deoxyribonucleotides"

<400> SEQUENCE: 29
gctgcaaggc gattaagttg ggua 24

<210> SEQ ID NO 30
<211> LENGTH: 24
<212> TYPE: DNA
<213> ORGANISM: Artificial
<220> FEATURE:
<223> OTHER INFORMATION: Designed oligonucleotide primer designated as MR1N3(24) to amplify a portion of plasmid pUC19-24 9 or plasmid pUC19-911. "nucleotides 22 to 24 are ribonucleotides -other nucleotides are deoxyribonucleotides"

<400> SEQUENCE: 30
ctttatgctt ccggctcgta tguu 24

<210> SEQ ID NO 31
<211> LENGTH: 25
<212> TYPE: DNA
<213> ORGANISM: Artificial
<220> FEATURE:
<223> OTHER INFORMATION: Designed chimeric oligonucleotide primer designated as pUC19 upper 249 to amplify a portion of plasmid pUC19. "nucleotides 24 to 25 are ribonucleotides-other nucleotides are deoxyribonucleotides"

<400> SEQUENCE: 31
cgcctccatc cagtctatta attgu 25

<210> SEQ ID NO 32
<211> LENGTH: 25
<212> TYPE: DNA
<213> ORGANISM: Artificial
<220> FEATURE:
<223> OTHER INFORMATION: Designed oligonucleotide primer designated as pUC19 upper 150 to amplify a portion of plasmid pUC19

<400> SEQUENCE: 32
ggtgtcacgc tcgtcgtttg gtatg 25

-continued

<210> SEQ ID NO 33
<211> LENGTH: 25
<212> TYPE: DNA
<213> ORGANISM: Artificial
<220> FEATURE:
<223> OTHER INFORMATION: Designed oligonucleotide primer designated as pUC19 upper 249 to amplify a portion of plasmid pUC19

<400> SEQUENCE: 33
cgcctccatc cagtctatta attgt 25

<210> SEQ ID NO 34
<211> LENGTH: 25
<212> TYPE: DNA
<213> ORGANISM: Artificial
<220> FEATURE:
<223> OTHER INFORMATION: Designed oligonucleotide primer designated as pUC19 lower NN to amplify a portion of plasmid pUC19

<400> SEQUENCE: 34
gataacactg cggccaactt acttc 25

<210> SEQ ID NO 35
<211> LENGTH: 30
<212> TYPE: DNA
<213> ORGANISM: Artificial
<220> FEATURE:
<223> OTHER INFORMATION: Designed chimeric oligonucleotide primer to amplify a portion of plasmid pUC19. "nucleotides 28 to 30 are ribonucleotides-other nucleotides are deoxyribonucleoti

<400> SEQUENCE: 35
ggatgtgctg caaggcgatt aagttgggua 30

<210> SEQ ID NO 36
<211> LENGTH: 30
<212> TYPE: DNA
<213> ORGANISM: Artificial
<220> FEATURE:
<223> OTHER INFORMATION: Designed chimeric oligonucleotide primer designated as MR1N3 to amplify a portion of plasmid pUC19. "nucleotides 28 to 30 are ribonucleotides-other nucleotides are deoxyribonucleoti

<400> SEQUENCE: 36
tttacacttt atgcttccgg ctcgtatguu 30

<210> SEQ ID NO 37
<211> LENGTH: 30
<212> TYPE: DNA
<213> ORGANISM: Artificial
<220> FEATURE:
<223> OTHER INFORMATION: Designed oligonucleotide primer to amplify a portion of plasmid pUC19

<400> SEQUENCE: 37
ggatgtgctg caaggcgatt aagttgggta 30

<210> SEQ ID NO 38
<211> LENGTH: 30
<212> TYPE: DNA
<213> ORGANISM: Artificial
<220> FEATURE:
<223> OTHER INFORMATION: Designed oligonucleotide primer designated as MR1N3 to amplify a portion of plasmid pUC19

<400> SEQUENCE: 38

-continued tttacacttt atgcttccgg ctcgtatgtt 30

<210> SEQ ID NO 39
<211> LENGTH: 30
<212> TYPE: DNA
<213> ORGANISM: Artificial
<220> FEATURE:
<223> OTHER INFORMATION: Synthetic RNA used as a probe for detecting an amplified portion of plasmid pUC19

<400> SEQUENCE: 39 ugaucccca uguugugcaa aaaagcgguu 30

<210> SEQ ID NO 40
<211> LENGTH: 25
<212> TYPE: DNA
<213> ORGANISM: Artificial
<220> FEATURE:
<223> OTHER INFORMATION: Designed chimeric oligonucleotide primer designated as pUC19 upper 150 to amplify a portion of plasmid pUC19. "nucleotides 24 to 25 are ribonucleotides-other nucleotides are deoxyribonucleotides"

<400> SEQUENCE: 40
ggtgtcacgc tcgtcgtttg gtaug 25

<210> SEQ ID NO 41
<211> LENGTH: 30
<212> TYPE: DNA
<213> ORGANISM: Artificial
<220> FEATURE:
<223> OTHER INFORMATION: Designed chimeric oligonucleotide primer designated as MR1N3 to amplify a portion of plasmid pUC19. "nucleotides 28 to 30 are ribonucleotides-other nucleotides are deoxyribonucleoti

<400> SEQUENCE: 41
tttacacttt atgcttccgg ctcgtatguu 30

<210> SEQ ID NO 42
<211> LENGTH: 17
<212> TYPE: DNA
<213> ORGANISM: Artificial
<220> FEATURE:
<223> OTHER INFORMATION: Designed oligonucleotide primer designated as M13M4

<400> SEQUENCE: 42
gttttcccag tcacgac 17

<210> SEQ ID NO 43
<211> LENGTH: 18
<212> TYPE: DNA
<213> ORGANISM: Artificial
<220> FEATURE:
<223> OTHER INFORMATION: Designed chimeric oligonucleotide primer to amplify a portion of vero toxin 1-encoding sequence from hemorrhagic Escherichia coli O-157. "nucleotides 16 to 18 are ribonucleotides-other nucleotides are deoxyribonucleotides"

<400> SEQUENCE: 43
agttaatgtg gtggcgaa 18

<210> SEQ ID NO 44
<211> LENGTH: 17
<212> TYPE: DNA
<213> ORGANISM: Artificial

-continued

<220> FEATURE:
<223> OTHER INFORMATION: Designed chimeric oligonucleotide primer to
amplify a portion of vero toxin 1-encoding sequence from
hemorrhagic Escherichia coli O-157. "nucleotides 15 to 17 are
ribonucleotides-other nucleotides are deoxyribonucleotides"

<400> SEQUENCE: 44
gactcttcca tctgcca 17

<210> SEQ ID NO 45
<211> LENGTH: 18
<212> TYPE: DNA
<213> ORGANISM: Artificial
<220> FEATURE:
<223> OTHER INFORMATION: Designed chimeric oligonucleotide primer to
amplify a portion of vero toxin 2-encoding sequence from
hemorrhagic Escherichia coli O-157. "nucleotides 16 to 18 are
ribonucleotides-other nucleotides are deoxyribonucleotides"

<400> SEQUENCE: 45
ttcggtatcc tattcccg 18

<210> SEQ ID NO 46
<211> LENGTH: 18
<212> TYPE: DNA
<213> ORGANISM: Artificial
<220> FEATURE:
<223> OTHER INFORMATION: Designed chimeric oligonucleotide primer to
amplify a portion of vero toxin 2-encoding sequence from
hemorrhagicEscherichia coli O-157. "nucleotides 16 to 18 are
ribonucleotides-other nucleotides are deoxyribonucleotides"

<400> SEQUENCE: 46
tctctggtca ttgtauua 18

<210> SEQ ID NO 47
<211> LENGTH: 22
<212> TYPE: DNA
<213> ORGANISM: Artificial
<220> FEATURE:
<223> OTHER INFORMATION: Designed oligonucleotide primer designated as
MCR-F to amplify along DNA fragment

<400> SEQUENCE: 47
ccattcaggc tgcgcaactg tt 22

<210> SEQ ID NO 48
<211> LENGTH: 22
<212> TYPE: DNA
<213> ORGANISM: Artificial
<220> FEATURE:
<223> OTHER INFORMATION: Designed oligonucleotide primer designated as
MCR-R to amplify along DNA fragment

<400> SEQUENCE: 48
tggcacgaca ggtttcccga ct 22

<210> SEQ ID NO 49
<211> LENGTH: 24
<212> TYPE: DNA
<213> ORGANISM: Artificial
<220> FEATURE:
<223> OTHER INFORMATION: Designed chimeric oligonucleotide primer
designated as MF2N3(24) to amplify a long DNA fragment.
"nucleotides 22 to 24 are ribonucleotides-other nucleotides
are deoxyribonucleoti

<400> SEQUENCE: 49

-continued

```
gctgcaaggc gattaagttg ggua                                              24


<210> SEQ ID NO 50
<211> LENGTH: 24
<212> TYPE: DNA
<213> ORGANISM: Artificial
<220> FEATURE:
<223> OTHER INFORMATION: Designed chimeric oligonucleotide primer
      designated as MR1N3(24) to amplify a long DNA fragment.
      "nucleotides 22 to 24 are ribonucleotides-other nucleotides
      are deoxyribonucleotides"

<400> SEQUENCE: 50

ctttatgctt ccggctcgta tguu                                              24


<210> SEQ ID NO 51
<211> LENGTH: 20
<212> TYPE: DNA
<213> ORGANISM: Artificial
<220> FEATURE:
<223> OTHER INFORMATION: Designed oligonucleotide primer to amplify a
      portion of bacteriophage lambda DNA

<400> SEQUENCE: 51

aacaacaaga aactggtttc                                                   20


<210> SEQ ID NO 52
<211> LENGTH: 20
<212> TYPE: DNA
<213> ORGANISM: Artificial
<220> FEATURE:
<223> OTHER INFORMATION: Designed oligonucleotide primer to amplify a
      portion of bacteriophage lambda DNA

<400> SEQUENCE: 52

gcaatgcatg acgactgggg                                                   20


<210> SEQ ID NO 53
<211> LENGTH: 17
<212> TYPE: DNA
<213> ORGANISM: Artificial
<220> FEATURE:
<223> OTHER INFORMATION: Designed chimeric oligonucleotide primer to
      amplify a portion of bacteriophage lambda DNA. "nucleotides 16
      to 17 are ribonucleotides-other nucleotides are
      deoxyribonucleotides"

<400> SEQUENCE: 53

gttttcccag tcacgac                                                      17


<210> SEQ ID NO 54
<211> LENGTH: 17
<212> TYPE: DNA
<213> ORGANISM: Artificial
<220> FEATURE:
<223> OTHER INFORMATION: Designed chimeric oligonucleotide primer to
      amplify a portion of bacteriophage lambda DNA. "nucleotides 16
      to 17 are ribonucleotides-other nucleotides are
      deoxyribonucleotides"

<400> SEQUENCE: 54

caggaaacag ctatgac                                                      17


<210> SEQ ID NO 55
<211> LENGTH: 20
<212> TYPE: DNA
<213> ORGANISM: Artificial
<220> FEATURE:
```

-continued

<223> OTHER INFORMATION: Designed oligonucleotide primer to amplify a portion of bacteriophage lambda DNA

<400> SEQUENCE: 55
gtacggtcat catctgacac 20

<210> SEQ ID NO 56
<211> LENGTH: 20
<212> TYPE: DNA
<213> ORGANISM: Artificial
<220> FEATURE:
<223> OTHER INFORMATION: Designed oligonucleotide primer to amplify a portion of bacteriophage lambda DNA

<400> SEQUENCE: 56
gcaatcggca tgttaaacgc 20

<210> SEQ ID NO 57
<211> LENGTH: 20
<212> TYPE: DNA
<213> ORGANISM: Artificial
<220> FEATURE:
<223> OTHER INFORMATION: Designed oligonucleotide primer to amplify a portion of bacteriophage lambda DNA

<400> SEQUENCE: 57
cgccatcctg ggaagactcc 20

<210> SEQ ID NO 58
<211> LENGTH: 44
<212> TYPE: DNA
<213> ORGANISM: Artificial
<220> FEATURE:
<223> OTHER INFORMATION: Designed oligonucleotide primer designated as R1-S1 to amplify a portion of bacteriophage lambda DNA

<400> SEQUENCE: 58
tttcacacag gaaacagcta tgacaacaac aagaaactgg tttc 44

<210> SEQ ID NO 59
<211> LENGTH: 44
<212> TYPE: DNA
<213> ORGANISM: Artificial
<220> FEATURE:
<223> OTHER INFORMATION: Designed oligonucleotide primer designated as R1-A3 to amplify a portion of bacteriophage lambda DNA

<400> SEQUENCE: 59
tttcacacag gaaacagcta tgacgcaatg catgacgact gggg 44

<210> SEQ ID NO 60
<211> LENGTH: 62
<212> TYPE: DNA
<213> ORGANISM: Artificial
<220> FEATURE:
<223> OTHER INFORMATION: Designed oligonucleotide primer designated as R2-S1 to amplify a portion of bacteriophage lambda DNA

<400> SEQUENCE: 60
attgtgagcg gataacaatt tcacacagga aacagctatg acaacaacaa gaaactggtt 60
tc 62

<210> SEQ ID NO 61
<211> LENGTH: 62
<212> TYPE: DNA
<213> ORGANISM: Artificial

-continued

<220> FEATURE:
<223> OTHER INFORMATION: Designed oligonucleotide primer designated as
      R2-A3 to amplify a portion of bacteriophage lambda DNA

<400> SEQUENCE: 61
attgtgagcg gataacaatt tcacacagga aacagctatg acgcaatgca tgacgactgg     60
gg                                                                    62

<210> SEQ ID NO 62
<211> LENGTH: 95
<212> TYPE: DNA
<213> ORGANISM: Artificial
<220> FEATURE:
<223> OTHER INFORMATION: Designed oligonucleotide primer designated as
      R3-S1 to amplify a portion of bacteriophage lambda DNA

<400> SEQUENCE: 62
cactttatgc ttccggctcg tatgttgtgt ggaattgtga gcggataaca atttcacaca     60
ggaaacagct atgacaacaa caagaaactg gtttc                                95

<210> SEQ ID NO 63
<211> LENGTH: 95
<212> TYPE: DNA
<213> ORGANISM: Artificial
<220> FEATURE:
<223> OTHER INFORMATION: Designed oligonucleotide primer designated as
      R3-A3 to amplify a portion of bacteriophage lambda DNA

<400> SEQUENCE: 63
cactttatgc ttccggctcg tatgttgtgt ggaattgtga gcggataaca atttcacaca     60
ggaaacagct atgacgcaat gcatgacgac tgggg                                95

<210> SEQ ID NO 64
<211> LENGTH: 17
<212> TYPE: DNA
<213> ORGANISM: Artificial
<220> FEATURE:
<223> OTHER INFORMATION: Designed chimeric oligonucleotide primer
      designated as M13RV-2N17mer. "nucleotides 16 to 17 are
      ribonucleotides-other nucleotides are deoxyribonucleotides"

<400> SEQUENCE: 64
caggaaacag ctatgac                                                    17

<210> SEQ ID NO 65
<211> LENGTH: 20
<212> TYPE: DNA
<213> ORGANISM: Artificial
<220> FEATURE:
<223> OTHER INFORMATION: Designed chimeric oligonucleotide primer
      designated as M13RV-2N20mer. "nucleotides 19 to 20 are
      ribonucleotides-other nucleotides are deoxyribonucleotides"

<400> SEQUENCE: 65
acacaggaaa cagctatgac                                                 20

<210> SEQ ID NO 66
<211> LENGTH: 70
<212> TYPE: DNA
<213> ORGANISM: Artificial
<220> FEATURE:
<223> OTHER INFORMATION: Designed oligonucleotide primer to amplify a
      portion of CDC2-related protein kinase PISSLRE gene

<400> SEQUENCE: 66

-continued

```
gagttcgtgt ccgtacaact atttcacaca ggaaacagct atgacccaac aagagcctat     60

agcttcgctc                                                            70


<210> SEQ ID NO 67
<211> LENGTH: 67
<212> TYPE: DNA
<213> ORGANISM: Artificial
<220> FEATURE:
<223> OTHER INFORMATION: Designed oligonucleotide primer to amplify a
      portion of CDC2-related protein kinase PISSLRE gene

<400> SEQUENCE: 67

tcgaaatcag ccacagcgcc atttcacaca ggaaacagct atgacccgct gtctttgagt     60

tgtggtg                                                               67


<210> SEQ ID NO 68
<211> LENGTH: 70
<212> TYPE: DNA
<213> ORGANISM: Artificial
<220> FEATURE:
<223> OTHER INFORMATION: Designed oligonucleotide primer to amplify
      a portion of type ii cytoskeltal 11 keratin gene

<400> SEQUENCE: 68

gagttcgtgt ccgtacaact atttcacaca ggaaacagct atgacgctat tctgacatca     60

ctttccagac                                                            70


<210> SEQ ID NO 69
<211> LENGTH: 66
<212> TYPE: DNA
<213> ORGANISM: Artificial
<220> FEATURE:
<223> OTHER INFORMATION: Designed oligonucleotide primer to amplify
      a portion of type ii cytoskeltal 11 keratin gene

<400> SEQUENCE: 69

tcgaaatcag ccacagcgcc atttcacaca ggaaacagct atgacgaatt ccactggtgg     60

cagtag                                                                66


<210> SEQ ID NO 70
<211> LENGTH: 62
<212> TYPE: DNA
<213> ORGANISM: Artificial
<220> FEATURE:
<223> OTHER INFORMATION: Designed oligonucleotide primer to amplify a
      portion of bacteriophage lambda DNA

<400> SEQUENCE: 70

attgtgagcg gataacaatt tcacacagga aacagctatg acgtacggtc atcatctgac     60

ac                                                                    62


<210> SEQ ID NO 71
<211> LENGTH: 62
<212> TYPE: DNA
<213> ORGANISM: Artificial
<220> FEATURE:
<223> OTHER INFORMATION: Designed oligonucleotide primer to amplify a
      portion of bacteriophage lambda DNA

<400> SEQUENCE: 71

attgtgagcg gataacaatt tcacacagga aacagctatg acatgcgccg cctgaaccac     60

ca                                                                    62
```

-continued

<210> SEQ ID NO 72
<211> LENGTH: 62
<212> TYPE: DNA
<213> ORGANISM: Artificial
<220> FEATURE:
<223> OTHER INFORMATION: Designed oligonucleotide primer to amplify a portion of bacteriophage lambda DNA

<400> SEQUENCE: 72
attgtgagcg gataacaatt tcacacagga aacagctatg acctgctctg ccgcttcacg 60
ca 62

<210> SEQ ID NO 73
<211> LENGTH: 62
<212> TYPE: DNA
<213> ORGANISM: Artificial
<220> FEATURE:
<223> OTHER INFORMATION: Designed oligonucleotide primer to amplify a portion of bacteriophage lambda DNA

<400> SEQUENCE: 73
attgtgagcg gataacaatt tcacacagga aacagctatg acgcaatcgg catgttaaac 60
gg 62

<210> SEQ ID NO 74
<211> LENGTH: 24
<212> TYPE: DNA
<213> ORGANISM: Artificial
<220> FEATURE:
<223> OTHER INFORMATION: Designed oligonucleotide primer designated as MF2N3(24) to amplify a portion of plasmid pUC19-249 or plasmid pUC19-911

<400> SEQUENCE: 74
gctgcaaggc gattaagttg ggta 24

<210> SEQ ID NO 75
<211> LENGTH: 24
<212> TYPE: DNA
<213> ORGANISM: Artificial
<220> FEATURE:
<223> OTHER INFORMATION: Designed oligonucleotide primer designated as MR1N3(24) to amplify a portion of plasmid pUC19-249 or plasmid pUC19-911

<400> SEQUENCE: 75
ctttatgctt ccggctcgta tgtt 24

<210> SEQ ID NO 76
<211> LENGTH: 20
<212> TYPE: DNA
<213> ORGANISM: Artificial
<220> FEATURE:
<223> OTHER INFORMATION: Designed chimeric oligonucleotide primer designated as M13M4-3N20mer. "nucleotides 18 to 20 are ribonucleotides-other nucleotides are deoxyribonucleotides"

<400> SEQUENCE: 76
agggttttcc cagtcacgac 20

<210> SEQ ID NO 77
<211> LENGTH: 20
<212> TYPE: DNA
<213> ORGANISM: Artificial
<220> FEATURE:
<223> OTHER INFORMATION: Designed chimeric oligonucleotide primer -continued designated as M13RV-3N20mer. "nucleotides 18 to 20 are ribonucleotides-other nucleotides are deoxyribonucleotides"

<400> SEQUENCE: 77
acacaggaaa cagctatgac 20

<210> SEQ ID NO 78
<211> LENGTH: 24
<212> TYPE: DNA
<213> ORGANISM: Artificial
<220> FEATURE:
<223> OTHER INFORMATION: Designed chimeric oligonucleotide primer designated as M13M4-3N24mer. "nucleotides 22 to 24 are ribonucleotides-other nucleotides are deoxyribonucleotides"

<400> SEQUENCE: 78
cgccagggtt ttcccagtca cgac 24

<210> SEQ ID NO 79
<211> LENGTH: 24
<212> TYPE: DNA
<213> ORGANISM: Artificial
<220> FEATURE:
<223> OTHER INFORMATION: Designed oligonucleotide primer designated as M13RV-3N 24mer."nucleotides 22 to 24 are ribonucleotides -other nucleotides are deoxyribonucleotides"

<400> SEQUENCE: 79
tttcacacag gaaacagcta tgac 24

<210> SEQ ID NO 80
<211> LENGTH: 69
<212> TYPE: DNA
<213> ORGANISM: Artificial
<220> FEATURE:
<223> OTHER INFORMATION: Designed oligonucleotide primer designated as 5'ID to amplify aportion of cyclin

<400> SEQUENCE: 80
tcgaaatcag ccacagcgcc atttcacaca ggaaacagct atgacatgtt ttgggagaat 60
taagtctga 69

<210> SEQ ID NO 81
<211> LENGTH: 69
<212> TYPE: DNA
<213> ORGANISM: Artificial
<220> FEATURE:
<223> OTHER INFORMATION: Designed oligonucleotide primer designated as 3'ID to amplify a portion of cyclin A DNA

<400> SEQUENCE: 81
gagttcgtgc cgtacaacta tttcacacag gaaacagcta tgacttacag atttagtgtc 60
tctggtggg 69

<210> SEQ ID NO 82
<211> LENGTH: 16
<212> TYPE: DNA
<213> ORGANISM: Artificial
<220> FEATURE:
<223> OTHER INFORMATION: Designed oligonucleotide primer designated as M13RV-2N 16mer. "nucleotides 15 to 16 are ribonucleotides-other nucleotides are deoxyribonucleotides"

<400> SEQUENCE: 82
aggaaacagc tatgac 16

-continued

<210> SEQ ID NO 83
<211> LENGTH: 27
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. "nucleotides 21 to 22 are ribonucleotides-other nucleotides are deoxyribonucleotides"

<400> SEQUENCE: 83
cagcaactgg gccagcaaag uugagaa 27

<210> SEQ ID NO 84
<211> LENGTH: 27
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. "nucleotides 21 to 22 are ribonucleotides-other nucleotides are deoxyribonucleotides"

<400> SEQUENCE: 84
gcaaaaacag aaagaaactg cucagaa 27

<210> SEQ ID NO 85
<211> LENGTH: 26
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. "nucleotides 21 to 22 are ribonucleotides-other nucleotides are deoxyribonucleotides"

<400> SEQUENCE: 85
cagcaactgg gccagcaaag uugaga 26

<210> SEQ ID NO 86
<211> LENGTH: 26
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. "nucleotides 21 to 22 are ribonucleotides-other nucleotides are deoxyribonucleotides"

<400> SEQUENCE: 86
gcaaaaacag aaagaaactg cucaga 26

<210> SEQ ID NO 87
<211> LENGTH: 25
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. "nucleotides 21 to 22 are ribonucleotides-other nucleotides are deoxyribonucleotides"

<400> SEQUENCE: 87
cagcaactgg gccagcaaag uugag 25

<210> SEQ ID NO 88
<211> LENGTH: 25
<212> TYPE: DNA

-continued

<213> ORGANISM: Artificial
<220> FEATURE:
<223> OTHER INFORMATION: Designed chimeric oligonucleotide primer to amplify a portion of human transferrin receptor-encoding sequence. "nucleotides 21 to 22 are ribonucleotides-other nucleotides are deoxyribonucleotides"

<400> SEQUENCE: 88
gcaaaaacag aaagaaactg cucag 25

<210> SEQ ID NO 89
<211> LENGTH: 24
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. "nucleotides 21 to 22 are ribonucleotides-other nucleotides are deoxyribonucleotides"

<400> SEQUENCE: 89
cagcaactgg gccagcaaag uuga 24

<210> SEQ ID NO 90
<211> LENGTH: 24
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. "nucleotides 21 to 22 are ribonucleotides-other nucleotides are deoxyribonucleotides"

<400> SEQUENCE: 90
gcaaaaacag aaagaaactg cuca 24

<210> SEQ ID NO 91
<211> LENGTH: 23
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. "nucleotides 21 to 22 are ribonucleotides-other nucleotides are deoxyribonucleotides"

<400> SEQUENCE: 91
cagcaactgg gccagcaaag uug 23

<210> SEQ ID NO 92
<211> LENGTH: 23
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. "nucleotides 21 to 22 are ribonucleotides-other nucleotides are deoxyribonucleotides"

<400> SEQUENCE: 92
gcaaaaacag aaagaaactg cuc 23

<210> SEQ ID NO 93
<211> LENGTH: 22
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence.

-continued

"nucleotides 21 to 22 are ribonucleotides-other nucleotides are deoxyribonucleotides"

<400> SEQUENCE: 93
cagcaactgg gccagcaaag uu 22

<210> SEQ ID NO 94
<211> LENGTH: 22
<212> TYPE: DNA
<213> ORGANISM: Artificial
<220> FEATURE:
<223> OTHER INFORMATION: Designed chimeric oligonucleotide primer to amplify a portion of human transferrin receptor-encoding sequence. "nucleotides 21 to 22 are ribonucleotides-other nucleotides are deoxyribonucleotides"

<400> SEQUENCE: 94
gcaaaaacag aaagaaactg cu 22

<210> SEQ ID NO 95
<211> LENGTH: 22
<212> TYPE: DNA
<213> ORGANISM: Artificial
<220> FEATURE:
<223> OTHER INFORMATION: Designed oligonucleotide primer to amplify a portion of human transferrin receptor-encoding sequence

<400> SEQUENCE: 95
caacttcaag gtttctgcca gc 22

<210> SEQ ID NO 96
<211> LENGTH: 21
<212> TYPE: DNA
<213> ORGANISM: Artificial
<220> FEATURE:
<223> OTHER INFORMATION: Designed oligonucleotide primer to amplify a portion of human transferrin receptor-encoding sequence

<400> SEQUENCE: 96
aatagtccaa gtagctagag c 21

<210> SEQ ID NO 97
<211> LENGTH: 20
<212> TYPE: DNA
<213> ORGANISM: Artificial
<220> FEATURE:
<223> OTHER INFORMATION: PCR primer BsuII-3 for cloning a gene encoding a polypeptide having a RNaseHII activity from Bacillus caldotenax
<220> FEATURE:
<221> NAME/KEY: misc_feature
<222> LOCATION: (15)..(15)
<223> OTHER INFORMATION: n is a, c, g, or t

<400> SEQUENCE: 97
gtcgccagcg cagtnathyt 20

<210> SEQ ID NO 98
<211> LENGTH: 20
<212> TYPE: DNA
<213> ORGANISM: Artificial
<220> FEATURE:
<223> OTHER INFORMATION: PCR primer BsuII-6 for cloning a gene encoding a polypeptide having a RNaseHII activity from Bacillus caldotenax
<220> FEATURE:
<221> NAME/KEY: misc_feature
<222> LOCATION: (18)..(18)
<223> OTHER INFORMATION: n is a, c, g, or t

<400> SEQUENCE: 98

-continued cggtccctcg tcacyttngc 20

<210> SEQ ID NO 99
<211> LENGTH: 20
<212> TYPE: DNA
<213> ORGANISM: Artificial
<220> FEATURE:
<223> OTHER INFORMATION: PCR primer RNII-S1 for cloning a gene encoding a polypeptide having a RNaseHII activity from Bacillus caldotenax

<400> SEQUENCE: 99
cgcgcttttc cggcgtcagc 20

<210> SEQ ID NO 100
<211> LENGTH: 20
<212> TYPE: DNA
<213> ORGANISM: Artificial
<220> FEATURE:
<223> OTHER INFORMATION: PCR primer RNII-S2 for cloning a gene encoding a polypeptide having a RNaseHII activity from Bacillus caldotenax

<400> SEQUENCE: 100
acggcgcacg cttcaatttg 20

<210> SEQ ID NO 101
<211> LENGTH: 20
<212> TYPE: DNA
<213> ORGANISM: Artificial
<220> FEATURE:
<223> OTHER INFORMATION: PCR primer RNII-S5 for cloning a gene encoding a polypeptide having a RNaseHII activity from Bacillus caldotenax

<400> SEQUENCE: 101
acgcctattt gccggggctt 20

<210> SEQ ID NO 102
<211> LENGTH: 20
<212> TYPE: DNA
<213> ORGANISM: Artificial
<220> FEATURE:
<223> OTHER INFORMATION: PCR primer RNII-S6 for cloning a gene encoding a polypeptide having a RNaseHII activity from Bacillus caldotenax

<400> SEQUENCE: 102
atgaccgacg cagcggcgat 20

<210> SEQ ID NO 103
<211> LENGTH: 39
<212> TYPE: DNA
<213> ORGANISM: Artificial
<220> FEATURE:
<223> OTHER INFORMATION: PCR primer RNII-Nde for cloning a gene encoding a polypeptide having a RNaseHII activity from Bacillus caldotenax

<400> SEQUENCE: 103
tagaagaggg agaggcatat gaagcggtat acggtgaaa 39

<210> SEQ ID NO 104
<211> LENGTH: 780
<212> TYPE: DNA
<213> ORGANISM: Bucillus caldotenax

<400> SEQUENCE: 104
atgaagcggt atacggtgaa agacattgaa gcgctgcttc cgaagcttgg cgcggacgac 60
ccgcgctggg agatgctgcg gcaggatgag cgaaaaagcg tgcaggcgct tcttgcccgt 120

-continued

```
tttgaaaggc agaaagcgcg ccggcacgcc atcgagcagc ggtgggaaga actaatgcgt    180

tatgagaggg aactatacgc cgctggcgtt agacggatcg ccggcattga tgaggccggg    240

cgcggcccgc tggccggccc ggtcgtcgcc gccgcggtca tcttgccgaa agacgcctat    300

ttgccggggc ttgacgactc gaagcggctg acgccggaaa agcgcgaggc attgtttgcg    360

caaattgaag cgtgcgccgt cgccatcggc atcggcatcg tcagcgcggc ggagatcgat    420

gaaaggaata tttacgaagc gacaaggcaa gcgatggcga aagcggtgaa cgccctttcc    480

ccgccgcctg aacatttgct tgttgatgcg atggcggtgc cgtgcccact gccgcaacag    540

cgcctcataa aaggagacgc caacagcgct tcaatcgccg ctgcgtcggt catcgccaaa    600

gtgacgcgcg accggtggat gaaagaactg gatcgccgct atccacaata cgggttcgcg    660

cgccatatgg gctacggaac gccggaacat ttcgaggcga tccgccgcta cggcgttacg    720

cctgagcacc gtcgttcgtt cgcaccggtg agggaggtgc tgaaggcgag cgagcagctc    780
```

```
<210> SEQ ID NO 105
<211> LENGTH: 260
<212> TYPE: PRT
<213> ORGANISM: Bucillus caldotenax

<400> SEQUENCE: 105

Met Lys Arg Tyr Thr Val Lys Asp Ile Glu Ala Leu Leu Pro Lys Leu
1               5                   10                  15

Gly Ala Asp Asp Pro Arg Trp Glu Met Leu Arg Gln Asp Glu Arg Lys
            20                  25                  30

Ser Val Gln Ala Leu Leu Ala Arg Phe Glu Arg Gln Lys Ala Arg Arg
        35                  40                  45

His Ala Ile Glu Gln Arg Trp Glu Glu Leu Met Arg Tyr Glu Arg Glu
    50                  55                  60

Leu Tyr Ala Ala Gly Val Arg Arg Ile Ala Gly Ile Asp Glu Ala Gly
65                  70                  75                  80

Arg Gly Pro Leu Ala Gly Pro Val Val Ala Ala Ala Val Ile Leu Pro
                85                  90                  95

Lys Asp Ala Tyr Leu Pro Gly Leu Asp Asp Ser Lys Arg Leu Thr Pro
            100                 105                 110

Glu Lys Arg Glu Ala Leu Phe Ala Gln Ile Glu Ala Cys Ala Val Ala
        115                 120                 125

Ile Gly Ile Gly Ile Val Ser Ala Ala Glu Ile Asp Glu Arg Asn Ile
    130                 135                 140

Tyr Glu Ala Thr Arg Gln Ala Met Ala Lys Ala Val Asn Ala Leu Ser
145                 150                 155                 160

Pro Pro Pro Glu His Leu Leu Val Asp Ala Met Ala Val Pro Cys Pro
                165                 170                 175

Leu Pro Gln Gln Arg Leu Ile Lys Gly Asp Ala Asn Ser Ala Ser Ile
            180                 185                 190

Ala Ala Ala Ser Val Ile Ala Lys Val Thr Arg Asp Arg Trp Met Lys
        195                 200                 205

Glu Leu Asp Arg Arg Tyr Pro Gln Tyr Gly Phe Ala Arg His Met Gly
    210                 215                 220

Tyr Gly Thr Pro Glu His Phe Glu Ala Ile Arg Arg Tyr Gly Val Thr
225                 230                 235                 240

Pro Glu His Arg Arg Ser Phe Ala Pro Val Arg Glu Val Leu Lys Ala
                245                 250                 255
```

-continued

```
Ser Glu Gln Leu
            260


<210> SEQ ID NO 106
<211> LENGTH: 20
<212> TYPE: DNA
<213> ORGANISM: Artificial
<220> FEATURE:
<223> OTHER INFORMATION: PCR primer BsuIII-1 for cloning a gene encoding
      a polypeptide having a RNaseHIII activity from Bacillus caldotenax

<400> SEQUENCE: 106

ggtaaggtct tgttycargg                                                  20


<210> SEQ ID NO 107
<211> LENGTH: 20
<212> TYPE: DNA
<213> ORGANISM: Artificial
<220> FEATURE:
<223> OTHER INFORMATION: PCR primer BsuIII-3 for cloning a gene encoding
      a polypeptide having a RNaseHIII activity from Bacillus caldotenax

<400> SEQUENCE: 107

ggaaccggag attayttygg                                                  20


<210> SEQ ID NO 108
<211> LENGTH: 20
<212> TYPE: DNA
<213> ORGANISM: Artificial
<220> FEATURE:
<223> OTHER INFORMATION: PCR primer BsuIII-6 for cloning a gene encoding
      a polypeptide having a RNaseHIII activity from Bacillus caldotenax
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 108

atgattgaag cagcngcnac                                                  20


<210> SEQ ID NO 109
<211> LENGTH: 20
<212> TYPE: DNA
<213> ORGANISM: Artificial
<220> FEATURE:
<223> OTHER INFORMATION: PCR primer BsuIII-8 for cloning a gene encoding
      a polypeptide having a RNaseHIII activity from Bacillus caldotenax
<220> FEATURE:
<221> NAME/KEY: misc_feature
<222> LOCATION: (15)..(15)
<223> OTHER INFORMATION: n is a, c, g, or t

<400> SEQUENCE: 109

gtattggcga aatgnarytt                                                  20


<210> SEQ ID NO 110
<211> LENGTH: 20
<212> TYPE: DNA
<213> ORGANISM: Artificial
<220> FEATURE:
<223> OTHER INFORMATION: PCR primer RNIII-S3 for cloning a gene encoding
      a polypeptide having a RNaseHIII activity from Bacillus caldotenax

<400> SEQUENCE: 110

cccgatcgtc gtcgccgccg                                                  20
```

-continued

<210> SEQ ID NO 111
<211> LENGTH: 20
<212> TYPE: DNA
<213> ORGANISM: Artificial
<220> FEATURE:
<223> OTHER INFORMATION: PCR primer BcaRNIII-3 for cloning a gene encoding a polypeptide having a RNaseHIII activity from Bacillus caldotenax

<400> SEQUENCE: 111

```
gatacgtgga cactttccgc                                              20
```

<210> SEQ ID NO 112
<211> LENGTH: 915
<212> TYPE: DNA
<213> ORGANISM: Bucillus caldotenax

<400> SEQUENCE: 112

```
gtgattcaag ccgaccaaca gctgcttgac gccttgcgcg cccactacca agacgcctta     60

tccgaccggc ttccggctgg agcgttgttt gccgtcaagc gcccggatgt cgtcatcacc    120

gcctaccgct caggcaaagt gctgtttcaa gggaaagcgg cggagcaaga agcagcgaaa    180

tggatatcag gggcgagcgc ctcaaacgaa acagctgacc accagccgtc cgctttggca    240

gctcatcaac tcgggtctct ttccgccatc ggttccgatg aagtcggcac cggcgattat    300

ttcggcccga tcgtcgtcgc cgccgcctac gtggatcggc cgcatatcgc caaaatcgcg    360

gcgcttggcg tgaaagattc gaaacaattg aacgatgagg caatcaaacg gatcgccccc    420

gccatcatgg aaaccgtgcc gcatgcggtc accgtgttgg acaatgccga atacaaccgc    480

tggcagcgaa gcggcatgcc gcagacgaaa atgaaagcgc tccttcacaa ccggacgctc    540

gtgaaactcg ttgacgccat cgcgcccgcc gaaccagaag caatcatcat cgacgaattt    600

ttaaaacggg attcgtattt ccgttacctt tccgatgaag atcgcattat ccgcgagcgg    660

gtgcactgcc ttcccaaggc ggaaagtgtc cacgtatcag tcgccgccgc ctcgatcatc    720

gcccgctatg tgtttttaga ggagatggag caattatccc gcgccgtcgg cctcctgctt    780

ccaaaaggcg ccggcgccat tgtcgatgaa gccgcggcca acatcatccg cgcgcggggg    840

gcggaagcgc ttgagacatg cgccaagctt catttcgcca atacaaaaaa ggcgctggac    900

atcgccaaac gccgg                                                    915
```

<210> SEQ ID NO 113
<211> LENGTH: 305
<212> TYPE: PRT
<213> ORGANISM: Bucillus caldotenax

<400> SEQUENCE: 113

```
Met Ile Gln Ala Asp Gln Gln Leu Leu Asp Ala Leu Arg Ala His Tyr
1               5                   10                  15

Gln Asp Ala Leu Ser Asp Arg Leu Pro Ala Gly Ala Leu Phe Ala Val
            20                  25                  30

Lys Arg Pro Asp Val Val Ile Thr Ala Tyr Arg Ser Gly Lys Val Leu
        35                  40                  45

Phe Gln Gly Lys Ala Ala Glu Gln Glu Ala Ala Lys Trp Ile Ser Gly
    50                  55                  60

Ala Ser Ala Ser Asn Glu Thr Ala Asp His Gln Pro Ser Ala Leu Ala
65                  70                  75                  80

Ala His Gln Leu Gly Ser Leu Ser Ala Ile Gly Ser Asp Glu Val Gly
```

-continued

```
                85                  90                  95

Thr Gly Asp Tyr Phe Gly Pro Ile Val Val Ala Ala Ala Tyr Val Asp
            100                 105                 110

Arg Pro His Ile Ala Lys Ile Ala Ala Leu Gly Val Lys Asp Ser Lys
        115                 120                 125

Gln Leu Asn Asp Glu Ala Ile Lys Arg Ile Ala Pro Ala Ile Met Glu
    130                 135                 140

Thr Val Pro His Ala Val Thr Val Leu Asp Asn Ala Glu Tyr Asn Arg
145                 150                 155                 160

Trp Gln Arg Ser Gly Met Pro Gln Thr Lys Met Lys Ala Leu Leu His
                165                 170                 175

Asn Arg Thr Leu Val Lys Leu Val Asp Ala Ile Ala Pro Ala Glu Pro
            180                 185                 190

Glu Ala Ile Ile Ile Asp Glu Phe Leu Lys Arg Asp Ser Tyr Phe Arg
        195                 200                 205

Tyr Leu Ser Asp Glu Asp Arg Ile Ile Arg Glu Arg Val His Cys Leu
    210                 215                 220

Pro Lys Ala Glu Ser Val His Val Ser Val Ala Ala Ala Ser Ile Ile
225                 230                 235                 240

Ala Arg Tyr Val Phe Leu Glu Glu Met Glu Gln Leu Ser Arg Ala Val
                245                 250                 255

Gly Leu Leu Leu Pro Lys Gly Ala Gly Ala Ile Val Asp Glu Ala Ala
            260                 265                 270

Ala Asn Ile Ile Arg Ala Arg Gly Ala Glu Ala Leu Glu Thr Cys Ala
        275                 280                 285

Lys Leu His Phe Ala Asn Thr Lys Lys Ala Leu Asp Ile Ala Lys Arg
    290                 295                 300

Arg
305
```

```
<210> SEQ ID NO 114
<211> LENGTH: 39
<212> TYPE: DNA
<213> ORGANISM: Artificial
<220> FEATURE:
<223> OTHER INFORMATION: PCR primer BcaRNIIINde for amplifying a
      gene encoding a polypeptide having a RNaseHIII activity from
      Bacillus caldotenax

<400> SEQUENCE: 114

cgaacgttgt caaaccatat gattcaagcc gaccaacag                          39


<210> SEQ ID NO 115
<211> LENGTH: 663
<212> TYPE: DNA
<213> ORGANISM: Pyrococcus horikoshii

<400> SEQUENCE: 115

atgaaggttg ctggagttga tgaagcgggg agggggccgg taattggccc gttagtaatt     60

ggagtagccg ttatagatga gaaaaatatt gagaggttac gtgacattgg ggttaaagac    120

tccaaacaat taactcctgg gcaacgtgaa aaactattta gcaaattaat agatatccta    180

gacgattatt atgttcttct cgttaccccc aaggaaatag atgagaggca tcattctatg    240

aatgaactag aagctgagaa attcgttgta gccttgaatt ctttaaggat caagccgcag    300

aagatatatg tggactctgc cgatgtagat cctaagaggt ttgctagtct aataaaggct    360

gggttgaaat atgaagccac ggttatcgcc gagcataaag ccgatgcaaa gtatgagata    420
```

-continued

```
gtatcggcag catcaataat tgcaaaggtc actagggata gagagataga gaagctaaag    480

caaaagtatg gggaatttgg ttctggctat ccgagtgatc cgagaactaa ggagtggctt    540

gaagaatatt acaaacaata tggtgacttt cctccaatag ttaggagaac ttgggaaacc    600

gctaggaaga tagaggaaag gtttagaaaa aatcagctaa cgcttgataa attccttaag    660

tga                                                                  663


<210> SEQ ID NO 116
<211> LENGTH: 33
<212> TYPE: DNA
<213> ORGANISM: Artificial
<220> FEATURE:
<223> OTHER INFORMATION: PCR primer 1650Nde for cloning a gene encoding
      a polypeptide having a RNaseHII activity from Pyrococcus furiosus

<400> SEQUENCE: 116

caggaggaga gacatatgaa aataggggga att                                  33


<210> SEQ ID NO 117
<211> LENGTH: 33
<212> TYPE: DNA
<213> ORGANISM: Artificial
<220> FEATURE:
<223> OTHER INFORMATION: PCR primer 1650Bam for cloning a gene encoding
      a polypeptide having a RNaseHII activity from Pyrococcus furiosus

<400> SEQUENCE: 117

gaaggttgtg gatccacttt ctaaggtttc tta                                  33


<210> SEQ ID NO 118
<211> LENGTH: 672
<212> TYPE: DNA
<213> ORGANISM: Pyrococcus furiosus

<400> SEQUENCE: 118

atgaaaatag ggggaattga cgaagcagga agaggaccag cgatagggcc attagtagta     60

gctactgtcg tcgttgatga gaaaaacatt gagaagctca gaaacattgg agtaaaagac    120

tccaaacaac taacaccccca tgaaaggaag aatttatttt cccagataac ctcaatagcg    180

gatgattaca aaatagtgat agtatcccca gaagaaatcg acaatagatc aggaacaatg    240

aacgagttag aggtagagaa gtttgctctc gccttaaatt cgcttcagat aaaaccagct    300

cttatatacg ctgatgcagc ggatgtagat gccaatagat ttgcaagctt gatagagaga    360

agactcaatt ataaggcgaa gattattgcc gaacacaagg ccgatgcaaa gtatccagta    420

gtttcagcag cttcaatact tgcaaaggtt gttagggatg aggaaattga aaaattaaaa    480

aagcaatatg gagactttgg ctctgggtat ccaagtgatc caaaaaccaa gaaatggctt    540

gaagagtact acaaaaaaca caactctttc cctccaatag tcagacgaac ctgggaaact    600

gtaagaaaaa tagaggaaag cattaaagcc aaaaaatccc agctaacgct tgataaattc    660

tttaagaaac ct                                                        672


<210> SEQ ID NO 119
<211> LENGTH: 224
<212> TYPE: PRT
<213> ORGANISM: Pyrococcus furiosus

<400> SEQUENCE: 119

Met Lys Ile Gly Gly Ile Asp Glu Ala Gly Arg Gly Pro Ala Ile Gly
1               5                   10                  15
```

-continued

```
Pro Leu Val Val Ala Thr Val Val Val Asp Glu Lys Asn Ile Glu Lys
            20                  25                  30

Leu Arg Asn Ile Gly Val Lys Asp Ser Lys Gln Leu Thr Pro His Glu
        35                  40                  45

Arg Lys Asn Leu Phe Ser Gln Ile Thr Ser Ile Ala Asp Asp Tyr Lys
    50                  55                  60

Ile Val Ile Val Ser Pro Glu Glu Ile Asp Asn Arg Ser Gly Thr Met
65                  70                  75                  80

Asn Glu Leu Glu Val Glu Lys Phe Ala Leu Ala Leu Asn Ser Leu Gln
                85                  90                  95

Ile Lys Pro Ala Leu Ile Tyr Ala Asp Ala Ala Asp Val Asp Ala Asn
            100                 105                 110

Arg Phe Ala Ser Leu Ile Glu Arg Arg Leu Asn Tyr Lys Ala Lys Ile
        115                 120                 125

Ile Ala Glu His Lys Ala Asp Ala Lys Tyr Pro Val Val Ser Ala Ala
    130                 135                 140

Ser Ile Leu Ala Lys Val Val Arg Asp Glu Glu Ile Glu Lys Leu Lys
145                 150                 155                 160

Lys Gln Tyr Gly Asp Phe Gly Ser Gly Tyr Pro Ser Asp Pro Lys Thr
                165                 170                 175

Lys Lys Trp Leu Glu Glu Tyr Tyr Lys Lys His Asn Ser Phe Pro Pro
            180                 185                 190

Ile Val Arg Arg Thr Trp Glu Thr Val Arg Lys Ile Glu Glu Ser Ile
        195                 200                 205

Lys Ala Lys Lys Ser Gln Leu Thr Leu Asp Lys Phe Phe Lys Lys Pro
    210                 215                 220
```

<210> SEQ ID NO 120
<211> LENGTH: 28
<212> TYPE: DNA
<213> ORGANISM: Artificial
<220> FEATURE:
<223> OTHER INFORMATION: PCR primer 915-F1 for cloning a gene encoding a polypeptide having a RNaseHII activity from Thermotoga maritima

<400> SEQUENCE: 120
aaaaagcttg ggaatagatg agctttac 28

<210> SEQ ID NO 121
<211> LENGTH: 26
<212> TYPE: DNA
<213> ORGANISM: Artificial
<220> FEATURE:
<223> OTHER INFORMATION: PCR primer 915-F2 for cloning a gene encoding a polypeptide having a RNaseHII activity from Thermotoga maritima

<400> SEQUENCE: 121
aaaccatggg aatagatgag ctttac 26

<210> SEQ ID NO 122
<211> LENGTH: 29
<212> TYPE: DNA
<213> ORGANISM: Artificial
<220> FEATURE:
<223> OTHER INFORMATION: PCR primer 915-R1 for cloning a gene encoding a polypeptide having a RNaseHII activity from Thermotoga maritima

<400> SEQUENCE: 122
aaatctagat cctcaacttt gtcgatgtg 29

-continued

<210> SEQ ID NO 123
<211> LENGTH: 30
<212> TYPE: DNA
<213> ORGANISM: Artificial
<220> FEATURE:
<223> OTHER INFORMATION: PCR primer 915-R2 for cloning a gene encoding a polypeptide having a RNaseHII activity from Thermotoga maritima

<400> SEQUENCE: 123
aatctagatt aaaaaagagg gagattatgg 30

<210> SEQ ID NO 124
<211> LENGTH: 22
<212> TYPE: DNA
<213> ORGANISM: Artificial
<220> FEATURE:
<223> OTHER INFORMATION: Designed oligonucleotide primer designated as MCS-F to amplify along DNA fragment

<400> SEQUENCE: 124
ccattcaggc tgcgcaactg tt 22

<210> SEQ ID NO 125
<211> LENGTH: 22
<212> TYPE: DNA
<213> ORGANISM: Artificial
<220> FEATURE:
<223> OTHER INFORMATION: Designed oligonucleotide primer designated as MCS-R to amplify along DNA fragment

<400> SEQUENCE: 125
tggcacgaca ggtttcccga ct 22

<210> SEQ ID NO 126
<211> LENGTH: 24
<212> TYPE: DNA
<213> ORGANISM: Artificial
<220> FEATURE:
<223> OTHER INFORMATION: Designed chimeric oligonucleotide primer designated as MF2N3(24) to amplify a long DNA fragment. "nucleotides 22 to 24 are ribonucleotides-other nucleotides are deoxyribonucleotides"

<400> SEQUENCE: 126
gctgcaaggc gattaagttg ggua 24

<210> SEQ ID NO 127
<211> LENGTH: 24
<212> TYPE: DNA
<213> ORGANISM: Artificial
<220> FEATURE:
<223> OTHER INFORMATION: Designed chimeric oligonucleotide primer designated as MR1N3(24) to amplify a long DNA fragment. "nucleotides 22 to 24 are ribonucleotides-other nucleotides are deoxyribonucleotides"

<400> SEQUENCE: 127
ctttatgctt ccggctcgta tguu 24

<210> SEQ ID NO 128
<211> LENGTH: 20
<212> TYPE: DNA
<213> ORGANISM: Artificial
<220> FEATURE:
<223> OTHER INFORMATION: Designed oligonucleotide primer to amplify a portion of lambda DNA. "nucleotides 18 to 20 are ribonucleotides -other nucleotides are deoxyribonucleotides"

-continued

<400> SEQUENCE: 128
cctttctctg tttttgtccg 20

<210> SEQ ID NO 129
<211> LENGTH: 20
<212> TYPE: DNA
<213> ORGANISM: Artificial
<220> FEATURE:
<223> OTHER INFORMATION: Designed chimeric oligonucleotide primer to amplify a portion of lambda DNA. "nucleotides 18 to 20 are ribonucleotides-other nucleotides are deoxyribonucleotides"

<400> SEQUENCE: 129
aagcacctca ttaccctugc 20

<210> SEQ ID NO 130
<211> LENGTH: 24
<212> TYPE: DNA
<213> ORGANISM: Artificial
<220> FEATURE:
<223> OTHER INFORMATION: Designed oligonucleotide primer to amplify a portion of lambda DNA

<400> SEQUENCE: 130
gggcggcgac ctcgcgggtt ttcg 24

<210> SEQ ID NO 131
<211> LENGTH: 24
<212> TYPE: DNA
<213> ORGANISM: Artificial
<220> FEATURE:
<223> OTHER INFORMATION: Designed oligonucleotide primer to amplify a portion of lambda DNA

<400> SEQUENCE: 131
gctgcttatg ctctataaag tagg 24

<210> SEQ ID NO 132
<211> LENGTH: 20
<212> TYPE: DNA
<213> ORGANISM: Artificial
<220> FEATURE:
<223> OTHER INFORMATION: Designed chimeric oligonucleotide primer to amplify a portion of Flavobacterium species DNA. "nucleotides 18 to 20 are ribonucleotides-other nucleotides are deoxyribonucleotides"

<400> SEQUENCE: 132
aggaatcttt atttaccaug 20

<210> SEQ ID NO 133
<211> LENGTH: 20
<212> TYPE: DNA
<213> ORGANISM: Artificial
<220> FEATURE:
<223> OTHER INFORMATION: Designed chimeric oligonucleotide primer to amplify a portion of Flavobacterium species DNA. "nucleotides 18 to 20 are ribonucleotides-other nucleotides are deoxyribonucleotides"

<400> SEQUENCE: 133
tggtgtttaa acttattgcg 20

<210> SEQ ID NO 134
<211> LENGTH: 24
<212> TYPE: DNA
<213> ORGANISM: Artificial

-continued

<220> FEATURE:
<223> OTHER INFORMATION: Designed oligonucleotide primer to amplify a portion of Flavobacterium species DNA.

<400> SEQUENCE: 134
ccatcagcta taaacacaaa cagc 24

<210> SEQ ID NO 135
<211> LENGTH: 24
<212> TYPE: DNA
<213> ORGANISM: Artificial
<220> FEATURE:
<223> OTHER INFORMATION: Designed oligonucleotide primer to amplify a portion of Flavobacterium species DNA.

<400> SEQUENCE: 135
tgttttgacc aaacatagta atgc 24

<210> SEQ ID NO 136
<211> LENGTH: 21
<212> TYPE: DNA
<213> ORGANISM: Artificial
<220> FEATURE:
<223> OTHER INFORMATION: Designed chimeric oligonucleotide primer to amplify a portion of vero toxin 2-encoding sequence from hemorrhagic Escherichia coli O-157. "nucleotides 19 to 21 are ribonucleotides-other nucleotides are deoxyribonucleotides"

<400> SEQUENCE: 136
tcgttaaata gtatacggac a 21

<210> SEQ ID NO 137
<211> LENGTH: 20
<212> TYPE: DNA
<213> ORGANISM: Artificial
<220> FEATURE:
<223> OTHER INFORMATION: Designed chimeric oligonucleotide primer to amplify a portion of vero toxin 2-encoding sequence from hemorrhagic Escherichia coli O-157. "nucleotides 18 to 20 are ribonucleotides-other nucleotides are deoxyribonucleotides"

<400> SEQUENCE: 137
tgctcaataa tcagacgaag 20

<210> SEQ ID NO 138
<211> LENGTH: 24
<212> TYPE: DNA
<213> ORGANISM: Artificial
<220> FEATURE:
<223> OTHER INFORMATION: Designed oligonucleotide primer to amplify a portion of vero toxin 2-encoding sequence from hemorrhagic Escherichia coli O-157.

<400> SEQUENCE: 138
aaatggggta ctgtgcctgt tact 24

<210> SEQ ID NO 139
<211> LENGTH: 24
<212> TYPE: DNA
<213> ORGANISM: Artificial
<220> FEATURE:
<223> OTHER INFORMATION: Designed oligonucleotide primer to amplify a portion of vero toxin 2-encoding sequence from hemorrhagic Escherichia coli O-157.

<400> SEQUENCE: 139
ctctgtatct gcctgaagcg taag 24

-continued

<210> SEQ ID NO 140
<211> LENGTH: 21
<212> TYPE: DNA
<213> ORGANISM: Artificial
<220> FEATURE:
<223> OTHER INFORMATION: Designed chimeric oligonucleotide primer to amplify a portion of vero toxin 2-encoding sequence from hemorrhagic Escherichia coli O-157. "nucleotides 18 to 20 are ribonucleotides-other nucleotides are deoxyribonucleotides"

<400> SEQUENCE: 140
tacctgggtt tttcttcggu a 21

<210> SEQ ID NO 141
<211> LENGTH: 20
<212> TYPE: DNA
<213> ORGANISM: Artificial
<220> FEATURE:
<223> OTHER INFORMATION: Designed chimeric oligonucleotide primer to amplify a portion of vero toxin 2-encoding sequence from hemorrhagic Escherichia coli O-157. "nucleotides 18 to 20 are ribonucleotides-other nucleotides are deoxyribonucleotides"

<400> SEQUENCE: 141
atagactttt cgacccaaca 20

<210> SEQ ID NO 142
<211> LENGTH: 20
<212> TYPE: DNA
<213> ORGANISM: Artificial
<220> FEATURE:
<223> OTHER INFORMATION: Designed chimeric oligonucleotide primer to amplify a portion of vero toxin 2-encoding sequence from hemorrhagic Escherichia coli O-157. "nucleotides 18 to 20 are ribonucleotides-other nucleotides are deoxyribonucleotides"

<400> SEQUENCE: 142
atagacatca agccctcgua 20

<210> SEQ ID NO 143
<211> LENGTH: 21
<212> TYPE: DNA
<213> ORGANISM: Artificial
<220> FEATURE:
<223> OTHER INFORMATION: Designed oligonucleotide primer to amplify a portion of vero toxin 2-encoding sequence from hemorrhagic Escherichia coli O-157.

<400> SEQUENCE: 143
tcgttaaata gtatacggac a 21

<210> SEQ ID NO 144
<211> LENGTH: 20
<212> TYPE: DNA
<213> ORGANISM: Artificial
<220> FEATURE:
<223> OTHER INFORMATION: Designed oligonucleotide primer to amplify a portion of vero toxin 2-encoding sequence from hemorrhagic Escherichia coli O-157.

<400> SEQUENCE: 144
atagacatca agccctcgta 20

<210> SEQ ID NO 145
<211> LENGTH: 20
<212> TYPE: DNA
<213> ORGANISM: Artificial
<220> FEATURE:

-continued

<223> OTHER INFORMATION: Designed chimeric oligonucleotide primer to amplify a portion of lambda DNA. "nucleotides 18 to 20 are ribonucleotides-other nucleotides are deoxyribonucleotides"

<400> SEQUENCE: 145
gaacaatgga agtcaacaaa 20

<210> SEQ ID NO 146
<211> LENGTH: 20
<212> TYPE: DNA
<213> ORGANISM: Artificial
<220> FEATURE:
<223> OTHER INFORMATION: Designed oligonucleotide primer to amplify a portion of viroid CSVd.

<400> SEQUENCE: 146
tacttgtggt tcctgtggtg 20

<210> SEQ ID NO 147
<211> LENGTH: 20
<212> TYPE: DNA
<213> ORGANISM: Artificial
<220> FEATURE:
<223> OTHER INFORMATION: Designed oligonucleotide primer to amplify a portion of viroid CSVd.

<400> SEQUENCE: 147
atactaaggt tccaagggct 20

<210> SEQ ID NO 148
<211> LENGTH: 18
<212> TYPE: DNA
<213> ORGANISM: Artificial
<220> FEATURE:
<223> OTHER INFORMATION: Designed chimeric oligonucleotide primer to amplify a portion of viroid CSVd. "nucleotides 16 to 18 are ribonucleotides-other nucleotides are deoxyribonucleotides"

<400> SEQUENCE: 148
ggaaacctgg aggaaguc 18

<210> SEQ ID NO 149
<211> LENGTH: 20
<212> TYPE: DNA
<213> ORGANISM: Artificial
<220> FEATURE:
<223> OTHER INFORMATION: Designed chimeric oligonucleotide primer to amplify a portion of viroid CSVd. "nucleotides 18 to 20 are ribonucleotides-other nucleotides are deoxyribonucleotides"

<400> SEQUENCE: 149
gtgaaaaccc tgtttaggau 20

<210> SEQ ID NO 150
<211> LENGTH: 20
<212> TYPE: DNA
<213> ORGANISM: Artificial
<220> FEATURE:
<223> OTHER INFORMATION: Designed chimeric oligonucleotide primer to amplify a portion of Flavobacterium species DNA. "nucleotides 18 to 20 are ribonucleotides-other nucleotides are deoxyribonucleotides"

<400> SEQUENCE: 150
acctagatat aagctctaca 20

<210> SEQ ID NO 151

-continued

```
<211> LENGTH: 20
<212> TYPE: DNA
<213> ORGANISM: Artificial
<220> FEATURE:
<223> OTHER INFORMATION: Designed chimeric oligonucleotide primer to
      amplify a portion of Flavobacterium species DNA. "nucleotides
      18 to 20 are ribonucleotides-other nucleotides are
      deoxyribonucleotides"

<400> SEQUENCE: 151

aaatagatgt tttagcagag                                                20


<210> SEQ ID NO 152
<211> LENGTH: 20
<212> TYPE: DNA
<213> ORGANISM: Artificial
<220> FEATURE:
<223> OTHER INFORMATION: Designed chimeric oligonucleotide primer to
      amplify a portion of Flavobacterium species DNA. "nucleotides
      18 to 20 are ribonucleotides-other nucleotides are
      deoxyribonucleotides"

<400> SEQUENCE: 152

atagataaaa aaaactccac                                                20


<210> SEQ ID NO 153
<211> LENGTH: 21
<212> TYPE: DNA
<213> ORGANISM: Artificial
<220> FEATURE:
<223> OTHER INFORMATION: Designed chimeric oligonucleotide primer to
      amplify a portion of vero toxin 2-encoding sequence from
      hemorrhagic Escherichia coli O-157. "nucleotides 19 to 21 are
      ribonucleotides-nucloetide
<220> FEATURE:
<221> NAME/KEY: misc_feature
<222> LOCATION: (18)..(18)
<223> OTHER INFORMATION: n is inosine-other nucleotides are
      deoxyribonucleotides

<400> SEQUENCE: 153

tcgttaaata gtatacgnac a                                              21


<210> SEQ ID NO 154
<211> LENGTH: 21
<212> TYPE: DNA
<213> ORGANISM: Artificial
<220> FEATURE:
<223> OTHER INFORMATION: Designed chimeric oligonucleotide primer to
      amplify a portion of vero toxin 2-encoding sequence from
      hemorrhagic Escherichia coli O-157. nucleotides 19 to 21 are
      ribonucleotides-nucleotide
<220> FEATURE:
<221> NAME/KEY: misc_feature
<222> LOCATION: (17)..(17)
<223> OTHER INFORMATION: n is inosine other nucleotides are
      deoxyribonucleotides

<400> SEQUENCE: 154

tcgttaaata gtatacngac a                                              21


<210> SEQ ID NO 155
<211> LENGTH: 21
<212> TYPE: DNA
<213> ORGANISM: Artificial
<220> FEATURE:
<223> OTHER INFORMATION: Designed chimeric oligonucleotide primer to
      amplify a portion of vero toxin 2-encoding sequence from
      hemorrhagic Escherichia coli O-157. nucleotides 19 to 21 are
      ribonucleotides-nucleotide
<220> FEATURE:
```

-continued

<221> NAME/KEY: misc_feature
<222> LOCATION: (16)..(16)
<223> OTHER INFORMATION: n is inosine-other nucleotides are
deoxyribonucleotides

<400> SEQUENCE: 155
tcgttaaata gtatanggac a 21

<210> SEQ ID NO 156
<211> LENGTH: 20
<212> TYPE: DNA
<213> ORGANISM: Artificial
<220> FEATURE:
<223> OTHER INFORMATION: Designed chimeric oligonucleotide primer to
amplify a portion of vero toxin 2-encoding sequence from
hemorrhagic Escherichia coli O-157. nucleotides 18 to 20 are
ribonucleotides-nucleotide
<220> FEATURE:
<221> NAME/KEY: misc_feature
<222> LOCATION: (17)..(17)
<223> OTHER INFORMATION: n is inosine-other nucleotides are
deoxyribonucleotides"

<400> SEQUENCE: 156
tgctcaataa tcagacnaag 20

<210> SEQ ID NO 157
<211> LENGTH: 20
<212> TYPE: DNA
<213> ORGANISM: Artificial
<220> FEATURE:
<223> OTHER INFORMATION: Designed chimeric oligonucleotide primer to
amplify a portion of vero toxin 2-encoding sequence from
hemorrhagic Escherichia coli O-157. "nucleotides 18 to 20 are
ribonucleotides-nucleotide
<220> FEATURE:
<221> NAME/KEY: misc_feature
<222> LOCATION: (16)..(16)
<223> OTHER INFORMATION: n is inosine-other nucleotides are
deoxyribonucleotides

<400> SEQUENCE: 157
tgctcaataa tcagangaag 20

<210> SEQ ID NO 158
<211> LENGTH: 20
<212> TYPE: DNA
<213> ORGANISM: Artificial
<220> FEATURE:
<223> OTHER INFORMATION: Designed chimeric oligonucleotide primer to
amplify a portion of vero toxin 2-encoding sequence from
hemorrhagic Escherichia coli O-157. "nucleotides 18 to 20 are
ribonucleotides-nucleotide
<220> FEATURE:
<221> NAME/KEY: misc_feature
<222> LOCATION: (15)..(15)
<223> OTHER INFORMATION: n is inosine-other nucleotides are
deoxyribonucleotides

<400> SEQUENCE: 158
tgctcaataa tcagncgaag 20

<210> SEQ ID NO 159
<211> LENGTH: 21
<212> TYPE: DNA
<213> ORGANISM: Artificial
<220> FEATURE:
<223> OTHER INFORMATION: Designed chimeric oligonucleotide primer to
amplify a portion of vero toxin 2-encoding sequence from
hemorrhagic Escherichia coli O-157. "nucleotides 9 to 11 and 19
to 21 are ribonucleotides-other nucleotides are -continued deoxyribonucleotides"

<400> SEQUENCE: 159
tacctggguu uttcttcggu a 21

<210> SEQ ID NO 160
<211> LENGTH: 20
<212> TYPE: DNA
<213> ORGANISM: Artificial
<220> FEATURE:
<223> OTHER INFORMATION: Designed chimeric oligonucleotide primer to amplify a portion of vero toxin 2-encoding sequence from hemorrhagic Escherichia coli O-157. "nucleotides 8 to 10 and 18 to 20 are ribonucleotides-other nucleotides are deoxyribonucleotides"

<400> SEQUENCE: 160
atagacauca agccctcgua 20

<210> SEQ ID NO 161
<211> LENGTH: 20
<212> TYPE: DNA
<213> ORGANISM: Artificial
<220> FEATURE:
<223> OTHER INFORMATION: Designed chimeric oligonucleotide primer to amplify a portion of vero toxin 2-encoding sequence from hemorrhagic Esche O-157. "nucleotides 18 to 20 are ribonucleotides-other nucleotides are deoxyribonucleotides"

<400> SEQUENCE: 161
gtcccctgag atatatguuc 20

<210> SEQ ID NO 162
<211> LENGTH: 30
<212> TYPE: DNA
<213> ORGANISM: Artificial
<220> FEATURE:
<223> OTHER INFORMATION: Designed oligonucleotide probe to detect a DNA fragment amplifing a portion of vero toxin 2-encoding sequence from hemorrhagic Escherichia coli O-157.

<400> SEQUENCE: 162
ccaacaaagt tatgtctctt cgttaaatag 30

<210> SEQ ID NO 163
<211> LENGTH: 20
<212> TYPE: DNA
<213> ORGANISM: Artificial
<220> FEATURE:
<223> OTHER INFORMATION: Designed chimeric oligonucleotide primer to amplify a portion of iNOS-encoding sequence from mouse. "nucleotides 18 to 20 are ribonucleotides-other nucleotides are deoxyribonucleotides"

<400> SEQUENCE: 163
atgccattga gttcatcaac 20

<210> SEQ ID NO 164
<211> LENGTH: 19
<212> TYPE: DNA
<213> ORGANISM: Artificial
<220> FEATURE:
<223> OTHER INFORMATION: Designed chimeric oligonucleotide primer to amplify a portion of iNOS-encoding sequence from mouse. "nucleotides 17 to 19 are ribonucleotides-other nucleotides are deoxyribonucleotides"

<400> SEQUENCE: 164

-continued

```
tcttggtggc aaagatgag                                                19


<210> SEQ ID NO 165
<211> LENGTH: 20
<212> TYPE: DNA
<213> ORGANISM: Artificial
<220> FEATURE:
<223> OTHER INFORMATION: Designed oligonucleotide primer to amplify
      a portion of iNOS-encoding sequence from mouse.

<400> SEQUENCE: 165

atgccattga gttcatcaac                                               20


<210> SEQ ID NO 166
<211> LENGTH: 19
<212> TYPE: DNA
<213> ORGANISM: Artificial
<220> FEATURE:
<223> OTHER INFORMATION: Designed oligonucleotide primer to amplify
      a portion of iNOS-encoding sequence from mouse

<400> SEQUENCE: 166

tcttggtggc aaagatgag                                                19


<210> SEQ ID NO 167
<211> LENGTH: 20
<212> TYPE: DNA
<213> ORGANISM: Artificial
<220> FEATURE:
<223> OTHER INFORMATION: Designed oligonucleotide primer designated as
      GMO-PCR-F 20mer

<400> SEQUENCE: 167

atcgttgaag atgcctctgc                                               20


<210> SEQ ID NO 168
<211> LENGTH: 20
<212> TYPE: DNA
<213> ORGANISM: Artificial
<220> FEATURE:
<223> OTHER INFORMATION: designed oligonucleotide primer designated as
      GMO-PCR-R 20mer

<400> SEQUENCE: 168

tccgtatgat cgcgcgtcat                                               20


<210> SEQ ID NO 169
<211> LENGTH: 20
<212> TYPE: DNA
<213> ORGANISM: Artificial
<220> FEATURE:
<223> OTHER INFORMATION: Designed chimeric oligonucleotide primer
      designated as GMO-S1 20mer. "nucleotides 19 to 20
      are ribonucleotides-other nucleotides are
      deoxyribonucleotides"

<400> SEQUENCE: 169

tttggagagg acacgctgac                                               20


<210> SEQ ID NO 170
<211> LENGTH: 20
<212> TYPE: DNA
<213> ORGANISM: Artificial
<220> FEATURE:
<223> OTHER INFORMATION: Designed oligonucleotide primer designated
      as GMO-S2 20mer. "nucleotides 19 to 20 are ribonucleotides-other
      nucleotides are deoxyribonucleotides"
```

-continued

<400> SEQUENCE: 170
ggacacgctg acaagctgac 20

<210> SEQ ID NO 171
<211> LENGTH: 20
<212> TYPE: DNA
<213> ORGANISM: Artificial
<220> FEATURE:
<223> OTHER INFORMATION: Designed oligonucleotide primer designated as GMO-A1 20mer. "nucleotides 19 to 20 are ribonucleotides-other nucleotides are deoxyribonucleotides"

<400> SEQUENCE: 171
ggctgtagcc actgatgcug 20

<210> SEQ ID NO 172
<211> LENGTH: 20
<212> TYPE: DNA
<213> ORGANISM: Artificial
<220> FEATURE:
<223> OTHER INFORMATION: Designed oligonucleotide primer designated as GMO-A2 20 mer. "nucleotides 19 to 20 are ribonucleotides-other nucleotides are deoxyribonucleotides"

<400> SEQUENCE: 172
ttccggaaag gccagaggau 20

<210> SEQ ID NO 173
<211> LENGTH: 20
<212> TYPE: DNA
<213> ORGANISM: Artificial
<220> FEATURE:
<223> OTHER INFORMATION: Designed chimeric oligonucleotide primer to amplify a portion of vero toxin 2-encoding sequence from hemorrhagic Escherichia coli O-157. "nucleotides 18 to 20 are (alpha-thio)ribonucleotides-other nucleotides are

<400> SEQUENCE: 173
tactgggttt ttcttcggua 20

<210> SEQ ID NO 174
<211> LENGTH: 20
<212> TYPE: DNA
<213> ORGANISM: Artificial
<220> FEATURE:
<223> OTHER INFORMATION: Designed chimeric oligonucleotide primer to amplify a portion of vero toxin 2-encoding sequence from hemorrhagic Escherichia coli O-157. "nucleotides 18 to 20 are (alpha-thio)ribonucleotides-other nucleotides are

<400> SEQUENCE: 174
atagacatca agccctcgua 20

<210> SEQ ID NO 175
<211> LENGTH: 22
<212> TYPE: DNA
<213> ORGANISM: Artificial
<220> FEATURE:
<223> OTHER INFORMATION: Designed chimeric oligonucleotide primer to amplify a portion of INOS-encoding sequence from mouse. "nucleotides 20 to 22 areribonucleotides-other nucleotides are deoxyribonucleotides"

<400> SEQUENCE: 175
tcatgccatt gagttcatca ac 22

<210> SEQ ID NO 176

-continued

<211> LENGTH: 22
<212> TYPE: DNA
<213> ORGANISM: Artificial
<220> FEATURE:
<223> OTHER INFORMATION: Designed chimeric oligonucleotide primer to amplify a portion of INOS-encoding sequence from mouse. "nucleotides 20 to 22 areribonucleotides-other nucleotides are deoxyribonucleotides"

<400> SEQUENCE: 176
tggtaggttc ctgttgtttc ua 22

<210> SEQ ID NO 177
<211> LENGTH: 22
<212> TYPE: DNA
<213> ORGANISM: Artificial
<220> FEATURE:
<223> OTHER INFORMATION: Designed oligonucleotide primer to amplify a portion of INOS-encoding sequence from mouse.

<400> SEQUENCE: 177
tcatgccatt gagttcatca ac 22

<210> SEQ ID NO 178
<211> LENGTH: 22
<212> TYPE: DNA
<213> ORGANISM: Artificial
<220> FEATURE:
<223> OTHER INFORMATION: Designed oligonucleotide primer to amplify a portion of INOS-encoding sequence from mouse.

<400> SEQUENCE: 178
tggtaggttc ctgttgtttc ta 22

<210> SEQ ID NO 179
<211> LENGTH: 20
<212> TYPE: DNA
<213> ORGANISM: Artificial
<220> FEATURE:
<223> OTHER INFORMATION: Designed chimeric oligonucleotide primer to amplify a portion of lambda DNA."nucleotides 18 to 20 are ribonucleotides-othernucleotides are deoxyribonucleotides"

<400> SEQUENCE: 179
ctgcgaggcg gtggcaaggg 20

<210> SEQ ID NO 180
<211> LENGTH: 21
<212> TYPE: DNA
<213> ORGANISM: Artificial
<220> FEATURE:
<223> OTHER INFORMATION: Designed chimeric oligonucleotide primer to amplify a portion of lambda DNA."nucleotides 19 to 21 are ribonucleotides-othernucleotides are deoxyribonucleotides"

<400> SEQUENCE: 180
ctgcctcgct ggccgtgccg c 21

<210> SEQ ID NO 181
<211> LENGTH: 23
<212> TYPE: DNA
<213> ORGANISM: Artificial
<220> FEATURE:
<223> OTHER INFORMATION: Designed chimeric oligonucleotide primer to amplify a portion of INOS-encoding sequence from mouse. "nucleotides 21 to 23 areribonucleotides-other nucleotides are deoxyribonucleotides"

-continued

<400> SEQUENCE: 181
ctcatgccat tgagttcatc aac 23

<210> SEQ ID NO 182
<211> LENGTH: 22
<212> TYPE: DNA
<213> ORGANISM: Artificial
<220> FEATURE:
<223> OTHER INFORMATION: Designed chimeric oligonucleotide primer to amplify a portion of INOS-encoding sequence from mouse. "nucleotides 20 to 22 areribonucleotides-other nucleotides are deoxyribonucleotides"

<400> SEQUENCE: 182
gctggtaggt tcctgttgtu uc 22

<210> SEQ ID NO 183
<211> LENGTH: 19
<212> TYPE: DNA
<213> ORGANISM: Artificial
<220> FEATURE:
<223> OTHER INFORMATION: Designed chimeric oligonucleotide primer to amplify a portion of pDON-AI DNA."nucleotides 17 to 19 are ribonucleotides-othernucleotides are deoxyribonucleotides"

<400> SEQUENCE: 183
agctctgtat ctggcggac 19

<210> SEQ ID NO 184
<211> LENGTH: 21
<212> TYPE: DNA
<213> ORGANISM: Artificial
<220> FEATURE:
<223> OTHER INFORMATION: Designed chimeric oligonucleotide primer to amplify a portion of pDON-AI DNA."nucleotides 19 to 21 are ribonucleotides-othernucleotides are deoxyribonucleotides"

<400> SEQUENCE: 184
gatcgggatt tttggactca g 21

<210> SEQ ID NO 185
<211> LENGTH: 21
<212> TYPE: DNA
<213> ORGANISM: Artificial
<220> FEATURE:
<223> OTHER INFORMATION: Designed chimeric oligonucleotide primer to amplify a portion of HPV type16 DNA."nucleotides 19 to 21 are ribonucleotides-othernucleotides are deoxyribonucleotides"

<400> SEQUENCE: 185
caaaagagaa ctgcaatguu u 21

<210> SEQ ID NO 186
<211> LENGTH: 25
<212> TYPE: DNA
<213> ORGANISM: Artificial
<220> FEATURE:
<223> OTHER INFORMATION: Designed chimeric oligonucleotide primer to amplify a portion of HPV type16 DNA."nucleotides 19 to 21 are ribonucleotides-othernucleotides are deoxyribonucleotides"

<400> SEQUENCE: 186
cgcctccatc cagtctatta atugu 25

-continued

<210> SEQ ID NO 187
<211> LENGTH: 27
<212> TYPE: DNA
<213> ORGANISM: Artificial
<220> FEATURE:
<223> OTHER INFORMATION: Designed oligonucleotide probe to detect a DNA fragment amplifing a portion of HPV DNA.

<400> SEQUENCE: 187
gaggacccac aggagcgacc cagaaag 27

<210> SEQ ID NO 188
<211> LENGTH: 20
<212> TYPE: DNA
<213> ORGANISM: Artificial
<220> FEATURE:
<223> OTHER INFORMATION: Designed oligonucleotide primer to amplify a portion of HCV.

<400> SEQUENCE: 188
cactccacca tgaatcactc 20

<210> SEQ ID NO 189
<211> LENGTH: 20
<212> TYPE: DNA
<213> ORGANISM: Artificial
<220> FEATURE:
<223> OTHER INFORMATION: Designed oligonucleotide primer to amplify a portion of HCV.

<400> SEQUENCE: 189
ggtgcacggt ctacgagacc 20

<210> SEQ ID NO 190
<211> LENGTH: 21
<212> TYPE: DNA
<213> ORGANISM: Artificial
<220> FEATURE:
<223> OTHER INFORMATION: Designed chimeric oligonucleotide primer to amplify a portion of HCV."nucleotides 19 to 21 are ribonucl eotides-other nucleotidesare deoxyribonucleotides"

<400> SEQUENCE: 190
ctgtgaggaa ctactgtcuu c 21

<210> SEQ ID NO 191
<211> LENGTH: 18
<212> TYPE: DNA
<213> ORGANISM: Artificial
<220> FEATURE:
<223> OTHER INFORMATION: Designed chimeric oligonucleotide primer to amplify a portion of HCV."nucleotides 16 to 18 are ribonucl eotides-other nucleotidesare deoxyribonucleotides"

<400> SEQUENCE: 191
gcagaccact atggcucu 18

<210> SEQ ID NO 192
<211> LENGTH: 30
<212> TYPE: DNA
<213> ORGANISM: Artificial
<220> FEATURE:
<223> OTHER INFORMATION: Designed oligonucleotide probe to detect a DNA fragment -continued

```
      amplifing portion o
<400> SEQUENCE: 192

gtatgagtgt cgtgcagcct ccaggacccc                                        30


<210> SEQ ID NO 193
<211> LENGTH: 21
<212> TYPE: DNA
<213> ORGANISM: Artificial
<220> FEATURE:
<223> OTHER INFORMATION: Designed chimeric oligonucleotide primer to
      amplify a portion of adenovirus."nucleotides 19 to 21
      are ribonucleotides-othernucleotides are
      deoxyribonucleotides"

<400> SEQUENCE: 193

tgagacatat tatctgccac g                                                 21


<210> SEQ ID NO 194
<211> LENGTH: 21
<212> TYPE: DNA
<213> ORGANISM: Artificial
<220> FEATURE:
<223> OTHER INFORMATION: Designed chimeric oligonucleotide primer to
      amplify a portion of adenovirus."nucleotides 19 to 21
      are ribonucleotides-othernucleotides are
      deoxyribonucleotides"

<400> SEQUENCE: 194

aaatggctag gaggtggaag a                                                 21


<210> SEQ ID NO 195
<211> LENGTH: 21
<212> TYPE: DNA
<213> ORGANISM: Artificial
<220> FEATURE:
<223> OTHER INFORMATION: Designed chimeric oligonucleotide primer to
      amplify a portion of adenovirus."nucleotides 19 to 21
      are ribonucleotides-othernucleotides are
      deoxyribonucleotides"

<400> SEQUENCE: 195

ttatcagcca gtacctctuc g                                                 21


<210> SEQ ID NO 196
<211> LENGTH: 21
<212> TYPE: DNA
<213> ORGANISM: Artificial
<220> FEATURE:
<223> OTHER INFORMATION: Designed oligonucleotide primer to amplify
      a portion of adenovirus

<400> SEQUENCE: 196

tgagacatat tatctgccac g                                                 21


<210> SEQ ID NO 197
<211> LENGTH: 21
<212> TYPE: DNA
<213> ORGANISM: Artificial
<220> FEATURE:
<223> OTHER INFORMATION: Designed oligonucleotide primer to amplify
      a portion of adenovirus.

<400> SEQUENCE: 197

aaatggctag gaggtggaag a                                                 21


<210> SEQ ID NO 198
<211> LENGTH: 20
```

-continued

```
<212> TYPE: DNA
<213> ORGANISM: Artificial
<220> FEATURE:
<223> OTHER INFORMATION: Designed oligonucleotide primer to amplify a
      portion of viroid CSVd.

<400> SEQUENCE: 198

ggggaaacct ggaggaagtc                                               20


<210> SEQ ID NO 199
<211> LENGTH: 20
<212> TYPE: DNA
<213> ORGANISM: Artificial
<220> FEATURE:
<223> OTHER INFORMATION: Designed oligonucleotide primer to amplify a
      portion of viroid CSVd.

<400> SEQUENCE: 199

cgggtagtag ccaaaggaag                                               20


<210> SEQ ID NO 200
<211> LENGTH: 19
<212> TYPE: DNA
<213> ORGANISM: Artificial
<220> FEATURE:
<223> OTHER INFORMATION: Designed oligonucleotide primer to amplify a
      portion of pDON-AI DNA.

<400> SEQUENCE: 200

agctctgtat ctggcggac                                                19


<210> SEQ ID NO 201
<211> LENGTH: 21
<212> TYPE: DNA
<213> ORGANISM: Artificial
<220> FEATURE:
<223> OTHER INFORMATION: Designed oligonucleotide primer to amplify a
      portion of pDON-AI DNA.

<400> SEQUENCE: 201

gatcgggatt tttggactca g                                             21


<210> SEQ ID NO 202
<211> LENGTH: 20
<212> TYPE: DNA
<213> ORGANISM: Artificial
<220> FEATURE:
<223> OTHER INFORMATION: Designed chimeric oligonucleotide primer to
      amplify a portion of verotoxin-1 encoding sequence from
      hemorrhagic Escherichia coli 0-157."nucleotides 18 to 20 are
      ribonucleotides-other nucleotides are deoxyribonucleotides"

<400> SEQUENCE: 202

ggggataatt tgtttgcagu                                               20


<210> SEQ ID NO 203
<211> LENGTH: 20
<212> TYPE: DNA
<213> ORGANISM: Artificial
<220> FEATURE:
<223> OTHER INFORMATION: Designed chimeric oligonucleotide primer to
      amplify a portion of verotoxin-1 encoding sequence from
      hemorrhagic Escherichia coli 0-157."nucleotides 18 to 20 are
      ribonucleotides-other nucleotides are deoxyribonucleotides"

<400> SEQUENCE: 203

tcgttcaaca ataagccgua                                               20
```

-continued

<210> SEQ ID NO 204
<211> LENGTH: 30
<212> TYPE: DNA
<213> ORGANISM: Artificial
<220> FEATURE:
<223> OTHER INFORMATION: Designed oligonucleotide probe to detect a DNA fragment amplifying a portion of verotoxin-1 encoding sequence from hemorrhagic Escherichia coli 0-157.

<400> SEQUENCE: 204
cgcccttcct ctggatctac ccctctgaca 30

<210> SEQ ID NO 205
<211> LENGTH: 21
<212> TYPE: DNA
<213> ORGANISM: Artificial
<220> FEATURE:
<223> OTHER INFORMATION: Designed chimeric oligonucleotide primer to amplify a portion of botulinum toxin A encoding sequence from Clostridiumbotulinum."nucleotides 19 to 21 are ribonucleotides -other nucleotides are deoxyribonucleotides"

<400> SEQUENCE: 205
caccagaagc aaaacaaguu c 21

<210> SEQ ID NO 206
<211> LENGTH: 23
<212> TYPE: DNA
<213> ORGANISM: Artificial
<220> FEATURE:
<223> OTHER INFORMATION: Designed chimeric oligonucleotide primer to amplify a portion of botulinum toxin A encoding sequence from Clostridiumbotulinum."nucleotides 21 to 23 are ribonucleotides -other nucleotides are deoxyribonucleotides"

<400> SEQUENCE: 206
ctattgatgt taacaacatt cuu 23

<210> SEQ ID NO 207
<211> LENGTH: 30
<212> TYPE: DNA
<213> ORGANISM: Artificial
<220> FEATURE:
<223> OTHER INFORMATION: Designed oligonucleotide probe to detect a DNA fragment amplifying a portion of botulinum toxin A encoding sequence from Clostridium botul
<400> SEQUENCE: 207
gggagttaca aaattatttg agagaattta 30

<210> SEQ ID NO 208
<211> LENGTH: 21
<212> TYPE: DNA
<213> ORGANISM: Artificial
<220> FEATURE:
<223> OTHER INFORMATION: Designed chimeric oligonucleotide primer to amplify a portion of viroid CSVd."nucleotides 19 to 21 are ribonucleotides-other nucleotides are deoxyribonucleotides"

<400> SEQUENCE: 208 caccettcct ttagtttccu u 21

<210> SEQ ID NO 209
<211> LENGTH: 20
<212> TYPE: DNA
<213> ORGANISM: Artificial
<220> FEATURE:
<223> OTHER INFORMATION: Designed chimeric oligonucleotide primer to amplify a portion of viroid CSVd."nucleotides 18 to 20 are -continued ribonucleotides-other nucleotides are deoxyribonucleotides"

<400> SEQUENCE: 209
cgttgaagct tcagttguuu         20

<210> SEQ ID NO 210
<211> LENGTH: 30
<212> TYPE: DNA
<213> ORGANISM: Artificial
<220> FEATURE:
<223> OTHER INFORMATION: Designed oligonucleotide probe to detect a
      DNA fragment amplifying a portion of viroid CSVd.

<400> SEQUENCE: 210
ccttcctctc ctggagaggt cttctgccct         30

<210> SEQ ID NO 211
<211> LENGTH: 21
<212> TYPE: DNA
<213> ORGANISM: Artificial
<220> FEATURE:
<223> OTHER INFORMATION: Designed chimeric oligonucleotide primer to
      amplify a portion of viroid CSVd."nucleotides 19 to 21 are
      ribonucleotides-other nucleotides are deoxyribonucleotides"

<400> SEQUENCE: 211
cacccttcct ttagtttccu u         21

<210> SEQ ID NO 212
<211> LENGTH: 21
<212> TYPE: DNA
<213> ORGANISM: Artificial
<220> FEATURE:
<223> OTHER INFORMATION: Designed chimeric oligonucleotide primer to
      amplify a portion of viroid CSVd."nucleotides 19 to 21 are
      ribonucleotides-other nucleotides are deoxyribonucleotides"

<400> SEQUENCE: 212
cgttgaagct tcagttgtuu c         21

<210> SEQ ID NO 213
<211> LENGTH: 21
<212> TYPE: DNA
<213> ORGANISM: Artificial
<220> FEATURE:
<223> OTHER INFORMATION: Designed oligonucleotide primer to amplify a
      portion of viroid CSVd.

<400> SEQUENCE: 213
cacccttcct ttagtttcct t         21

<210> SEQ ID NO 214
<211> LENGTH: 21
<212> TYPE: DNA
<213> ORGANISM: Artificial
<220> FEATURE:
<223> OTHER INFORMATION: Designed oligonucleotide primer to amplify a
      portion of viroid CSVd.

<400> SEQUENCE: 214
cgttgaagct tcagttgttt c         21

<210> SEQ ID NO 215
<211> LENGTH: 20
<212> TYPE: DNA
<213> ORGANISM: Artificial
<220> FEATURE:

-continued

<223> OTHER INFORMATION: Designed chimeric oligonucleotide primer to amplify a portion of c-ki-ras oncogene."nucleotides 18 to 20 are ribonucleotides-other nucleotides are deoxyribonucleotides"

<400> SEQUENCE: 215
gactgaatat aaacttgugg 20

<210> SEQ ID NO 216
<211> LENGTH: 20
<212> TYPE: DNA
<213> ORGANISM: Artificial
<220> FEATURE:
<223> OTHER INFORMATION: Designed chimeric oligonucleotide primer to amplify a portion of c-ki-ras oncogene."nucleotides 18 to 20 are ribonucleotides-other nucleotides are deoxyribonucleotides"

<400> SEQUENCE: 216
ctattgttgg atcatatucg 20

<210> SEQ ID NO 217
<211> LENGTH: 20
<212> TYPE: DNA
<213> ORGANISM: Artificial
<220> FEATURE:
<223> OTHER INFORMATION: Designed oligonucleotide primer to amplify a portion of c-ki-rasoncogene.

<400> SEQUENCE: 217
gactgaatat aaacttgtgg 20

<210> SEQ ID NO 218
<211> LENGTH: 20
<212> TYPE: DNA
<213> ORGANISM: Artificial
<220> FEATURE:
<223> OTHER INFORMATION: Designed oligonucleotide primer to amplify a portion of c-ki-rasoncogene.

<400> SEQUENCE: 218
ctattgttgg atcatattcg 20

<210> SEQ ID NO 219
<211> LENGTH: 20
<212> TYPE: DNA
<213> ORGANISM: Artificial
<220> FEATURE:
<223> OTHER INFORMATION: Designed chimeric oligonucleotide primer to amplify a portion of verotoxin-2 encoding sequence from hemorrhagic Escherichia coli O-157."nucleotides 18 to 20 are ribonucleotides-other nucleotides are deoxyribonucleotides"

<400> SEQUENCE: 219
gacttttcga cccaacaaag 20

<210> SEQ ID NO 220
<211> LENGTH: 20
<212> TYPE: DNA
<213> ORGANISM: Artificial
<220> FEATURE:
<223> OTHER INFORMATION: Designed chimeric oligonucleotide primer to amplify a portion of verotoxin-2 encoding sequence from hemorrhagic Escherichia coli O-157."nucleotides 18 to 20 are ribonucleotides-other nucleotides are deoxyribonucleotides"

<400> SEQUENCE: 220
atatccacag caaaataacu 20

-continued

<210> SEQ ID NO 221
<211> LENGTH: 21
<212> TYPE: DNA
<213> ORGANISM: Artificial
<220> FEATURE:
<223> OTHER INFORMATION: Designed oligonucleotide primer to amplify a portion of INOS-encoding sequence from mouse.

<400> SEQUENCE: 221
cacaaggcca catcggattt c 21

<210> SEQ ID NO 222
<211> LENGTH: 21
<212> TYPE: DNA
<213> ORGANISM: Artificial
<220> FEATURE:
<223> OTHER INFORMATION: Designed oligonucleotide primer to amplify a portion of INOS-encoding sequence from mouse.

<400> SEQUENCE: 222
tgcataccac ttcaacccga g 21

<210> SEQ ID NO 223
<211> LENGTH: 25
<212> TYPE: DNA
<213> ORGANISM: Artificial
<220> FEATURE:
<223> OTHER INFORMATION: Designed oligonucleotide primer designated as pUC19 upper 150 to amplify a portion of plasmid pUC19.

<400> SEQUENCE: 223
ggtgtcacgc tcgtcgtttg gtatg 25

<210> SEQ ID NO 224
<211> LENGTH: 25
<212> TYPE: DNA
<213> ORGANISM: Artificial
<220> FEATURE:
<223> OTHER INFORMATION: Designed chimeric oligonucleotide primer designated as pUC19 lower NN to amplify a portion of plasmid pUC19.

<400> SEQUENCE: 224
gataacactg cggccaactt acttc 25

<210> SEQ ID NO 225
<211> LENGTH: 21
<212> TYPE: DNA
<213> ORGANISM: Artificial
<220> FEATURE:
<223> OTHER INFORMATION: Designed chimeric oligonucleotide primer designated as SEA-1 to amplify a portion of Staphylococcus aureus. "nucleotides 19 to 21 are ribonucleotides-other nucleotides are deoxyribonucleotides"

<400> SEQUENCE: 225
tgtatgtatg gtggtgtaac g 21

<210> SEQ ID NO 226
<211> LENGTH: 21
<212> TYPE: DNA
<213> ORGANISM: Artificial
<220> FEATURE:
<223> OTHER INFORMATION: Designed chimeric oligonucleotide primer designated as SEA-2 to amplify a portion of Staphylococcus aureus. "nucleotides 19 to 21 are ribonucleotides-other nucleotides are deoxyribonucleotides"

<400> SEQUENCE: 226

-continued

```
taaccgtttc caaaggtacu g                                               21


<210> SEQ ID NO 227
<211> LENGTH: 19
<212> TYPE: DNA
<213> ORGANISM: Artificial
<220> FEATURE:
<223> OTHER INFORMATION: Designed chimeric oligonucleotide primer
      designated as HCV-F3 to amplify a portion of HCV.
      "nucleotides 17 to 19 are ribonucleotides-other
      nucleotides are deoxyribonucleotides"

<400> SEQUENCE: 227

gcgtctagcc atggcguua                                                  19


<210> SEQ ID NO 228
<211> LENGTH: 18
<212> TYPE: DNA
<213> ORGANISM: Artificial
<220> FEATURE:
<223> OTHER INFORMATION: Designed chimeric oligonucleotide primer
      designated as HCV-R1 to amplify a portion of HCV. "nucleotides
      16 to 18 are ribonucleotides-other nucleotides are
      deoxyribonucleotides"

<400> SEQUENCE: 228

gcagaccact atggcucu                                                   18


<210> SEQ ID NO 229
<211> LENGTH: 30
<212> TYPE: DNA
<213> ORGANISM: Artificial
<220> FEATURE:
<223> OTHER INFORMATION: Designed oligonucleotide primer designated as
      MF2 to amplify a portion of pUC19 plasmid DNA.

<400> SEQUENCE: 229

ggatgtgctg caaggcgatt aagttgggta                                      30


<210> SEQ ID NO 230
<211> LENGTH: 30
<212> TYPE: DNA
<213> ORGANISM: Artificial
<220> FEATURE:
<223> OTHER INFORMATION: Designed oligonucleotide primer designated as
      MR1 to amplify a portion of pUC19 plasmid DNA.

<400> SEQUENCE: 230

tttacacttt atgcttccgg ctcgtatgtt                                      30


<210> SEQ ID NO 231
<211> LENGTH: 21
<212> TYPE: DNA
<213> ORGANISM: Artificial
<220> FEATURE:
<223> OTHER INFORMATION: Designed oligonucleotide primer to
      amplify a portion of adenovirus.

<400> SEQUENCE: 231

ttatcagcca gtacctcttc g                                               21


<210> SEQ ID NO 232
<211> LENGTH: 714
<212> TYPE: DNA
<213> ORGANISM: Thermotoga maritima

<400> SEQUENCE: 232
```

-continued

```
atgggaatag atgagcttta caaaaaagag tttggaatcg tagcaggtgt ggatgaagcg     60

ggaagagggt gcctcgcagg tcccgttgtg gcggccgctg tcgttctgga aaaagaaata    120

gaaggaataa acgattcaaa acagctttcc cctgcgaaga gggaaagact tttagatgaa    180

ataatggaga aggcagcagt tgggttagga attgcgtctc cagaggaaat agatctctac    240

aacatattca atgccacaaa acttgctatg aatcgagcac tggagaacct gtctgtgaaa    300

ccatcatttg tactcgttga cgggaaagga atcgagttga gcgttcccgg tacatgctta    360

gtgaagggag accagaaaag caaattgata ggagcagctt ccattgttgc gaaggtcttc    420

agagatagat tgatgagcga gtttcacagg atgtatccac agttttcctt ccacaaacac    480

aaaggttacg ccacaaaaga acatctgaac gaaatcagaa agaacggagt tttaccaatc    540

caccggctga gttttgaacc tgttttagaa cttctgaccg atgatttgtt gagggagttc    600

ttcgaaaaag gcctcatctc cgaaaatcga ttcgaacgaa tattgaatct tctgggggcg    660

agaaaaagtg tggttttccg gaaagaaaga acaaaccata atctccctct tttt          714


<210> SEQ ID NO 233
<211> LENGTH: 238
<212> TYPE: PRT
<213> ORGANISM: Thermotoga maritime

<400> SEQUENCE: 233

Met Gly Ile Asp Glu Leu Tyr Lys Lys Glu Phe Gly Ile Val Ala Gly
1               5                   10                  15

Val Asp Glu Ala Gly Arg Gly Cys Leu Ala Gly Pro Val Val Ala Ala
            20                  25                  30

Ala Val Val Leu Glu Lys Glu Ile Glu Gly Ile Asn Asp Ser Lys Gln
        35                  40                  45

Leu Ser Pro Ala Lys Arg Glu Arg Leu Leu Asp Glu Ile Met Glu Lys
    50                  55                  60

Ala Ala Val Gly Leu Gly Ile Ala Ser Pro Glu Glu Ile Asp Leu Tyr
65                  70                  75                  80

Asn Ile Phe Asn Ala Thr Lys Leu Ala Met Asn Arg Ala Leu Glu Asn
                85                  90                  95

Leu Ser Val Lys Pro Ser Phe Val Leu Val Asp Gly Lys Gly Ile Glu
            100                 105                 110

Leu Ser Val Pro Gly Thr Cys Leu Val Lys Gly Asp Gln Lys Ser Lys
        115                 120                 125

Leu Ile Gly Ala Ala Ser Ile Val Ala Lys Val Phe Arg Asp Arg Leu
    130                 135                 140

Met Ser Glu Phe His Arg Met Tyr Pro Gln Phe Ser Phe His Lys His
145                 150                 155                 160

Lys Gly Tyr Ala Thr Lys Glu His Leu Asn Glu Ile Arg Lys Asn Gly
                165                 170                 175

Val Leu Pro Ile His Arg Leu Ser Phe Glu Pro Val Leu Glu Leu Leu
            180                 185                 190

Thr Asp Asp Leu Leu Arg Glu Phe Phe Glu Lys Gly Leu Ile Ser Glu
        195                 200                 205

Asn Arg Phe Glu Arg Ile Leu Asn Leu Leu Gly Ala Arg Lys Ser Val
    210                 215                 220

Val Phe Arg Lys Glu Arg Thr Asn His Asn Leu Pro Leu Phe
225                 230                 235
```

-continued

<210> SEQ ID NO 234
<211> LENGTH: 663
<212> TYPE: DNA
<213> ORGANISM: Pyrococcus horikoshii

<400> SEQUENCE: 234
atgaaggttg ctggagttga tgaagcgggg agggggccgg taattggccc gttagtaatt 60
ggagtagccg ttatagatga gaaaaatatt gagaggttac gtgacattgg ggttaaagac 120
tccaaacaat taactcctgg gcaacgtgaa aaactattta gcaaattaat agatatccta 180
gacgattatt atgttcttct cgttaccccc aaggaaatag atgagaggca tcattctatg 240
aatgaactag aagctgagaa attcgttgta gccttgaatt ctttaaggat caagccgcag 300
aagatatatg tggactctgc cgatgtagat cctaagaggt ttgctagtct aataaaggct 360
gggttgaaat atgaagccac ggttatcgcc gagcataaag ccgatgcaaa gtatgagata 420
gtatcggcag catcaataat tgcaaaggtc actagggata gagagataga gaagctaaag 480
caaaagtatg gggaatttgg ttctggctat ccgagtgatc cgagaactaa ggagtggctt 540
gaagaatatt acaaacaata tggtgacttt cctccaatag ttaggagaac ttgggaaacc 600
gctaggaaga tagaggaaag gtttagaaaa aatcagctaa cgcttgataa attccttaag 660
tga 663

<210> SEQ ID NO 235
<211> LENGTH: 30
<212> TYPE: DNA
<213> ORGANISM: Artificial
<220> FEATURE:
<223> OTHER INFORMATION: PCR primer PhoNde for cloning a gene encoding a polypeptide having a RNaseHII activity from Pyrococcus horikoshii

<400> SEQUENCE: 235
aggaggaaaa tcatatgaag gttgctggag 30

<210> SEQ ID NO 236
<211> LENGTH: 30
<212> TYPE: DNA
<213> ORGANISM: Artificial
<220> FEATURE:
<223> OTHER INFORMATION: PCR primer PhoBam for cloning a gene encoding a polypeptide having a RNaseHII activity from Pyrococcus horikoshii

<400> SEQUENCE: 236
ttacatgaag gatccaagat cacttaagga 30

<210> SEQ ID NO 237
<211> LENGTH: 673
<212> TYPE: DNA
<213> ORGANISM: Pyrococcus horikoshii

<400> SEQUENCE: 237
atgaaggttg ctggagttga tgaagcgggg agggggccgg taattggccc gttagtaatt 60
ggagtagccg ttatagatga gaaaaatatt gagaggttac gtgacattgg ggttaaagac 120
tccaaacaat taactcctgg gcaacgtgaa aaactattta gcaaattaat agatatccta 180
gacgattatt atgttcttct cgttaccccc aaggaaatag atgagaggca tcattctatg 240
aatgaactag aagctgagaa attcgttgta gccttgaatt ctttaaggat caagccgcag 300
aagatatatg tggactctgc cgatgtagat cctaagaggt ttgctagtct aataaaggct 360

-continued gggttgaaat atgaagccac ggttatcgcc gagcataaag ccgatgcaaa gtatgagata 420
gtatcggcag catcaataat tgcaaaggtc actagggata gagagataga gaagctaaag 480
caaaagtatg gggaatttgg ttctggctat ccgagtgatc cgagaactaa ggagtggctt 540
gaagaatatt acaaacaata tggtgacttt cctccaatag ttaggagaac ttgggaaacc 600
gctaggaaga tagaggaaag gtttagaaaa aatcagctaa cgcttgataa attccttaag 660
tgatcttgga tcc 673

<210> SEQ ID NO 238
<211> LENGTH: 220
<212> TYPE: PRT
<213> ORGANISM: Pyrococcus horikoshii

<400> SEQUENCE: 238

Met Lys Val Ala Gly Val Asp Glu Ala Gly Arg Gly Pro Val Ile Gly
1 5 10 15

Pro Leu Val Ile Gly Val Ala Val Ile Asp Glu Lys Asn Ile Glu Arg
20 25 30

Leu Arg Asp Ile Gly Val Lys Asp Ser Lys Gln Leu Thr Pro Gly Gln
35 40 45

Arg Glu Lys Leu Phe Ser Lys Leu Ile Asp Ile Leu Asp Asp Tyr Tyr
50 55 60

Val Leu Leu Val Thr Pro Lys Glu Ile Asp Glu Arg His His Ser Met
65 70 75 80

Asn Glu Leu Glu Ala Glu Lys Phe Val Val Ala Leu Asn Ser Leu Arg
85 90 95

Ile Lys Pro Gln Lys Ile Tyr Val Asp Ser Ala Asp Val Asp Pro Lys
100 105 110

Arg Phe Ala Ser Leu Ile Lys Ala Gly Leu Lys Tyr Glu Ala Thr Val
115 120 125

Ile Ala Glu His Lys Ala Asp Ala Lys Tyr Glu Ile Val Ser Ala Ala
130 135 140

Ser Ile Ile Ala Lys Val Thr Arg Asp Arg Glu Ile Glu Lys Leu Lys
145 150 155 160

Gln Lys Tyr Gly Glu Phe Gly Ser Gly Tyr Pro Ser Asp Pro Arg Thr
165 170 175

Lys Glu Trp Leu Glu Glu Tyr Tyr Lys Gln Tyr Gly Asp Phe Pro Pro
180 185 190

Ile Val Arg Arg Thr Trp Glu Thr Ala Arg Lys Ile Glu Glu Arg Phe
195 200 205

Arg Lys Asn Gln Leu Thr Leu Asp Lys Phe Leu Lys
210 215 220

<210> SEQ ID NO 239
<211> LENGTH: 626
<212> TYPE: DNA
<213> ORGANISM: Archaeogobus fulgidus

<400> SEQUENCE: 239
atgaaggcag gcatcgatga ggctggaaag ggctgcgtca tcggcccact ggttgttgca 60
ggagtggctt gcagcgatga ggataggctg agaaagcttg gtgtgaaaga ctccaaaaag 120
ctaagtcagg ggaggagaga ggaactagcc gaggaaataa ggaaaatctg cagaacggag 180
gttttgaaag tttctcccga aaatctcgac gaaaggatgg ctgctaaaac cataaacgag 240
attttgaagg agtgctacgc tgaaataatt ctcaggctga agccggaaat tgcttatgtt 300

-continued

```
gacagtcctg atgtgattcc cgagagactt tcgagggagc ttgaggagat tacggggttg    360

agagttgtgg ccgagcacaa ggcggacgag aagtatcccc tggtagctgc ggcttcaatc    420

atcgcaaagg tggaaaggga gcgggagatt gagaggctga aagaaaaatt cggggatttc    480

ggcagcggct atgcgagcga tccgaggaca agagaagtgc tgaaggagtg gatagcttca    540

ggcagaattc cgagctgcgt gagaatgcgc tggaagacgg tgtcaaatct gaggcagaag    600

acgcttgacg atttctaaac gaaacc                                         626
```

<210> SEQ ID NO 240
<211> LENGTH: 30
<212> TYPE: DNA
<213> ORGANISM: Artificial
<220> FEATURE:
<223> OTHER INFORMATION: PCR primer AfuNde for cloning a gene encoding a polypeptide having a RNaseHII activity from Archaeoglobus fulgidus

<400> SEQUENCE: 240

```
aagctgggtt tcatatgaag gcaggcatcg                                      30
```

<210> SEQ ID NO 241
<211> LENGTH: 30
<212> TYPE: DNA
<213> ORGANISM: Artificial
<220> FEATURE:
<223> OTHER INFORMATION: PCR primer AfuBam for cloning a gene encoding a polypeptide having a RNaseHII activity from Archaeoglobus fulgidus

<400> SEQUENCE: 241

```
tggtaataac ggatccgttt agaaatcgtc                                      30
```

<210> SEQ ID NO 242
<211> LENGTH: 638
<212> TYPE: DNA
<213> ORGANISM: Archaeoglobus fulgidus

<400> SEQUENCE: 242

```
catatgaagg caggcatcga tgaggctgga aagggctgcg tcatcggccc actggttgtt     60

gcaggagtgg cttgcagcga tgaggatagg ctgagaaagc ttggtgtgaa agactccaaa    120

aagctaagtc aggggaggag agaggaacta gccgaggaaa taaggaaaat ctgcagaacg    180

gaggttttga aagtttctcc cgaaaatctc gacgaaagga tggctgctaa aaccataaac    240

gagattttga aggagtgcta cgctgaaata attctcaggc tgaagccgga aattgcttat    300

gttgacagtc ctgatgtgat tcccgagaga ctttcgaggg agcttgagga gattacgggg    360

ttgagagttg tggccgagca caaggcggac gagaagtatc ccctggtagc tgcggcttca    420

atcatcgcaa aggtggaaag ggagcgggag attgagaggc tgaaagaaaa attcggggat    480

ttcggcagcg gctatgcgag cgatccgagg acaagagaag tgctgaagga gtggatagct    540

tcaggcagaa ttccgagctg cgtgagaatg cgctggaaga cggtgtcaaa tctgaggcag    600

aagacgcttg acgatttcta aacggatccc cgggtacc                             638
```

<210> SEQ ID NO 243
<211> LENGTH: 205
<212> TYPE: PRT
<213> ORGANISM: Archaeoglobus fulgidus

<400> SEQUENCE: 243

-continued

```
Met Lys Ala Gly Ile Asp Glu Ala Gly Lys Gly Cys Val Ile Gly Pro
1               5                   10                  15

Leu Val Val Ala Gly Val Ala Cys Ser Asp Glu Asp Arg Leu Arg Lys
            20                  25                  30

Leu Gly Val Lys Asp Ser Lys Lys Leu Ser Gln Gly Arg Arg Glu Glu
        35                  40                  45

Leu Ala Glu Glu Ile Arg Lys Ile Cys Arg Thr Glu Val Leu Lys Val
    50                  55                  60

Ser Pro Glu Asn Leu Asp Glu Arg Met Ala Ala Lys Thr Ile Asn Glu
65                  70                  75                  80

Ile Leu Lys Glu Cys Tyr Ala Glu Ile Ile Leu Arg Leu Lys Pro Glu
                85                  90                  95

Ile Ala Tyr Val Asp Ser Pro Asp Val Ile Pro Glu Arg Leu Ser Arg
            100                 105                 110

Glu Leu Glu Glu Ile Thr Gly Leu Arg Val Val Ala Glu His Lys Ala
        115                 120                 125

Asp Glu Lys Tyr Pro Leu Val Ala Ala Ala Ser Ile Ile Ala Lys Val
    130                 135                 140

Glu Arg Glu Arg Glu Ile Glu Arg Leu Lys Glu Lys Phe Gly Asp Phe
145                 150                 155                 160

Gly Ser Gly Tyr Ala Ser Asp Pro Arg Thr Arg Glu Val Leu Lys Glu
                165                 170                 175

Trp Ile Ala Ser Gly Arg Ile Pro Ser Cys Val Arg Met Arg Trp Lys
            180                 185                 190

Thr Val Ser Asn Leu Arg Gln Lys Thr Leu Asp Asp Phe
        195                 200                 205
```

<210> SEQ ID NO 244
<211> LENGTH: 18
<212> TYPE: DNA
<213> ORGANISM: Artificial
<220> FEATURE:
<223> OTHER INFORMATION: Designed chimeric oligonucleotide primer designated as MTIS2F to amplify a portion of Mycobacterium tuberculosis DNA."nucleotides 16 to 18 are ribonucleotides -other nucleotides are deoxyribonucleotides."

<400> SEQUENCE: 244
tctcgtccag cgccgcuu 18

<210> SEQ ID NO 245
<211> LENGTH: 21
<212> TYPE: DNA
<213> ORGANISM: Artificial
<220> FEATURE:
<223> OTHER INFORMATION: Designed chimeric oligonucleotide primer designated as MTIS2R to amplify a portion of Mycobacterium tuberculosis DNA."nucleotides 19 to 21 are ribonucleotides -other nucleotides are deoxyribonucleotides."

<400> SEQUENCE: 245
gacaaaggcc acgtaggcga a 21

<210> SEQ ID NO 246
<211> LENGTH: 20
<212> TYPE: DNA
<213> ORGANISM: Artificial
<220> FEATURE:
<223> OTHER INFORMATION: Designed chimeric oligonucleotide primer designated as CT2F to amplify a portion of Chlamydia trachomatis cryptic plasmid DNA."nucleotides 18 to 20 are ribonucleotides-other nucleotides are deoxyribonucleotides."

-continued

<400> SEQUENCE: 246
ctggatttat cggaaaccuu 20

<210> SEQ ID NO 247
<211> LENGTH: 18
<212> TYPE: DNA
<213> ORGANISM: Artificial
<220> FEATURE:
<223> OTHER INFORMATION: Designed chimeric oligonucleotide primer designated as CT2R to amplify a portion of Chlamydia trachomatis cryptic plasmid DNA."nucleotides 16 to 18 are ribonucleotides -other nucleotides are deoxyribonucleotides."

<400> SEQUENCE: 247
aggcctctga aacgacuu 18

<210> SEQ ID NO 248
<211> LENGTH: 19
<212> TYPE: DNA
<213> ORGANISM: Artificial
<220> FEATURE:
<223> OTHER INFORMATION: Designed chimeric oligonucleotide primer designated as K-F-1033(60) to amplify a portion of Mycobacterium tuberculosis DNA."nucleotides 17 to 19 are ribonucleotides-other nucleotides are deoxyribonucleotides."

<400> SEQUENCE: 248
cacatcgatc cggttcagc 19

<210> SEQ ID NO 249
<211> LENGTH: 20
<212> TYPE: DNA
<213> ORGANISM: Artificial
<220> FEATURE:
<223> OTHER INFORMATION: Designed chimeric oligonucleotide primer designated as K-R-1133(62) to amplify a portion of Mycobacterium tuberculosis DNA."nucleotides 18 to 20 are ribonucleotides-other nucleotides are deoxyribonucleotides."

<400> SEQUENCE: 249
tgatcgtctc ggctagtgca 20

<210> SEQ ID NO 250
<211> LENGTH: 22
<212> TYPE: DNA
<213> ORGANISM: Artificial
<220> FEATURE:
<223> OTHER INFORMATION: Designed chimeric oligonucleotide primer designated as K-F-1033(68) to amplify a portion of Mycobacterium tuberculosis DNA."nucleotides 20 to 22 are ribonucleotides-other nucleotides are deoxyribonucleotides."

<400> SEQUENCE: 250
gtacacatcg atccggttca gc 22

<210> SEQ ID NO 251
<211> LENGTH: 22
<212> TYPE: DNA
<213> ORGANISM: Artificial
<220> FEATURE:
<223> OTHER INFORMATION: Designed chimeric oligonucleotide primer designated as K-R-1133(68) to amplify a portion of Mycobacterium tuberculosis DNA."nucleotides 20 to 22 are ribonucleotides-other nucleotides are deoxyribonucleotides."

<400> SEQUENCE: 251
gttgatcgtc tcggctagtg ca 22

-continued

<210> SEQ ID NO 252
<211> LENGTH: 20
<212> TYPE: DNA
<213> ORGANISM: Artificial
<220> FEATURE:
<223> OTHER INFORMATION: Designed oligonucleotide primer designated as F26 to amplify a portion of Mycobacterium tuberculosis DNA.

<400> SEQUENCE: 252
ccggagactc cagttcttgg 20

<210> SEQ ID NO 253
<211> LENGTH: 20
<212> TYPE: DNA
<213> ORGANISM: Artificial
<220> FEATURE:
<223> OTHER INFORMATION: Designed oligonucleotide primer designated as R1310 to amplify a portion of Mycobacterium tuberculosis DNA.

<400> SEQUENCE: 253
gtctctggcg ttgagcgtag 20

<210> SEQ ID NO 254
<211> LENGTH: 22
<212> TYPE: DNA
<213> ORGANISM: Artificial
<220> FEATURE:
<223> OTHER INFORMATION: Designed chimeric oligonucleotide primer designated as pDON-AI-68-1 to amplify a portion of pDON-AI. "nucleotides 20 to 22 are ribonucleotides-other nucleotides are deoxyribonucleotides."

<400> SEQUENCE: 254
actagctctg tatctggcgg ac 22

<210> SEQ ID NO 255
<211> LENGTH: 23
<212> TYPE: DNA
<213> ORGANISM: Artificial
<220> FEATURE:
<223> OTHER INFORMATION: Designed chimeric oligonucleotide primer designated as pDON-AI-68-2 to amplify a portion of pDON-AI. "nucleotides 21 to 23 are ribonucleotides-other nucleotides are deoxyribonucleotides."

<400> SEQUENCE: 255
acgatcggga tttttggact cag 23

<210> SEQ ID NO 256
<211> LENGTH: 300
<212> TYPE: DNA
<213> ORGANISM: Homo sapiens proto-oncogene Wnt-5a

<400> SEQUENCE: 256
cactagattt tttgtttggg gaggttggct tgaacataaa tgaaatatcc tgtattttct 60
tagggatact tggttagtaa attataatag tagaaataat acatgaatcc cattcacagg 120
tttctcagcc caagcaacaa ggtaattgcg tgccattcag cactgcacca gagcagacaa 180
cctatttgag gaaaaacagt gaaatccacc ttcctcttca cactgagccc tctctgattc 240
ctccgtgttg tgatgtgatg ctggccacgt ttccaaacgg cagctccact gggtcccctt 300

<210> SEQ ID NO 257
<211> LENGTH: 300
<212> TYPE: DNA

-continued

<213> ORGANISM: Homo sapiens ribosomal protein S5

<400> SEQUENCE: 257
cgccgagtga cagagacgct caggctgtgt tctcaggatg accgagtggg agacagcagc 60
accagcggtg gcagagaccc cagacatcaa gctctttggg aagtggagca ccgatgatgt 120
gcagatcaat gacatttccc tgcaggatta cattgcagtg aaggagaagt atgccaagta 180
cctccctcac agtgcagggc ggtatgccgc aaacgctttc cgcaaagctc agtgtcccat 240
tgtggagcgc ctcactaact ccatgatgat gcacggccgc aacaacggca agaagctcat 300

<210> SEQ ID NO 258
<211> LENGTH: 300
<212> TYPE: DNA
<213> ORGANISM: Homo sapiens diaphorase

<400> SEQUENCE: 258
tctatacaaa ttttcagaag gttattttct ttatcattgc taaactgatg acttaccatg 60
ggatggggtc cagtcccatg accttggggt acaattgtaa acctagagtt ttatcaactt 120
tggtgaacag ttttggcata atagtcaatt tctacttctg gaagtcatct cattccactg 180
ttggtattat ataattcaag gagaatatga taaaacactg ccctcttgtg gtgcattgaa 240
agaagagatg agaaatgatg aaaaggttgc ctgaaaaatg ggagacagcc tcttacttgc 300

<210> SEQ ID NO 259
<211> LENGTH: 300
<212> TYPE: DNA
<213> ORGANISM: Human protocadherin

<400> SEQUENCE: 259
agtctcttgg gatcccctaa ccagagcctt tttgccatag ggctgcacac tggtcaaatc 60
agtactgccc gtccagtcca agacacagat tcacccaggc agactctcac ggtcttgatc 120
aaagacaatg gggagccttc gctctccacc actgctaccc tcactgtgtc agtaaccgag 180
gactctcctg aagcccgagc cgagttcccc tctggctctg ccccccggga gcagaaaaaa 240
aatctcacct tttatctact tctttcccta atcctggttt ctgtggggtt tgtggtcaca 300

<210> SEQ ID NO 260
<211> LENGTH: 80
<212> TYPE: DNA
<213> ORGANISM: Artificial
<220> FEATURE:
<223> OTHER INFORMATION: Designed oligonucleotide for making of pIC62.

<400> SEQUENCE: 260
catgtacatc acagtagtcg ttcacagggt tttccggcca taatggcctt tcctgtgtgt 60
gtgctacagc tagtcagtca 80

<210> SEQ ID NO 261
<211> LENGTH: 20
<212> TYPE: DNA
<213> ORGANISM: Artificial
<220> FEATURE:
<223> OTHER INFORMATION: Designed chimeric oligonucleotide primer
designated as ICAN2."nucleotides 19 to 20 are ribonucleotides
-other nucleotides are deoxyribonucleotides."

<400> SEQUENCE: 261
actgactagc tgtagcacac 20

-continued

<210> SEQ ID NO 262
<211> LENGTH: 20
<212> TYPE: DNA
<213> ORGANISM: Artificial
<220> FEATURE:
<223> OTHER INFORMATION: Designed chimeric oligonucleotide primer designated as ICAN6."nucleotides 19 to 20 are ribonucleotides -other nucleotides are deoxyribonucleotides."

<400> SEQUENCE: 262
acatcacagt agtcgttcac 20

<210> SEQ ID NO 263
<211> LENGTH: 20
<212> TYPE: DNA
<213> ORGANISM: Artificial
<220> FEATURE:
<223> OTHER INFORMATION: Designed oligonucleotide primer designated as ICAN2 DNA."

<400> SEQUENCE: 263
actgactagc tgtagcacac 20

<210> SEQ ID NO 264
<211> LENGTH: 20
<212> TYPE: DNA
<213> ORGANISM: Artificial
<220> FEATURE:
<223> OTHER INFORMATION: Designed oligonucleotide primer designated as ICAN6 DNA.

<400> SEQUENCE: 264
acatcacagt agtcgttcac 20

<210> SEQ ID NO 265
<211> LENGTH: 23
<212> TYPE: DNA
<213> ORGANISM: Artificial
<220> FEATURE:
<223> OTHER INFORMATION: Designed oligonucleotide primer to amplify a portion of ribosomal protein S18-encoding sequence from mouse.

<400> SEQUENCE: 265
gtctctagtg atccctgaga agt 23

<210> SEQ ID NO 266
<211> LENGTH: 23
<212> TYPE: DNA
<213> ORGANISM: Artificial
<220> FEATURE:
<223> OTHER INFORMATION: Designed oligonucleotide primer to amplify a portion of ribosomal protein S18-encoding sequence from mouse.

<400> SEQUENCE: 266
tggatacacc cacagttcgg ccc 23

<210> SEQ ID NO 267
<211> LENGTH: 23
<212> TYPE: DNA
<213> ORGANISM: Artificial
<220> FEATURE:
<223> OTHER INFORMATION: Designed oligonucleotide primer to amplify a portion of transferrin receptor (TFR)-encoding sequence from mouse.

<400> SEQUENCE: 267
ccgcgctccg acaagtagat gga 23

-continued

<210> SEQ ID NO 268
<211> LENGTH: 23
<212> TYPE: DNA
<213> ORGANISM: Artificial
<220> FEATURE:
<223> OTHER INFORMATION: Designed oligonucleotide primer to amplify a portion of transferrin receptor (TFR)-encoding sequence from mouse.

<400> SEQUENCE: 268
ccaaagagtg caaggtctgc ctc 23

<210> SEQ ID NO 269
<211> LENGTH: 23
<212> TYPE: DNA
<213> ORGANISM: Artificial
<220> FEATURE:
<223> OTHER INFORMATION: Designed oligonucleotide primer to amplify a portion of stromal cell derived factor 4 (Sdf4)-encoding sequence from mouse.

<400> SEQUENCE: 269
tctgatggat gcaaccgcta gac 23

<210> SEQ ID NO 270
<211> LENGTH: 23
<212> TYPE: DNA
<213> ORGANISM: Artificial
<220> FEATURE:
<223> OTHER INFORMATION: Designed oligonucleotide primer to amplify a portion of stromal cell derived factor 4 (Sdf4)-encoding sequence from mouse.

<400> SEQUENCE: 270
gaactcttca tgcacgttgc ggg 23

<210> SEQ ID NO 271
<211> LENGTH: 23
<212> TYPE: DNA
<213> ORGANISM: Artificial
<220> FEATURE:
<223> OTHER INFORMATION: Designed oligonucleotide primer to amplify a portion of cytoplasmic beta-actin encoding sequence from mouse.

<400> SEQUENCE: 271
tgatggtggg aatgggtcag aag 23

<210> SEQ ID NO 272
<211> LENGTH: 23
<212> TYPE: DNA
<213> ORGANISM: Artificial
<220> FEATURE:
<223> OTHER INFORMATION: Designed oligonucleotide primer to amplify a portion of cytoplasmic beta-actin encoding sequence from mouse.

<400> SEQUENCE: 272
agaagcactt gcggtgcacg atg 23

<210> SEQ ID NO 273
<211> LENGTH: 23
<212> TYPE: DNA
<213> ORGANISM: Artificial
<220> FEATURE:
<223> OTHER INFORMATION: Designed oligonucleotide primer to amplify a portion of ornithine decarboxylase-encoding sequence from mouse.

<400> SEQUENCE: 273

-continued

```
gatgaaagtc gccagagcac atc                                          23


<210> SEQ ID NO 274
<211> LENGTH: 23
<212> TYPE: DNA
<213> ORGANISM: Artificial
<220> FEATURE:
<223> OTHER INFORMATION: Designed oligonucleotide primer to amplify a
      portion of ornithine decarboxylase-encoding sequence from mouse.

<400> SEQUENCE: 274

ttgatcctag cagaagcaca ggc                                          23


<210> SEQ ID NO 275
<211> LENGTH: 23
<212> TYPE: DNA
<213> ORGANISM: Artificial
<220> FEATURE:
<223> OTHER INFORMATION: Designed oligonucleotide primer to
      amplify a portion of hypoxanthine guanine phosphoribosyl
      transferase (HPRT)-encoding sequence from mouse.

<400> SEQUENCE: 275

ggacaggact gaaagacttg ctc                                          23


<210> SEQ ID NO 276
<211> LENGTH: 23
<212> TYPE: DNA
<213> ORGANISM: Artificial
<220> FEATURE:
<223> OTHER INFORMATION: Designed oligonucleotide primer to amplify
      a portion of hypoxanthine guanine phosphoribosyl transferase
      (HPRT)-encoding sequence from mouse.

<400> SEQUENCE: 276

gtctggcctg tatccaacac ttc                                          23


<210> SEQ ID NO 277
<211> LENGTH: 23
<212> TYPE: DNA
<213> ORGANISM: Artificial
<220> FEATURE:
<223> OTHER INFORMATION: Designed oligonucleotide primer to amplify a
      portion of tyrosine 3-monooxygenase encoding sequence from mouse.

<400> SEQUENCE: 277

atgagctggt gcagaaggcc aag                                          23


<210> SEQ ID NO 278
<211> LENGTH: 23
<212> TYPE: DNA
<213> ORGANISM: Artificial
<220> FEATURE:
<223> OTHER INFORMATION: Designed oligonucleotide primer to amplify a
      portion of tyrosine 3-monooxygenase encoding sequence from mouse.

<400> SEQUENCE: 278

ttcccctcct tctcctgctt ctg                                          23


<210> SEQ ID NO 279
<211> LENGTH: 21
<212> TYPE: DNA
<213> ORGANISM: Artificial
<220> FEATURE:
<223> OTHER INFORMATION: Designed oligonucleotide primer designated
      as MCS-F.

<400> SEQUENCE: 279
```

-continued

```
ccattcaggc tgcgcaatgt t                                              21


<210> SEQ ID NO 280
<211> LENGTH: 22
<212> TYPE: DNA
<213> ORGANISM: Artificial
<220> FEATURE:
<223> OTHER INFORMATION: Designed oligonucleotide primer designated
      as MCS-R

<400> SEQUENCE: 280

tggcacgaca ggtttcccga ct                                             22


<210> SEQ ID NO 281
<211> LENGTH: 24
<212> TYPE: DNA
<213> ORGANISM: Artificial
<220> FEATURE:
<223> OTHER INFORMATION: Designed chimeric oligonucleotide primer
      designated as MF2N3(24). "nucleotides 22 to 24 are
      ribonucleoitdes-other nucleotides are deoxyribonucleotides."

<400> SEQUENCE: 281

gctgcaaggc gattaagttg ggua                                           24


<210> SEQ ID NO 282
<211> LENGTH: 24
<212> TYPE: DNA
<213> ORGANISM: Artificial
<220> FEATURE:
<223> OTHER INFORMATION: Designed chimeric oligonucleotide primer
      designated as MR1N3(24). "nucleotides 22 to 24 are
      ribonucleoitdes-other nucleotides are deoxyribonucleotides."

<400> SEQUENCE: 282

ctttatgctt ccggctcgta tguu                                           24


<210> SEQ ID NO 283
<211> LENGTH: 16
<212> TYPE: DNA
<213> ORGANISM: Artificial
<220> FEATURE:
<223> OTHER INFORMATION: Designed chimeric oligonucleotide primer
      designated as MTIS2F-16 to amplify a portion of Mycobacterium
      tuberculosis DNA."nucleotides 14 to 16 are ribonucleotides-other
      nucleotides are deoxyribonucleotides."

<400> SEQUENCE: 283

tcgtccagcg ccgcuu                                                    16


<210> SEQ ID NO 284
<211> LENGTH: 20
<212> TYPE: DNA
<213> ORGANISM: Artificial
<220> FEATURE:
<223> OTHER INFORMATION: Designed chimeric oligonucleotide primer
      designated as MTIS2R-ACC to amplify a portion of Mycobacterium
      tuberculosis DNA."nucleotides 18 to 20 are ribonucleotides-other
      nucleotides are deoxyribonucleotides."

<400> SEQUENCE: 284

caaaggccac gtaggcgaac                                                20


<210> SEQ ID NO 285
<211> LENGTH: 20
<212> TYPE: DNA
<213> ORGANISM: Artificial
```

-continued

<220> FEATURE:
<223> OTHER INFORMATION: Designed oligonucleotide primer designated as
MTIS-PCR-F-2 to amplify a portion of Mycobacterium tuberculosis
DNA.

<400> SEQUENCE: 285
cgaccgcatc aaccgggagc 20

<210> SEQ ID NO 286
<211> LENGTH: 20
<212> TYPE: DNA
<213> ORGANISM: Artificial
<220> FEATURE:
<223> OTHER INFORMATION: Designed oligonucleotide primer designated as
MTIS-PCR-R-2 to amplify a portion of Mycobacterium tuberculosis
DNA.

<400> SEQUENCE: 286
cccaggatcc tgcgagcgta 20

<210> SEQ ID NO 287
<211> LENGTH: 45
<212> TYPE: DNA
<213> ORGANISM: Artificial
<220> FEATURE:
<223> OTHER INFORMATION: Designed oligonucleotide primer designated
as SP6-HCV-F to amplify a portion of
HCV.

<400> SEQUENCE: 287
ccatttaggt gacactatag aatactgatg ggggcgacac tccac 45

<210> SEQ ID NO 288
<211> LENGTH: 45
<212> TYPE: DNA
<213> ORGANISM: Artificial
<220> FEATURE:
<223> OTHER INFORMATION: Designed oligonucleotide primer designated as
SP6-HCV-R to amplify a portion of HCV

<400> SEQUENCE: 288
agctctaata cgactcacta tagggtcgca agcaccctat caggc 45

<210> SEQ ID NO 289
<211> LENGTH: 20
<212> TYPE: DNA
<213> ORGANISM: Artificial
<220> FEATURE:
<223> OTHER INFORMATION: Designed chimeric oligonucleotide primer
designated as HCV-A S to amplify a portion of HCV."nucleotides 18
to 20 are ribonucleotides-other nucleotides are
deoxyribonucleotides."

<400> SEQUENCE: 289
gggtcctttc ttggatcaac 20

<210> SEQ ID NO 290
<211> LENGTH: 20
<212> TYPE: DNA
<213> ORGANISM: Artificial
<220> FEATURE:

-continued

```
<223> OTHER INFORMATION: Designed chimeric oligonucleotide primer
      designated as HCV-A A to amplify a portion of HCV. "nucleotides 18
      to 20 are ribonucleotides-other nucleotides are
      deoxyribonucleotides."

<400> SEQUENCE: 290

gacccaacac tactcggcua                                              20
```